US009051265B2

(12) United States Patent
Kamenecka et al.

(10) Patent No.: US 9,051,265 B2
(45) Date of Patent: *Jun. 9, 2015

(54) N-BENZYLINDOLE MODULATORS OF PPARG

(75) Inventors: Theodore Mark Kamenecka, Palm Beach Gardens, FL (US); Patrick R. Griffin, Jupiter, FL (US); Marcel Koenig, Palm Beach Gardens, FL (US); Alice Asteian, Jupiter, FL (US); Anne-Laure Blayo, Jupiter, FL (US); Yuanjun He, Palm Beach Gardens, FL (US); Youseung Shin, Jupiter, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/490,342

(22) Filed: Jun. 6, 2012

(65) Prior Publication Data

US 2012/0309769 A1 Dec. 6, 2012

Related U.S. Application Data

(60) Provisional application No. 61/493,895, filed on Jun. 6, 2011, provisional application No. 61/554,703, filed on Nov. 2, 2011, provisional application No. 61/617,138, filed on Mar. 29, 2012.

(51) Int. Cl.
| | |
|---|---|
| C07D 209/08 | (2006.01) |
| C07D 405/12 | (2006.01) |
| C07D 409/12 | (2006.01) |
| C07D 401/06 | (2006.01) |
| C07D 403/12 | (2006.01) |
| C07D 413/12 | (2006.01) |
| A61K 31/4439 | (2006.01) |
| A61K 31/497 | (2006.01) |
| A61K 31/41 | (2006.01) |
| A61K 31/4245 | (2006.01) |
| C07D 209/42 | (2006.01) |
| C07D 209/04 | (2006.01) |
| C07D 413/10 | (2006.01) |
| C07D 419/12 | (2006.01) |
| A61K 31/404 | (2006.01) |

(52) U.S. Cl.
CPC .......... *C07D 209/42* (2013.01); *C07D 209/04* (2013.01); *C07D 413/10* (2013.01); *C07D 419/12* (2013.01); *A61K 31/404* (2013.01); *C07D 401/06* (2013.01); *C07D 403/12* (2013.01); *C07D 405/12* (2013.01); *C07D 409/12* (2013.01)

(58) Field of Classification Search
None
See application file for complete search history.

(56) References Cited

U.S. PATENT DOCUMENTS

| 5,541,229 | A | 7/1996 | Narr et al. |
| 6,348,032 | B1 | 2/2002 | Sperl et al. |
| 7,544,707 | B2 | 6/2009 | Connor et al. |
| 2009/0062363 | A1* | 3/2009 | Kaku et al. ............... 514/394 |
| 2009/0325956 | A1 | 12/2009 | Taniguchi et al. |
| 2011/0028527 | A1 | 2/2011 | Chiang et al. |
| 2012/0309757 | A1 | 12/2012 | Kamenecka et al. |

FOREIGN PATENT DOCUMENTS

| EP | 0179619 A1 | 4/1986 |
| EP | 1445250 A1 | 8/2004 |
| EP | 1595866 A1 | 11/2005 |
| EP | 1988076 A1 | 11/2008 |
| JP | 08048671 A | 2/1996 |
| JP | 2005162657 | * 6/2005 |
| WF | WO0112187 | * 2/2001 |
| WO | WO-0112187 A2 | 2/2001 |
| WO | WO-2004/072025 A2 | 8/2004 |
| WO | WO-2006/045478 A1 | 5/2006 |
| WO | WO-2009/083526 A1 | 7/2009 |
| WO | WO-2012/170554 A1 | 12/2012 |
| WO | WO-2012/170561 A1 | 12/2012 |
| WO | WO-2013/078233 A1 | 5/2013 |
| WO | WO-2013/078237 A1 | 5/2013 |
| WO | WO-2013/078240 A1 | 5/2013 |

OTHER PUBLICATIONS

Chemical Abstract Registry No. 932514-67-5, indexed in the Registry File on STN CAS Online Apr. 26, 2007.*
Ito et al., A medium-term rat liver bioassay for rapid in vivo detection of carcinogenic potential of chemicals. Cancer Science 2003, 94, 3-8.*
Chemical abstract Registry No. 895116-51-5, indexed in the Registry File on STN CAS Online Jul. 23, 2006.*
Chemical Abstract Registry No. 895115-61-4, indexed in the Registry File on STN CAS Online Jul. 23, 2006.*
International Application Serial No. PCT/US2012/066123, International Search Report mailed Jan. 29, 2013, 3 pgs.
International Application Serial No. PCT/US2012/066123, Written Opinion mailed Jan. 29, 2013, 6 pgs.

(Continued)

*Primary Examiner* — Michael Barker
*Assistant Examiner* — Po-Chih Chen
(74) *Attorney, Agent, or Firm* — Geoffrey K. Cooper; Thomas Fitting

(57) ABSTRACT

The invention provides molecular entities that bind with high affinity to PPARG (PPARγ), and inhibit kinase-mediated (e.g., cdk5-mediated) phosphorylation of PPARG, but do not exert an agonistic effect on PPARG. Compounds of the invention can be used for treatment of conditions in patients wherein PPARG plays a role, such as diabetes, insulin resistance, impaired glucose tolerance, pre-diabetes, hyperglycemia, hyperinsulinemia, obesity, or inflammation. Side effects such as significant weight gain, edema, impairment of bone growth or formation, or cardiac hypertrophy, or any combination thereof, can be avoided in the mammal receiving the compound. Methods of preparation of the compounds, bioassay methods for evaluating compounds of the invention as non-agonistic PPARG binding compounds, and pharmaceutical compositions are also provided.

15 Claims, No Drawings

(56) References Cited

OTHER PUBLICATIONS

International Application Serial No. PCT/US2012/066135, International Search Report mailed Feb. 8, 2013, 4 pgs.
International Application Serial No. PCT/US2012/066135, Written Opinion mailed Feb. 8, 2013, 7 pgs.
Motani, Alykhan, et al., "INT131: A Selective Modulator of PPARgamma", J. Mol. Biol. 386, [Online] Retrieved From Internet: <http://www.intekrin.com/files/JMB386()1301_PPARg_T131-09.pdf>, (2009), 1301-1311.
International Application Serial No. PCT/US2012/041129, International Search Report mailed Jul. 24, 2012, 4 pgs.
International Application Serial No. PCT/US2012/041129, Written Opinion mailed Jul. 24, 2012, 9 pgs.
International Application Serial No. PCT/US2012/041137, International Search Report mailed Jul. 30, 2012, 8 pgs.
International Application Serial No. PCT/US2012/041137, Written Opinion mailed Jul. 30, 2012, 11 pgs.
Haggarty, S, "Dissecting cellular processes using small molecule: identification of colchicine-like. taxol-like and other small molecules that perturb mitosis.", Chemistry & Biology. vol. 7. No. 4, (Apr. 1, 2000), 275-286.
Hitoshi, Takami, et al., "Indole and benzimidazole derivatives as steroid 5[alpha]-reductase inhibitors in the rat prostate.", Bioorganic & Medicinal Chemistry. vol. 6. No. 12., (Dec. 1, 1998), 2441-2448.
Hitoshi, Takami, et al., "Synthesis of Tricyclic Compounds as Steroid 5.Alpha.-Reductase Inhibitors.", Chemical & Pharmaceutical Bulletin. vol. 48. No. 4., (Jan. 1, 2000), 552-555.
Jacobs, Robert T, et al., "Substituted 3-(phenylmethyl)-1H-indole-5-carboxamides and 1-(phenylmethyl)indole-6-carboxamides as potent. selective. orally active antagonists of the peptidoleukotrienes.", Journal of Medicinal Chemistry. American Chemical Society. US. vol. 36. No. 3., (Jan. 1, 1993), 394-409.
Jang, Hyun Choi, et al., "Antidiabetic actions of a non-agonist PPAR[gamma] ligand blocking Cdk5-mediated phosphorylation.", Nature, vol. 477, No. 7365, (Nov. 22, 2011), 477-481.
Jang Hyun, Choi, et al., "Antidiabetic actions of a non-agonist PPAR[gamma] ligand blocking Cdk5-mediated phosphorylation.", Nature val. 477, No. 7365, (Nov. 22, 2011), 477-481.
Kttcha, Daniel M, "The manganese(III) acetate oxidation of N-protected indolines.", Tetrahedron Letters. vol. 29. No. 18., (Jan. 1, 1988), 2151-2154.
Lamotte, Y., et al., "Synthesis and biological activities of novel indole derivatives as potent and selective PPAR<3> modulators", Bioorg Med Chem Lett., 20(4), (Feb. 15, 2010), 1399-1404.
Page, et al., "New 1.2.3.4-tetrahydropyrrolo[3.4-b]indole derivatives as selective CB2 receptor agonists.", Bioorganic & Medicinal Chemistry Letters. Ergamon. Elsevier Science. GB. vol. 17. No. 22., (Oct. 12, 2007), 6183-6187.
U.S. Appl. No. 13/490,324, Response filed Aug. 13, 2013 to Non Final Office Action mailed May 17, 2013, 78 pgs.
Bhattarai, B. R., et al., "Novel thiazolidinedione derivatives with anti-obesity effects: Dual action as PTP1B inhibitors and PPAR-y activators", *Bioorganic and Medicinal Chemistry Letters*, 20, (Sep. 2010), 6758-6763.
Chen, H., et al., "Cevoglitazar, a Novel Peroxisome Proliferator-Activated Receptor-α/y Dual Agonist, Potently Reduces Food intake and Body Weight in Obese Mice and Cynomolgus Monkeys", *Endocrinology*, 151(7), (Jul. 2010), 3115-3124.
Foryst-Ludwig, A., et al., "PPARgamma activation attenuates T-Iymphocyte-dependent inflammation of adipose tissue and development of insulin resistance in obese mice", *Cardiovascular Diabetology*, 9::64, (2010), 9 pgs.
Lu, M., et al., "Brain PPAR-y promotes obesity and is required for the insulin—sensitizing effect of thiazolidinediones", *Nature Medicine*, 17(51 (2011), 618-623.
Olefsky, J. M., et al., "Macrophages, Inflammation, and Insulin Resistance", *Ann. Rev. Physiol.*. 72, (Oct. 2009), 219-246.
U.S. Appl. No. 13/490,324, Non Final Office Action mailed May 17, 2013, 15 pgs.
"Diabetes Mellitus", Diabetes [Online], retrieved on Mar. 15, 2009, [Online]. Retrieved from the Internet: <URL; http://www.merck.com.mmpe/print/sec12/ch158/ch158b.html>, 1 pg.
Andersen, Henrik Sune, et al., "Preparation of aryl(carboxamido)azoles and analogs as modulators of molecules with phosphotyrosine recognition units", Document No. 128:3688, retrieved from CAPLUS, (Nov. 13, 1997), 1 pg. (Caplus printout only).
Lamotte, Yann, et al., "Synthesis and biological activities of novel indole derivatives as potent and selective PPARy modulators", Document No. 152:429458, retrieved from CAPLUS, Source: Bioorganic & Medicinal Chemistry Letters (2010), 20 (4), 1399-1404, (Feb. 10, 2010), 1 pg.(Caplus printout only).
Narr, Berthold, et al., "Preparation of 1-(4-biphenylyl)benzimidazoles as angiotensin II antagonists", Document No. 117:48554, retrieved from CAPLUS, (Aug. 8, 1992), 1 pg. (Caplus printout only).
U.S. Appl. No. 13/490,324, Non Final Office Action mailed May 16, 2014, 15 pgs.
U.S. Appl. No. 13/490,324, Preliminary Amendment filed Jan. 17, 2013, 71 pgs.
U.S. Appl. No. 13/490,324, Response filed Apr. 7, 2014 to Final Office Action mailed Nov. 7, 2013, 66 pgs.
U.S. Appl. No. 13/811,969, Non Final Office Action mailed Jun. 19, 2014, 33 pgs.
International Application Serial No. PCT/US2012/066116, International Preliminary Report on Patentability mailed Jun. 5, 2014, 6 pgs.
International Application Serial No. PCT/US2012/066123, International Preliminary Report on Patentability mailed Jun. 5, 2014, 6 pgs.
International Application Serial No. PCT/US2012/066135, International Preliminary Report on Patentability mailed Jun. 5, 2014, 9 pgs.
"Is there a Diabetes Cure?", [Online]. Retrieved from the Internet: <http://www.webmd.com/diabetesis-there-adiabetes-cure?page=2.>, (May 13, 2014), 4 pgs.
Bruno, et al., "Expert Opinion Emerging Drugs", 10(4), (2005), 747-771.
Colagiuri, et al., "The Answer to Diabetes Prevention: Science, Surgery, Service Delivery, or Social Policy?", American Journal of Public Health, vol. 96, No. 9, (Sep. 2006), 1562-1569.
Curtis, et al., "The Journal of the American Board of Family Practice", vol. 18, (2005), 37-43.
Park, Kyong Soo, "Prevention of type 2 diabetes mellitus from the viewpoint of genetics", Diabetes Research and Clinical Practice 66S (2004), (2004), S33-S35.
Sime, et al., "Discovery of GSK1997132B a novel centrally penetrant benzimidazole PPARy partial agonist", Bioorganic & Medicinal Chemistry Letters (published online Jun. 29, 2011), 21 (18), (Jun. 29, 2011), 5568-5572 (Caplus printout only).
Yanaka, et al., "An English translation of JP 08-048671", (1996).

* cited by examiner

N-BENZYLINDOLE MODULATORS OF PPARG

CROSS-REFERENCE TO RELATED APPLICATIONS

This application claims the benefit of priority to U.S. provisional patent applications, Ser. Nos. 61/493,895, filed Jun. 6, 2011, 61/554,703, filed Nov. 2, 2011, and 61/617,138, filed Mar. 29, 2012, which are incorporated by reference herein in their entireties.

BACKGROUND

The peroxisome proliferator active receptors (PPARs), members of the nuclear hormone receptor superfamily, comprise several subtypes, such as PPARα, PPARβ, and PPARγ. The PPARγ subtype, also referred to as PPARG, is the target of the glitazone pharmaceutical agents used for treatment of type II diabetes. PPARG is NR1C3 (the gene ID) and has two major isoforms—PPARG1 and PPARG2. The glitazones, such as pioglitazone and rosiglitazone, act as PPARG receptor agonists. However, other classes of pharmaceutical agents, such as Telmisartan, have been reported to act as partial agonists, binding in a different mode to PPARG and having different cofactor requirements. See Y. Lamotte, et al., *Bioorg. Med. Chem. Lett.* (2010), 20, 1399-1404.

SUMMARY

The present invention is directed to compounds that are non-activating (non-agonist) PPARG modulators, and to the use of these compounds in modulating the activity of PPARG, such as in treatment of conditions wherein non-activating modulation of PPARG is medically indicated, such as diabetes, insulin resistance, impaired glucose tolerance, pre-diabetes, hyperglycemia, hyperinsulinemia, obesity, or inflammation. Compounds of the invention can block kinase-mediated, such as cdk5-mediated, phosphorylation of PPARG, but are not agonists of the receptor itself. By avoiding agonism of the receptor, it is believed that the compounds may exhibit no or reduced side effects associated with administration of full and partial agonists of PPARG, such as significant weight gain, edema, impairment of bone growth or formation, or cardiac hypertrophy, or any combination thereof, in the mammal receiving the compound.

In various embodiments, the invention provides a non-agonist PPARG modulatory compound of formula (I) or a pharmaceutically acceptable salt thereof:

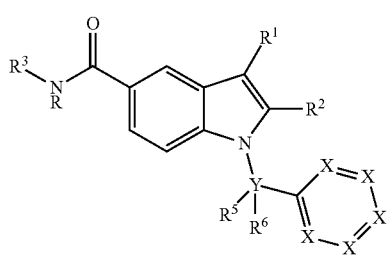

(I)

wherein:

R is H, $(C_1-C_6)$alkyl, $(C_3-C_9)$cycloalkyl, or $(C_1-C_6)$haloalkyl;

each X is independently N, CH, or $CR^4$, provided that no more than two instances of X are N, and no more than three instances of X are $CR^4$;

$R^1$ and $R^2$ are independently H, $(C_1-C_6)$alkyl, $(C_3-C_9)$cycloalkyl, or $(C_1-C_6)$haloalkyl; or $R^1$ and $R^2$ together with the atoms to which they are bonded form a 5- to 9-membered ring, comprising 0-3 heteroatoms selected from the group consisting of O, NR, and $SO_q$ wherein q is 0, 1, or 2, and optionally mono- or pluri-substituted with independently selected $(C_1-C_6)$alkyl, $(C_2-C_6)$alkenyl, $(C_2-C_6)$alkynyl, $(C_6-C_{10})$aryl, $(C_3-C_9)$cycloalkyl, halo, $(C_1-C_6)$haloalkyl, nitro, cyano-$(C_0-C_6)$alkyl, $R'O_2C$—$(C_0-C_6)$alkyl, methylenedioxy, $R'O$—$(C_0-C_6)$alkyl, $(R')_2N$—$(C_0-C_6)$alkyl, $(R')_2NC(=O)$—$(C_0-C_6)$alkyl, $(C_1-C_6)$alkyl-$S(O)_q(C_0-C_6)$alkyl, aryl, aroyl, or $SO_2NR'_2$; $R^3$ is optionally mono- or multi-substituted $(C_1-C_6)$alkyl, $(C_1-C_6)$alkenyl, $(C_1-C_6)$alkynyl, aryl, arylalkyl, heteroaryl, heteroarylalkyl, cycloalkyl, heterocyclyl, cycloalkylalkyl, or heterocyclylalkyl; wherein if present each substituent on $R^3$ is independently selected from the group consisting of $(C_1-C_6)$alkyl, $(C_2-C_6)$alkenyl, $(C_2-C_6)$alkynyl, $(C_6-C_{10})$aryl, $(C_3-C_9)$cycloalkyl, 3-9 membered mono- and bicyclic heterocyclyl, 3-9 membered mono- and bicyclic heteroaryl, halo, haloalkyl, haloalkoxy, nitro, cyano, $CO_2R'$, methylenedioxy, OR', $N(R')_2$, $C(O)N(R')_2$, $(C_1-C_4)$alkyl-$S(O)_q$, $SO_2NR'_2$, and $(C_1-C_6)$alkoxyl, wherein R' is independently H, $(C_1-C_6)$ alkyl, $(C_1-C_6)$ haloalkyl, or $(C_3-C_9)$cycloalkyl, or wherein two R' bonded to an atom together with the atom form a 3-8 membered ring optionally further comprising a heteroatom selected from the group consisting of O, NR', and $S(O)_q$, and wherein alkyl, alkenyl, alkynyl, aryl, arylalkyl, or cycloalkyl is optionally mono- or independently multi-substituted with $(C_1-C_6)$alkyl, $(C_1-C_6)$haloalkyl, $(C_1-C_6)$alkoxy, $(C_1-C_6)$haloalkoxy, halo, OR', $N(R')_2$, aryl, or aroyl; and wherein an alkyl or an alkyl group of a cycloalkylalkyl, heterocyclylalkyl, arylalkyl or heteroarylalkyl can be substituted with oxo;

each $R^4$ is independently halo, nitro, $(C_1-C_6)$fluoroalkyl, $R''$—$(C_1-C_6)$alkyl, $R''O_2C$—$(C_0-C_6)$alkyl, NC—$(C_0-C_6)$alkyl, $R''O$—$(C_0-C_6)$alkyl, $(R'')_2N$—$(C_0-C_6)$alkyl, $(R')_2NC(=O)$—$(C_0-C_6)$alkyl, C-bonded tetrazolyl, (1,3,4-oxadiazol-2(3H)-on)-yl, (1,2,4-oxadiazol-5(4H)-on)-3-yl, $(C_1-C_6)$alkyl-$S(O)_q(C_0-C_6)$alkyl, an unsubstituted or substituted aryl, an unsubstituted or substituted heteroaryl, $(C_1-C_6)$alkyl or $(C_3-C_9)$cycloalkyl-$(C_0-C_6)$alkyl, wherein any alkyl or cycloalkyl is optionally mono- or independently multi-substituted with R'', OR'', $N(R'')_2$, C-bonded tetrazolyl, $(C_1-C_6)$alkyl-$S(O)_q(C_0-C_6)$alkyl, an unsubstituted or substituted aryl, or an unsubstituted or substituted heteroaryl; or $R^4$ is —$(C(R'')_2)_mCO_2R''$, —$(C(R'')_2)_mCON(R'')_2$, or —$(C(R'')_2)_mCN$; m is 1, 2, 3, 4, 5, or 6;

R'' is independently H, OH, $(C_1-C_6)$alkyl or $(C_3-C_9)$cycloalkyl-$(C_0-C_6)$alkyl; or R'' is independently $(C_1-C_6)$haloalkyl, —$(C(R')_2)_mCO_2R$, —$(C(R')_2)_mCON(R)_2$, —$(C(R')_2)_mCON(R)OH$, or —$(C(R')_2)_mCN$; or R'' is C-bonded tetrazolyl, C-bonded oxadiazolonyl, $(C_1-C_6)$alkyl-(1,3,4-oxadiazol-2(3H)-on)-yl, $(C_1-C_6)$alkyl-(1,2,4-oxadiazol-5(4H)-on)-3-yl, $(C_1-C_4)$alkyl-$S(O)_q(C_0-C_6)$alkyl, an unsubstituted or substituted aryl, or an unsubstituted or substituted heteroaryl; or two R'' bonded to an atom together with the atom form a 3-8 membered ring optionally further comprising a heteroatom selected from the group consisting of O, NR, and $S(O)_q$; and wherein any alkyl or cycloalkyl moiety of R'' is optionally mono- or independently multi-substituted with $(C_1-C_6)$alkyl, $(C_1-C_6)$haloalkyl, $(C_1-C_6)$alkoxy, $(C_1-C_6)$haloalkoxy, halo, cyano, $CO_2R$, OR, $N(R)_2$, aryl, or aroyl; and wherein an alkyl, or an alkyl moiety or a cycloalkyl moiety or a heterocyclyl moiety of a cycloalkylalkyl, heterocyclylalkyl, arylalkyl or heteroarylalkyl, can be substituted with oxo;

q is 0, 1, or 2;

Y is ($C_1$-$C_2$)alkyl, or sulfur;

when Y is ($C_1$-$C_2$)alkyl, $R^5$ and $R^6$ are independently H or ($C_1$-$C_4$)alkyl or independently each $R^5$ and $R^6$ together with the carbon atom to which they are bonded form a carbonyl; and, when Y is sulfur, $R^5$ and $R^6$ are both oxygen.

In various embodiments, the invention provides a pharmaceutical composition comprising a compound of the invention, and a pharmaceutically acceptable excipient.

In various embodiments, the invention provides a method of inhibiting kinase-mediated, such as cdk5-mediated, phosphorylation of PPARG in a mammal, comprising administering to the mammal an effective amount of a compound of the invention. Compounds can bind both PPARG1 and PPARG2.

In various embodiments, the invention provides a method of treating a condition in a mammal, wherein binding of a ligand to PPARG or inhibition of kinase-mediated, such as cdk5-mediated, phosphorylation of PPARG, or both, is medically indicated, comprising administering to the mammal an effective amount of a compound of the invention at a frequency of dosing and for a duration of dosing effective to provide a beneficial effect to the mammal. For example, the condition can be diabetes, insulin resistance, impaired glucose tolerance, pre-diabetes, hyperglycemia, hyperinsulinemia, obesity, or inflammation. In methods of treatment of these conditions using a compound of the invention, the compound can avoid producing side effects of significant weight gain, edema, impairment of bone growth or formation, or cardiac hypertrophy, or any combination thereof, in the mammal receiving the compound.

In various embodiments, the invention provides a method of treatment of diabetes, insulin resistance, impaired glucose tolerance, pre-diabetes, hyperglycemia, hyperinsulinemia, obesity, or inflammation in a human, comprising administering to the human regularly over a duration of time an effective amount of a compound of the invention, optionally in conjunction with a second medicament effective for the treatment of the condition.

DETAILED DESCRIPTION

Overview

PPARG (also known as PPARγ) is a member of the nuclear receptor family of transcription factors. This protein is a dominant regulator of adipose cell differentiation and development. It is also the functioning receptor for the thiazolidinedione (TZD) class of anti-diabetic drugs, such as rosiglitazone and pioglitazone. These drugs were developed before their molecular modes of action were known, but later compounds were developed specifically as anti-diabetic drugs with high affinity and full agonism toward PPARG transcriptional activity. It has therefore been assumed that the therapeutic actions of these drugs result from their functional agonism on this receptor. From a clinical perspective, rosiglitazone (Avandia®) and pioglitazone (Actos®) are both highly effective oral medications for type 2 diabetes and are well tolerated by the majority of patients. Unfortunately, a substantial number of patients experience side effects from these drugs, including fluid retention, congestive heart failure and loss of bone mineral density. Since many diabetics have pre-existing cardiovascular disease or are at risk for heart problems, the fluid retention is particularly troubling. While some of the non-TZD full agonists also have good anti-diabetic activity, they also cause many of the same side effects, including fluid retention.

The therapeutic role of classical agonism of PPARG was made somewhat confusing by the development of several compounds that have less than full agonist properties (partial agonists) but retain substantial insulin-sensitizing and anti-diabetic actions in experimental models. Furthermore, we have recently shown that many anti-diabetic PPARG ligands of the TZD and other chemical classes have a second, distinct biochemical function: blocking the obesity-linked phosphorylation of PPARG by cyclin-dependent kinase 5 (cdk5) at serine 273. This is a direct action of the ligands and requires binding to the PPARG ligand binding domain (LBD) causing a conformational change that interferes with the ability of cdk5 to phosphorylate serine 273. Other kinase enzymes than cdk-5 can also mediate the phosphorylation of PPARG, and compounds of the invention can block the phosphorylation of PPARG without acting as PPARG agonists.

Rosiglitazone and MRL24 (a selective PPARG partial agonist) both modulate serine 273 phosphorylation at therapeutic doses in mice. Furthermore, a small clinical trial of newly diagnosed type 2 diabetics showed a remarkably close association in individual patients between the clinical effects of rosiglitazone and the blocking of this phosphorylation in PPARG. Thus, the contribution made by classical agonism to the therapeutic effects of these drugs or to their side effects can be deleterious.

The inventors herein have developed entirely new classes of compounds than can be effective anti-diabetic drugs that are optimized for the inhibition of cdk5-mediated phosphorylation of PPARG while being devoid of classical agonism. In this application we describe the development of a class of synthetic small molecules that bind tightly to PPARG and effectively inhibit phosphorylation at serine 273, yet are completely devoid of classical agonism. These compounds have unique binding modes in the ligand binding pocket of PPARG. An example possessing this type of bioactivity has been found to exhibits potent and dose-dependent anti-diabetic effects in obese mice. Importantly, this compound does not cause the fluid retention, weight gain, or impact mineralization in MC3T3 cells as is seen with rosiglitazone and other drugs that are full or partial agonists of PPARG.

Development of Novel Non-agonistic PPARG Ligands

In order to develop a suitable ligand, we optimized compounds for (i) high binding affinity for PPARG (ii) blocking the cdk5-mediated PPARG phosphorylation, and (iii) lacking classical agonism. Classical agonism is defined here, as is standard in the nuclear receptor field, as an increased level of transcription through a tandem PPAR response element luciferase reporter (PPRE::Luc).

Our central hypothesis is that "classical agonism of PPARG correlates with the adverse side effects of TZDs (and likely partial agonists as well), and that the blockage of cdk5-mediated phosphorylation of PPARG correlates with insulin sensitization efficacy."

The compounds we identify as non-agonist PPARG modulators are non-agonists that are potent blockers of cdk5-mediated phosphorylation of PPARG. Such a compound will have the following properties:

1. High affinity binding to PPARG
2. Minimal or no classical agonism
   a. Classical agonism is defined as AF-2 mediated coactivator interaction. Coactivator can be anyone of the p160 family or TRAP220 family members, as well as any coactivator shown to interact with PPARG 3. Compound is cell penetrant as determined by the cell based blockage of S273-P in differentiated preadipocytes or when a fixed concentration of compound added to cells alters the transcriptional activity of rosiglitazone on a tandem PPRE::Luc reporter. The compounds do not stimulate increased lipid accumulation or changes in morphology characteristic of differentiating fat cells.
4. Compounds may be antagonist of PPARG but not inverse agonists (they do not repress PPARG target genes).

In vivo such compounds do not increase the expression of a classified agonist gene set but do modulate the cdk5 gene set (Choi et al Nature. 2011 Sep. 4; 477(7365):477-81. doi: 10.1038/nature10383).

We currently believe a compound of the invention (i.e., a compound with the desirable properties recited above) is a compound that shows, at a concentration 10 times its IC50 in the lanthascreen assay, less than 5% transactivation relative to rosiglitazone in a receptor promoter reporter cotransfection assay with wild type human or mouse PPARG and a PPRE reporter. Specific protocols for the two assays, lanthascreen ($IC_{50}$) and PPRE ($EC_{50}$), and exemplary results are presented below.

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein PPARG plays a role in the biochemical mechanisms involved in the disease or condition or symptom(s) thereof such that a therapeutically beneficial effect can be achieved by acting on PPARG. "Acting on" PPARG, or "modulating" PPARG, can include binding to PPARG and/or inhibiting the bioactivity of PPARG and/or allosterically regulating the bioactivity of PPARG in vivo. When the term "modulator" is used herein, the term alludes to a compound of the invention, and it is understood that the terms "modulator" and "compound" or "compound of the invention" are synonymous when the context indicates that a compound of the present invention is being referred to.

In various embodiments, the compounds of the invention are not agonists of PPARG, i.e., binding of the compound to PPARG does not activate the receptor, as discussed in greater detail below. In various embodiments, compounds of the invention bring about inhibition of cdk5-mediated phosphorylation of PPARG while being devoid of classical agonism. Such compounds are referred to herein as "non-agonist PPARG modulatory compounds."

The expression "effective amount", when used to describe therapy to an individual suffering from a disorder, refers to the amount of a compound of the invention that is effective to inhibit or otherwise act on PPARG in the individual's tissues wherein PPARG involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

A "small molecule" refers to an organic compound, including an organometallic compound, of a molecular weight less than about 2 kDa, that is not a polynucleotide, a polypeptide, a polysaccharide, or a synthetic polymer composed of a plurality of repeating units.

As to any of the groups described herein, which contain one or more substituents, it is understood that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein can be present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis. Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

When a group, e.g., an "alkyl" group, is referred to without any limitation on the number of atoms in the group, it is understood that the claim is definite and limited with respect to the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1H$), deuterium ($^2H$), or tritium ($^3H$) in any combination. Similarly, any carbon atom or set thereof in a molecule can be any of the isotopic form of carbons, such as $^{11}C$, $^{12}C$, $^{13}C$, or $^{14}C$, or any nitrogen atom or set thereof in a molecule can be any of the isotopic forms of nitrogen, such as $^{13}N$, $^{14}N$, or $^{15}N$. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}C$ radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}N$ and $^{15}N$, $^{32}S$ and $^{34}S$, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}C$ and $^3H$ can be prepared using neutrons generated in a nuclear reactor. Following nuclear transformation, $^{14}C$ and $^3H$ are incorporated into precursor molecules, followed by further elaboration as needed.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle.

Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

C(O) and S(O)$_2$ groups can also be bound to one or two heteroatoms, such as nitrogen or oxygen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a "urea." When a C(O) is bonded to one oxygen and one nitrogen atom, the resulting group is termed a "carbamate" or "urethane." When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N-1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, —CH$_2$CH$_2$—S(=O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH₃)—CH₃, —CH₂—CH=CH—CH₂—SH, and —CH=CH—O—CH₂CH₂—O—CH₃.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl-1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]

azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "$(C_x-C_y)$perfluoroalkyl," wherein x<y, means an alkyl group with a minimum of x carbon atoms and a maximum of y carbon atoms, wherein all hydrogen atoms are replaced by fluorine atoms. Preferred is —$(C_1-C_6)$perfluoroalkyl, more preferred is —$(C_1-C_3)$perfluoroalkyl, most preferred is —$CF_3$.

The term "$(C_x-C_y)$perfluoroalkylene," wherein x<y, means an alkyl group with a minimum of x carbon atoms and a maximum of y carbon atoms, wherein all hydrogen atoms are replaced by fluorine atoms. Preferred is —$(C_1-C_6)$perfluoroalkylene, more preferred is —$(C_1-C_3)$perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula $N(group)_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —$C(O)NR_2$, and —NRC(O)R groups, respectively. Amide groups therefore include but are not limited to primary carboxamide groups (—$C(O)NH_2$) and formamide groups (—NHC(O)H). A "carboxamido" group is a group of the formula $C(O)NR_2$, wherein R can be H, alkyl, aryl, etc.

The term "azido" refers to an $N_3$ group. An "azide" can be an organic azide or can be a salt of the azide ($N_3^-$) anion. The term "nitro" refers to an $NO_2$ group bonded to an organic moiety. The term "nitroso" refers to an NO group bonded to an organic moiety. The term nitrate refers to an $ONO_2$ group bonded to an organic moiety or to a salt of the nitrate ($NO_3^-$) anion.

The term "urethane" ("carbamoyl" or "carbamyl") includes N- and O-urethane groups, i.e., —NRC(O)OR and —$OC(O)NR_2$ groups, respectively.

The term "sulfonamide" (or "sulfonamido") includes S- and N-sulfonamide groups, i.e., —$SO_2NR_2$ and —$NRSO_2R$ groups, respectively. Sulfonamide groups therefore include but are not limited to sulfamoyl groups (—$SO_2NH_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$. The term "guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds of the Invention
Tautomerism

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

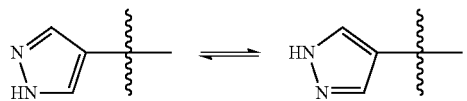

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

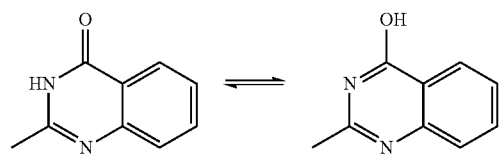

is an example of tautomerism. Accordingly, a structure depicted herein as one tautomer is intended to also include the other tautomer.

Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

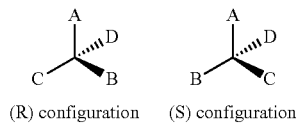

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of formula (I) which are biologically active in the treatment of cancer or other proliferative disease

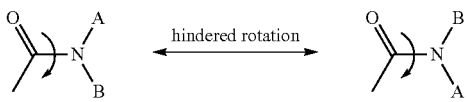

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

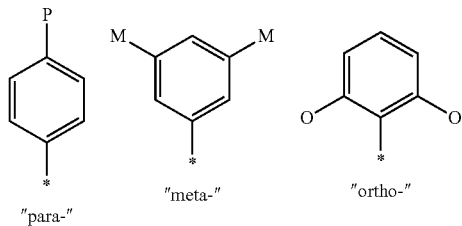

In various embodiments, the compound or set of compounds, such as are among the inventive compounds or are used in the inventive methods, can be any one of any of the combinations and/or sub-combinations of the above-listed embodiments.

DETAILED DESCRIPTION

In various embodiments, the invention provides a non-agonist PPARG modulatory compound of formula (I) or a pharmaceutically acceptable salt thereof:

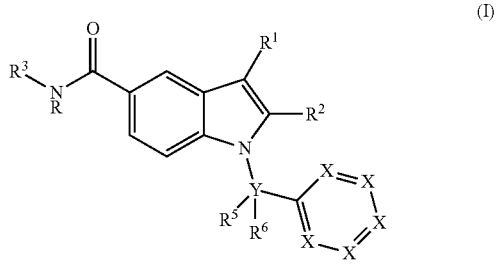

wherein:

R is H, $(C_1-C_6)$alkyl, $(C_3-C_9)$cycloalkyl, or $(C_1-C_6)$haloalkyl;

each X is independently N, CH, or $CR^4$, provided that no more than two instances of X are N, and no more than three instances of X are $CR^4$;

$R^1$ and $R^2$ are independently H, $(C_1-C_6)$alkyl, $(C_3-C_9)$cycloalkyl, or $(C_1-C_6)$haloalkyl; or $R^1$ and $R^2$ together with the atoms to which they are bonded form a 5- to 9-membered ring, comprising 0-3 heteroatoms selected from the group consisting of O, NR, and $SO_q$ wherein q is 0, 1, or 2, and optionally mono- or pluri-substituted with independently selected $(C_1-C_6)$alkyl, $(C_2-C_6)$alkenyl, $(C_2-C_6)$alkynyl, $(C_6-C_{10})$aryl, $(C_3-C_9)$cycloalkyl, halo, $(C_1-C_6)$haloalkyl, nitro, cyano-$(C_0-C_6)$alkyl, R'O$_2$C—$(C_0-C_6)$alkyl, methylenedioxy, R'O—$(C_0-C_6)$alkyl, (R')$_2$N—$(C_0-C_6)$alkyl, (R')$_2$NC(=O)—$(C_0-C_6)$alkyl, $(C_1-C_6)$alkyl-S(O)$_q$$(C_0-C_6)$alkyl, aryl, aroyl, or SO$_2$NR'$_2$; $R^3$ is optionally mono- or multi-substituted $(C_1-C_6)$alkyl, $(C_1-C_6)$alkenyl, $(C_1-C_6)$alkynyl, aryl, arylalkyl, heteroaryl, heteroarylalkyl, cycloalkyl, heterocyclyl, cycloalkylalkyl, or heterocyclylalkyl; wherein if present each substituent on $R^3$ is independently selected from the group consisting of $(C_1-C_6)$alkyl, $(C_2-C_6)$alkenyl, $(C_2-C_6)$alkynyl, $(C_6-C_{10})$aryl, $(C_3-C_9)$cycloalkyl, 3-9 membered mono- and bicyclic heterocyclyl, 3-9 membered mono- and bicyclic heteroaryl, halo, haloalkyl, haloalkoxy, nitro, cyano, CO$_2$R', methylenedioxy, OR', N(R')$_2$, C(O)N(R')$_2$, $(C_1-C_4)$alkyl-S(O)$_q$, SO$_2$NR'$_2$, and $(C_1-C_6)$alkoxyl, wherein R' is independently H, $(C_1-C_6)$ alkyl, $(C_1-C_6)$ haloalkyl, or $(C_3-C_9)$cycloalkyl, or wherein two R' bonded to an atom together with the atom form a 3-8 membered ring optionally further comprising a heteroatom selected from the group consisting of O, NR', and S(O)$_q$, and wherein alkyl, alkenyl, alkynyl, aryl, arylalkyl, or cycloalkyl is optionally mono- or independently multi-substituted with $(C_1-C_6)$alkyl, $(C_1-C_6)$haloalkyl, $(C_1-C_6)$alkoxy, $(C_1-C_6)$haloalkoxy, halo, OR', N(R')$_2$, aryl, or aroyl; and wherein an alkyl or an alkyl group of a cycloalkylalkyl, heterocyclylalkyl, arylalkyl or heteroarylalkyl can be substituted with oxo; each $R^4$ is independently halo, nitro, $(C_1-C_6)$fluoroalkyl, R"—$(C_0-C_6)$alkyl, R"O$_2$C—$(C_0-C_6)$alkyl, NC—$(C_0-C_6)$alkyl, R"O—$(C_0-C_6)$alkyl, (R")$_2$N—$(C_0-C_6)$alkyl, (R')$_2$NC(=O)—$(C_0-C_6)$alkyl, C-bonded tetrazolyl, $(C_1-C_6)$alkyl-S(O)$_q$$(C_0-C_6)$alkyl, an unsubstituted or substituted aryl, an unsubstituted or substituted heteroaryl, $(C_1-C_6)$alkyl or $(C_3-C_9)$cycloalkyl-$(C_0-C_6)$alkyl, wherein any alkyl or cycloalkyl is optionally mono- or independently multi-substituted with R", OR", N(R")$_2$, C-bonded tetrazolyl, $(C_1-C_6)$alkyl-S(O)$_q$$(C_0-C_6)$alkyl, an unsubstituted or substituted aryl, or an unsubstituted or substituted heteroaryl; or $R^4$ is —$(C(R")_2)_m$CO$_2$R", —$(C(R")_2)_m$CON(R")$_2$, or —$(C(R")_2)_m$CN;

m is 1, 2, 3, 4, 5, or 6;

R" is independently H, OH, $(C_1-C_6)$alkyl or $(C_3-C_9)$cycloalkyl-$(C_0-C_6)$alkyl; or R" is independently $(C_1-C_6)$haloalkyl, —$(C(R')_2)_m$CO$_2$R, —$(C(R')_2)_m$CON(R)$_2$, —$(C(R')_2)_m$CON(R)OH, or —$(C(R')_2)_m$CN; or R" is C-bonded tetrazolyl, C-bonded oxadiazolonyl, $(C_1-C_6)$alkyl-(1,3,4-oxadiazol-2(3H)-on)-yl, $(C_1-C_6)$alkyl-(1,2,4-oxadiazol-5(4H)-on)-3-yl, $(C_1-C_4)$alkyl-S(O)$_q$$(C_0-C_6)$alkyl, an unsubstituted or substituted aryl, or an unsubstituted or substituted heteroaryl; or two R" bonded to an atom together with the atom form a 3-8 membered ring optionally further comprising a heteroatom selected from the group consisting of O, NR, and S(O)$_q$; and wherein any alkyl or cycloalkyl moiety of R" is optionally mono- or independently multi-substituted with $(C_1-C_6)$alkyl, $(C_1-C_6)$haloalkyl, $(C_1-C_6)$alkoxy, $(C_1-C_6)$haloalkoxy, halo, cyano, CO$_2$R, OR, N(R)$_2$, aryl, or aroyl; and wherein an alkyl, or an alkyl moiety or a cycloalkyl moiety or a heterocyclyl moiety of a cycloalkylalkyl, heterocyclylalkyl, arylalkyl or heteroarylalkyl, can be substituted with oxo;

q is 0, 1, or 2;
Y is $(C_1-C_2)$alkyl, or sulfur;
when Y is $(C_1-C_2)$alkyl, $R^5$ and $R^6$ are independently H or $(C_1-C_4)$alkyl or independently each $R^5$ and $R^6$ together with the carbon atom to which they are bonded form a carbonyl; and,
when Y is sulfur, $R^5$ and $R^6$ are both oxygen.

In various embodiments, $R^1$ and $R^2$ are independently H or methyl.

In various embodiments, one X is N.

In various embodiments, $R^3$ is benzyl, α-phenethyl, α-phenpropyl, cycloalkyl or cycloalkylalkyl, any of which is unsubstituted or substituted.

Alternatively, $R^3$ is unsubstituted or substituted naphthyl or naphthylalkyl.

Additionally, $R^3$ can be heterocyclyl, heterocyclylalkyl, heteroaryl, or heteroarylalkyl, any of which is unsubstituted or substituted.

In various embodiments, the compound is of formula (II), or a pharmaceutically acceptable salt thereof

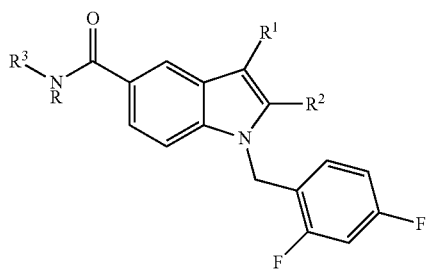

(II)

wherein R', $R^2$ and $R^3$ are as defined above for formula (I).

In various embodiments, $YR^5R^6$ is $SO_2$. Alternatively, Y is C1-alkyl; and $R^5$ and $R^6$ are H, providing a methylene group. Or, Y is C2-alkyl, and $R^5$ and $R^6$ are H, providing an ethylene group.

In various embodiments, $R^4$ is —$CO_2H$, —$(CH_2)_mCO_2H$, —$O(CH_2)_mCO_2H$, —CN, —$(CH_2)_mCN$, —$O(CH_2)_mCN$, —$C(CH_3)_2CO_2H$, —$C(CH_3)_2CN$, —$OC(CH_3)_2CO_2H$, —$OC(CH_3)_2CN$,
—$CH(CH_3)CO_2H$, —$CH(CH_3)CN$, —$OCH(CH_3)CO_2H$, —$OCH(CH_3)CN$; —$CH(CH_2CH_3)CO_2H$, —$CH(CH_2CH_3)CN$, —$OCH(CH_2CH_3)CO_2H$, —$OCH(CH_2CH_3)CN$; —CH(i-Pr)$CO_2H$, —CH(i-Pr)CN, —OCH(i-Pr)$CO_2H$, —OCH(i-Pr)CN, wherein iPr indicates isopropyl; —CH(t-Bu)$CO_2H$, —CH(t-Bu)CN, —OCH(t-Bu)$CO_2H$, —OCH(t-Bu)CN, wherein t-Bu indicates t-butyl; —$(CHR")_mC(=O)N(R")_2$, —$O(CHR")_mC(=O)N(R")_2$,

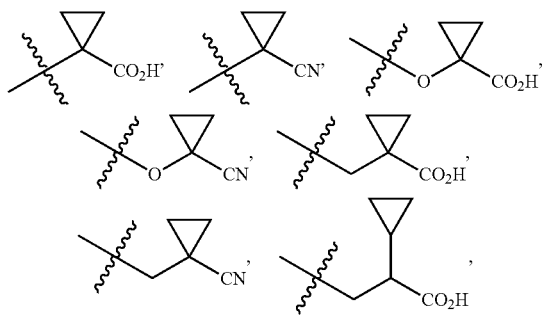

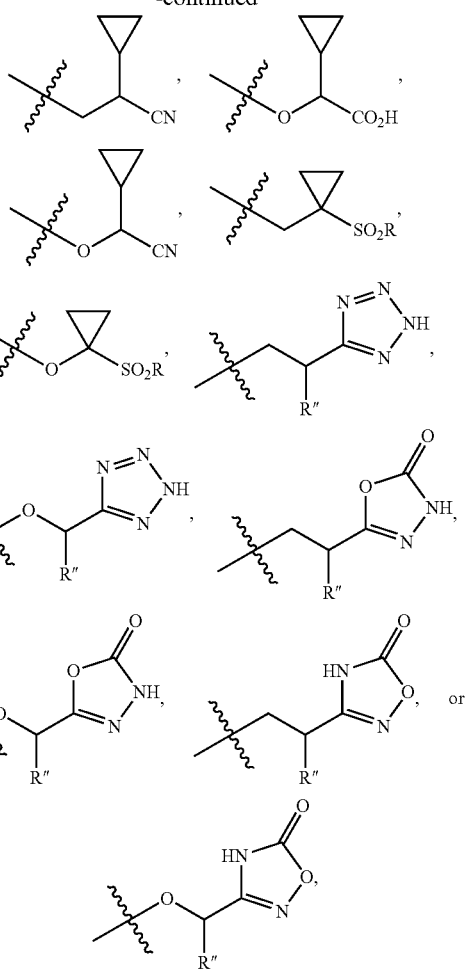

wherein m and R" are as defined above for formula (I); wherein a wavy line indicates a point of attachment.

In various embodiments, n is 1 and $R^4$ is disposed para to Y.

In various embodiments, $R^3$ is any one of:

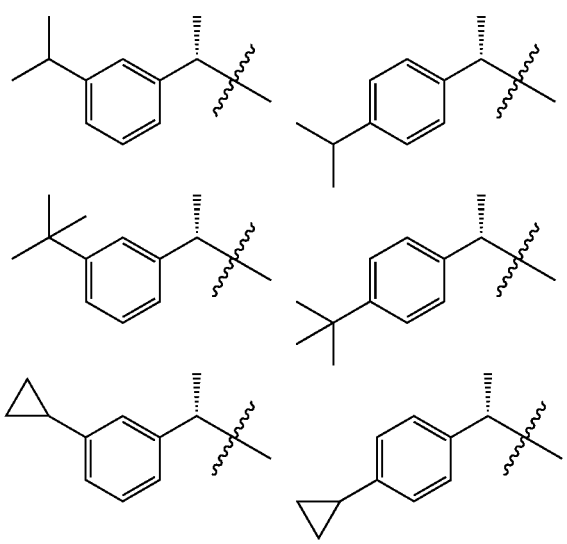

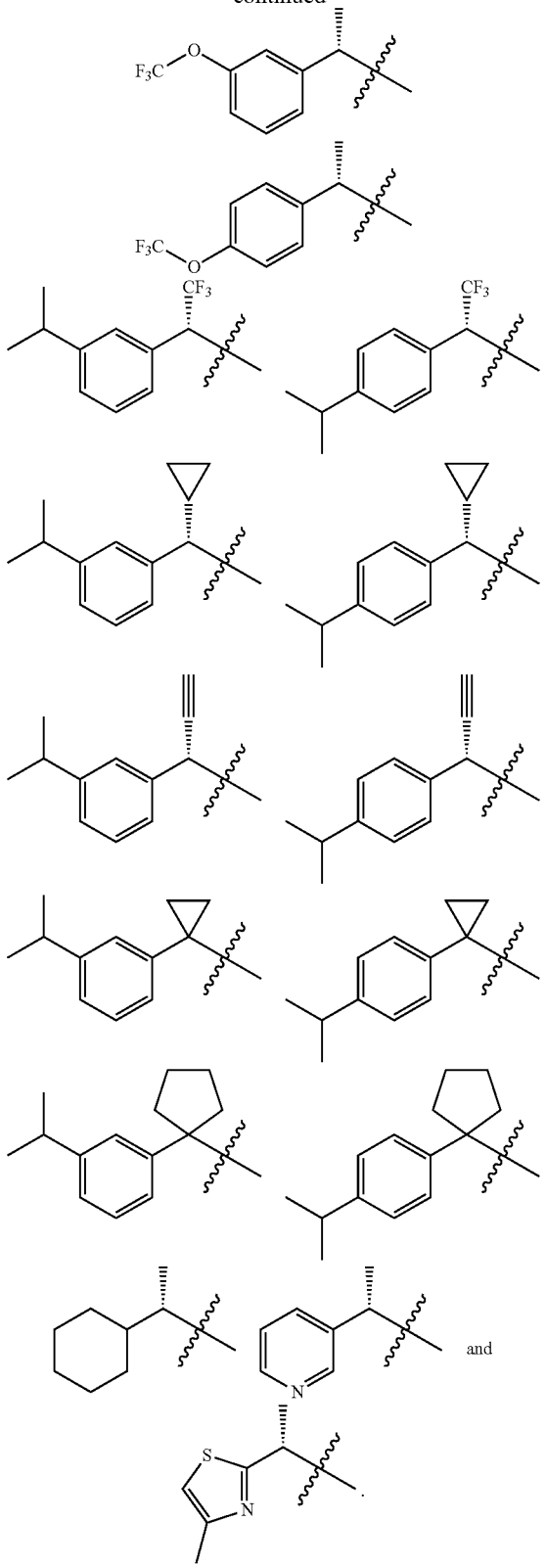

wherein a wavy line indicates a point of attachment.

In various embodiments, the compound is any of those shown in Table 1, below. A compound shown in Table 1 listed as a "prophetic example" is a compound believed by the inventors herein to be a compound of the invention, but which has not yet been specifically synthesized. Such compounds can be prepared by synthetic methods disclosed herein in combination with the knowledge of a person of ordinary skill in the art of organic synthesis, including the use of appropriately selected precursors, intermediates, reagents, and reaction mechanisms.

In various embodiments, the invention provides a pharmaceutical composition, comprising a compound of the invention; and a pharmaceutically acceptable excipient.

Another aspect of the invention is a composition, comprising a compound of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy,* 19th Ed., 1995, or later versions thereof, incorporated by reference herein. The compositions can appear in conventional forms, for example, capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly (anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tabletting techniques can contain:

| Core: | |
|---|---|
| Active compound (as free compound or salt thereof) | 250 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | Ad. |

| -continued | |
|---|---|
| Coating: | |
| HPMC approx. | 9 mg |
| *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 μg to about 1250 mg, preferably from about 250 μg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

Methods Of The Invention

In various embodiments, the invention provides method of inhibiting kinase-mediated, such as cdk5-mediated, phosphorylation of PPARG in a mammal, comprising administering to the mammal an effective amount of a compound of the invention. The effective amount of the compound for inhibiting kinase-mediated, e.g., cdk5-mediated, phosphorylation of PPARG can avoid producing an agonistic effect on PPARG. By avoiding agonism of PPARG, various side effects can be avoided, including significant weight gain, edema, impairment of bone growth or formation, or cardiac hypertrophy, or any combination thereof, in the mammal receiving the compound. Compounds of the invention can be useful for administration of effective amounts to patients suffering from diabetes, insulin resistance, impaired glucose tolerance, pre-diabetes, hyperglycemia, hyperinsulinemia, obesity, or inflammation.

In various embodiments, the invention provides a method of treating a condition in a mammal, wherein binding of a ligand to PPARG or inhibition of cdk5-mediated phosphorylation of PPARG, or both, is medically indicated, comprising administering to the mammal an effective amount of a compound of the invention at a frequency of dosing and for a duration of dosing effective to provide a beneficial effect to the mammal. The mammal under treatment can be a human. In various embodiments, the effective amount, frequency of dosing, and duration of dosing of the compound for binding of a ligand to PPARG or inhibition of cdk5-mediated phosphorylation of PPARG, or both, do not produce an agonistic effect on PPARG. For example, administration of a compound of the invention can be used for treatment of diabetes or obesity. Due to the avoidance of agonism of PPARG, an effective amount, frequency of dosing, and duration of dosing of the compound does not significantly produce side effects of significant weight gain, edema, impairment of bone growth or formation, or cardiac hypertrophy, or any combination thereof, in the mammal receiving the compound. in the mammal receiving the compound.

In particular, the invention provides a method of treatment of diabetes, insulin resistance, impaired glucose tolerance, pre-diabetes, hyperglycemia, hyperinsulinemia, obesity, or inflammation, in a human, comprising administering to the human regularly over a duration of time an effective amount of a compound of the invention, optionally in conjunction with a second medicament effective for the treatment of diabetes. The compound can be any suitable drug approved for diabetes treatment, such as biguanides, such as metformin and the like, sulfonylureas, such as gliburide and the like, or thiazolidinediones, such as rosiglitazone and the like. For treatment of inflammation, a second medicament suitable for suppression of an inflammatory response can also be administered.

EXAMPLES

TABLE 1

Specific Compounds of the Invention

| # | Formula | Substituents |
|---|---------|--------------|
| 1 | | R1 = H<br>R2 = H<br>R3 = 2,4-dimethoxybenzyl<br>R4 = F<br>Y = C<br>R5 = H<br>R6 = H |
| 2 | | R1 = H<br>R2 = H<br>R3 = 3-trifluoromethoxybenzyl<br>R4 = F<br>Y = C<br>R5 = H<br>R6 = H |
| 3 | | R1 = H<br>R2 = H<br>R3 = 3,4-dimethoxybenzyl<br>R4 = F<br>Y = C<br>R5 = H<br>R6 = H |
| 4 | | R1 = H<br>R2 = H<br>R3 = 1-(4-nitrophenyl)ethyl<br>R4 = F<br>Y = C<br>R5 = H<br>R6 = H |

TABLE 1-continued

Specific Compounds of the Invention

| # | Formula | Subsituents |
|---|---------|-------------|
| 5 | 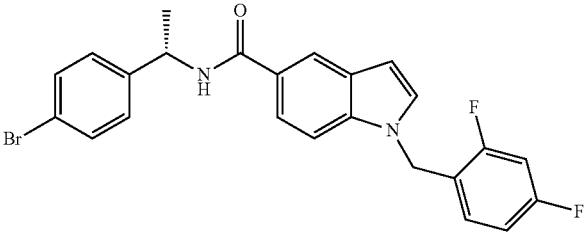 [SMILES: C[C@H](NC(=O)c1ccc2c(ccn2Cc2ccc(F)cc2F)c1)c1ccc(Br)cc1] | R1 = H<br>R2 = H<br>R3 = 1-(4-bromophenyl)ethyl<br>R4 = F<br>Y = C<br>R5 = H<br>R6 = H |
| 6 | 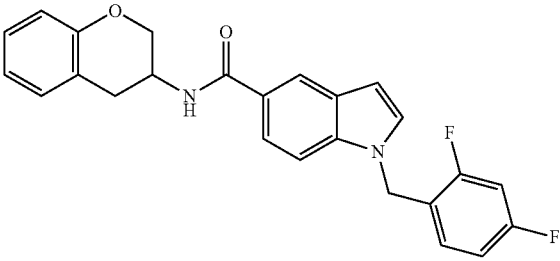 [SMILES: O=C(NC1COc2ccccc2C1)c1ccc2c(ccn2Cc2ccc(F)cc2F)c1] | R1 = H<br>R2 = H<br>R3 = chroman-3yl<br>R4 = F<br>Y = C<br>R5 = H<br>R6 = H |
| 7 | 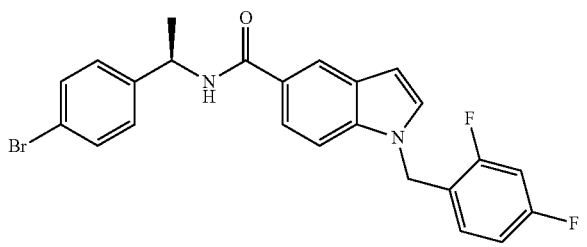 [SMILES: C[C@@H](NC(=O)c1ccc2c(ccn2Cc2ccc(F)cc2F)c1)c1ccc(Br)cc1] | R1 = H<br>R2 = H<br>R3 = 1-(4-bromophenyl)ethyl<br>R4 = F<br>Y = C<br>R5 = H<br>R6 = H |
| 8 | 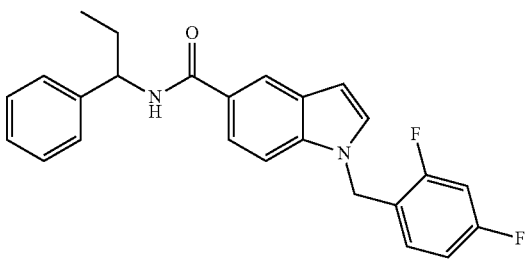 [SMILES: CCC(NC(=O)c1ccc2c(ccn2Cc2ccc(F)cc2F)c1)c1ccccc1] | R1 = H<br>R2 = H<br>R3 = 1-phenylpropyl<br>R4 = F<br>Y = C<br>R5 = H<br>R6 = H |
| 9 | 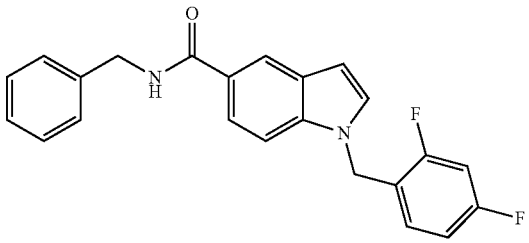 [SMILES: O=C(NCc1ccccc1)c1ccc2c(ccn2Cc2ccc(F)cc2F)c1] | R1 = H<br>R2 = H<br>R3 = benzyl<br>R4 = F<br>Y = C<br>R5 = H<br>R6 = H |
| 10 | 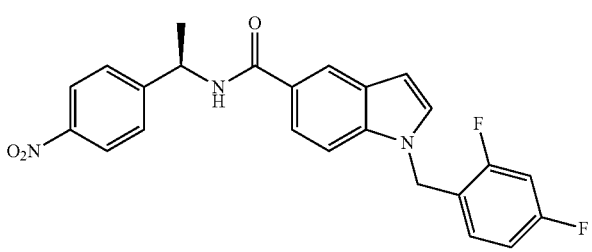 | R1 = H<br>R2 = H<br>R3 = 1-(4-nitrophenyl)ethyl<br>R4 = F<br>Y = C<br>R5 = H<br>R6 = H |

TABLE 1-continued

Specific Compounds of the Invention

| # | Formula | Subsituents |
|---|---------|-------------|
| 11 | | R1 = H<br>R2 = H<br>R3 = 1-methyl-1-phenylethyl<br>R4 = F<br>Y = C<br>R5 = H<br>R6 = H |
| 12 | | R1 = H<br>R2 = H<br>R3 = thiophen-2-ylmethyl<br>R4 = F<br>Y = C<br>R5 = H<br>R6 = H |
| 13 | | R1 = H<br>R2 = H<br>R3 = 2-methoxyethyl<br>R4 = F<br>Y = C<br>R5 = H<br>R6 = H |
| 14 | | R1 = H<br>R2 = H<br>R3 = 2,3-dihydro-benzo[1,4]dioxin-2-ylmethyl<br>R4 = F<br>Y = C<br>R5 = H<br>R6 = H |
| 15 | | R1 = H<br>R2 = H<br>R3 = 1-(naphthalen-1-yl)ethyl<br>R4 = F<br>Y = C<br>R5 = H<br>R6 = H |
| 16 | | R1 = H<br>R2 = H<br>R3 = 1-(4-fluorophenyl)ethyl<br>R4 = F<br>Y = C<br>R5 = H<br>R6 = H |

TABLE 1-continued

Specific Compounds of the Invention

| # | Formula | Substituents |
|---|---------|--------------|
| 17 | | R1 = H<br>R2 = H<br>R3 = 1-(4-fluorophenyl)ethyl<br>R4 = F<br>Y = C<br>R5 = H<br>R6 = H |
| 18 | | R1 = H<br>R2 = H<br>R3 = cyclopentyl<br>R4 = F<br>Y = C<br>R5 = H<br>R6 = H |
| 19 | | R1 = H<br>R2 = H<br>R3 = 2-phenylcyclopropyl<br>R4 = F<br>Y = C<br>R5 = H<br>R6 = H |
| 20 | | R1 = H<br>R2 = H<br>R3 = 4-aminobenzyl<br>R4 = F<br>Y = C<br>R5 = H<br>R6 = H |
| 21 | | R1 = methyl<br>R2 = methyl<br>R3 = 1-phenylpropyl<br>R4 = F<br>Y = C<br>R5 = H<br>R6 = H |
| 22 | | R1 = methyl<br>R2 = methyl<br>R3 = 1-phenylpropyl<br>R4 = Cl<br>Y = C<br>R5 = H<br>R6 = H |

TABLE 1-continued

Specific Compounds of the Invention

| # | Formula | Substituents |
|---|---------|--------------|
| 24 | | R1 = H<br>R2 = H<br>R3 = 1-phenylpropyl<br>R4 = Cl<br>Y = C—C<br>R5 = H<br>R6 = H |
| 25 | | R1 = H<br>R2 = H<br>R3 = 1-phenylpropyl<br>R4 = Absent<br>Y = C<br>R5 and R6 together are oxo (=O) |
| 26 | | R1 = H<br>R2 = H<br>R3 = 1-phenylpropyl<br>R4 = NO$_2$<br>Y = C<br>R5 and R6 together are oxo (=O) |
| 27 | | R1 = H<br>R2 = H<br>R3 = 1-phenylpropyl<br>R4 = F<br>Y = C<br>R5 and R6 together are oxo (=O) |
| 28 | | R1 = H<br>R2 = H<br>R3 = 1-phenylpropyl<br>R4 = methyl<br>Y, R5 and R6 are together sulfonyl (O=S=O) |

TABLE 1-continued

Specific Compounds of the Invention

| # | Formula | Substituents |
|---|---------|--------------|
| 30 | | R1 = H<br>R2 = H<br>R3 = 1-phenylpropyl<br>R4 = Absent<br>ring bearing R4 fused with phenyl<br>Y, R5 and R6 are together sulfonyl (O=S=O) |
| 31 | | R1 = H<br>R2 = H<br>R3 = 1-phenylpropyl<br>R4 = NO2<br>Y, R5 and R6 are together sulfonyl (O=S=O) |
| 32 | | R1 = H<br>R2 = H<br>R3 = 1-phenylpropyl<br>R4 = Cl<br>ring = 1N<br>Y = C<br>R5 and R6 = H |
| 33<br>P | | R1 = methyl<br>R2 = methyl<br>F3 = 6-cyclopropylpyrazin-2-yl-1-ethyl<br>R4 = 1-carboxy-1-methylethyl<br>Y = C<br>R5 = H<br>R6 = H |
| 34<br>P | | R1 = methyl<br>R2 = methyl<br>R3 = 7-isopropyl-2,3-dihydrobenzofuran-3-yl<br>R4 = 1-carboxy-1-methylethyl<br>Y = C<br>R5 = H<br>R6 = H |

TABLE 1-continued

Specific Compounds of the Invention

| # | Formula | Subsituents |
|---|---------|-------------|
| 35 | | R1 = methyl<br>R2 = methyl<br>R3 = 1-(3-isopropylphenyl)ethyl<br>R4 = 1-carboxy-1-cyclopropyl<br>Y = C<br>R5 = H<br>R6 = H |
| 36 | | R1 = methyl<br>R2 = methyl<br>R3 = 1-(3-cyclopropylphenyl)ethyl<br>R4 = 1-carboxy-1-methoxy<br>Y = C<br>R5 = H<br>R6 = H |
| 37 | | R1 = methyl<br>R2 = methyl<br>R3 = 1-(3-isopropylphenyl)ethyl<br>R4 = 1-carboxy-1-methoxy<br>Y = C<br>R5 = H<br>R6 = H |
| 38 | | R1 = methyl<br>R2 = methyl<br>R3 = 1-(4-t-butylphenyl)ethyl<br>R4 = 1-carboxy-1-methoxy<br>Y = C<br>R5 = H<br>R6 = H |
| 39 | | R1 = methyl<br>R2 = methyl<br>R3 = 1-(3-cyclopropylphenyl)ethyl<br>R4 = 1-carboxy-1-methoxy<br>Y = C<br>R5 = H<br>R6 = H |
| 40 | | R1 = methyl<br>R2 = methyl<br>R3 = 1-(3-isopropylphenyl)ethyl<br>R4 = 1-carboxy-1-methoxy<br>Y = C<br>R5 = H<br>R6 = H |

TABLE 1-continued

Specific Compounds of the Invention

| # | Formula | Substituents |
|---|---------|--------------|
| 41 | | R1 = methyl<br>R2 = methyl<br>R3 = 1-(4-t-butylphenyl)ethyl<br>R4 = 1-carboxy-1-methoxy<br>Y = C<br>R5 = H<br>R6 = H |
| 42 | | R1 = methyl<br>R2 = methyl<br>R3 = 1-(3-isopropylphenyl)ethyl<br>R4 = 1-carboxy-1-ethoxy<br>Y = C<br>R5 = H<br>R6 = H |
| 43 | | R1 = methyl<br>R2 = methyl<br>R3 = 1-(4-t-butylphenyl)ethyl<br>R4 = 1-carboxy-1-ethoxy<br>Y = C<br>R5 = H<br>R6 = H |
| 44 | | R1 = methyl<br>R2 = methyl<br>R3 = 1-(3-isopropylphenyl)ethyl<br>R4 = 1-carboxy-1-ethoxy<br>Y = C<br>R5 = H<br>R6 = H |
| 45 | | R1 = methyl<br>R2 = methyl<br>R3 = 1-(4-t-butylphenyl)ethyl<br>R4 = 1-carboxy-1-ethoxy<br>Y = C<br>R5 = H<br>R6 = H |
| 46 | | R1 = methyl<br>R2 = methyl<br>R3 = 1-(3-cyclopropylphenyl)ethyl<br>R4 = 1-carboxy-1-ethoxy<br>Y = C<br>R5 = H<br>R6 = H |

TABLE 1-continued

Specific Compounds of the Invention

| # | Formula | Substituents |
|---|---------|--------------|
| 47 | 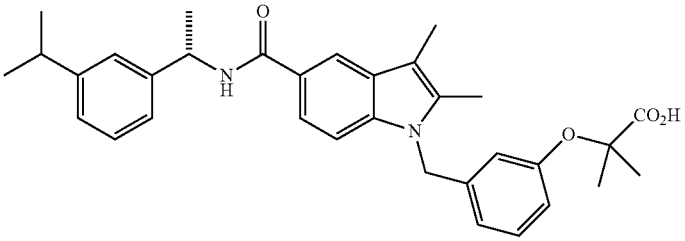 [SMILES: Cc1c(C)n(Cc2cccc(OC(C)(C)C(=O)O)c2)c2ccc(C(=O)N[C@@H](C)c3cccc(C(C)C)c3)cc12] | R1 = methyl<br>R2 = methyl<br>R3 = 1-(3-isopropylphenyl)ethyl<br>R4 = 1-carboxy-1-ethoxy-1-methyl<br>Y = C<br>R5 = H<br>R6 = H |
| 48 | 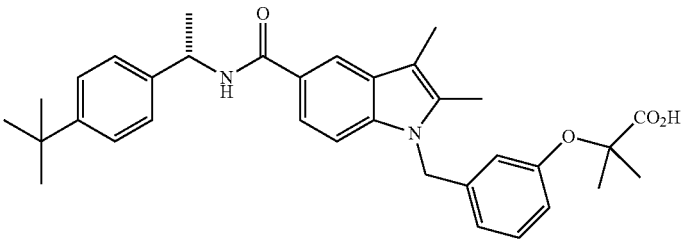 [SMILES: Cc1c(C)n(Cc2cccc(OC(C)(C)C(=O)O)c2)c2ccc(C(=O)N[C@@H](C)c3ccc(C(C)(C)C)cc3)cc12] | R1 = methyl<br>R2 = methyl<br>R3 = 1-(4-t-butylphenyl)ethyl<br>R4 = 1-carboxy-1-ethoxy-1-methyl<br>Y = C<br>R5 = H<br>R6 = H |
| 49 | 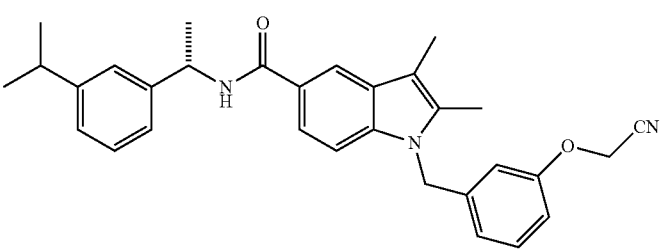 [SMILES: Cc1c(C)n(Cc2cccc(OCC#N)c2)c2ccc(C(=O)N[C@@H](C)c3cccc(C(C)C)c3)cc12] | R1 = methyl<br>R2 = methyl<br>R3 = 1-(3-isopropylphenyl)ethyl<br>R4 = 1-cyano-1-methoxy<br>Y = C<br>R5 = H<br>R6 = H |
| 50 | 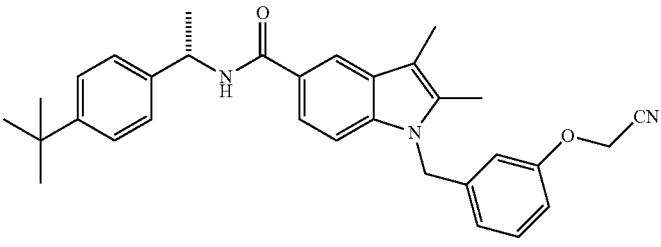 [SMILES: Cc1c(C)n(Cc2cccc(OCC#N)c2)c2ccc(C(=O)N[C@@H](C)c3ccc(C(C)(C)C)cc3)cc12] | R1 = methyl<br>R2 = methyl<br>R3 = 1-(4-t-butylphenyl)ethyl<br>R4 = 1-cyano-1-methoxy<br>Y = C<br>R5 = H<br>R6 = H |
| 51 | 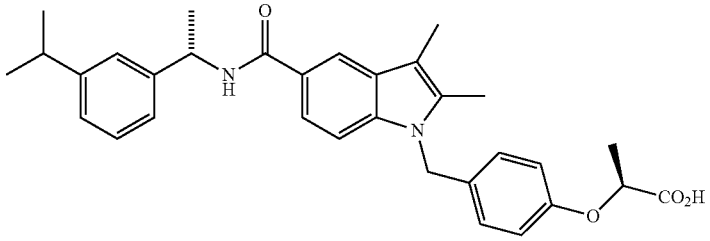 [SMILES: Cc1c(C)n(Cc2ccc(O[C@@H](C)C(=O)O)cc2)c2ccc(C(=O)N[C@@H](C)c3cccc(C(C)C)c3)cc12] | R1 = methyl<br>R2 = methyl<br>R3 = 1-(3-isopropylphenyl)ethyl<br>R4 = 1-carboxy-1-ethoxy<br>Y = C<br>R5 = H<br>R6 = H |
| 52 | 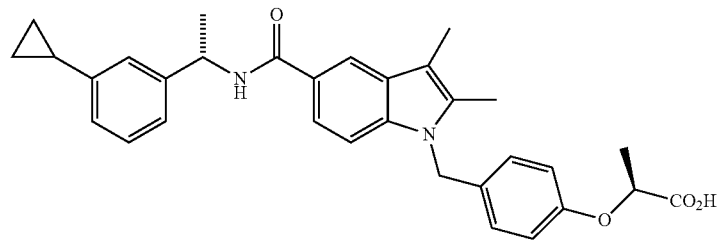 [SMILES: Cc1c(C)n(Cc2ccc(O[C@@H](C)C(=O)O)cc2)c2ccc(C(=O)N[C@@H](C)c3cccc(C4CC4)c3)cc12] | R1 = methyl<br>R2 = methyl<br>R3 = 1-(3-cyclopropylphenyl)ethyl<br>R4 = 1-carboxy-1-ethoxy<br>Y = C<br>R5 = H<br>R6 = H |

TABLE 1-continued

Specific Compounds of the Invention

| # | Formula | Subsituents |
|---|---------|-------------|
| 53 | | R1 = methyl<br>R2 = methyl<br>R3 = 1-(3-isoproylphenyl)ethyl<br>R4 = 1-carboxy-1-ethoxy<br>Y = C<br>R5 = H<br>R6 = H |
| 54 | | R1 = methyl<br>R2 = methyl<br>R3 = 1-(3-isopropylphenyl)ethyl<br>R4 = 1-carboxy-1-ethoxy-1-methyl<br>Y = C<br>R5 = H<br>R6 = H |
| 55 | | R1 = methyl<br>R2 = methyl<br>R3 = 1-(3-isoproylphenyl)ethyl<br>R4 = 1-carboxy-1-ethoxy, Cl<br>Y = C<br>R5 = H<br>R6 = H |
| 56 | | R1 = methyl<br>R2 = methyl<br>R3 = 1-(3-cyclopropylphenyl)ethyl<br>R4 = 1-carboxy-1-ethoxy, Cl<br>Y = C<br>R5 = H<br>R6 = H |
| 57 | | R1 = methyl<br>R2 = methyl<br>R3 = 1-(4-bromophenyl)ethyl<br>R4 = 1-carboxy-1-ethoxy, Cl<br>n = 1<br>Y = CH |
| 58 | | R1 = methyl<br>R2 = methyl<br>R3 = 1-(4-t-butylphenyl)ethyl<br>R4 = 1-carboxy-1-ethoxy, Cl<br>Y = C<br>R5 = H<br>R6 = H |

TABLE 1-continued

Specific Compounds of the Invention

| # | Formula | Substituents |
|---|---------|--------------|
| 59 | | R1 = methyl<br>R2 = methyl<br>R3 = 1-(3-t-butylphenyl)ethyl<br>R4 = 1-carboxy-1-ethoxy, Cl<br>Y = C<br>R5 = H<br>R6 = H |
| 60 | | R1 = methyl<br>R2 = methyl<br>R3 = 1-(3-isopropoxyphenyl)ethyl<br>R4 = 1-carboxy-1-ethoxy, Cl<br>Y = C<br>R5 = H<br>R6 = H |
| 61 | | R1 = methyl<br>R2 = methyl<br>R3 = 1-(3-isoproylphenyl)ethyl<br>R4 = 1-carboxy-1-ethoxy, Cl<br>Y = C<br>R5 = H<br>R6 = H |
| 62 | | R1 = methyl<br>R2 = methyl<br>R3 = 1-(3-cyclopropylphenyl)ethyl<br>R4 = 1-carboxy-1-ethoxy, Cl<br>Y = C<br>R5 = H<br>R6 = H |
| 63 | | R1 = methyl<br>R2 = methyl<br>R3 = 1-(4-bromophenyl)ethyl<br>R4 = 1-carboxy-1-ethoxy, Cl<br>Y = C<br>R5 = H<br>R6 = H |

TABLE 1-continued

Specific Compounds of the Invention

| # | Formula | Substituents |
|---|---------|--------------|
| 64 | 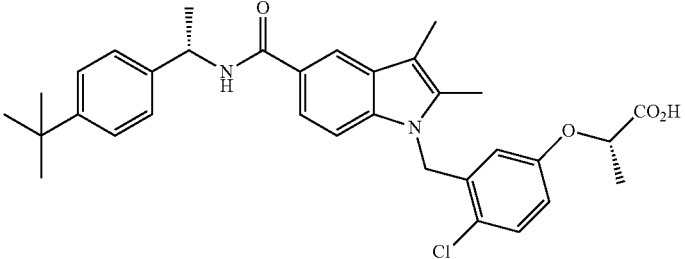 [SMILES: Cc1c(C)n(Cc2cc(O[C@@H](C)C(=O)O)ccc2Cl)c2ccc(C(=O)N[C@@H](C)c3ccc(C(C)(C)C)cc3)cc12] | R1 = methyl<br>R2 = methyl<br>R3 = 1-(3-t-butylphenyl)ethyl<br>R4 = 1-carboxy-1-ethoxy, Cl<br>Y = C<br>R5 = H<br>R6 = H |
| 65 | 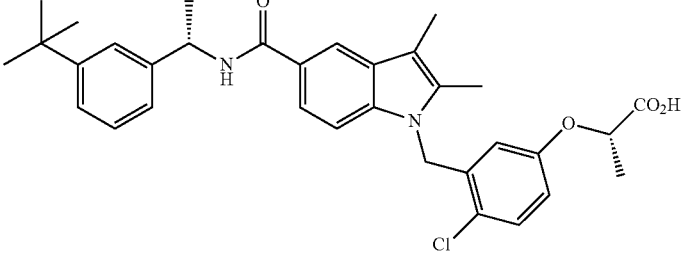 | R1 = methyl<br>R2 = methyl<br>R3 = 1-(3-t-butylphenyl)ethyl<br>R4 = 1-carboxy-1-ethoxy, Cl<br>Y = C<br>R5 = H<br>R6 = H |
| 66 | 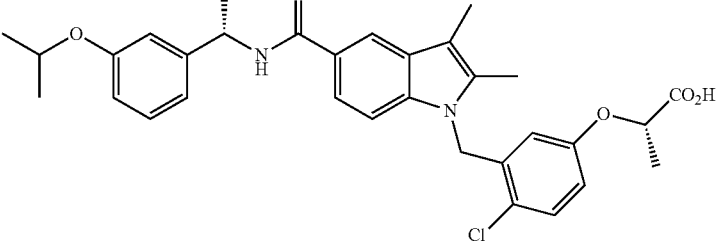 | R1 = methyl<br>R2 = methyl<br>R3 = 1-(3-isopropoxyphenyl)ethyl<br>R4 = 1-carboxy-1-ethoxy, Cl<br>Y = C<br>R5 = H, R6 = H |
| 67 | 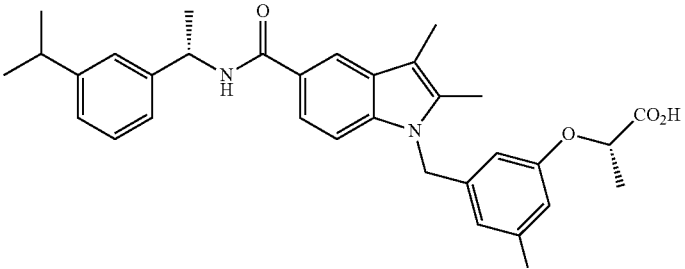 | R1 = methyl<br>R2 = methyl<br>R3 = 1-(3-isoproylphenyl)ethyl<br>R4 = 1-carboxy-1-ethoxy, Cl<br>Y = C<br>R5 = H<br>R6 = H |
| 68 | 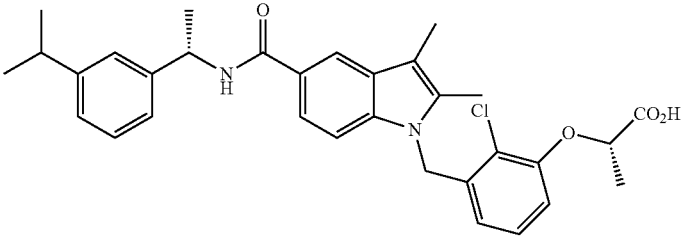 [SMILES: Cc1c(C)n(Cc2cccc(O[C@@H](C)C(=O)O)c2Cl)c2ccc(C(=O)N[C@@H](C)c3cccc(C(C)C)c3)cc12] | R1 = methyl<br>R2 = methyl<br>R3 = 1-(3-isoproylphenyl)ethyl<br>R4 = 1-carboxy-1-ethoxy, Cl<br>Y = C<br>R5 = H<br>R6 = H |

TABLE 1-continued

Specific Compounds of the Invention

| # | Formula | Substituents |
|---|---------|--------------|
| 69 | | R1 = methyl<br>R2 = methyl<br>R3 = 1-(3-isoproylphenyl)ethyl<br>R4 = 1-carboxy-1-ethoxy, Cl<br>Y = C<br>R5 = H<br>R6 = H |
| 70 | | R1 = methyl<br>R2 = methyl<br>R3 = 1-(3-isopropylphenyl)ethyl<br>R4 = 1-carboxy-1-ethoxy, Cl<br>Y = C<br>R5 = H<br>R6 = H |
| 71 | | R1 = methyl<br>R2 = methyl<br>R3 = 1-(3-isopropylphenyl)ethyl<br>R4 = 1-carboxy-1-ethoxy, Cl<br>Y = C<br>R5 = H<br>R6 = H |
| 72 | | R1 = methyl<br>R2 = methyl<br>R3 = 1-(3-isopropylphenyl)ethyl<br>R4 = 1-carboxy-1-ethoxy, Cl<br>Y = C<br>R5 = H<br>R6 = H |
| 73 | | R1 = methyl<br>R2 = methyl<br>R3 = 1-(3-isopropylphenyl)ethyl<br>R4 = 1-carboxy-1-ethoxy, Cl<br>Y = C<br>R5 = H<br>R6 = H |

TABLE 1-continued

Specific Compounds of the Invention

| # | Formula | Substituents |
|---|---------|--------------|
| 74 | | R1 = methyl<br>R2 = methyl<br>R3 = 1-(3-isopropylphenyl)ethyl<br>R4 = 1-carboxy-1-ethoxy, Cl<br>Y = C<br>R5 = H<br>R6 = H |
| 75 | | R1 = methyl<br>R2 = methyl<br>R3 = 1-(3-isopropylphenyl)ethyl<br>R4 = 1-carboxy-1-ethoxy, Cl<br>Y = C<br>R5 = H<br>R6 = H |
| 76 | | R1 = methyl<br>R2 = methyl<br>R3 = 1-(3-isopropylphenyl)ethyl<br>R4 = 1-carboxy-1-ethoxy, Cl<br>Y = C<br>R5 = H<br>R6 = H |
| 77 | | R1 = methyl<br>R2 = methyl<br>R3 = 1-(3-isopropylphenyl)ethyl<br>R4 = 1-carboxy-1-propoxy<br>Y = C<br>R5 = H<br>R6 = H |
| 78 | | R1 = methyl<br>R2 = methyl<br>R3 = 1-(3-isopropylphenyl)ethyl<br>R4 = 1-carboxy-1-propoxy<br>Y = C<br>R5 = H<br>R6 = H |
| 79 | | R1 = methyl<br>R2 = methyl<br>R3 = 1-(3-isopropylphenyl)ethyl<br>R4 = 1-carboxy-2-methyl-1-propoxy<br>Y = C<br>R5 = H<br>R6 = H |

TABLE 1-continued

Specific Compounds of the Invention

| # | Formula | Substituents |
|---|---------|--------------|
| 80 | | R1 = methyl<br>R2 = methyl<br>R3 = 1-(3-isopropylphenyl)ethyl<br>R4 = 1-carboxy-2-methyl-1-propoxy<br>Y = C<br>R5 = H<br>R6 = H |
| 81 | | R1 = methyl<br>R2 = methyl<br>R3 = 1-(3-isopropylphenyl)ethyl<br>R4 = 1-carboxy-1-propoxy, Cl<br>Y = C<br>R5 = H<br>R6 = H |
| 82 | | R1 = methyl<br>R2 = methyl<br>R3 = 1-(3-isopropylphenyl)ethyl<br>R4 = 1-carboxy-1-propoxy, Cl<br>Y = C<br>R5 = H<br>R6 = H |
| 83 | | R1 = methyl<br>R2 = methyl<br>R3 = 1-(3-isopropylphenyl)ethyl<br>R4 = 1-carboxy-1-propoxy, Cl<br>Y = C<br>R5 = H<br>R6 = H |
| 84 | | R1 = methyl<br>R2 = methyl<br>R3 = 1-(3-isopropylphenyl)ethyl<br>R4 = 1-carboxy-1-propoxy, Cl<br>Y = C<br>R5 = H<br>R6 = H |
| 85 | | R1 = methyl<br>R2 = methyl<br>R3 = 1-(3-isopropylphenyl)ethyl<br>R4 = 1-carboxy-2-methyl-1-propoxy, Cl<br>Y = C<br>R5 = H<br>R6 = H |

TABLE 1-continued

Specific Compounds of the Invention

| # | Formula | Substituents |
|---|---------|--------------|
| 86 | | R1 = methyl<br>R2 = methyl<br>R3 = 1-(3-isopropylphenyl)ethyl<br>R4 = 1-carboxy-2-methyl-1-propoxy, Cl<br>R5 = H<br>R6 = H |
| 87 | | R1 = methyl<br>R2 = methyl<br>R3 = 1-(3-isopropylphenyl)ethyl<br>R4 = 1-carboxy-2-methyl-1-propoxy, Cl<br>Y = C<br>R5 = H<br>R6 = H |
| 88 | | R1 = methyl<br>R2 = methyl<br>R3 = 1-(3-isopropylphenyl)ethyl<br>R4 = 1-carboxy-2-methyl-1-propoxy, Cl<br>Y = C<br>R5 = H<br>R6 = H |
| 89 | | R1 = methyl<br>R2 = methyl<br>R3 = 1-phenylpropyl<br>R4 = 1-carboxy-1-cyclopropyl<br>Y = C<br>R5 = H<br>R6 = H |
| 90 | | R1 = methyl<br>R2 = methyl<br>R3 = 1-(4-bromophenyl)ethyl<br>R4 = 1-carboxy-1-cyclopropyl<br>Y = C<br>R5 = H<br>R6 = H |

TABLE 1-continued

Specific Compounds of the Invention

| # | Formula | Substituents |
|---|---------|--------------|
| 91 | 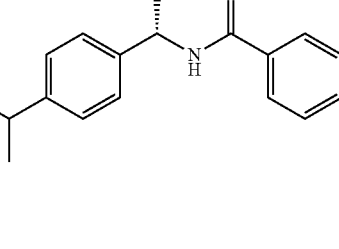 | R1 = methyl<br>R2 = methyl<br>R3 = 1-(4-isopropylphenyl)ethyl<br>R4 = 1-carboxy-1-cyclopropyl<br>Y = C<br>R5 = H<br>R6 = H |
| 92 | 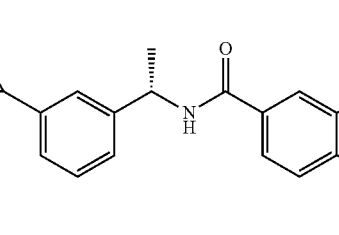 | R1 = methyl<br>R2 = methyl<br>R3 = 1-(3-cyclopropylphenyl)ethyl<br>R4 = 1-carboxy-1-ethoxy, Cl<br>Y = C<br>R5 = H<br>R6 = H |
| 93 | 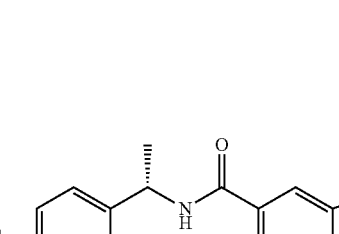 | R1 = methyl<br>R2 = methyl<br>R3 = 1-(4-tert-butylphenyl)ethyl<br>R4 = 1-carboxy-1-ethoxy, Cl<br>Y = C<br>R5 = H<br>R6 = H |
| 94 | 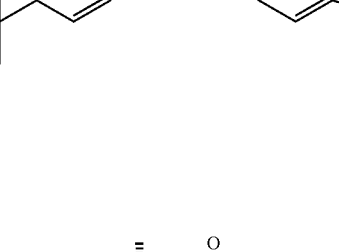 | R1 = methyl<br>R2 = methyl<br>R3 = 1-(3-cyclopropylphenyl)ethyl<br>R4 = 1-carboxy-1-ethoxy, Cl<br>Y = C<br>R5 = H<br>R6 = H |
| 95 | 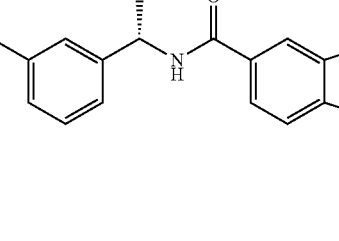 | R1 = methyl<br>R2 = methyl<br>R3 = 1-(4-tert-butylphenyl)ethyl<br>R4 = 1-carboxy-1-ethoxy, Cl<br>Y = C<br>R5 = H<br>R6 = H |

TABLE 1-continued

Specific Compounds of the Invention

| # | Formula | Subsituents |
|---|---|---|
| 96 | 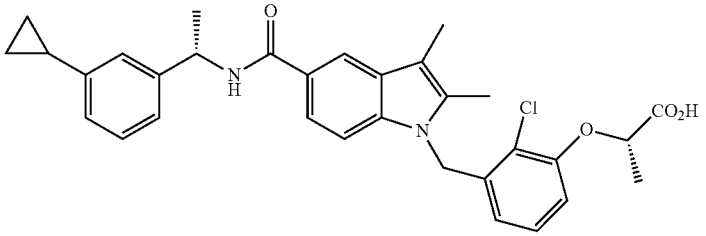 [SMILES: Cc1c(C)n(Cc2cccc(O[C@@H](C)C(=O)O)c2Cl)c2ccc(C(=O)N[C@@H](C)c3cccc(C4CC4)c3)cc12] | R1 = methyl<br>R2 = methyl<br>R3 = 1-(3-cyclopropylphenyl)ethyl<br>R4 = 1-carboxy-1-ethoxy, Cl<br>Y = C<br>R5 = H<br>R6 = H |
| 97 | 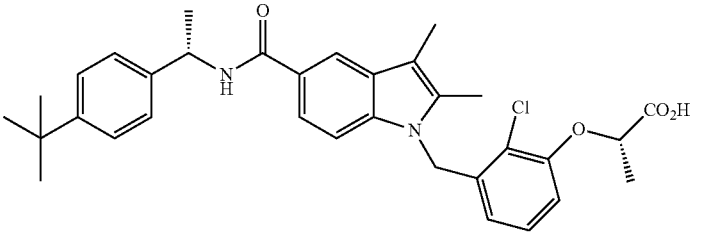 [SMILES: Cc1c(C)n(Cc2cccc(O[C@@H](C)C(=O)O)c2Cl)c2ccc(C(=O)N[C@@H](C)c3ccc(C(C)(C)C)cc3)cc12] | R1 = methyl<br>R2 = methyl<br>R3 = 1-(4-tert-butylphenyl)ethyl<br>R4 = 1-carboxy-1-ethoxy, Cl<br>Y = C<br>R5 = H<br>R6 = H |
| 98 | 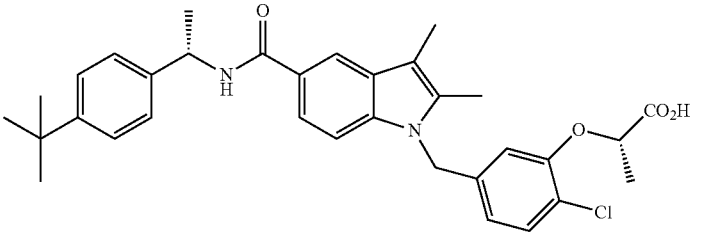 [SMILES: Cc1c(C)n(Cc2ccc(Cl)c(O[C@@H](C)C(=O)O)c2)c2ccc(C(=O)N[C@@H](C)c3ccc(C(C)(C)C)cc3)cc12] | R1 = methyl<br>R2 = methyl<br>R3 = 1-(4-tert-butylphenyl)ethyl<br>R4 = 1-carboxamide-1-ethoxy, Cl<br>Y = C<br>R5 = H<br>R6 = H |
| 99 | 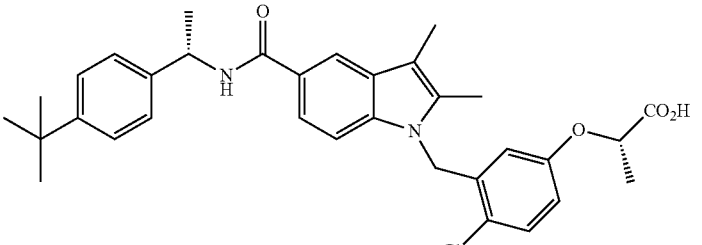 | R1 = methyl<br>R2 = methyl<br>R3 = 1-(4-tert-butylphenyl)ethyl<br>R4 = 1-carboxamide-1-ethoxy, Cl<br>Y = C<br>R5 = H<br>R6 = H |
| 100 | 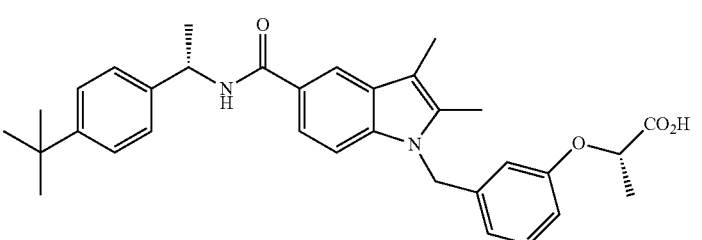 | R1 = methyl<br>R2 = methyl<br>R3 = 1-(4-tert-butylphenyl)ethyl<br>R4 = 1-carboxamide-1-ethoxy<br>Y = C<br>R5 = H<br>R6 = H |
| 101 | 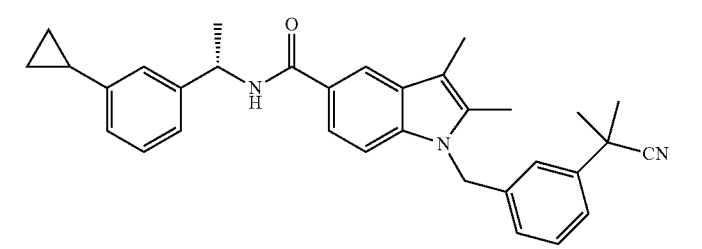 [SMILES: Cc1c(C)n(Cc2cccc(C(C)(C)C#N)c2)c2ccc(C(=O)N[C@@H](C)c3cccc(C4CC4)c3)cc12] | R1 = methyl<br>R2 = methyl<br>R3 = 1-(3-cyclopropylphenyl)ethyl<br>R4 = 1-cyano-1-methylethyl<br>Y = C<br>R5 = H<br>R6 = H |

TABLE 1-continued

Specific Compounds of the Invention

| # | Formula | Substituents |
|---|---------|--------------|
| 102 | | R1 = methyl<br>R2 = methyl<br>R3 = 1-(3-cylcopropylphenyl)ethyl<br>R4 = 1-carboxamide-1-methylethyl<br>Y = C<br>R5 = H<br>R6 = H |
| 103 | | R1 = methyl<br>R2 = methyl<br>R3 = 1-(3-cyclopropylphenyl)ethyl<br>R4 = 1-carboxy-1-ethoxy<br>Y = C<br>R5 = methyl<br>R6 = H |
| 104 | | R1 = methyl<br>R2 = methyl<br>R3 = 1-(4-tert-butylphenyl)ethyl<br>R4 = 1-carboxy-1-ethoxy<br>Y = C<br>R5 = methyl<br>R6 = H |
| 105 | | R1 = methyl<br>R2 = methyl<br>R3 = 1-(3-isopropoxyphenyl)ethyl<br>R4 = 1-carboxy-1-ethoxy<br>Y = C<br>R5 = H<br>R6 = H |
| 106 | | R1 = methyl<br>R2 = methyl<br>R3 = 1-(3-t-butylphenyl)ethyl<br>R4 = 1-carboxy-1-ethoxy<br>Y = C<br>R5 = H<br>R6 = H |
| 107 | | R1 = methyl<br>R2 = methyl<br>R3 = 1-(4-bromophenyl)ethyl<br>R4 = 1-carboxy-1-ethoxy<br>Y = C<br>R5 = H<br>R6 = H |

TABLE 1-continued

Specific Compounds of the Invention

| # | Formula | Substituents |
|---|---------|--------------|
| 108 | | R1 = methyl<br>R2 = methyl<br>R3 = 1-(4-trifluoromethylphenyl)ethyl<br>R4 = 1-carboxy-1-ethoxy<br>Y = C<br>R5 = H<br>R6 = H |
| 109 | | R1 = methyl<br>R2 = methyl<br>R3 = 1-(3-chlorophenyl)ethyl<br>R4 = 1-carboxy-1-ethoxy<br>Y = C<br>R5 = H<br>R6 = H |
| 110 | | R1 = methyl<br>R2 = methyl<br>R3 = 1-(4-chlorophenyl)ethyl<br>R4 = 1-carboxy-1-ethoxy<br>Y = C<br>R5 = H<br>R6 = H |
| 111 | | R1 = methyl<br>R2 = methyl<br>R3 = 1-(2-chlorophenyl)ethyl<br>R4 = 1-carboxy-1-ethoxy<br>Y = C<br>R5 = H<br>R6 = H |
| 112 | | R1 = methyl<br>R2 = methyl<br>R3 = 1-(4-t-butylphenyl)ethyl<br>R4 = 1-carboxy-1-ethoxy, OMe<br>Y = C<br>R5 = H<br>R6 = H |
| 113 | | R1 = methyl<br>R2 = methyl<br>R3 = 1-(3-cyclopropylphenyl)ethyl<br>R4 = 1-carboxy-1-ethoxy, OMe<br>Y = C<br>R5 = H<br>R6 = H |

TABLE 1-continued

Specific Compounds of the Invention

| # | Formula | Substituents |
|---|---------|--------------|
| 114 | | R1 = methyl<br>R2 = methyl<br>R3 = 1-(4-t-butylphenyl)ethyl<br>R4 = 1-carboxy-1-ethoxy, F<br>Y = C<br>R5 = H<br>R6 = H |
| 115 | | R1 = methyl<br>R2 = methyl<br>R3 = 1-(4-t-butylphenyl)ethyl<br>R4 = 1-carboxy-1-ethoxy, F<br>Y = C<br>R5 = H<br>R6 = H |
| 116 | | R1 = methyl<br>R2 = methyl<br>R3 = 1-(3-cyclopropylphenyl)ethyl<br>R4 = 1-carboxy-1-ethoxy, F<br>Y = C<br>R5 = H<br>R6 = H |
| 117 | | R1 = methyl<br>R2 = methyl<br>R3 = 1-(4-methoxyphenyl)ethyl<br>R4 = 1-carboxy-1-ethoxy<br>Y = C<br>R5 = H<br>R6 = H |
| 118 | | R1 = methyl<br>R2 = methyl<br>R3 = 1-(4-tert-butylphenyl)ethyl<br>R4 = 1-carboxy-1-ethoxy<br>Y = C<br>R5 = methyl<br>R6 = H |
| 119 | | R1 = methyl<br>R2 = methyl<br>R3 = 1-(4-tert-butylphenyl)ethyl<br>R4 = 1-carboxy-1-ethoxy<br>Y = C<br>R5 = methyl<br>R6 = H |

TABLE 1-continued

Specific Compounds of the Invention

| # | Formula | Substituents |
|---|---------|--------------|
| 120 | | R1 = methyl<br>R2 = methyl<br>R3 = 1-(3-cyclopropylphenyl)ethyl<br>R4 = 1-carboxy-1-cyclopropyl<br>Y = C<br>R5 = H<br>R6 = H |
| 121 | | R1 = methyl<br>R2 = methyl<br>R3 = 1-(3-cyclopropylphenyl)ethyl<br>R4 = 1-carboxy<br>Y = C<br>R5 = H<br>R6 = H |
| 122 | | R1 = methyl<br>R2 = methyl<br>R3 = 1-(3-cyclopropylphenyl)ethyl<br>R4 = 1-carboxamide<br>Y = C<br>R5 = H<br>R6 = H |
| 123 | | R1 = methyl<br>R2 = methyl<br>R3 = 3-isopropylphenyl-1-ethyl<br>R4 = 1-carboxyethyl, methoxy<br>Y = C<br>R5 = H<br>R6 = H |
| 124 | | R1 = methyl<br>R2 = methyl<br>R3 = 1-(3-isopropylphenyl)ethyl<br>R4 = 1-carboxy-1-ethoxy, F<br>Y = C<br>R5 = H<br>R6 = H |
| 125<br>P | | R1 = methyl<br>R2 = methyl<br>R3 = 1-(3-isopropylphenyl)ethyl<br>R4 = 1-carboxy-1-ethoxy, CH3<br>Y = C<br>R5 = H<br>R6 = H |

TABLE 1-continued

Specific Compounds of the Invention

| # | Formula | Substituents |
|---|---|---|
| 126 P | 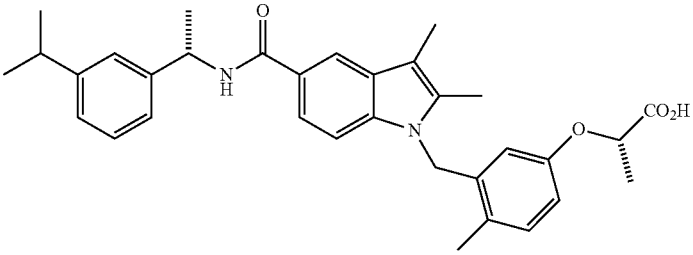 [SMILES: Cc1ccc(O[C@@H](C)C(=O)O)cc1Cn1c(C)c(C)c2cc(C(=O)N[C@@H](C)c3cccc(C(C)C)c3)ccc21] | R1 = methyl<br>R2 = methyl<br>R3 = 1-(3-isopropylphenyl)ethyl<br>R4 = 1-carboxy-1-ethoxy, CH₃<br>Y = C<br>R5 = H<br>R6 = H |
| 127 P | 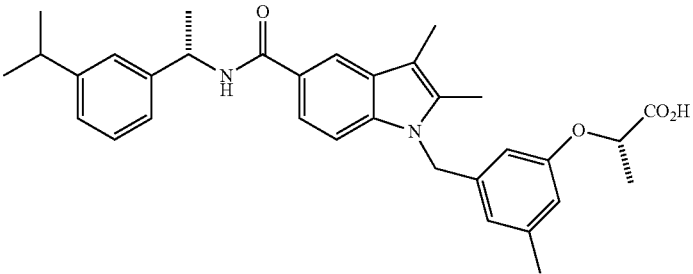 [SMILES: Cc1cc(Cn2c(C)c(C)c3cc(C(=O)N[C@@H](C)c4cccc(C(C)C)c4)ccc32)cc(O[C@@H](C)C(=O)O)c1] | R1 = methyl<br>R2 = methyl<br>R3 = 1-(3-isopropylphenyl)ethyl<br>R4 = 1-carboxy-1-ethoxy, CH₃<br>Y = C<br>R5 = H<br>R6 = H |
| 128 P | 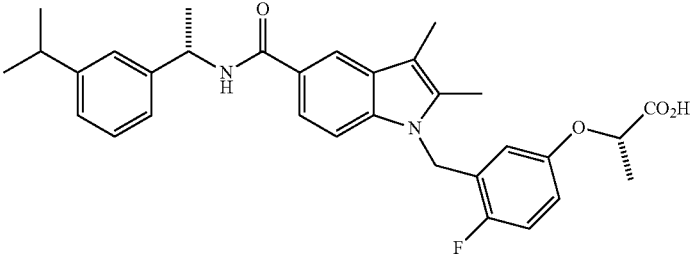 [SMILES: Cc1c(C)n(Cc2cc(O[C@@H](C)C(=O)O)ccc2F)c2ccc(C(=O)N[C@@H](C)c3cccc(C(C)C)c3)cc12] | R1 = methyl<br>R2 = methyl<br>R3 = 1-(3-isopropylphenyl)ethyl<br>R4 = 1-carboxy-1-ethoxy, F<br>Y = C<br>R5 = H<br>R6 = H |
| 129 P | 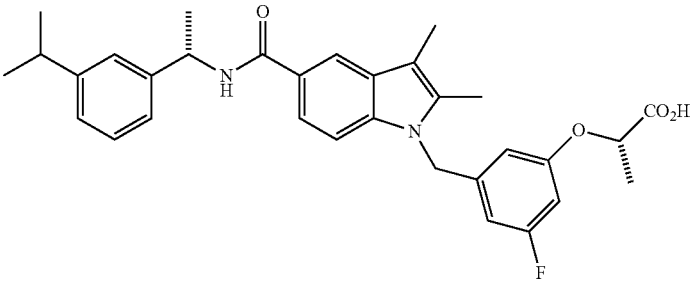 [SMILES: Cc1c(C)n(Cc2cc(F)cc(O[C@@H](C)C(=O)O)c2)c2ccc(C(=O)N[C@@H](C)c3cccc(C(C)C)c3)cc12] | R1 = methyl<br>R2 = methyl<br>R3 = 1-(3-isopropylphenyl)ethyl<br>R4 = 1-carboxy-1-ethoxy, F<br>Y = C<br>R5 = H<br>R6 = H |
| 130 P | 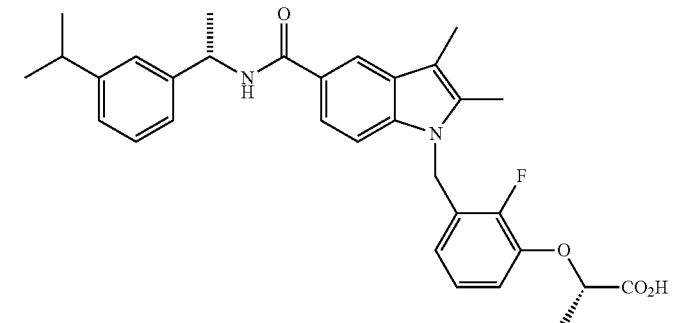 [SMILES: Cc1c(C)n(Cc2cccc(O[C@@H](C)C(=O)O)c2F)c2ccc(C(=O)N[C@@H](C)c3cccc(C(C)C)c3)cc12] | R1 = methyl<br>R2 = methyl<br>R3 = 1-(3-isopropylphenyl)ethyl<br>R4 = 1-carboxy-1-ethoxy, F<br>Y = C<br>R5 = H<br>R6 = H |

TABLE 1-continued

Specific Compounds of the Invention

| # | Formula | Substituents |
|---|---|---|
| 131 P | | R1 = methyl<br>R2 = methyl<br>R3 = 1-(3-isopropylphenyl)ethyl<br>R4 = 1-carboxy-1-ethoxy, CH$_3$<br>Y = C<br>R5 = H<br>R6 = H |
| 132 P | | R1 = methyl<br>R2 = methyl<br>R3 = 1-(3-isopropylphenyl)ethyl<br>R4 = 1-carboxy-1-ethoxy, CF$_3$<br>Y = C<br>R5 = H<br>R6 = H |
| 133 P | | R1 = methyl<br>R2 = methyl<br>R3 = 1-(3-isopropylphenyl)ethyl<br>R4 = 1-carboxy-1-ethoxy, CF$_3$<br>Y = C<br>R5 = H<br>R6 = H |
| 134 P | | R1 = methyl<br>R2 = methyl<br>R3 = 1-(3-isopropylphenyl)ethyl<br>R4 = 1-carboxy-1-ethoxy, CF$_3$<br>Y = C<br>R5 = H<br>R6 = H |
| 135 P | | R1 = methyl<br>R2 = methyl<br>R3 = 1-(3-isopropylphenyl)ethyl<br>R4 = 1-carboxy-1-ethoxy, CF$_3$<br>Y = C<br>R5 = H<br>R6 = H |

TABLE 1-continued

Specific Compounds of the Invention

| # | Formula | Substituents |
|---|---------|--------------|
| 136 P | | R1 = methyl<br>R2 = methyl<br>R3 = 1-(3-isopropylphenyl)ethyl<br>R4 = 1-carboxy-1-ethoxy, CN<br>Y = C<br>R5 = H<br>R6 = H |
| 137 P | | R1 = methyl<br>R2 = methyl<br>R3 = 1-(3-isopropylphenyl)ethyl<br>R4 = 1-carboxy-1-ethoxy, CN<br>Y = C<br>R5 = H<br>R6 = H |
| 138 P | | R1 = methyl<br>R2 = methyl<br>R3 = 1-(3-isopropylphenyl)ethyl<br>R4 = 1-carboxy-1-ethoxy, cyclopropyl<br>Y = C<br>R5 = H<br>R6 = H |
| 139 P | | R1 = methyl<br>R2 = methyl<br>R3 = 1-(3-isopropylphenyl)ethyl<br>R4 = 1-carboxy-1-cyclopropylmethoxy, Cl<br>Y = C<br>R5 = H<br>R6 = H |
| 140 P | | R1 = methyl<br>R2 = methyl<br>R3 = 1-(3-isopropylphenyl)ethyl<br>R4 = 1-carboxy-1-cyclopropylmethoxy, Cl<br>Y = C<br>R5 = H<br>R6 = H |
| 141 P | | R1 = methyl<br>R2 = methyl<br>R3 = 1-(3-isopropylphenyl)ethyl<br>R4 = 1-carboxy-1-cyclopropylmethoxy, Cl<br>Y = C<br>R5 = H<br>R6 = H |

TABLE 1-continued

Specific Compounds of the Invention

| # | Formula | Substituents |
|---|---------|--------------|
| 142 P | | R1 = methyl<br>R2 = methyl<br>R3 = 1-(3-isopropylphenyl)ethyl<br>R4 = 1-carboxy-1-cyclopropylmethoxy, Cl<br>Y = C<br>R5 = H, R6 = H |
| 143 P | | R1 = methyl<br>R2 = methyl<br>R3 = 1-(3-isopropylphenyl)ethyl<br>R4 = 2-(1-carboxy-1-ethoxy)<br>R4 ring is 4-pyridyl<br>Y = C<br>R5 = H; R6 = H |
| 144 P | | R1 = methyl<br>R2 = methyl<br>R3 = 1-(3-isopropylphenyl)ethyl R4 = 4-(1-carboxy-1-ethoxy)<br>R4 ring is 2-pyridyl<br>Y = C<br>R5 = H<br>R6 = H |
| 145 P | | R1 = methyl<br>R2 = methyl<br>R3 = 1-(3-isopropylphenyl)ethyl<br>R4 = 3-(1-carboxy-1-ethoxy)<br>R4 ring is 3-pyridyl<br>Y = C<br>R5 = H<br>R6 = H |
| 146 P | | R1 = methyl<br>R2 = methyl<br>R3 = 1-(3-isopropylphenyl)ethyl<br>R4 = 6-(1-carboxy-1-ethoxy)<br>R4 ring is 2-pyridyl<br>Y = C<br>R5 = H<br>R6 = H |
| 147 P | | R1 = methyl<br>R2 = methyl<br>R3 = 1-(3-isopropylphenyl)ethyl<br>R4 = 1-carboxy-1-ethoxy, F<br>Y = C<br>R5 = H<br>R6 = H |

TABLE 1-continued

Specific Compounds of the Invention

| # | Formula | Substituents |
|---|---------|--------------|
| 148 P | | R1 = methyl<br>R2 = methyl<br>R3 = 1-(3-isopropylphenyl)ethyl R4 = 1-carboxy-1-ethoxy, F<br>Y = C<br>R5 = H<br>R6 = H |
| 149 P | | R1 = methyl<br>R2 = methyl<br>R3 = 1-(3-isopropylphenyl)ethyl R4 = 1-carboxy-1-ethoxy, F, Cl<br>Y = C<br>R5 = H<br>R6 = H |
| 150 P | | R1 = methyl<br>R2 = methyl<br>R3 = 1-(3-isopropylphenyl)ethyl<br>R4 = 1-carboxy-1-ethoxy, F, Cl<br>Y = C<br>R5 = H<br>R6 = H |
| 151 P | | R1 = methyl<br>R2 = methyl<br>R3 = 1-(3-isopropylphenyl)ethyl<br>R4 = 1-carboxy-1-ethoxy, F<br>Y = C<br>R5 = H<br>R6 = H |
| 152 P | | R1 = methyl<br>R2 = methyl<br>R3 = 1-(3-isopropylphenyl)ethyl<br>R4 = 1-carboxy-1-ethoxy, F, Cl<br>Y = C<br>R5 = H<br>R6 = H |

TABLE 1-continued

Specific Compounds of the Invention

| # | Formula | Substituents |
|---|---|---|
| 153 P | | R1 = methyl<br>R2 = methyl<br>R3 = 1-(3-isopropylphenyl)ethyl<br>R4 = 1-carboxy-1-ethoxy, F, Cl<br>Y = C<br>R5 = H<br>R6 = H |
| 154 P | | R1 = methyl<br>R2 = methyl<br>R3 = 1-(3-isopropylphenyl)ethyl R4 = 1-carboxy-1-ethoxy, F<br>Y = C<br>R5 = H<br>R6 = H |
| 155 P | | R1 = methyl<br>R2 = methyl<br>R3 = 1-(3-isopropylphenyl)ethyl<br>R4 = 1-carboxyethyl<br>Y = C<br>R5 = H<br>R6 = H |
| 156 P | | R1 = methyl<br>R2 = methyl<br>R3 = 1-(3-isopropylphenyl)ethyl<br>R4 = 1-carboxyethyl<br>Y = C<br>R5 = H<br>R6 = H |
| 157 P | | R1 = methyl<br>R2 = methyl<br>R3 = 1-(4-isopropoxyphenyl)ethyl<br>R4 = 1-carboxy-1-ethoxy, Cl<br>Y = C<br>R5 = H<br>R6 = H |

TABLE 1-continued

Specific Compounds of the Invention

| # | Formula | Substituents |
|---|---|---|
| 158 P | | R1 = methyl<br>R2 = methyl<br>R3 = 1-(4-isopropoxyphenyl)ethyl<br>R4 = carboxy<br>Y = C<br>R5 = H<br>R6 = H |
| 159 P | | R1 = methyl<br>R2 = methyl<br>R3 = 1-(4-isopropoxyphenyl)ethyl<br>R4 = carboxy<br>Y = C<br>R5 = H<br>R6 = H |
| 160 P | | R1 = methyl<br>R2 = methyl<br>R3 = 1-(3-isopropylphenyl)ethyl<br>R4 = 1-carboxamide-1-ethoxy<br>Y = C<br>R5 = H<br>R6 = H |
| 161 P | | R1 = methyl<br>R2 = methyl<br>R3 = 1-(3-isopropylphenyl)ethyl<br>R4 = 1-tetrazolyl-1-ethoxy<br>Y = C<br>R5 = H<br>R6 = H |
| 162 P | | R1 = methyl<br>R2 = methyl<br>R3 = 1-(3-isopropylphenyl)ethyl<br>R4 = 1-oxadiazolonyl-1-ethoxy<br>Y = C<br>R5 = H<br>R6 = H |
| 163 P | | R1 = methyl<br>R2 = methyl<br>R3 = 1-(3-isopropylphenyl)ethyl<br>R4 = 1-oxadiazolonyl-1-ethoxy<br>Y = C<br>R5 = H<br>R6 = H |

TABLE 1-continued

Specific Compounds of the Invention

| # | Formula | Substituents |
|---|---------|--------------|
| 164 P | | R1 = methyl<br>R2 = methyl<br>R3 = 1-(3-isopropylphenyl)ethyl<br>R4 = 1-N-hydroxyacetamide-1-ethoxy<br>Y = C<br>R5 = H<br>R6 = H |
| 165 P | | R1 = methyl<br>R2 = methyl<br>R3 = 1-(3-isopropylphenyl)ethyl<br>R4 = 1-N-methylcarboxamide-1-ethoxy<br>Y = C<br>R5 = H<br>R6 = H |
| 166 P | | R1 = methyl<br>R2 = methyl<br>R3 = 1-(3-isopropylphenyl)ethyl<br>R4 = 1-methylsulfonyl-1-ethoxy<br>Y = C<br>R5 = H<br>R6 = H |
| 167 P | | R1 = methyl<br>R2 = methyl<br>R3 = 1-(3-isopropylphenyl)ethyl<br>R4 = 1-carboxy-1-ethoxy<br>Y = C<br>R5 = $CH_3$<br>R6 = H |
| 168 P | | R1 = methyl<br>R2 = methyl<br>R3 = 1-(3-isopropylphenyl)ethyl<br>R4 = 1-carboxy-1-ethoxy<br>Y = C<br>R5 = H<br>R6 = $CH_3$ |
| 169 P | | R1 = methyl<br>R2 = methyl<br>R3 = 1-(3-isopropylphenyl)ethyl<br>R4 = 1-carboxy-1-ethoxy<br>Y = C<br>R5 = $CH_3$<br>R6 = $CH_3$ |

TABLE 1-continued

Specific Compounds of the Invention

| # | Formula | Substituents |
|---|---------|--------------|
| 170 P | | R1 = methyl<br>R2 = methyl<br>R3 = 1-(3-isopropylphenyl)ethyl<br>R4 = 1-carboxy-1-ethoxy, Cl, Cl<br>Y = C<br>R5 = H<br>R6 = H |
| 171 P | | R1 = methyl<br>R2 = methyl<br>R3 = 1-(3-isopropylphenyl)ethyl<br>R4 = 1-carboxamide-1-ethoxy, Cl, Cl<br>Y = C<br>R5 = H<br>R6 = H |
| 172 P | | R1 = methyl<br>R2 = methyl<br>R3 = 1-(3-isopropylphenyl)ethyl<br>R4 = 1-N-methylcarboxamide-1-ethoxy, Cl, Cl<br>Y = C<br>R5 = H<br>R6 = H |
| 172 P | | R1 = methyl<br>R2 = methyl<br>R3 = 1-(3-cyclopropylphenyl)ethyl<br>R4 = 1-N-methylcarboxamide-1-methyl, 1-ethoxy<br>Y = C<br>R5 = H<br>R6 = H |
| 173 P | | R1 = methyl<br>R2 = methyl<br>R3 = 1-(3-cyclopropylphenyl)ethyl<br>R4 = 1-carboxy-1-ethylamino<br>Y = C<br>R5 = H<br>R6 = H |
| 174 P | | R1 = methyl<br>R2 = methyl<br>R3 = 1-(3-cyclopropylphenyl)ethyl<br>R4 = 1-carboxy-1-ethylamino-ethyl<br>Y = C<br>R5 = H<br>R6 = H |

TABLE 1-continued

Specific Compounds of the Invention

| # | Formula | Substituents |
|---|---------|--------------|
| 175 P | 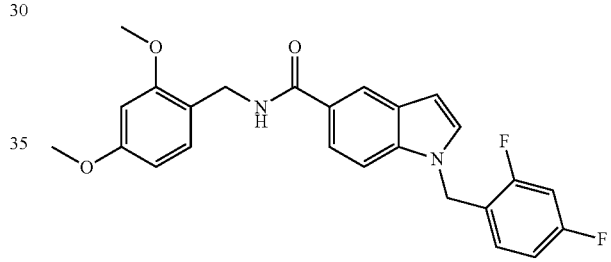 | R1 = methyl<br>R2 = methyl<br>R3 = 1-(3-cyclopropylphenyl)ethyl<br>R4 = 1-carboxamide-1-ethylamino<br>Y = C<br>R5 = H<br>R6 = H |

Note: With reference to Formula I, the ring bearing R4 has no nitrogen (N) unless noted.
P = prophetic example Synthetic Methods The following abbreviations are used throughout this document.

BOP Benzotriazol-1-yl-oxy-tris-(dimethylamino)phosphonium hexafluorophosphate
CDI Carbonyl diimidazole
DBU Diazabicycloundecane
DCM Dichloromethane
DIAD Diisopropylazodicarboxylate
DIPEA, $^i$Pr$_2$EtN N,N-Diisopropylethylamine
DMAP 4-(N,N-dimethylamino)pyridine
DMF N,N-Dimethylformamide
DMSO Dimethylsulfoxide
EDAC 1-Ethyl-3-(3-dimethylaminopropyl)carbodiimide hydrochloride
eq Equivalents
Et$_2$O Diethyl ether
EtOAc Ethyl acetate
h, hr Hours
HATU O-(7-Azabenzotriazole-1-yl)-N,N,N'N'-tetramethyluronium hexafluorophosphate
HCl Hydrochloric acid
HOAT Hydroxyazabenztriazole
HOBT Hydroxybenzotriazole
LiHDMS Lithium hexamethyldisilazide
LiOH Lithium hydroxide
mg Milligrams
min Minutes
mL Milliliters
μL Microliters
mM millimolar
μM micromolar
nM nanomolar
mmole Millimoles
MS Mass spectroscopy
MeOH Methanol
NaBH$_3$CN Sodium cyanoborohydride
NaH Sodium hydride
NaIO$_4$ Sodium periodate
NMM N-Methylmorpholine
rb Round-bottom
RT Room temperature
sat. Saturated
TEA Triethylamine
TFA Trifluoroacetic acid
THF Tetrahydrofuran
~ approximately (~10° C.) or, to (range, e.g., X~Y=X to Y)

Example 1

1-(2,4-Difluorobenzyl)-N-(2,4-dimethoxybenzyl)-1H-indole-5-carboxamide

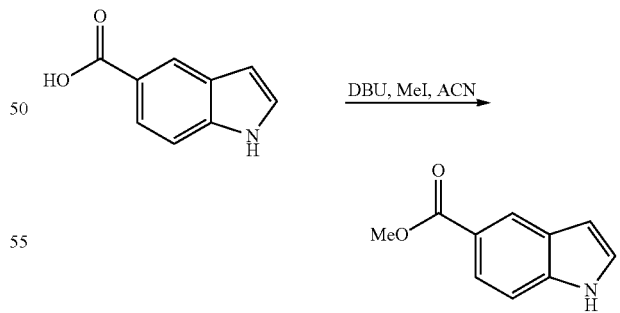

Step 1: Methyl 1H-indole-5-carboxylate

To a solution of 1H-indole-5-carboxylic acid (1 g, 6.2 mmol, 1.0 equiv) in acetonitrile (40 mL) were added 1,8-Diazabicyclo[5.4.0]undec-7-ene (1.1 mL, 7.4 mmol, 1.2 equiv) and iodomethane (2.3 mL, 37.2 mmol, 6 equiv). The solution was stirred under reflux overnight. The reaction mixture was concentrated in vacuo. The residue was dissolved in AcOEt, washed with a 0.5 N HCl aqueous solution, a saturated NaHCO$_3$ solution and brine, dried over MgSO$_4$ and concentrated in vacuo. The obtained oil was used in the next step without further purification.

Step 2: Methyl 1-(2,4-difluorobenzyl)-1H-indole-5-carboxylate

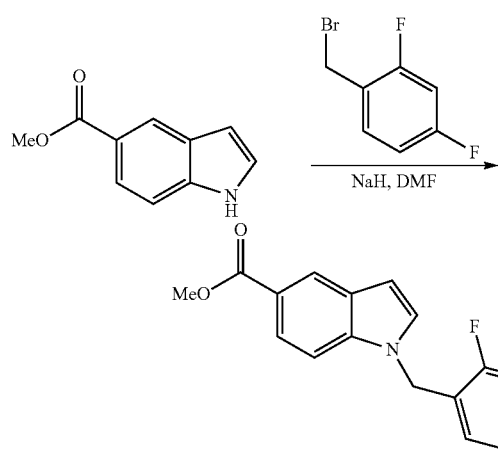

To a solution of methyl 1H-indole-5-carboxylate (2 g, 11.4 mmol, 1 equiv) and 1-(bromomethyl)-2,4-difluorobenzene (1.61 mL, 12.6 mmol, 1.1 equiv) in anhydrous DMF (50 mL) under argon atmosphere was added sodium hydride (913 mg, 22.8 mmol, 2 equiv) in small portions. The mixture was stirred 2 h at room temperature. The reaction mixture was then neutralized by addition of methanol and concentrated in vacuo. The residue was dissolved in AcOEt, washed with brine and dried over MgSO$_4$. The crude was purified by flash chromatography (Hexane/AcOEt 7/3) to afford the title compound as a colorless oil (3.14 g, 10.4 mmol, 91%). ESI-MS (m/z): 302 [M+H]$^+$.

Step 3: 1-(2,4-Difluorobenzyl)-1H-indole-5-carboxylic acid

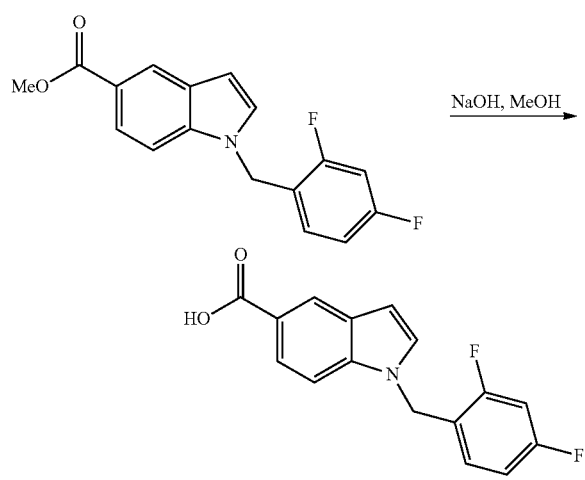

To a solution of methyl 1-(2,4-difluorobenzyl)-1H-indole-5-carboxylate (3.14 g, 10.4 mmol, 1 equiv) in methanol (50 mL) was added a 5 N NaOH solution (50 mL, 104 mmol, 10 equiv). The reaction mixture was stirred 2 h at 40° C. The mixture was then acidified and extracted with DCM. After concentration in vacuo, the title compound was precipitated in Et$_2$O to afford a white powder (2.82 g, 9.8 mmol, 96%). ESI-MS (m/z): 288 [M+H]$^+$.

Step 4: 1-(2,4-Difluorobenzyl)-N-(2,4-dimethoxybenzyl)-1H-indole-5-carboxamide

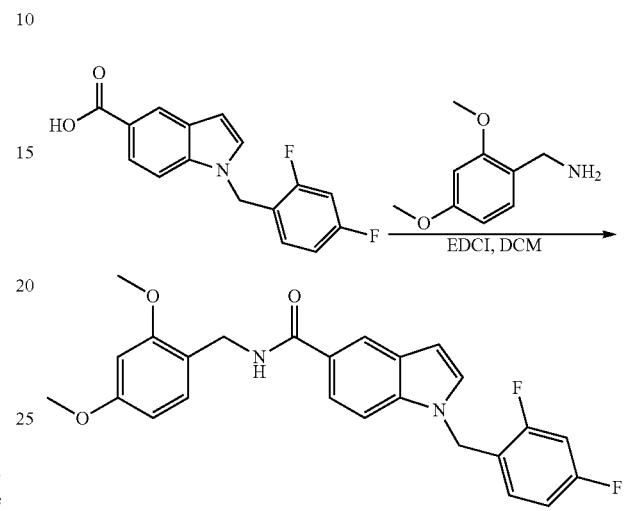

To a solution of 1-(2,4-difluorobenzyl)-1H-indole-5-carboxylic acid (50 mg, 0.17 mmol, 1 equiv) in DCM (2 mL) were added the (2,4-dimethoxyphenyl)methanamine (27 µL, 0.18 mmol, 1.05 equiv) and 1-Ethyl-3-(3-dimethylaminopropyl)carbodiimide (35 mg, 0.18 mmol, 1.05 equiv). The reaction mixture was stirred 2 h at room temperature. The solvent was removed in vacuo. The residue was dissolved in AcOEt and washed with a 0.5 N HCl aqueous solution, a saturated NaHCO$_3$ solution and brine, dried over MgSO$_4$ and concentrated in vacuo to afford a beige powder (56 mg, 0.13 mmol, 76%). ESI-MS (m/z): 437 [M+H]$^+$.

Example 2

1-(2,4-Difluorobenzyl)-N-(3-(trifluoromethoxy)benzyl)-1H-indole-5-carboxamide

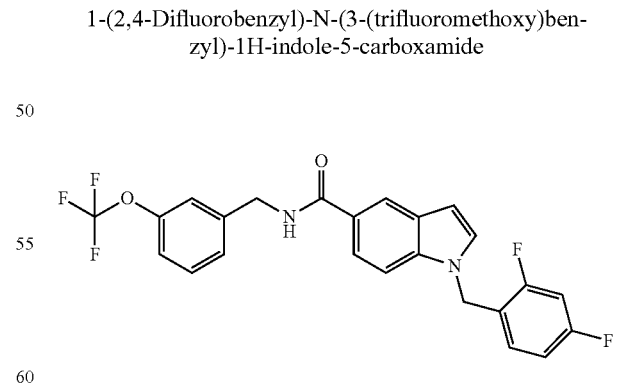

The title compound was prepared following the same general protocol as described in Step 4, Example 1, using (3-(trifluoromethoxy)phenyl)methanamine instead of the (2,4-dimethoxyphenyl)methanamine. A white powder was obtained (55 mg, 0.12 mmol, 70%). ESI-MS (m/z): 461 [M+H]$^+$.

Example 3

1-(2,4-Difluorobenzyl)-N-(3,4-dimethoxybenzyl)-1H-indole-5-carboxamide

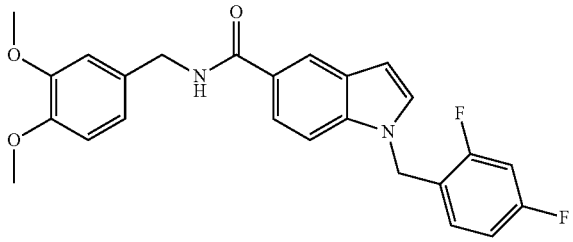 [SMILES: COc1ccc(CNC(=O)c2ccc3c(ccn3Cc3ccc(F)cc3F)c2)cc1OC]

The title compound was prepared following the same general protocol as described in Step 4, Example 1, using (3,4-dimethoxyphenyl)methanamine instead of the (2,4-dimethoxyphenyl)methanamine. A white powder was obtained (44 mg, 0.10 mmol, 59%). ESI-MS (m/z): 437 [M+H]$^+$.

Example 4

(S)-1-(2,4-Difluorobenzyl)-N-(1-(4-nitrophenyl)ethyl)-1H-indole-5-carboxamide

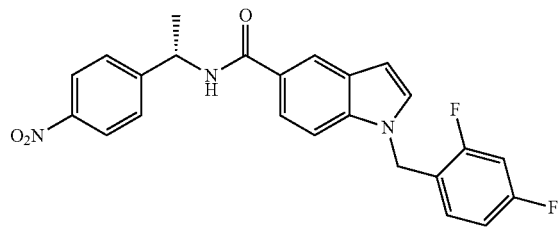 [SMILES: C[C@H](NC(=O)c1ccc2c(ccn2Cc2ccc(F)cc2F)c1)c1ccc([N+](=O)[O-])cc1]

The title compound was prepared following the same general protocol as described in Step 4, Example 1, using (S)-1-(4-nitrophenyl)ethanamine instead of the (2,4-dimethoxyphenyl)methanamine. A beige powder was obtained (46 mg, 0.11 mmol, 62%). ESI-MS (m/z): 436 [M+H]$^+$.

Example 5

(S)-N-(1-(4-Bromophenyl)ethyl)-1-(2,4-difluorobenzyl)-1H-indole-5-carboxamide

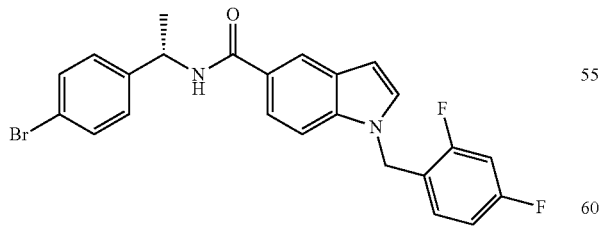

The title compound was prepared following the same general protocol as described in Step 4, Example 1, using (S)-1-(4-bromophenyl)ethanamine instead of the (2,4-dimethoxyphenyl)methanamine. A white powder was obtained (50 mg, 0.11 mmol, 63%). ESI-MS (m/z): 469/471 [M+H]$^+$.

Example 6

N-(Chroman-3-yl)-1-(2,4-difluorobenzyl)-1H-indole-5-carboxamide

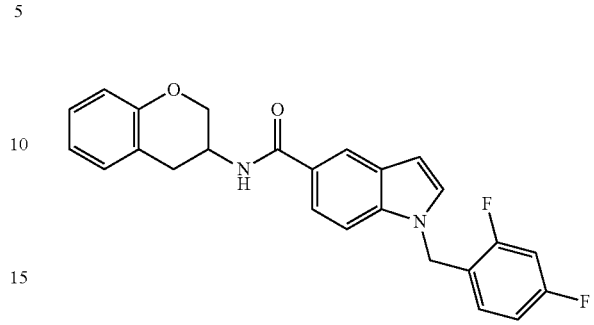

The title compound was prepared following the same general protocol as described in Step 4, Example 1, using chroman-3-amine instead of the (2,4-dimethoxyphenyl)methanamine. A white powder was obtained (52 mg, 0.12 mmol, 73%). ESI-MS (m/z): 419 [M+H]$^+$.

Example 7

(R)-N-(1-(4-Bromophenyl)ethyl)-1-(2,4-difluorobenzyl)-1H-indole-5-carboxamide

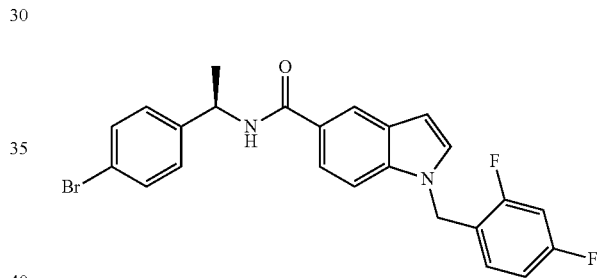

The title compound was prepared following the same general protocol as described in Step 4, Example 1, using (R)-1-(4-bromophenyl)ethanamine instead of the (2,4-dimethoxyphenyl)methanamine. A white powder was obtained (55 mg, 0.12 mmol, 69%). ESI-MS (m/z): 469/471 [M+H]$^+$.

Example 8

1-(2,4-Difluorobenzyl)-N-(1-phenylpropyl)-1H-indole-5-carboxamide

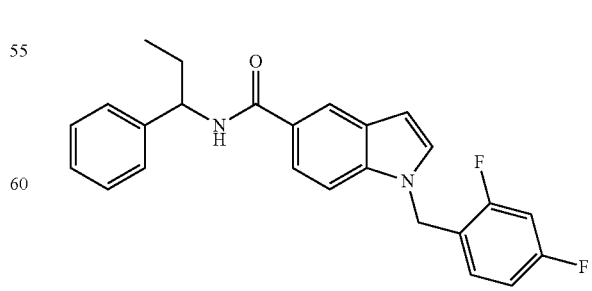

The title compound was prepared following the same general protocol as described in Step 4, Example 1, using 1-phenylpropan-1-amine instead of the (2,4-dimethoxyphenyl) methanamine. A beige powder was obtained (46 mg, 0.12 mmol, 67%). ESI-MS (m/z): 405 [M+H]+.

Example 9

N-Benzyl-1-(2,4-difluorobenzyl)-1H-indole-5-carboxamide

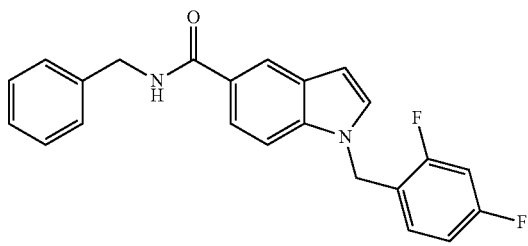 [SMILES: O=C(NCc1ccccc1)c1ccc2c(ccn2Cc2ccc(F)cc2F)c1]

The title compound was prepared following the same general protocol as described in Step 4, Example 1, using phenylmethanamine instead of the (2,4-dimethoxyphenyl) methanamine. A light green powder was obtained (49 mg, 0.13 mmol, 77%). ESI-MS (m/z): 377 [M+H]+.

Example 10

(R)-1-(2,4-Difluorobenzyl)-N-(1-(4-nitrophenyl)ethyl)-1H-indole-5-carboxamide

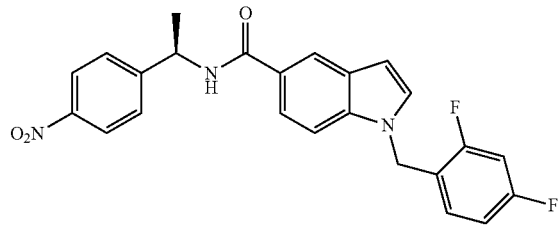 [SMILES: C[C@@H](NC(=O)c1ccc2c(ccn2Cc2ccc(F)cc2F)c1)c1ccc([N+](=O)[O-])cc1]

The title compound was prepared following the same general protocol as described in Step 4, Example 1, using (R)-1-(4-nitrophenyl)ethanamine instead of the (2,4-dimethoxyphenyl)methanamine. A beige powder was obtained (45 mg, 0.10 mmol, 60%). ESI-MS (m/z): 436 [M+H]+.

Example 11

1-(2,4-Difluorobenzyl)-N-(2-phenylpropan-2-yl)-1H-indole-5-carboxamide

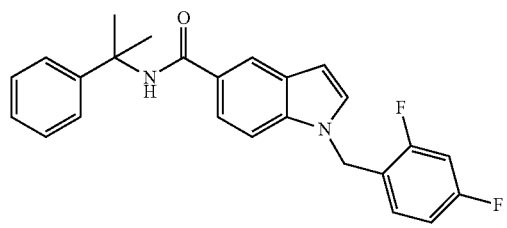

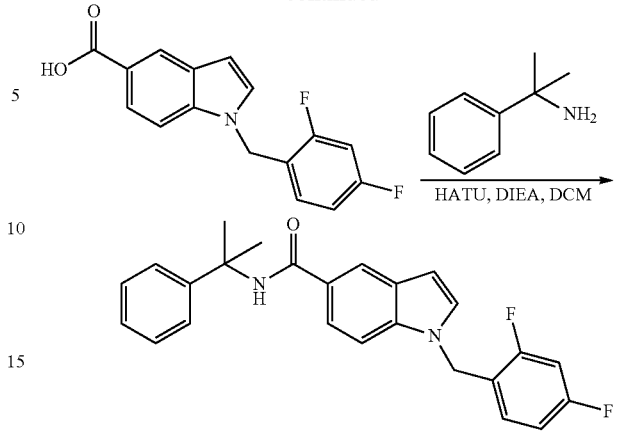

To a solution of 1-(2,4-difluorobenzyl)-1H-indole-5-carboxylic acid (50 mg, 0.17 mmol, 1 equiv) in DCM (2 mL) was added 2-phenylpropane-2-amine (27 µL, 0.18 mmol, 1.05 equiv), DIEA (30 µL, 0.17 mmol, 1 equiv) and HATU (68 mg, 0.18 mmol, 1.05 equiv). The reaction mixture was stirred 2 h at room temperature.

The solvent was removed in vacuo. The residue was dissolved in AcOEt and washed with a 0.5N HCl aqueous solution, a saturated NaHCO3 solution and brine, dried over MgSO4 and concentrated in vacuo to afford a white powder (63 mg, 0.15 mmol, 92%). ESI-MS (m/z): 405 [M+H]+.

Example 12

1-(2,4-Difluorobenzyl)-N-(thiophen-2-ylmethyl)-1H-indole-5-carboxamide

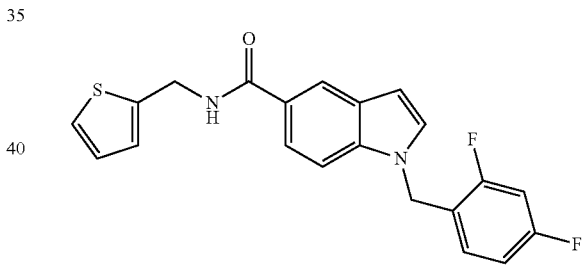

The title compound was prepared following the same general protocol as described in Step 4, Example 1, using thiophen-2-ylmethanamine instead of the (2,4-dimethoxyphenyl)methanamine. A white powder was obtained (45 mg, 0.12 mmol, 69%). ESI-MS (m/z): 383 [M+H]+.

Example 13

1-(2,4-Difluorobenzyl)-N-(2-methoxyethyl)-1H-indole-5-carboxamide

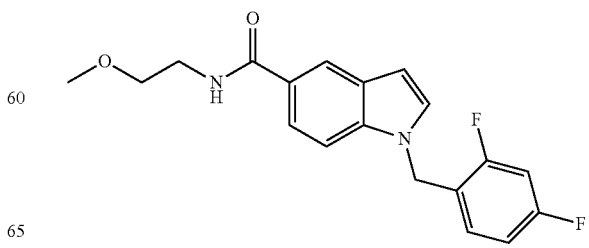

The title compound was prepared following the same general protocol as described in Step 4, Example 1, using 2-methoxyethanamine instead of the (2,4-dimethoxyphenyl)methanamine. A light green powder was obtained (47 mg, 0.14 mmol, 80%). ESI-MS (m/z): 345 [M+H]+.

Example 14

1-(2,4-Difluorobenzyl)-N-((2,3-dihydrobenzo[b][1,4]dioxin-2-yl)methyl)-1H-indole-5-carboxamide

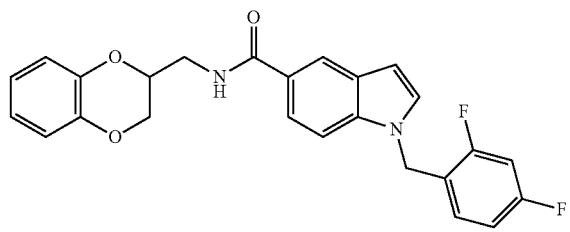 [SMILES: O=C(NCC1COc2ccccc2O1)c1ccc2c(ccn2Cc2ccc(F)cc2F)c1]

The title compound was prepared following the same general protocol as described in Step 4, Example 1, using (2,3-dihydrobenzo[b][1,4]dioxin-2-yl)methanamine instead of the (2,4-dimethoxyphenyl)methanamine. A beige powder was obtained (65 mg, 0.15 mmol, 88%). ESI-MS (m/z): 435 [M+H]+.

Example 15

1-(2,4-Difluorobenzyl)-N-(1-(naphthalen-1-yl)ethyl)-1H-indole-5-carboxamide

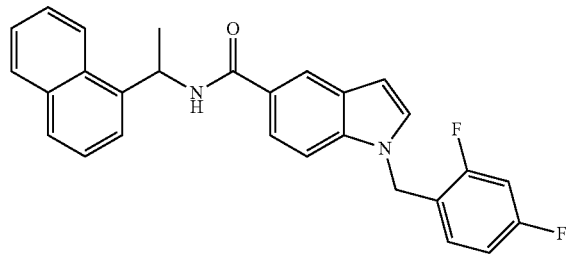 [SMILES: CC(NC(=O)c1ccc2c(ccn2Cc2ccc(F)cc2F)c1)c1cccc2ccccc12]

The title compound was prepared following the same general protocol as described in Step 4, Example 1, using 1-(naphthalen-1-yl)ethanamine instead of the (2,4-dimethoxyphenyl)methanamine. A white powder was obtained (55 mg, 0.12 mmol, 73%). ESI-MS (m/z): 441 [M+H]+.

Example 16

(S)-1-(2,4-Difluorobenzyl)-N-(1-(4-fluorophenyl)ethyl)-1H-indole-5-carboxamide

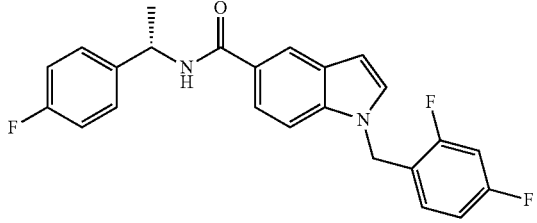 [SMILES: C[C@H](NC(=O)c1ccc2c(ccn2Cc2ccc(F)cc2F)c1)c1ccc(F)cc1]

The title compound was prepared following the same general protocol as described in Step 4, Example 1, using (S)-1-(4-fluorophenyl)ethanamine instead of the (2,4-dimethoxyphenyl)methanamine. A white powder was obtained (45 mg, 0.11 mmol, 65%). ESI-MS (m/z): 409 [M+H]+.

Example 17

(R)-1-(2,4-Difluorobenzyl)-N-(1-(4-fluorophenyl)ethyl)-1H-indole-5-carboxamide

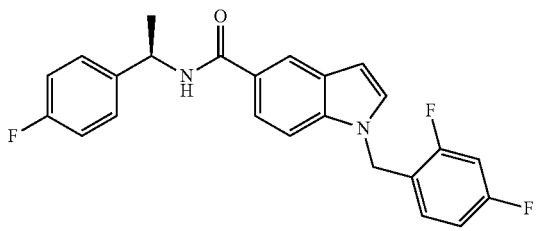 [SMILES: C[C@@H](NC(=O)c1ccc2c(ccn2Cc2ccc(F)cc2F)c1)c1ccc(F)cc1]

The title compound was prepared following the same general protocol as described in Step 4, Example 1, using (R)-1-(4-fluorophenyl)ethanamine instead of the (2,4-dimethoxyphenyl)methanamine. A white powder was obtained (41 mg, 0.10 mmol, 59%). ESI-MS (m/z): 409 [M+H]+.

Example 18

N-Cyclopentyl-1-(2,4-difluorobenzyl)-1H-indole-5-carboxamide

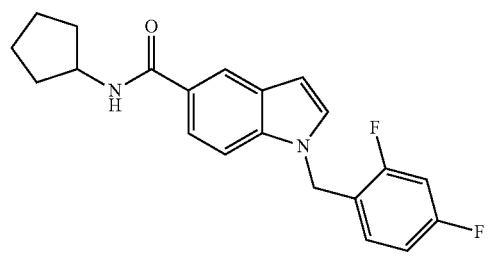 [SMILES: O=C(NC1CCCC1)c1ccc2c(ccn2Cc2ccc(F)cc2F)c1]

The title compound was prepared following the same general protocol as described in Step 4, Example 1, using cyclopentanamine instead of the (2,4-dimethoxyphenyl)methanamine. A white powder was obtained (35 mg, 0.10 mmol, 58%). ESI-MS (m/z): 355 [M+H]+.

Example 19

1-(2,4-Difluorobenzyl)-N-((1R,2S)-2-phenylcyclopropyl)-1H-indole-5-carboxamide

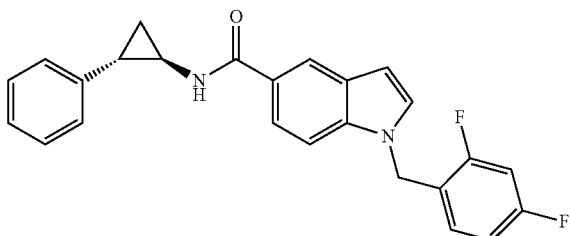

The title compound was prepared following the same general protocol as described in Step 4, Example 1, using (1R,2S)-2-phenylcyclopropanamine instead of the (2,4-dimethoxyphenyl)methanamine. A beige powder was obtained (49 mg, 0.12 mmol, 72%). ESI-MS (m/z): 403 [M+H]+.

Example 20

N-(4-Aminobenzyl)-1-(2,4-difluorobenzyl)-1H-indole-5-carboxamide

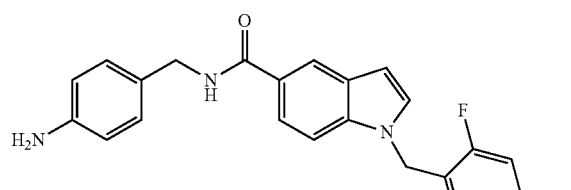

The title compound was prepared following the same general protocol as described in Example 11, using 4-(aminomethyl)aniline instead of the 2-phenylpropane-2-amine. A yellow powder was obtained (19 mg, 0.05 mmol, 29%).

ESI-MS (m/z): 392 [M+H]+.

Example 21

1-(2,4-difluorobenzyl)-2,3-dimethyl-N-(1-phenylpropyl)-1H-indole-5-carboxamide

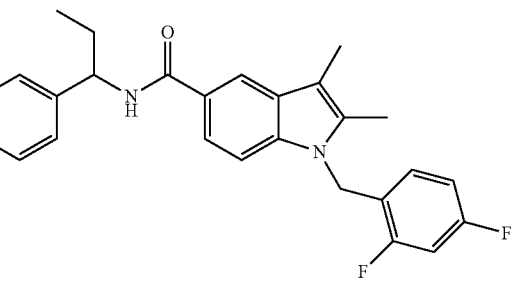

Step 1: ethyl 1-(2,4-difluorobenzyl)-2,3-dimethyl-1H-indole-5-carboxylate

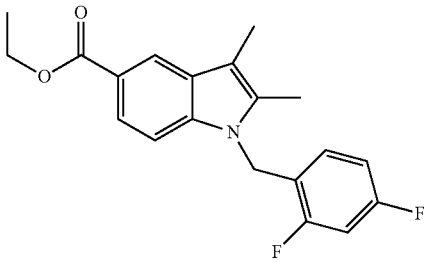 [SMILES: CCOC(=O)c1ccc2c(c1)c(C)c(C)n2Cc1ccc(F)cc1F]

NaH (1.1 equiv) was added to a solution of ethyl 2,3-dimethyl-1H-indole-5-carboxylate in DMF at room temperature. After 30 min, 2,4-difluorobenzyl bromide (1.1 equiv) was added to the reaction mixture and stirred for 1 h. After the reaction was completed, the solvent was removed in vacuo to obtain the crude which was purified by flash chromatography to obtain the compound. LC-MS 344 (M+H).

Step 2: 1-(2,4-difluorobenzyl)-2,3-dimethyl-1H-indole-5-carboxylic acid

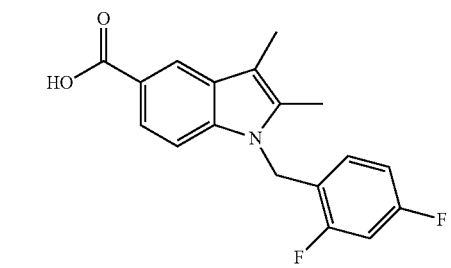 [SMILES: Cc1c(C)n(Cc2ccc(F)cc2F)c2ccc(C(=O)O)cc12]

A mixture of above compound and NaOH (10 equiv) in EtOH was refluxed at 100° C. for 2 h. The reaction mixture was cooled to rt, then acidified to pH~4 with sat'd citric acid. The mixture was evaporated in vacuo to obtain the crude, which was precipitated in water and filtered to obtain the compound. LC-MS 316 (M+H).

Step 3: 1-(2,4-difluorobenzyl)-2,3-dimethyl-N-(1-phenylpropyl)-1H-indole-5-carboxamide To a mixture of 1-(2,4-difluorobenzyl)-2,3-dimethyl-1H-indole-5-carboxylic acid in DMF was added DIPEA (1.3 equiv) and HATU (1.2 equiv). The mixture was stirred for 5 min, and then α-ethylbenzylamine (1.1 equiv) was added. The reaction mixture was stirred at rt for 1 h. After the reaction was completed, the solvent was removed in vacuo to obtain the crude which was purified by flash chromatography to obtain the title compound. LC-MS 433 (M+H).

Example 22

1-(4-chlorobenzyl)-2,3-dimethyl-N-(1-phenylpropyl)-1H-indole-5-carboxamide

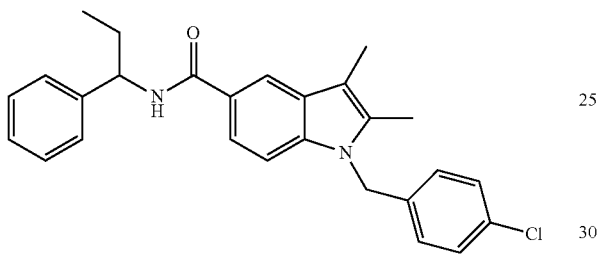

The title compound was prepared following the same general protocol as described in Steps 1, 2, and 3 of Example 21, using 4-chloro-benzylchloride and ethyl 2,3-dimethyl-1H-indole-5-carboxylate. LC-MS 431 (M+H).

Example 24

1-(3-chlorophenethyl)-N-(1-phenylpropyl)-1H-indole-5-carboxamide

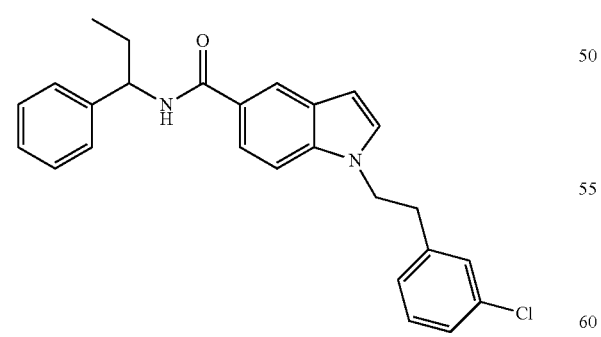

The title compound was prepared following the same general protocol as described in Step 1 of Example 21, using 2-(3-chlorophenyl)ethyl chloride and N-(1-phenylpropyl)-1H-indole-5-carboxamide. LC-MS 417 (M+H).

Example 25

1-benzoyl-N-(1-phenylpropyl)-1H-indole-5-carboxamide

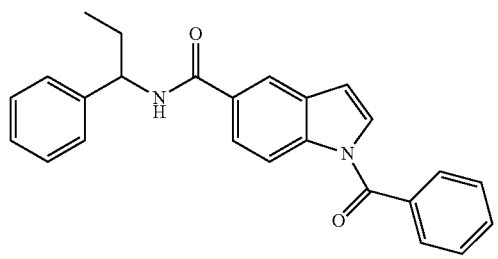 [SMILES: CCC(NC(=O)c1ccc2c(ccn2C(=O)c2ccccc2)c1)c1ccccc1]

Benzoyl chloride (1.1 equiv) was added to a solution of N-(1-phenylpropyl)-1H-indole-5-carboxamide in $CH_2Cl_2$, $Et_3N$ (1.3 equiv) at room temperature. After the reaction was completed, the solvent was evaporated and the residual was purified by silica gel column chromatography to get the product. LC-MS 383 (M+H).

Example 26

1-(4-nitrobenzoyl)-N-(1-phenylpropyl)-1H-indole-5-carboxamide

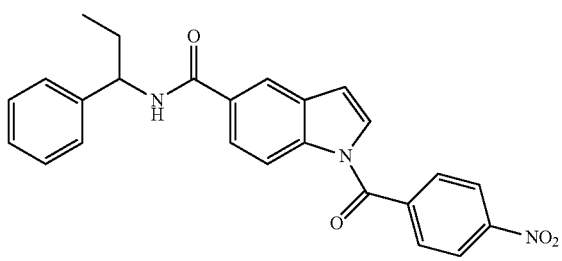 [SMILES: CCC(NC(=O)c1ccc2c(ccn2C(=O)c2ccc([N+](=O)[O-])cc2)c1)c1ccccc1]

The title compound was prepared following the same general protocol as described in Example 25, using 4-nitrobenzoylchloride and N-(1-phenylpropyl)-1H-indole-5-carboxamide. LC-MS 428 (M+H)

Example 27

1-(2,3-difluorobenzoyl)-N-(1-phenylpropyl)-1H-indole-5-carboxamide

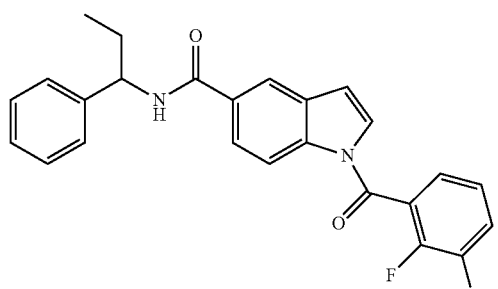

The title compound was prepared following the same general protocol as described in Example 25, using 2,3-difluorobenzoylchloride and N-(1-phenylpropyl)-1H-indole-5-carboxamide. LC-MS 419 (M+H).

Example 28

N-(1-phenylpropyl)-1-tosyl-1H-indole-5-carboxamide

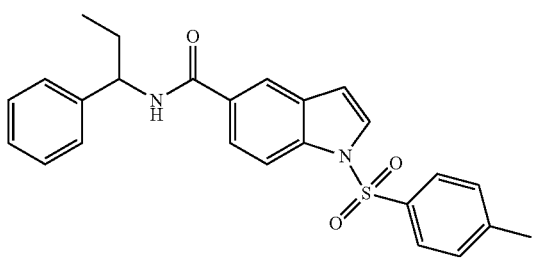 [SMILES: CCC(NC(=O)c1ccc2c(ccn2S(=O)(=O)c2ccc(C)cc2)c1)c1ccccc1]

Tosyl chloride (1.1 equiv), benzyltriethylammonium chloride (0.5 equiv) was added to a solution of N-(1-phenylpropyl)-1H-indole-5-carboxamide in $CH_2Cl_2$, KOH (1.3 equiv) at room temperature. After the reaction was completed, the solvent was evaporated and the residual was purified by silica gel column chromatography to get the product. LC-MS 433 (M+H).

Example 30

1-(naphthalen-1-ylsulfonyl)-N-(1-phenylpropyl)-1H-indole-5-carboxamide

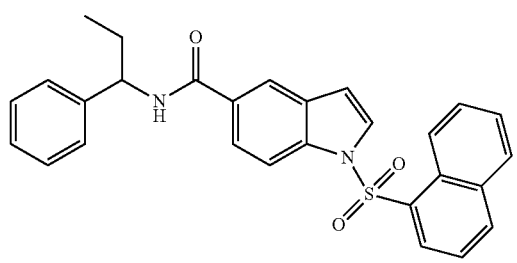 [SMILES: CCC(NC(=O)c1ccc2c(ccn2S(=O)(=O)c2cccc3ccccc23)c1)c1ccccc1]

The title compound was prepared following the same general protocol as described in Example 28, using 1-naphthylsulfonyl chloride and N-(1-phenylpropyl)-1H-indole-5-carboxamide. LC-MS 469 (M+H).

Example 31

1-(4-nitrophenylsulfonyl)-N-(1-phenylpropyl)-1H-indole-5-carboxamide

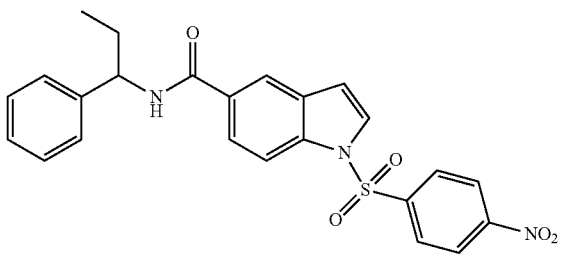 [SMILES: CCC(NC(=O)c1ccc2c(ccn2S(=O)(=O)c2ccc([N+](=O)[O-])cc2)c1)c1ccccc1]

The title compound was prepared following the same general protocol as described in Example 28, using 4-nitrophenylsulfonyl chloride and N-(1-phenylpropyl)-1H-indole-5-carboxamide. LC-MS 464 (M+H).

Example 32

1-((6-chloropyridin-3-yl)methyl)-N-(1-phenylpropyl)-1H-indole-5-carboxamide

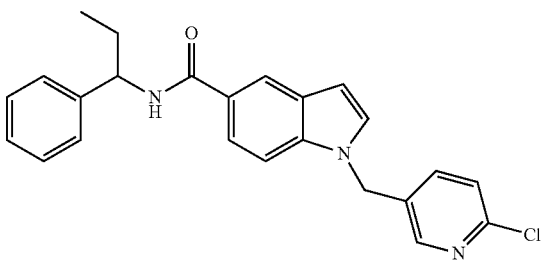 [SMILES: CCC(NC(=O)c1ccc2c(ccn2Cc2ccc(Cl)nc2)c1)c1ccccc1]

The title compound was prepared following the same general protocol as described in Step 1, Example 21, using 5-(bromomethyl)-2-chloropyridine and N-(1-phenylpropyl)-1H-indole-5-carboxamide. LC-MS 404 (M+H).

Examples 33, 34

33

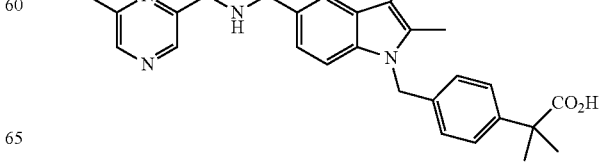

34

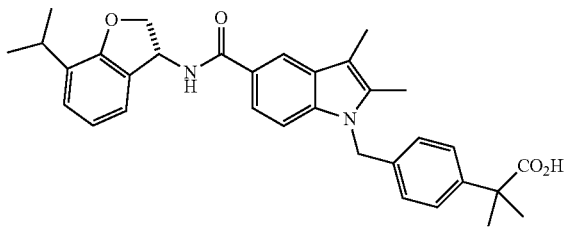

The title compounds can be prepared analogously to Example 35, below, but substituting

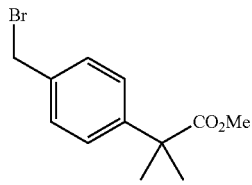

This bromomethyl compound can be prepared as described in Example 35, step 2, below, substituting methyl 1-methyl-1-(p-tolyl)-propionate for methyl 1-(p-tolyl)cyclopropanecarboxylate in the bromination reaction. Alternatively the bromomethyl compound can be purchased from Chinglu Pharmaceutical Research LLC, 705 North Mountain Rd., Suite C115, Newington, Conn.

Various compounds such as 33 and 34 can then be prepared, as is apparent to a person of skill in the art, by use of the appropriate precursors and reagents as indicated in Example 35, steps 3-8.

Example 35

(S)-1-(4-((5-((1-(3-Isopropylphenyl)ethyl)carbamoyl)-2,3-dimethyl-1H-indol-1-yl)methyl)phenyl)cyclopropanecarboxylic acid

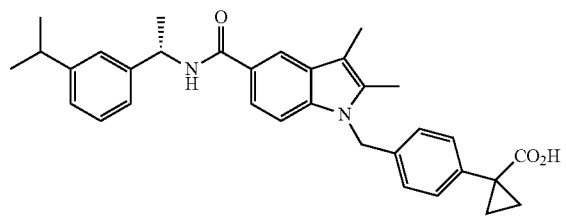 [SMILES: Cc1c(C)n(Cc2ccc(C3(C(=O)O)CC3)cc2)c2ccc(C(=O)N[C@@H](C)c3cccc(C(C)C)c3)cc12]

Step 1: Methyl 1-(p-tolyl)cyclopropanecarboxylate

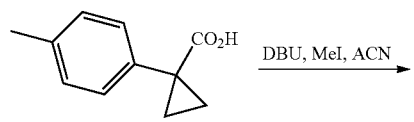

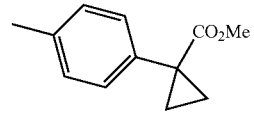

To a solution of 1-(p-tolyl)cyclopropanecarboxylic acid (900 mg, 5.1 mmol) in acetonitrile (20 mL) was added DBU (917 µL) followed by methyl iodide (1.91 mL). The resulting solution was heated at reflux overnight, and then diluted with AcOEt. The mixture was washed with a 0.5 N HCl solution, a saturated solution of NaHCO$_3$, and brine, dried on MgSO$_4$, and concentrated. The resulting colorless oil was purified by chromatography on silica gel (Hexane/ethyl acetate 9/1) to afford the title compound as a colorless oil (622 mg, 64%).

Step 2: Methyl 1-(4-(bromomethyl)phenyl)cyclopropanecarboxylate

To a solution of methyl 1-(p-tolyl)cyclopropanecarboxylate (622 mg, 3.27 mmol) in carbon tetrachloride (16 mL) was added N-bromosuccinimide (611 mg) followed by benzoyl peroxide (40 mg). The resulting solution was heated at reflux overnight, and then diluted with methylene chloride. The mixture was washed with brine, dried on MgSO$_4$, and concentrated to afford a colorless oil (860 mg, 97%).

Step 3: 2,3-Dimethyl-1H-indole-5-carboxylic acid

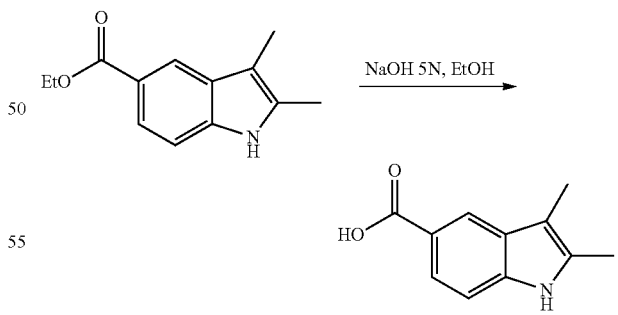

To a solution of ethyl 2,3-dimethyl-1H-indole-5-carboxylate (500 mg, 2.3 mmol) in ethanol (10 mL) was added a 5N NaOH solution (9.2 mL). The resulting solution was heated at 50° C. for 4 h, and then quenched carefully by addition of a 6N HCl solution (10 mL). The mixture was diluted with ethyl acetate, washed with a 0.5 N HCl solution and brine, dried on MgSO$_4$, and concentrated to afford a yellow powder (500 mg, 100%). ESI-MS (m/z): 190 [MH]$^+$

Step 4: 1-(4-(1-(Methoxycarbonyl)cyclopropyl)benzyl)-2,3-dimethyl-1H-indole-5-carboxylic acid

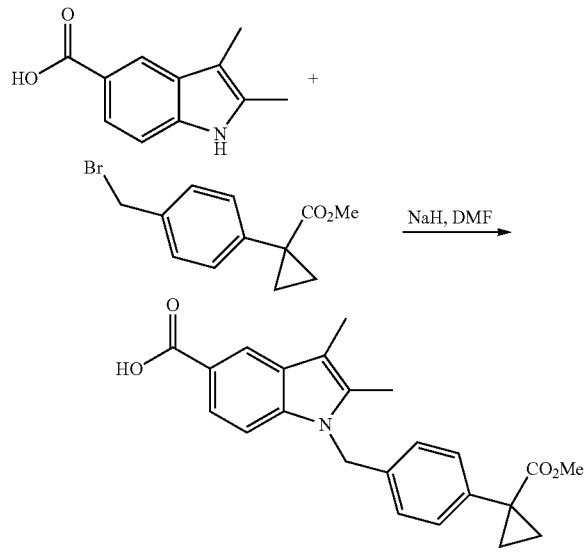

To a solution of 2,3-dimethyl-1H-indole-5-carboxylic acid (500 mg, 2.3 mmol) in anhydrous DMF (20 mL) was added methyl 1-(4-(bromomethyl)phenyl)cyclopropanecarboxylate (620 mg) followed by NaH (230 mg). The resulting solution was allowed to stir overnight under argon atmosphere. The remaining NaH was hydrolyzed by the careful addition of a 0.5 N HCl solution. The mixture was diluted with ethyl acetate, washed with a 0.5 N HCl solution and brine, dried on MgSO$_4$, and concentrated. The crude residue was purified by chromatography on silica gel (Hexane/Ethyl acetate 5/5) to afford an orange powder (361 mg). ESI-MS (m/z): 378 [MH]$^+$

Step 5: (S)-Methyl 1-(4-((5-((1-(3-bromophenyl)ethyl)carbamoyl)-2,3-dimethyl-1H-indol-1-yl)methyl)phenyl)cyclopropanecarboxylate

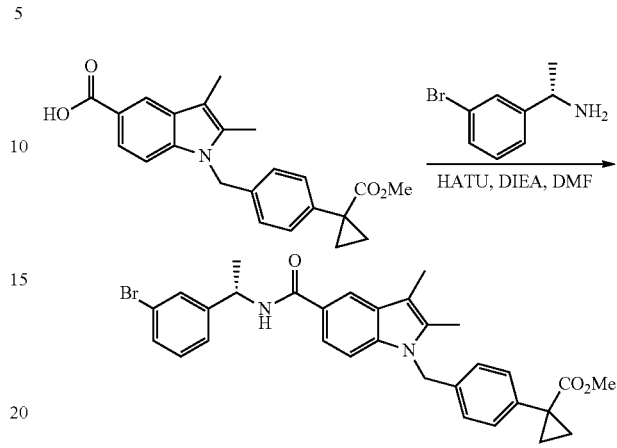

To a solution of 1-(4-(1-(methoxycarbonyl)cyclopropyl)benzyl)-2,3-dimethyl-1H-indole-5-carboxylic acid (50 mg, 0.13 mmol) in DMF (1 mL) was added (S)-1-(3-bromophenyl)ethylamine (21 µL), DIEA (45 µL) and HATU (54 mg). The reaction mixture was allowed to stir at rt for 30 min, and then was diluted by ethyl acetate. The resulting mixture was washed with a 0.5 N HCl solution, a saturated solution of NaHCO$_3$, and brine, dried on MgSO$_4$, and concentrated to afford a yellow oil (73 mg) which was directly used without further purification.

ESI-MS (m/z): 559/561 [MH]$^+$

Step 6: (S)-Methyl 1-(4-((2,3-dimethyl-5-al-(3-(prop-1-en-2-yl)phenyl)ethyl)carbamoyl)-1H-indol-1-yl)methyl)phenyl)cyclopropanecarboxylate

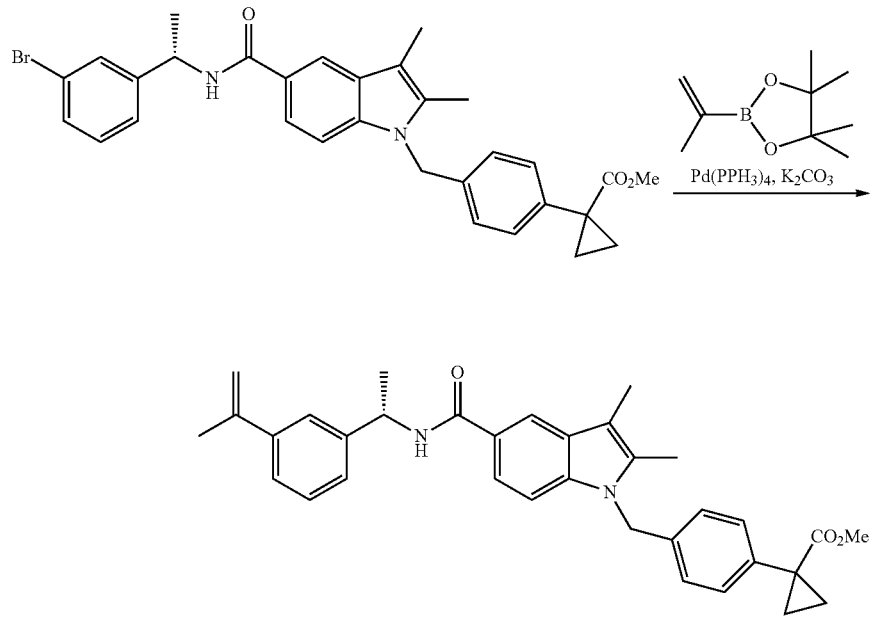

To a solution of (S)-methyl 1-(4-((5-((1-(3-bromophenyl)ethyl)carbamoyl)-2,3-dimethyl-1H-indol-1-yl)methyl)phenyl)cyclopropanecarboxylate (73 mg) in dioxane/water (1.2 mL/0.3 mL) was added isopropenylboronic acid pinacol ester (49 µL), K$_2$CO$_3$ (36 mg) and Pd(PPh$_3$)$_4$ (15 mg). The solution was degassed with argon and then stirred for 1 h at 100° C. under microwave. The resulting mixture was diluted with ethyl acetate washed with a 0.5 N HCl solution, a saturated solution of NaHCO$_3$, and brine, dried on MgSO$_4$, and concentrated to afford a yellow oil which was directly used without further purification. ESI-MS (m/z): 521 [MH]$^+$ Step 7: (S)-Methyl 1-(4-((5-((1-(3-isopropylphenyl)ethyl)carbamoyl)-2,3-dimethyl-1H-indol-1-yl)methyl)phenyl)cyclopropanecarboxylate

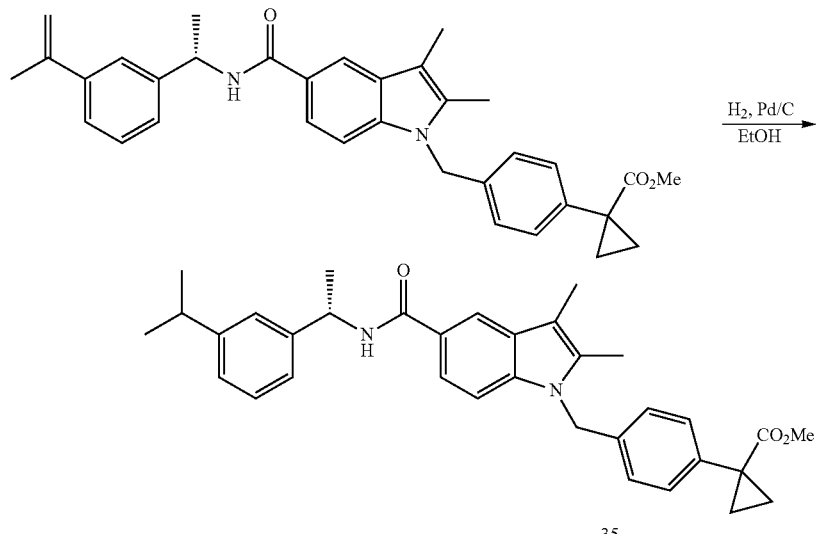

To a solution of (S)-methyl 1-(4-((2,3-dimethyl-5-((1-(3-(prop-1-en-2-yl)phenyl)ethyl)carbamoyl)-1H-indol-1-yl)methyl)phenyl)cyclopropanecarboxylate in EtOH (5 mL) was added Pd/C 10%. The resulting mixture was stirred for 5 h under hydrogen atmosphere. The solution was then filtered and concentrated to afford a yellow oil which was directly used without further purification. ESI-MS (m/z): 523 [MH]$^+$ Step 8: (S)-1-(4-((5-((1-(3-Isopropylphenyl)ethyl)carbamoyl)-2,3-dimethyl-1H-indol-1-yl)methyl)phenyl)cyclopropanecarboxylic acid

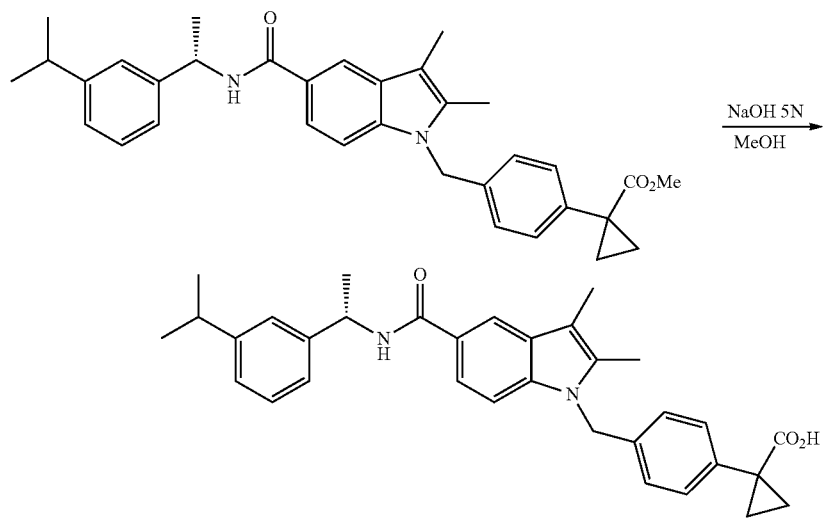

To a solution of (S)-1-(4-((5-((1-(3-isopropylphenyl)ethyl)carbamoyl)-2,3-dimethyl-1H-indol-1-yl)methyl)phenyl)cyclopropanecarboxylic acid in methanol (1 mL) was added a 5 N NaOH solution (1 mL). The resulting solution was heated at 50° C. for 4 h, and then quenched carefully by addition of a 6 N HCl solution (1 mL). The mixture was diluted with ethyl acetate, washed with a 0.5 N HCl solution and brine, dried on MgSO$_4$, and concentrated. The resulting oil was purified by preparative HPLC to afford a white powder (9 mg). ESI-MS (m/z): 509 [MH]$^+$ Example 36

(S)-2-(4-((5-(β1-(3-Cyclopropylphenyl)ethyl)carbamoyl)-2,3-dimethyl-1H-indol-1-yl)methyl)phenoxy)acetic acid

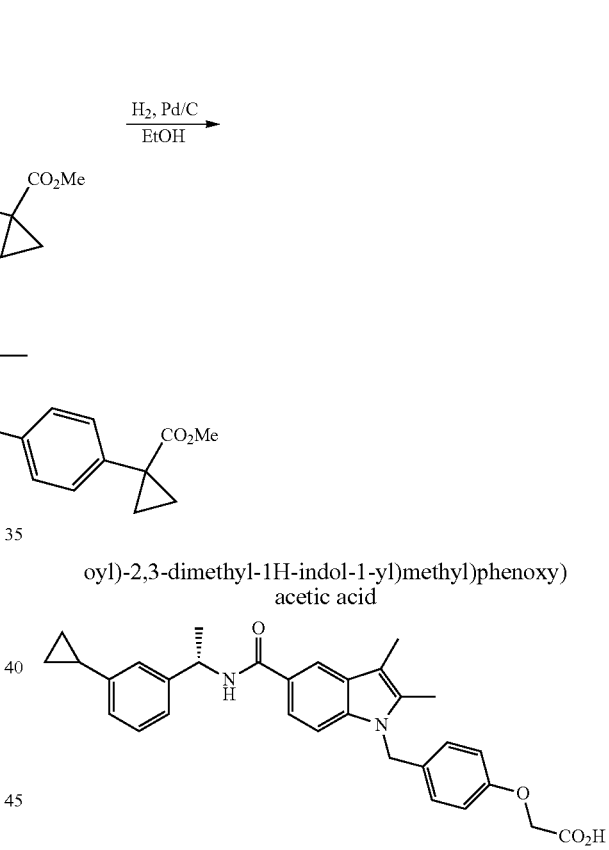

Step 1: Methyl 2-(p-tolyloxy)acetate

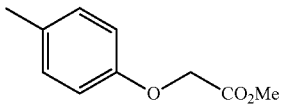

To a solution of p-cresol (2 mL, 19.1 mmol) in anhydrous DMF (50 mL) were added Cs$_2$CO$_3$ (8.1 g, 24.9 mmol) and methyl bromoacetate (1.9 mL, 20.1 mmol). The suspension was stirred at room temperature for 3 h. After dilution with ethyl acetate, the reaction mixture was washed with a 0.5 N HCl solution, a saturated solution of NaHCO$_3$, and brine, dried on MgSO$_4$, and concentrated. The resulting oil was purified by chromatography on silica gel (Hexane/ethyl acetate 8/2) to afford the title compound as a colorless oil (3.10 g, 90%).

Step 2: Methyl 2-(4-(bromomethyl)phenoxy)acetate

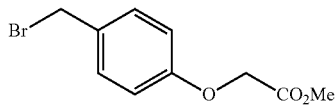

To a solution of the methyl 2-(p-tolyloxy)acetate (3.10 g, 17.2 mmol) in carbon tetrachloride (60 mL) was added N-bromosuccinimide (3.57 g, 20 mmol) followed by benzoyl peroxide (463 mg, 1.9 mmol). The resulting solution was heated at reflux overnight, and then diluted with methylene chloride. The mixture was washed with brine, dried on MgSO$_4$, and concentrated. The resulting colorless oil was purified by chromatography on silica gel (Hexane/ethyl acetate 9/1) to afford a colorless oil (2.5 g, 56%).

Step 3: Allyl 1-(4-(2-methoxy-2-oxoethoxy)benzyl)-2,3-dimethyl-1H-indole-5-carboxylate

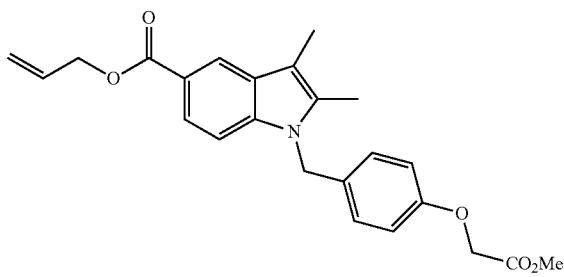 [SMILES: C=CCOC(=O)c1ccc2c(c1)c(C)c(C)n2Cc1ccc(OCC(=O)OC)cc1]

To a solution of the allyl 2,3-dimethyl-1H-indole-5-carboxylate (500 mg, 2.2 mmol) in anhydrous DMF (20 mL) was added the methyl 2-(4-(bromomethyl)phenoxy)acetate (565 mg, 2.2 mmol) followed by NaH (131 mg, 3.3 mmol). The resulting solution was allowed to stir overnight under argon atmosphere. The remaining NaH was hydrolyzed by the careful addition of a 0.5 N HCl solution. The mixture was diluted with ethyl acetate, washed with a 0.5 N HCl solution and brine, dried on MgSO$_4$, and concentrated. The crude residue was purified by chromatography on silica gel (Hexane/Ethyl acetate 5/5) to afford yellow oil (536 mg, 61%). ESI-MS (m/z): 408 [M+H]$^+$

Step 4: 1-(4-(2-Methoxy-2-oxoethoxy)benzyl)-2,3-dimethyl-1H-indole-5-carboxylic acid

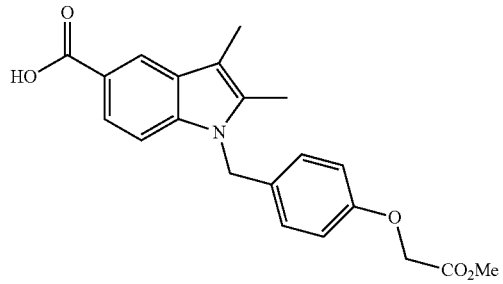 [SMILES: COC(=O)COc1ccc(Cn2c(C)c(C)c3cc(C(=O)O)ccc32)cc1]

A solution of the allyl 1-(4-(2-methoxy-2-oxoethoxy)benzyl)-2,3-dimethyl-1H-indole-5-carboxylate (536 mg, 1.3 mmol) and morpholine (1.14 mL, 13.2 mmol) in anhydrous THF was degassed with argon. Then Pd(PPh$_3$)$_4$ (152 mg, 0.13 mmol) was added and the reaction stirred under argon protection for 1.5 h. The reaction mixture was diluted with ethyl acetate, washed with brine, concentrated. The title compound was precipitated in ethyl ether as a beige powder (430 mg, 89%). ESI-MS (m/z): 368 [M+H]$^+$.

Step 5: (S)-Methyl 2-(4-((5-((1-(3-cyclopropylphenyl)ethyl)carbamoyl)-2,3-dimethyl-1H-indol-1-yl)methyl)phenoxy)acetate

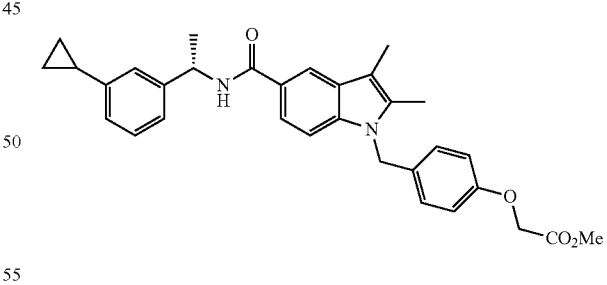

To a solution of the 1-(4-(2-methoxy-2-oxoethoxy)benzyl)-2,3-dimethyl-1H-indole-5-carboxylic acid (50 mg, 0.14 mmol) in DCM (1 mL) was added the (S)-1-(3-cyclopropylphenyl)ethanamine hydrochloride (28 mg), DIEA (73 μL) and HATU (53 mg). The reaction mixture was allowed to stir at rt for 30 min, and then was diluted by ethyl acetate. The resulting mixture was washed with a 0.5 N HCl solution, a saturated solution of NaHCO$_3$, and brine, dried on MgSO$_4$, and concentrated to afford a yellow oil (73 mg) which was directly used without further purification. ESI-MS (m/z): 497 [M+H]$^+$

Step 6: (S)-2-(4-((5-((1-(3-Cyclopropylphenyl)ethyl)carbamoyl)-2,3-dimethyl-1H-indol-1-yl)methyl)phenoxy)acetic acid

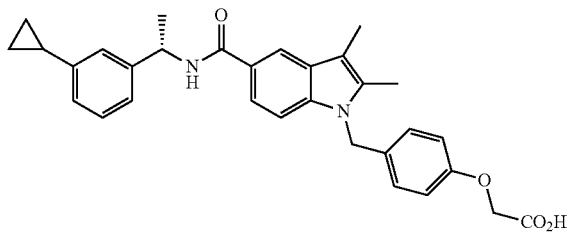 [SMILES: Cc1c(C)n(Cc2ccc(OCC(=O)O)cc2)c2ccc(C(=O)N[C@@H](C)c3cccc(C4CC4)c3)cc12]

To a solution of the (S)-methyl 2-(4-((5-((1-(3-cyclopropylphenyl)ethyl)carbamoyl)-2,3-dimethyl-1H-indol-1-yl)methyl)phenoxy)acetate in methanol (1 mL) was added a 5N NaOH solution (1 mL). The resulting solution was heated at 50° C. for 4 h, and then quenched carefully by addition of a 6N HCl solution (1 mL). The mixture was diluted with ethyl acetate, washed with a 0.5 N HCl solution and brine, dried on $MgSO_4$, and concentrated. The resulting oil was purified by preparative HPLC to afford a white powder (46 mg). ESI-MS (m/z): 497 $[MH]^+$

Example 37

(S)-2-(4-((5-((1-(3-Isopropylphenyl)ethyl)carbamoyl)-2,3-dimethyl-1H-indol-1-yl)methyl)phenoxy)acetic acid

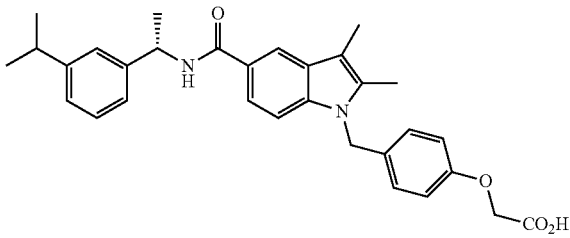 [SMILES: Cc1c(C)n(Cc2ccc(OCC(=O)O)cc2)c2ccc(C(=O)N[C@@H](C)c3cccc(C(C)C)c3)cc12]

Step 1: (S)-Methyl 2-(4-((5-((1-(3-isopropylphenyl)ethyl)carbamoyl)-2,3-dimethyl-1H-indol-1-yl)methyl)phenoxy)acetate

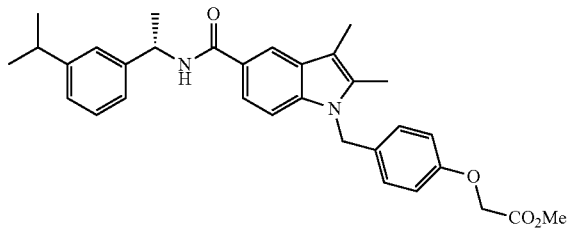 [SMILES: COC(=O)COc1ccc(Cn2c(C)c(C)c3cc(C(=O)N[C@@H](C)c4cccc(C(C)C)c4)ccc32)cc1]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride.

Step 2: (S)-2-(4-((5-((1-(3-Isopropylphenyl)ethyl)carbamoyl)-2,3-dimethyl-1H-indol-1-yl)methyl)phenoxy)acetic acid

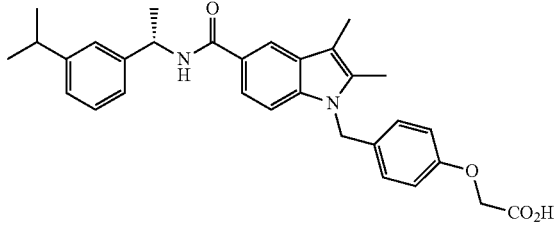 [SMILES: Cc1c(C)n(Cc2ccc(OCC(=O)O)cc2)c2ccc(C(=O)N[C@@H](C)c3cccc(C(C)C)c3)cc12]

The title compound was prepared following the same protocol as described in Step 6, Example 36, using the (S)-methyl 2-(4-((5-((1-(3-isopropylphenyl)ethyl)carbamoyl)-2,3-dimethyl-1H-indol-1-yl)methyl)phenoxy)acetate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 499 $[MH]^+$

Example 38

(S)-2-(4-((5-((1-(4-(tert-Butyl)phenyl)ethyl)carbamoyl)-2,3-dimethyl-1H-indol-1-yl)methyl)phenoxy)acetic acid

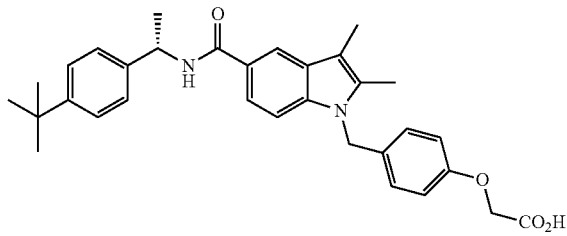 [SMILES: Cc1c(C)n(Cc2ccc(OCC(=O)O)cc2)c2ccc(C(=O)N[C@@H](C)c3ccc(C(C)(C)C)cc3)cc12]

Step 1: (S)-Methyl 2-(4-((5-((1-(4-(tert-butyl)phenyl)ethyl)carbamoyl)-2,3-dimethyl-1H-indol-1-yl)methyl)phenoxy)acetate

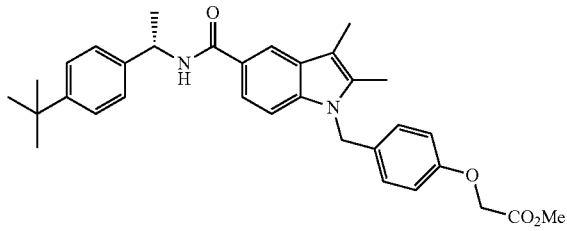 [SMILES: COC(=O)COc1ccc(Cn2c(C)c(C)c3cc(C(=O)N[C@@H](C)c4ccc(C(C)(C)C)cc4)ccc32)cc1]

The title compound was prepared following the same protocol as described in Step 5, Example 36, using the (S)-1-(4-

(tert-butyl)phenyl)ethanamine hydrochloride instead of the (S)-1-(3-cyclopropylphenyl)ethanamine hydrochloride.

Step 2: (S)-2-(4-((5-((1-(4-(tert-Butyl)phenyl)ethyl) carbamoyl)-2,3-dimethyl-1H-indol-1-yl)methyl)phenoxy)acetic acid

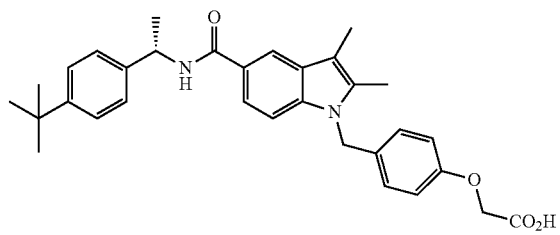 [SMILES: Cc1c(C)n(Cc2ccc(OCC(=O)O)cc2)c2ccc(C(=O)N[C@@H](C)c3ccc(C(C)(C)C)cc3)cc12]

The title compound was prepared following the same protocol as described in Step 6, Example 36, using the (S)-methyl 2-(4((5-((1-(4-(tert-butyl)phenyl)ethyl)carbamoyl)-2,3-dimethyl-1H-indol-1-yl)methyl)phenoxy)acetate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 513 [MH]+

Example 39

(S)-2-(3-((5-((1-(3-Cyclopropylphenyl)ethyl)carbamoyl)-2,3-dimethyl-1H-indol-1-yl)methyl)phenoxy)acetic acid

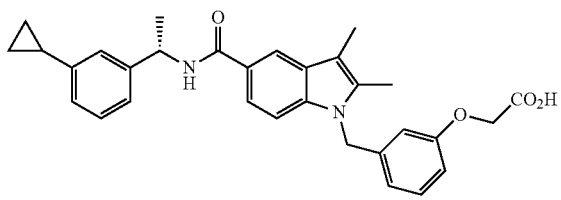 [SMILES: Cc1c(C)n(Cc2cccc(OCC(=O)O)c2)c2ccc(C(=O)N[C@@H](C)c3cccc(C4CC4)c3)cc12]

Step 1: Methyl 2-(m-tolyloxy)acetate

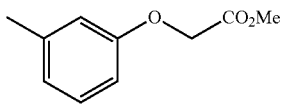

The title compound was prepared following the same protocol as described in Step 1, Example 36, using the m-cresol instead of the p-cresol.

Step 2: Methyl 2-(3-(bromomethyl)phenoxy)acetate

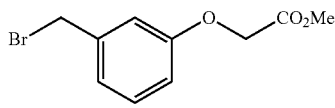 [SMILES: COC(=O)COc1cccc(CBr)c1]

The title compound was prepared following the same protocol as described in Step 2, Example 36, using the methyl 2-(m-tolyloxy)acetate instead of the methyl 2-(p-tolyloxy)acetate.

Step 3: Allyl 1-(3-(2-methoxy-2-oxoethoxy)benzyl)-2,3-dimethyl-1H-indole-5-carboxylate

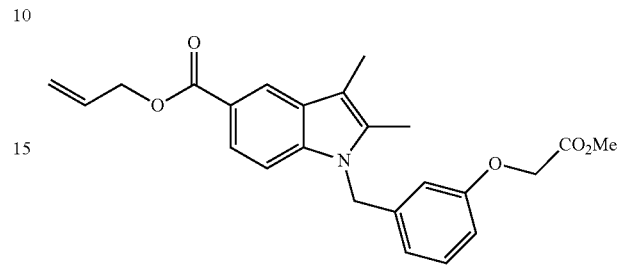

The title compound was prepared following the same general protocol as described in Step 3, Example 36, using the methyl 2-(3-(bromomethyl)phenoxy)acetate instead of the methyl 2-(4-(bromomethyl)phenoxy)acetate. ESI-MS (m/z): 408 [M+H]+.

Step 4: 1-(3-(2-Methoxy-2-oxoethoxy)benzyl)-2,3-dimethyl-1H-indole-5-carboxylic acid

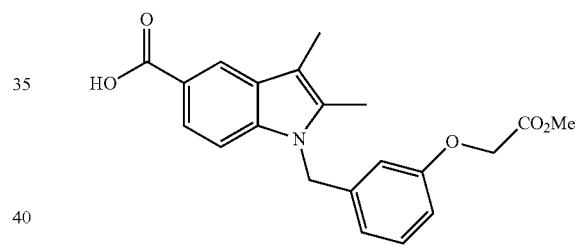

The title compound was prepared following the same general protocol as described in Step 4, Example 36, using the allyl 1-(3-(2-methoxy-2-oxoethoxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 368 [M+H]+.

Step 5: (S)-Methyl 2-(3-((5-((1-(3-cyclopropylphenyl)ethyl)carbamoyl)-2,3-dimethyl-1H-indol-1-yl) methyl)phenoxy)acetate

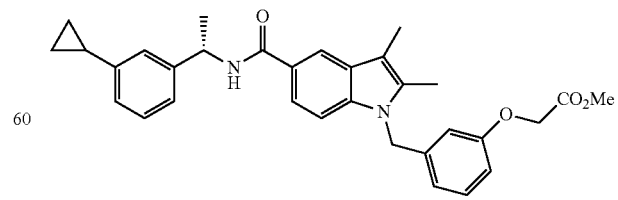

The title compound was prepared following the same protocol as described in Step 5, Example 36, using the 1-(3-(2-methoxy-2-oxoethoxy)benzyl)-2,3-dimethyl-1H-indole-5- carboxylic acid instead of the 1-(4-(2-methoxy-2-oxoethoxy)benzyl)-2,3-dimethyl-1H-indole-5-carboxylic acid.

Step 6: (S)-2-(3-((5-((1-(3-Cyclopropylphenyl)ethyl)carbamoyl)-2,3-dimethyl-1H-indol-1-yl)methyl)phenoxy)acetic acid

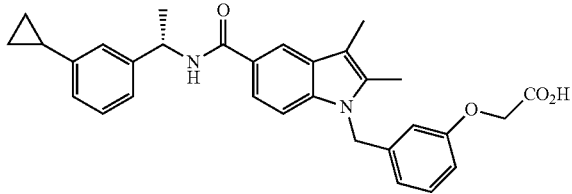 [SMILES: Cc1c(C)n(Cc2cccc(OCC(=O)O)c2)c2ccc(C(=O)N[C@@H](C)c3cccc(C4CC4)c3)cc12]

The title compound was prepared following the same protocol as described in Step 6, Example 36, using the (S)-methyl 2-(3-((5-((1-(3-cyclopropylphenyl)ethyl)carbamoyl)-2,3-dimethyl-1H-indol-1-yl)methyl)phenoxy)acetate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 497 [MH]$^+$ Example 40

(S)-2-(3-((5-((1-(3-Isopropylphenyl)ethyl)carbamoyl)-2,3-dimethyl-1H-indol-1-yl)methyl)phenoxy)acetic acid

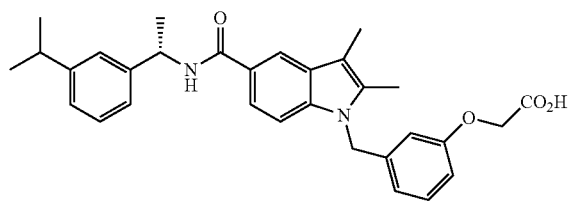 [SMILES: Cc1c(C)n(Cc2cccc(OCC(=O)O)c2)c2ccc(C(=O)N[C@@H](C)c3cccc(C(C)C)c3)cc12]

Step 1: (S)-Methyl 2-(3-((5-((1-(3-isopropylphenyl)ethyl)carbamoyl)-2,3-dimethyl-1H-indol-1-yl)methyl)phenoxy)acetate

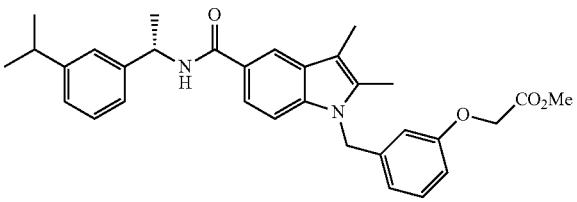 [SMILES: COC(=O)COc1cccc(Cn2c(C)c(C)c3cc(C(=O)N[C@@H](C)c4cccc(C(C)C)c4)ccc32)c1]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the 1-(3-(2-methoxy-2-oxoethoxy)benzyl)-2,3-dimethyl- 1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-((1-(3-Isopropylphenyl)ethyl)carbamoyl)-2,3-dimethyl-1H-indol-1-yl)methyl)phenoxy)acetic acid

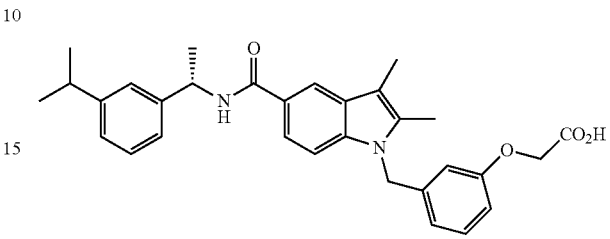

The title compound was prepared following the same protocol as described in Step 6, Example 36, using the (S)-methyl 2-(3-((5-((1-(3-isopropylphenyl)ethyl)carbamoyl)-2,3-dimethyl-1H-indol-1-yl)methyl)phenoxy)acetate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 499 [MH]$^+$ Example 41

(S)-2-(3-((5-((1-(4-(tert-Butyl)phenyl)ethyl)carbamoyl)-2,3-dimethyl-1H-indol-1-yl)methyl)phenoxy)acetic acid

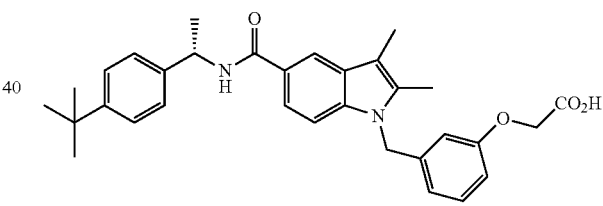

Step 1: (S)-Methyl 2-(3-((5-((1-(4-(tert-butyl)phenyl)ethyl)carbamoyl)-2,3-dimethyl-1H-indol-1-yl)methyl)phenoxy)acetate

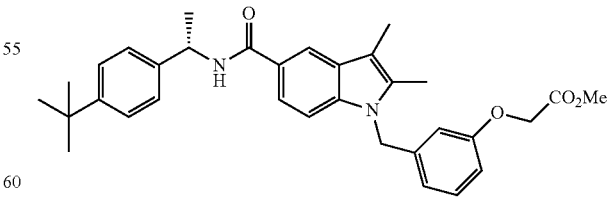

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride and the 1-(3-(2-methoxy-2-oxoethoxy)benzyl)-2,3-dimethyl- 1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-((1-(4-(tert-Butyl)phenyl)ethyl)carbamoyl)-2,3-dimethyl-1H-indol-1-yl)methyl)phenoxy)acetic acid

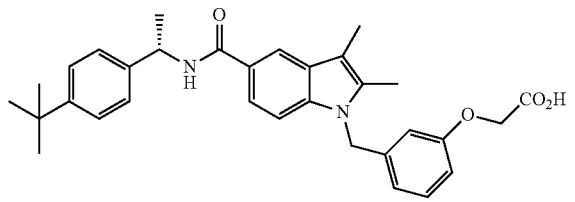 [SMILES: Cc1c(C)n(Cc2cccc(OCC(=O)O)c2)c2ccc(C(=O)N[C@@H](C)c3ccc(C(C)(C)C)cc3)cc12]

The title compound was prepared following the same protocol as described in Step 6, Example 36, using the (S)-methyl 2-(3-((5-((1-(4-(tert-butyl)phenyl)ethyl)carbamoyl)-2,3-dimethyl-1H-indol-1-yl)methyl)phenoxy)acetate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 513 [M+H]+

Example 42

(R)-2-(3-((5-(((S)-1-(3-Isopropylphenyl)ethyl)carbamoyl)-2,3-dimethyl-1H-indol-1-yl)methyl)phenoxy)propanoic acid

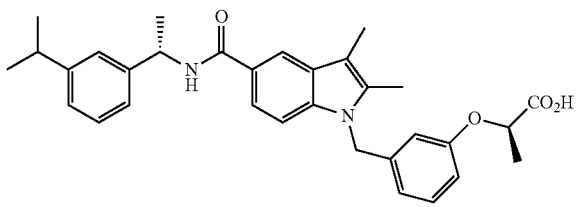 [SMILES: Cc1c(C)n(Cc2cccc(O[C@H](C)C(=O)O)c2)c2ccc(C(=O)N[C@@H](C)c3cccc(C(C)C)c3)cc12]

Step 1: (R)-Methyl 2-(m-tolyloxy)propanoate

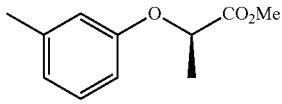

To a solution of the m-cresol (1.0 g, 9.2 mmol) in anhydrous THF (15 mL) at 0° C. under argon protection was added triphenylphosphine (2.55 g, 9.7 mmol), followed by addition of the (S)-methyl 2-hydroxypropanoate (926 µL, 9.7 mmol). Then diisopropylazodicarboxylate (DIAD) (2.85 mL, 13.8 mmol) was added dropwise at 0° C. The reaction mixture was stirred at room temperature overnight. The resulting mixture was diluted by ethyl acetate, washed with a 0.5 N HCl solution, a saturated solution of NaHCO$_3$, and brine, dried on MgSO$_4$, and concentrated. The obtained oil was purified by flash chromatography (Hexane/Ethyl acetate 0~50%) to afford a colorless oil (820 mg, 46%).

Step 2: (R)-Methyl 2-(3-(bromomethyl)phenoxy)propanoate

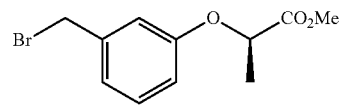

The title compound was prepared following the same protocol as described in Step 2, Example 36, using the (R)-methyl 2-(m-tolyloxy)propanoate instead of the methyl 2-(p-tolyloxy)acetate.

Step 3: (R)-Allyl 1-(3-((1-methoxy-1-oxopropan-2-yl)oxy)benzyl)-2,3-dimethyl-1H-indole-5-carboxylate

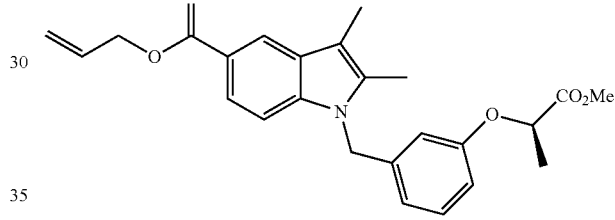

The title compound was prepared following the same general protocol as described in Step 3, Example 36, using the (R)-methyl 2-(3-(bromomethyl)phenoxy)propanoate instead of the methyl 2-(4-(bromomethyl)phenoxy)acetate. ESI-MS (m/z): 422 [M+H]+.

Step 4: (R)-1-(3-((1-Methoxy-1-oxopropan-2-yl)oxy)benzyl)-2,3-dimethyl-1H-indole-5-carboxylic acid

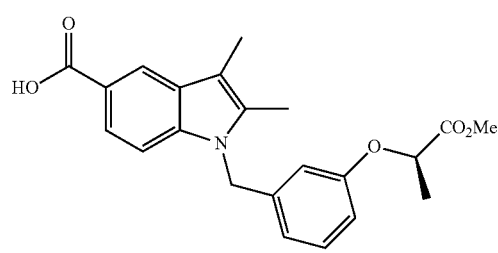 [SMILES: COC(=O)[C@@H](C)Oc1cccc(Cn2c(C)c(C)c3cc(C(=O)O)ccc32)c1]

The title compound was prepared following the same general protocol as described in Step 4, Example 36, using the (R)-allyl 1-(3-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 368 [M+H]+.

123

Step 5: (R)-Methyl 2-(3-((5-(((S)-1-(3-isopropylphenyl)ethyl)carbamoyl)-2,3-dimethyl-1H-indol-1-yl)methyl)phenoxy)propanoate

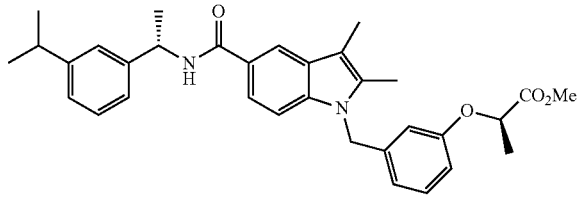 [SMILES: COC(=O)[C@@H](C)Oc1cccc(Cn2c(C)c(C)c3cc(C(=O)N[C@@H](C)c4cccc(C(C)C)c4)ccc32)c1]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-((5-(((S)-1-(3-Isopropylphenyl)ethyl)carbamoyl)-2,3-dimethyl-1H-indol-1-yl)methyl)phenoxy)propanoic acid

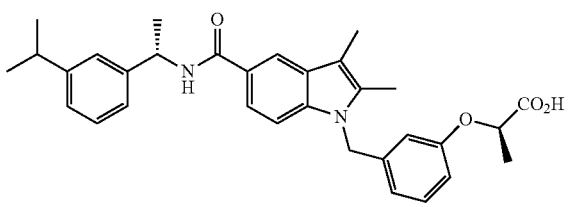 [SMILES: Cc1c(C)n(Cc2cccc(O[C@H](C)C(=O)O)c2)c2ccc(C(=O)N[C@@H](C)c3cccc(C(C)C)c3)cc12]

The title compound was prepared following the same protocol as described in Step 6, Example 36, using the (R)-methyl 2-(3-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 513 [MH]+

Example 43

(R)-2-(3-((5-(((S)-1-(4-(tert-Butyl)phenyl)ethyl)carbamoyl)-2,3-dimethyl-1H-indol-1-yl)methyl)phenoxy)propanoic acid

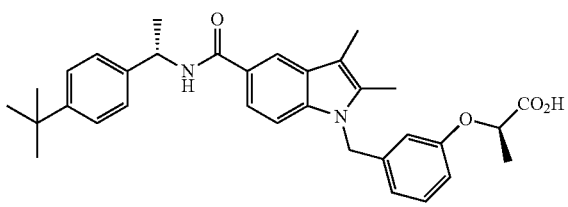 [SMILES: Cc1c(C)n(Cc2cccc(O[C@H](C)C(=O)O)c2)c2ccc(C(=O)N[C@@H](C)c3ccc(C(C)(C)C)cc3)cc12]

124

Step 1: (R)-Methyl 2-(3-((5-(((S)-1-(4-(tert-butyl)phenyl)ethyl)carbamoyl)-2,3-dimethyl-1H-indol-1-yl)methyl)phenoxy)propanoate

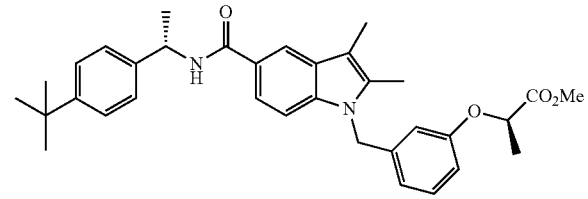 [SMILES: COC(=O)[C@@H](C)Oc1cccc(Cn2c(C)c(C)c3cc(C(=O)N[C@@H](C)c4ccc(C(C)(C)C)cc4)ccc32)c1]

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride and the (R)-1-(3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (R)-2-(3-((5-(((S)-1-(4-(tert-Butyl)phenyl)ethyl)carbamoyl)-2,3-dimethyl-1H-indol-1-yl)methyl)phenoxy)propanoic acid

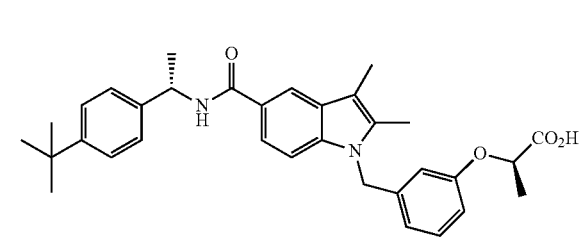 [SMILES: Cc1c(C)n(Cc2cccc(O[C@H](C)C(=O)O)c2)c2ccc(C(=O)N[C@@H](C)c3ccc(C(C)(C)C)cc3)cc12]

The title compound was prepared following the same protocol as described in Step 6, Example 36, using the (R)-methyl 2-(3-((5-(((S)-1-(4-(tert-butyl)phenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 527 [MH]+

Example 44

(S)-2-(3-((5-(((S)-1-(3-Isopropylphenyl)ethyl)carbamoyl)-2,3-dimethyl-1H-indol-1-yl)methyl)phenoxy)propanoic acid

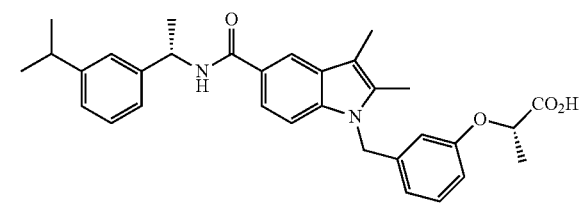 [SMILES: Cc1c(C)n(Cc2cccc(O[C@@H](C)C(=O)O)c2)c2ccc(C(=O)N[C@@H](C)c3cccc(C(C)C)c3)cc12]

Step 1: (S)-Methyl 2-(m-tolyloxy)propanoate

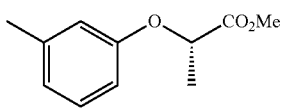

The title compound was prepared following the same protocol as described in Step 1, Example 42, using the (R)-methyl 2-hydroxypropanoate instead of the (S)-methyl 2-hydroxypropanoate.

Step 2: (S)-Methyl 2-(3-(bromomethyl)phenoxy)propanoate

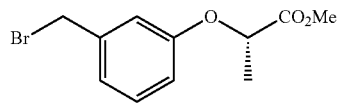

The title compound was prepared following the same protocol as described in Step 2, Example 36, using the (S)-methyl 2-(m-tolyloxy)propanoate instead of the methyl 2-(p-tolyloxy)acetate.

Step 3: (S)-Allyl 1-(3-((1-methoxy-1-oxopropan-2-yl)oxy)benzyl)-2,3-dimethyl-1H-indole-5-carboxylate

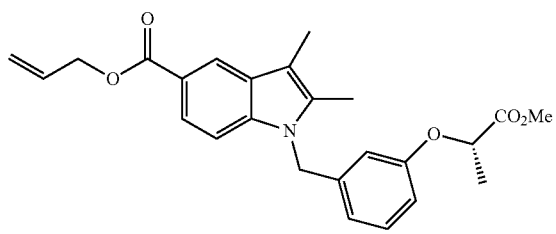 [SMILES: C=CCOC(=O)c1ccc2c(c1)c(C)c(C)n2Cc1cccc(O[C@@H](C)C(=O)OC)c1]

The title compound was prepared following the same general protocol as described in Step 3, Example 36, using the (S)-methyl 2-(3-(bromomethyl)phenoxy)propanoate instead of the methyl 2-(4-(bromomethyl)phenoxy)acetate. ESI-MS (m/z): 422 [M+H]$^+$.

Step 4: (S)-1-(3-((1-Methoxy-1-oxopropan-2-yl)oxy)benzyl)-2,3-dimethyl-1H-indole-5-carboxylic acid

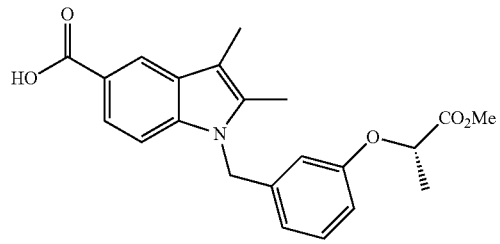 [SMILES: COC(=O)[C@H](C)Oc1cccc(Cn2c(C)c(C)c3cc(C(=O)O)ccc32)c1]

The title compound was prepared following the same general protocol as described in Step 4, Example 36, using the (S)-allyl 1-(3-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 368 [M+H]$^+$.

Step 5: (S)-Methyl 2-(3-((5-(((S)-1-(3-isopropylphenyl)ethyl)carbamoyl)-2,3-dimethyl-1H-indol-1-yl)methyl)phenoxy)propanoate

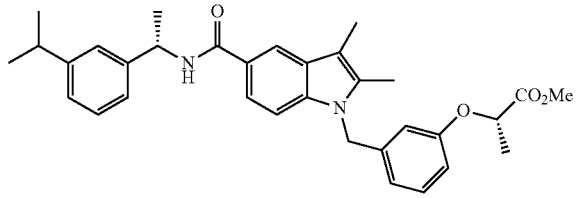 [SMILES: COC(=O)[C@H](C)Oc1cccc(Cn2c(C)c(C)c3cc(C(=O)N[C@@H](C)c4cccc(C(C)C)c4)ccc32)c1]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-((5-(((S)-1-(3-Isopropylphenyl)ethyl)carbamoyl)-2,3-dimethyl-1H-indol-1-yl)methyl)phenoxy)propanoic acid

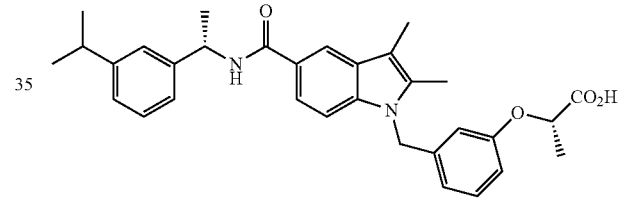

The title compound was prepared following the same protocol as described in Step 6, Example 36, using the (S)-methyl 2-(3-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 513 [M+H]$^+$

Example 45

(S)-2-(3-((5-(((S)-1-(4-(tert-Butyl)phenyl)ethyl)carbamoyl)-2,3-dimethyl-1H-indol-1-yl)methyl)phenoxy)propanoic acid

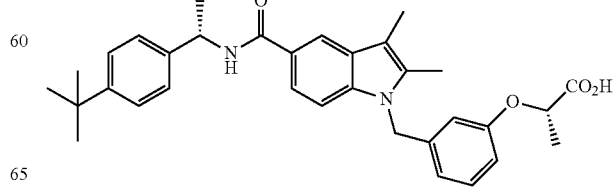

127

Step 1: (S)-Methyl 2-(3-((5-(((S)-1-(4-(tert-butyl)phenyl)ethyl)carbamoyl)-2,3-dimethyl-1H-indol-1-yl)methyl)phenoxy)propanoate

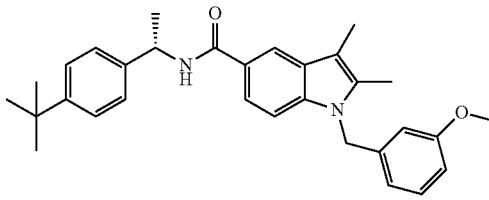

The title compound was prepared following the same protocol as described in Step 5, Example 36, using the (S)-1-(4-(tent-Butyl)phenyl)ethanamine hydrochloride instead of the (S)-1-(3-cyclopropylphenyl)ethanamine hydrochloride and the (S)-1-(3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-(((S)-1-(4-(tert-Butyl)phenyl)ethyl)carbamoyl)-2,3-dimethyl-1H-indol-1-yl)methyl)phenoxy)propanoic acid

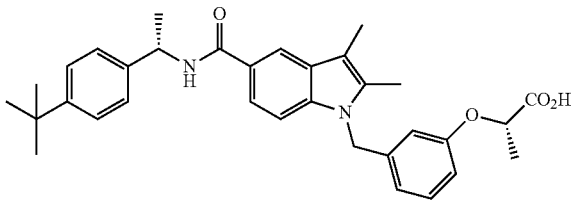 [SMILES: Cc1c(C)n(Cc2cccc(O[C@@H](C)C(=O)O)c2)c2ccc(C(=O)N[C@@H](C)c3ccc(C(C)(C)C)cc3)cc12]

The title compound was prepared following the same protocol as described in Step 6, Example 36, using the (S)-methyl 2-(3-((5-(((S)-1-(4-(tert-Butyl)phenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 527 [MH]$^+$ Example 46

(S)-2-(3-((5-(((S)-1-(3-Cyclopropylphenyl)ethyl)carbamoyl)-2,3-dimethyl-1H-indol-1-yl)methyl)phenoxy)propanoic acid

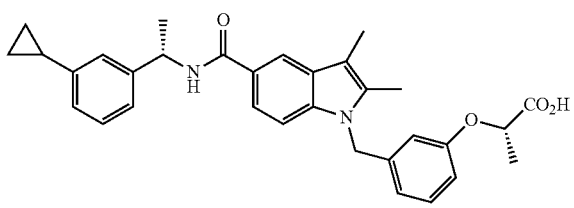 [SMILES: Cc1c(C)n(Cc2cccc(O[C@@H](C)C(=O)O)c2)c2ccc(C(=O)N[C@@H](C)c3cccc(C4CC4)c3)cc12]

128

Step 1: (S)-Methyl 2-(3-((5-(((S)-1-(3-cyclopropylphenyl)ethyl)carbamoyl)-2,3-dimethyl-1H-indol-1-yl)methyl)phenoxy)propanoate

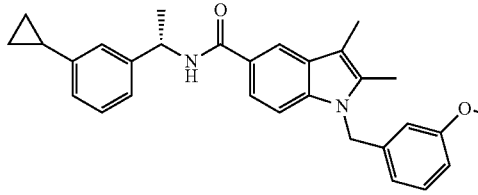

The title compound was prepared following the same protocol as described in Step 5, Example 36, using the (S)-1-(3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-(((S)-1-(3-Cyclopropylphenyl)ethyl)carbamoyl)-2,3-dimethyl-1H-indol-1-yl)methyl)phenoxy)propanoic acid

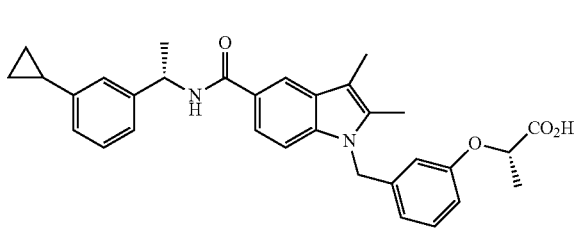 [SMILES: Cc1c(C)n(Cc2cccc(O[C@@H](C)C(=O)O)c2)c2ccc(C(=O)N[C@@H](C)c3cccc(C4CC4)c3)cc12]

The title compound was prepared following the same protocol as described in Step 6, Example 36, using the (S)-methyl 2-(3-((5-((S)-1-(3-cyclopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 511 [MH]$^+$ Example 47

(S)-2-(3-((5-((1-(3-Isopropylphenyl)ethyl)carbamoyl)-2,3-dimethyl-1H-indol-1-yl)methyl)phenoxy)-2-methylpropanoic acid

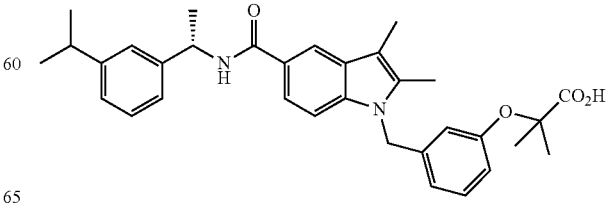

Step 1: Methyl 2-methyl-2-(m-tolyloxy)propanoate

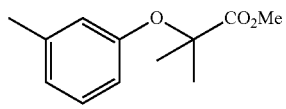

The title compound was prepared following the same protocol as described in Step 1, Example 36, using the m-cresol instead of the p-cresol and the methyl α-bromoisobutyrate instead of the methyl bromoacetate.

Step 2: Methyl 2-(3-(bromomethyl)phenoxy)-2-methylpropanoate

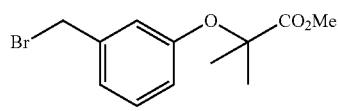 [SMILES: COC(=O)C(C)(C)Oc1cccc(CBr)c1]

The title compound was prepared following the same protocol as described in Step 2, Example 36, using the methyl 2-methyl-2-(m-tolyloxy)propanoate instead of the methyl 2-(p-tolyloxy)acetate.

Step 3: Allyl 1-(3-((1-methoxy-2-methyl-1-oxopropan-2-yl)oxy)benzyl)-2,3-dimethyl-1H-indole-5-carboxylate

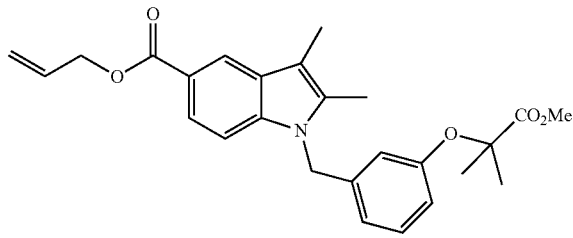 [SMILES: C=CCOC(=O)c1ccc2c(c1)c(C)c(C)n2Cc1cccc(OC(C)(C)C(=O)OC)c1]

The title compound was prepared following the same general protocol as described in Step 3, Example 36, using the methyl 2-(3-(bromomethyl)phenoxy)-2-methylpropanoate instead of the methyl 2-(4-(bromomethyl)phenoxy)acetate. ESI-MS (m/z): 436 [M+H]⁺.

Step 4: 1-(3-((1-Methoxy-2-methyl-1-oxopropan-2-yl)oxy)benzyl)-2,3-dimethyl-1H-indole-5-carboxylic acid

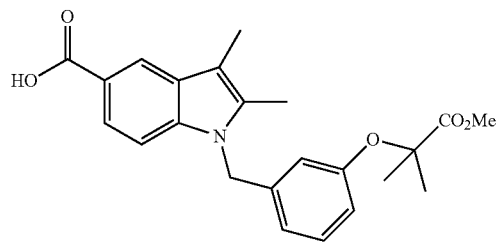 [SMILES: COC(=O)C(C)(C)Oc1cccc(Cn2c(C)c(C)c3cc(C(=O)O)ccc32)c1]

The title compound was prepared following the same general protocol as described in Step 4, Example 36, using the allyl 1-(3-((1-methoxy-2-methyl-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.
ESI-MS (m/z): 396 [M+H]⁺.

Step 5: (S)-Methyl 2-(3-((5-((1-(3-isopropylphenyl)ethyl)carbamoyl)-2,3-dimethyl-1H-indol-1-yl)methyl)phenoxy)-2-methylpropanoate

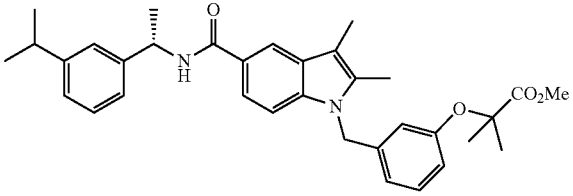 [SMILES: COC(=O)C(C)(C)Oc1cccc(Cn2c(C)c(C)c3cc(C(=O)N[C@@H](C)c4cccc(C(C)C)c4)ccc32)c1]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the 1-(3-((1-methoxy-2-methyl-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-((5-((1-(3-Isopropylphenyl)ethyl)carbamoyl)-2,3-dimethyl-1H-indol-1-yl)methyl)phenoxy)-2-methylpropanoic acid

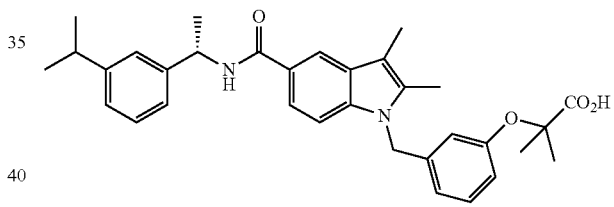

The title compound was prepared following the same protocol as described in Step 6, Example 36, using the (S)-methyl 2-(3-((5-((1-(3-isopropylphenyl)ethyl)carbamoyl)-2,3-dimethyl-1H-indol-1-yl)methyl)phenoxy)-2-methylpropanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 527 [MH]⁺

Example 48

(S)-2-(3-((5-((1-(4-(tert-Butyl)phenyl)ethyl)carbamoyl)-2,3-dimethyl-1H-indol-1-yl)methyl)phenoxy)-2-methylpropanoic acid

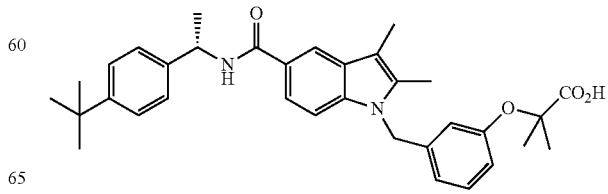

Step 1: (S)-Methyl 2-(3-((5-((1-(4-(tert-butyl)phenyl)
ethyl)carbamoyl)-2,3-dimethyl-1H-indol-1-yl)me-
thyl)phenoxy)-2-methylpropanoate

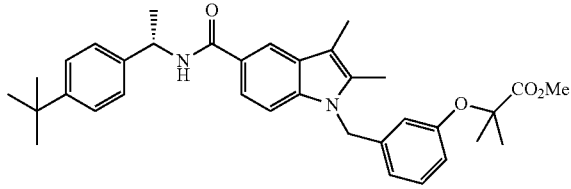 [SMILES: COC(=O)C(C)(C)Oc1cccc(Cn2c(C)c(C)c3cc(C(=O)N[C@@H](C)c4ccc(C(C)(C)C)cc4)ccc32)c1]

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride and the 1-(3-((1-methoxy-2-methyl-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-((1-(4-(tert-Butyl)phenyl)ethyl)
carbamoyl)-2,3-dimethyl-1H-indol-1-yl)methyl)phe-
noxy)-2-methylpropanoic acid

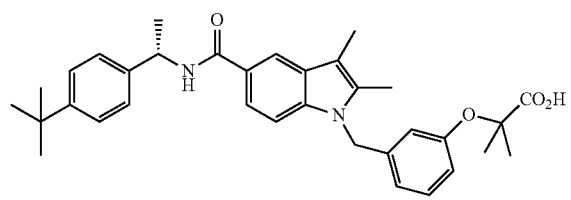 [SMILES: Cc1c(C)n(Cc2cccc(OC(C)(C)C(=O)O)c2)c2ccc(C(=O)N[C@@H](C)c3ccc(C(C)(C)C)cc3)cc12]

The title compound was prepared following the same protocol as described in Step 6, Example 36, using the (S)-methyl 2-(3-((5-((1-(4-(tert-butyl)phenyl)ethyl)carbamoyl)-2,3-dimethyl-1H-indol-1-yl)methyl)phenoxy)-2-methylpropanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 541 [MH]$^+$ Example 49

(S)-1-(3-(Cyanomethoxy)benzyl)-N-(1-(3-isopropylphenyl)ethyl)-2,3-dimethyl-1H-indole-5-carboxamide

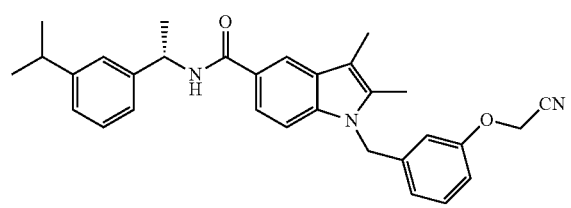 [SMILES: Cc1c(C)n(Cc2cccc(OCC#N)c2)c2ccc(C(=O)N[C@@H](C)c3cccc(C(C)C)c3)cc12]

Step 1: 2-(m-Tolyloxy)acetonitrile

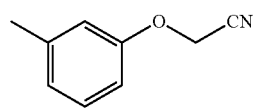

The title compound was prepared following the same protocol as described in Step 1, Example 36, using the m-cresol instead of the p-cresol and the bromoacetonitrile instead of the methyl bromoacetate.

Step 2: 2-(3-(Bromomethyl)phenoxy)acetonitrile

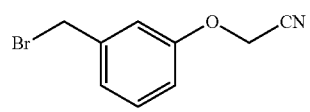 [SMILES: N#CCOc1cccc(CBr)c1]

The title compound was prepared following the same protocol as described in Step 2, Example 36, using the 2-(m-Tolyloxy)acetonitrile instead of the methyl 2-(p-tolyloxy)acetate.

Step 3: Allyl 1-(3-(cyanomethoxy)benzyl)-2,3-dimethyl-1H-indole-5-carboxylate

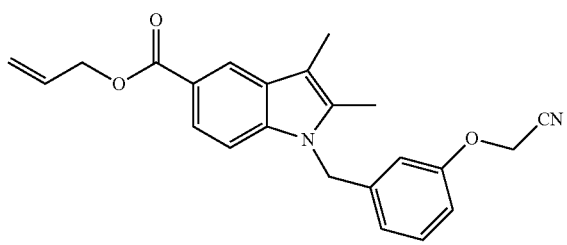 [SMILES: C=CCOC(=O)c1ccc2c(c1)c(C)c(C)n2Cc1cccc(OCC#N)c1]

The title compound was prepared following the same general protocol as described in Step 3, Example 36, using the 2-(3-(Bromomethyl)phenoxy)acetonitrile instead of the methyl 2-(4-(bromomethyl)phenoxy)acetate. ESI-MS (m/z): 375 [M+H]$^+$.

Step 4: 1-(3-(Cyanomethoxy)benzyl)-2,3-dimethyl-1H-indole-5-carboxylic acid

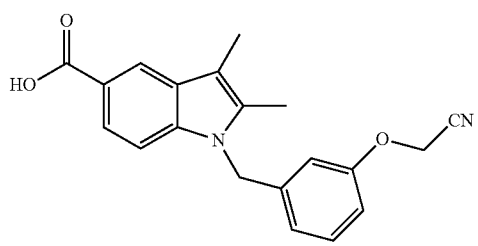 [SMILES: Cc1c(C)n(Cc2cccc(OCC#N)c2)c2ccc(C(=O)O)cc12]

The title compound was prepared following the same general protocol as described in Step 4, Example 36, using the allyl 1-(3-(cyanomethoxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 335 [M+H]$^+$.

Step 5: (S)-1-(3-(Cyanomethoxy)benzyl)-N-(1-(3-isopropylphenyl)ethyl)-2,3-dimethyl-1H-indole-5-carboxamide

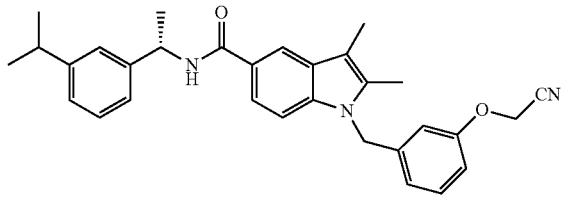 [SMILES: Cc1c(C)n(Cc2cccc(OCC#N)c2)c2ccc(C(=O)N[C@@H](C)c3cccc(C(C)C)c3)cc12]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the 1-(3-(cyanomethoxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid. ESI-MS (m/z): 480 [M+H]$^+$.

Example 50

(S)-N-(1-(4-(tert-Butyl)phenyl)ethyl)-1-(3-(cyanomethoxy)benzyl)-2,3-dimethyl-1H-indole-5-carboxamide

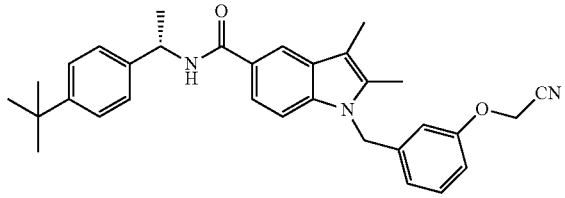 [SMILES: Cc1c(C)n(Cc2cccc(OCC#N)c2)c2ccc(C(=O)N[C@@H](C)c3ccc(C(C)(C)C)cc3)cc12]

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride and the 1-(3-(cyanomethoxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid. ESI-MS (m/z): 494 [M+H]$^+$.

Example 51

(S)-2-(4-((5-(((S)-1-(3-Isopropylphenyl)ethyl)carbamoyl)-2,3-dimethyl-1H-indol-1-yl)methyl)phenoxy)propanoic acid

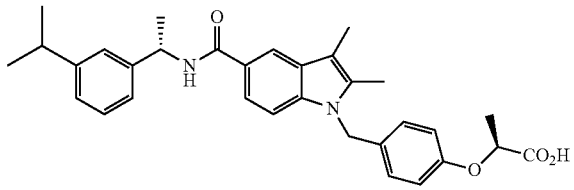 [SMILES: Cc1c(C)n(Cc2ccc(O[C@@H](C)C(=O)O)cc2)c2ccc(C(=O)N[C@@H](C)c3cccc(C(C)C)c3)cc12]

Step 1: (S)-Methyl 2-(p-tolyloxy)propanoate

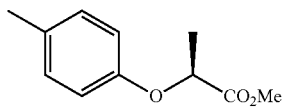

The title compound was prepared following the same protocol as described in Step 1, Example 42, using the p-cresol instead of the m-cresol and the (R)-methyl 2-hydroxypropanoate instead of the (S)-methyl 2-hydroxypropanoate.

Step 2: (S)-Methyl 2-(4-(bromomethyl)phenoxy)propanoate

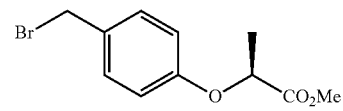

The title compound was prepared following the same protocol as described in Step 2, Example 36, using the (S)-methyl 2-(p-tolyloxy)propanoate instead of the methyl 2-(p-tolyloxy)acetate.

Step 3: (S)-Allyl 1-(4-((1-methoxy-1-oxopropan-2-yl)oxy)benzyl)-2,3-dimethyl-1H-indole-5-carboxylate

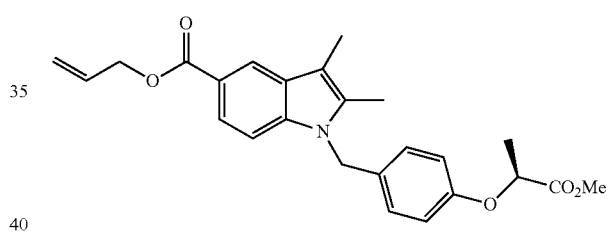

The title compound was prepared following the same general protocol as described in Step 3, Example 36, using the (S)-methyl 2-(4-(bromomethyl)phenoxy)propanoate instead of the methyl 2-(4-(bromomethyl)phenoxy)acetate. ESI-MS (m/z): 422 [M+H]$^+$.

Step 4: (S)-1-(4-((1-Methoxy-1-oxopropan-2-yl)oxy)benzyl)-2,3-dimethyl-1H-indole-5-carboxylic acid

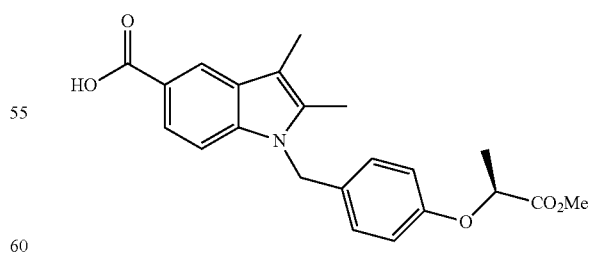

The title compound was prepared following the same general protocol as described in Step 4, Example 36, using the (S)-allyl 1-(4-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 368 [M+H]$^+$.

Step 5: (S)-Methyl 2-(4-((5-(((S)-1-(3-isopropylphenyl)ethyl)carbamoyl)-2,3-dimethyl-1H-indol-1-yl)methyl)phenoxy)propanoate

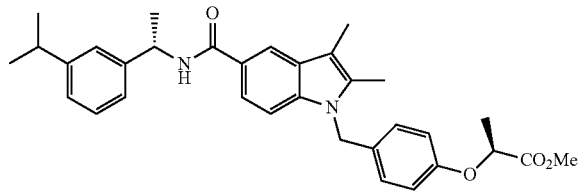 [SMILES: COC(=O)[C@H](C)Oc1ccc(Cn2c(C)c(C)c3cc(C(=O)N[C@@H](C)c4cccc(C(C)C)c4)ccc32)cc1]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(4-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(4-((5-(((S)-1-(4-Isopropylphenyl)ethyl)carbamoyl)-2,3-dimethyl-1H-indol-1-yl)methyl)phenoxy)propanoic acid

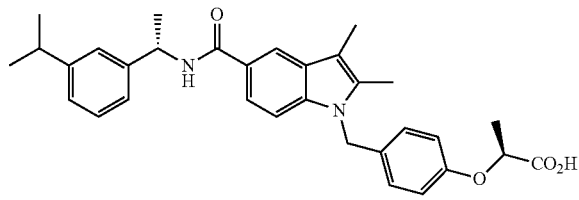 [SMILES: Cc1c(C)n(Cc2ccc(O[C@@H](C)C(=O)O)cc2)c2ccc(C(=O)N[C@@H](C)c3cccc(C(C)C)c3)cc12]

The title compound was prepared following the same protocol as described in Step 6, Example 36, using the (S)-methyl 2-(4-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 513 [MH]+

Example 52

(S)-2-(4-((5-(((S)-1-(3-Cyclopropylphenyl)ethyl)carbamoyl)-2,3-dimethyl-1H-indol-1-yl)methyl)phenoxy)propanoic acid

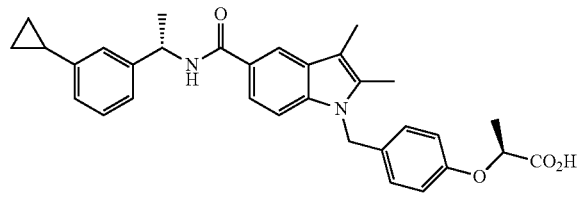 [SMILES: Cc1c(C)n(Cc2ccc(O[C@@H](C)C(=O)O)cc2)c2ccc(C(=O)N[C@@H](C)c3cccc(C4CC4)c3)cc12]

Step 1: (S)-Methyl 2-(4-((5-(((S)-1-(3-cyclopropylphenyl)ethyl)carbamoyl)-2,3-dimethyl-1H-indol-1-yl)methyl)phenoxy)propanoate

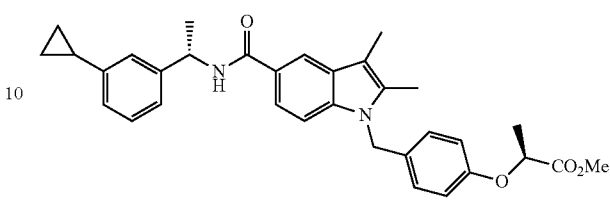

The title compound was prepared following the same protocol as described in Step 5, Example 36, using the (S)-1-(4-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(4-((5-(((S)-1-(3-Cyclopropylphenyl)ethyl)carbamoyl)-2,3-dimethyl-1H-indol-1-yl)methyl)phenoxy)propanoic acid

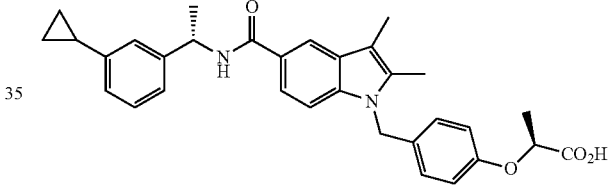

The title compound was prepared following the same protocol as described in Step 6, Example 36, using the (S)-methyl 2-(4-((5-(((S)-1-(3-cyclopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 511 [MH]+

Example 53

(R)-2-(4-((5-(((S)-1-(3-Isopropylphenyl)ethyl)carbamoyl)-2,3-dimethyl-1H-indol-1-yl)methyl)phenoxy)propanoic acid

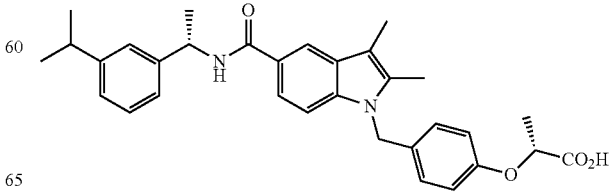

Step 1: (R)-Methyl 2-(p-tolyloxy)propanoate

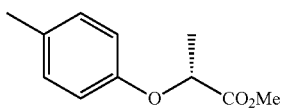

The title compound was prepared following the same protocol as described in Step 1, Example 42, using the p-cresol instead of the m-cresol.

Step 2: (R)-Methyl 2-(4-(bromomethyl)phenoxy)propanoate

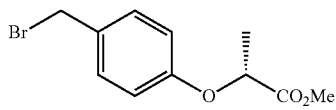

The title compound was prepared following the same protocol as described in Step 2, Example 36, using the (R)-methyl 2-(p-tolyloxy)propanoate instead of the methyl 2-(p-tolyloxy)acetate.

Step 3: (R)-Allyl 1-(4-((1-methoxy-1-oxopropan-2-yl)oxy)benzyl)-2,3-dimethyl-1H-indole-5-carboxylate

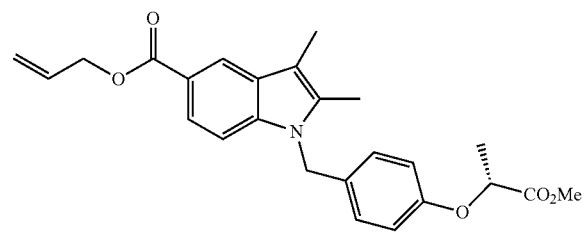 [SMILES: C=CCOC(=O)c1ccc2c(c1)c(C)c(C)n2Cc1ccc(O[C@H](C)C(=O)OC)cc1]

The title compound was prepared following the same general protocol as described in Step 3, Example 36, using the (R)-methyl 2-(4-(bromomethyl)phenoxy)propanoate instead of the methyl 2-(4-(bromomethyl)phenoxy)acetate. ESI-MS (m/z): 422 [M+H]⁺.

Step 4: (R)-1-(4-((1-Methoxy-1-oxopropan-2-yl)oxy)benzyl)-2,3-dimethyl-1H-indole-5-carboxylic acid

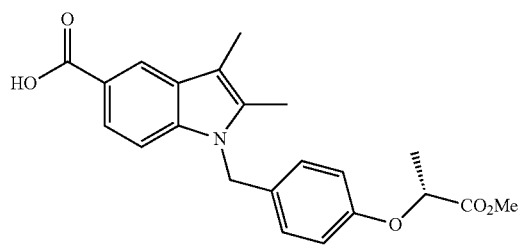 [SMILES: COC(=O)[C@@H](C)Oc1ccc(Cn2c(C)c(C)c3cc(C(=O)O)ccc32)cc1]

The title compound was prepared following the same general protocol as described in Step 4, Example 36, using the (R)-allyl 1-(4-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 368 [M+H]⁺.

Step 5: (R)-Methyl 2-(4-((5-(((S)-1-(3-isopropylphenyl)ethyl)carbamoyl)-2,3-dimethyl-1H-indol-1-yl)methyl)phenoxy)propanoate

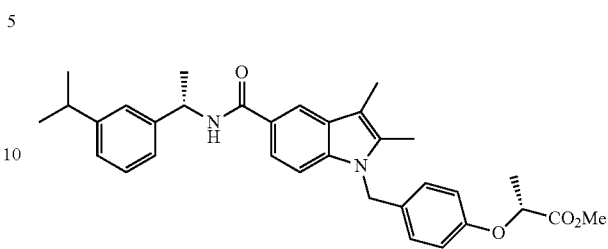

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(4-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-((5-(((S)-1-(4-Isopropylphenyl)ethyl)carbamoyl)-2,3-dimethyl-1H-indol-1-yl)methyl)phenoxy)propanoic acid

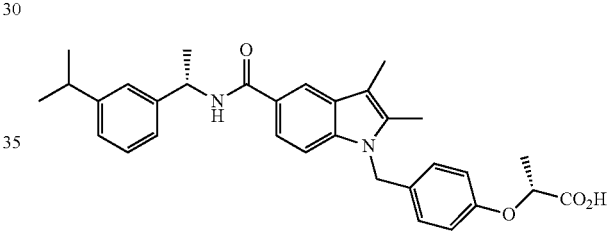

The title compound was prepared following the same protocol as described in Step 6, Example 36, using the (R)-methyl 2-(4-((5-(((S)-1-(3-isopropylphenyl)ethyl)carbamoyl)-2,3-dimethyl-1H-indol-1-yl)methyl)phenoxy) propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 513 [MH]⁺

Example 54

(S)-2-(4-((5-((1-(3-Isopropylphenyl)ethyl)carbamoyl)-2,3-dimethyl-1H-indol-1-yl)methyl)phenoxy)-2-methylpropanoic acid

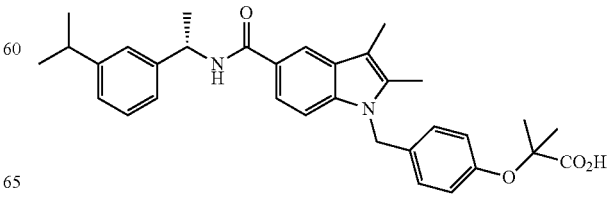

Step 1: Methyl 2-methyl-2-(p-tolyloxy)propanoate

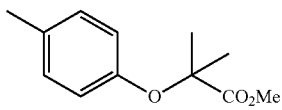

The title compound was prepared following the same protocol as described in Step 1, Example 36, using the methyl α-bromoisobutyrate instead of the methyl bromoacetate.

Step 2: Methyl 2-(4-(bromomethyl)phenoxy)-2-methylpropanoate

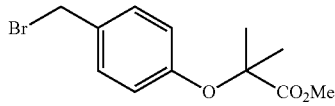

The title compound was prepared following the same protocol as described in Step 2, Example 36, using the methyl 2-methyl-2-(p-tolyloxy)propanoate instead of the methyl 2-(p-tolyloxy)acetate.

Step 3: Allyl 1-(4-((1-methoxy-2-methyl-1-oxopropan-2-yl)oxy)benzyl)-2,3-dimethyl-1H-indole-5-carboxylate

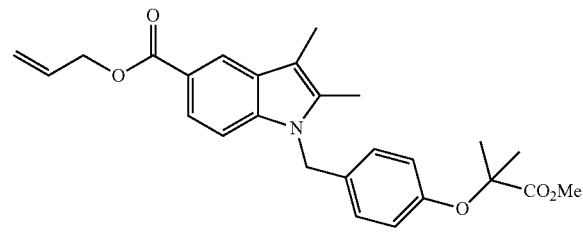 [SMILES: C=CCOC(=O)c1ccc2c(c1)c(C)c(C)n2Cc1ccc(OC(C)(C)C(=O)OC)cc1]

The title compound was prepared following the same general protocol as described in Step 3, Example 36, using the methyl 2-(4-(bromomethyl)phenoxy)-2-methylpropanoate instead of the methyl 2-(4-(bromomethyl)phenoxy)acetate. ESI-MS (m/z): 436 [M+H]$^+$.

Step 4: 1-(4-((1-Methoxy-2-methyl-1-oxopropan-2-yl)oxy)benzyl)-2,3-dimethyl-1H-indole-5-carboxylic acid

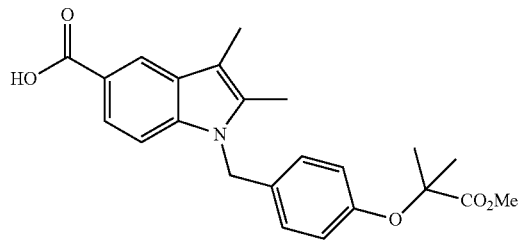 [SMILES: COC(=O)C(C)(C)Oc1ccc(Cn2c(C)c(C)c3cc(C(=O)O)ccc32)cc1]

The title compound was prepared following the same general protocol as described in Step 4, Example 36, using the allyl 1-(4-((1-methoxy-2-methyl-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 396 [M+H]$^+$.

Step 5: (S)-Methyl 2-(4-((5-((1-(3-isopropylphenyl)ethyl)carbamoyl)-2,3-dimethyl-1H-indol-1-yl)methyl)phenoxy)-2-methylpropanoate

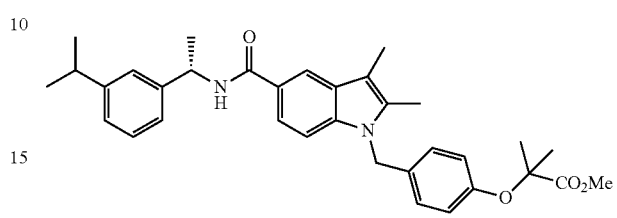

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the 1-(4-((1-methoxy-2-methyl-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(4-((5-((1-(3-Isopropylphenyl)ethyl)carbamoyl)-2,3-dimethyl-1H-indol-1-yl)methyl)phenoxy)-2-methylpropanoic acid

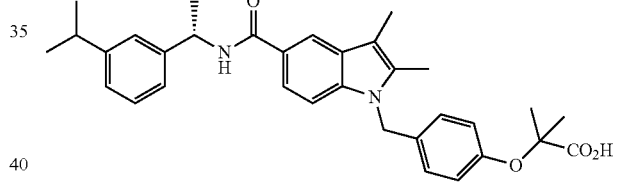

The title compound was prepared following the same protocol as described in Step 6, Example 36, using the (S)-methyl 2-(4-((5-((1-(3-isopropylphenyl)ethyl)carbamoyl)-2,3-dimethyl-1H-indol-1-yl)methyl)phenoxy)-2-methylpropanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 527 [MH]$^+$

Example 55

(S)-2-(2-Chloro-5-((5-(((S)-1-(3-isopropylphenyl)ethyl)carbamoyl)-2,3-dimethyl-1H-indol-1-yl)methyl)phenoxy)propanoic acid

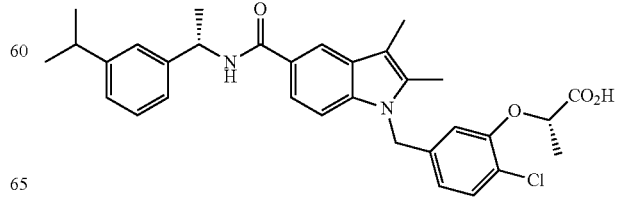

Step 1: (S)-Methyl 2-(2-chloro-5-methylphenoxy)propanoate

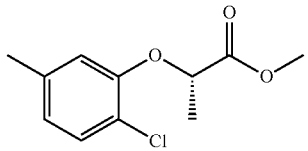

To a solution of the 2-chloro-5-methylphenol (4.0 g, 28 mmol) in anhydrous THF (24 mL) at 0° C. under argon protection was added triphenylphosphine (9.5 g, 36.4 mmol), followed by addition of the (R)-methyl 2-hydroxypropanoate (3.89 g, 31 mmol). Then DIAD (8.2 mL, 42 mmol) was added slowly to the solution at 0° C. The reaction mixture was stirred at room temperature for 20 h. The solvent was removed and the crude was purified by flash chromatography (AcOEt/hexane 0~30%) to obtain the title compound.

Step 2: (S)-Methyl 2-(5-(bromomethyl)-2-chlorophenoxy)propanoate

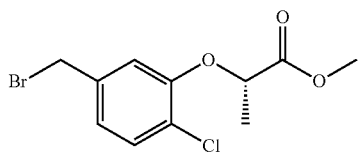 [SMILES: COC(=O)[C@H](C)Oc1cc(CBr)ccc1Cl]

To (S)-methyl 2-(2-chloro-5-methylphenoxy)propanoate (2.4 g, 10.5 mmol) in $CCl_4$ (20 mL) was added NBS (1.92 g, 11.55 mmol) and AIBN (0.35 g, 2.1 mmol). The mixture was refluxed overnight. The reaction mixture was cooled and the solvent was removed to obtain the crude. The crude was purified by flash chromatography (AcOEt/Hexane 0~30%) to obtain the title compound.

Step 3: (S)-Allyl 1-(4-chloro-3-((1-methoxy-1-oxopropan-2-yl)oxy)benzyl)-2,3-dimethyl-1H-indole-5-carboxylate

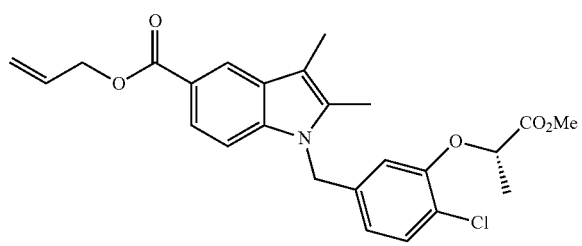 [SMILES: C=CCOC(=O)c1ccc2c(c1)c(C)c(C)n2Cc1ccc(Cl)c(O[C@@H](C)C(=O)OC)c1]

The title compound was prepared following the same general protocol as described for the synthesis of the (S)-allyl 1-(2-chloro-5-((1-methoxy-1-oxopropan-2-yl)oxy)benzyl)-2,3-dimethyl-1H-indole-5-carboxylate (Step 3, Example 26), using the (S)-methyl 2-(5-(bromomethyl)-2-chlorophenoxy) propanoate instead of the (S)-methyl 2-(3-(bromomethyl)-4-chlorophenoxy)propanoate ESI-MS (m/z): 456 $[M+1]^+$.

Step 4: (S)-1-(4-Chloro-3-((1-methoxy-1-oxopropan-2-yl)oxy)benzyl)-2,3-dimethyl-1H-indole-5-carboxylic acid

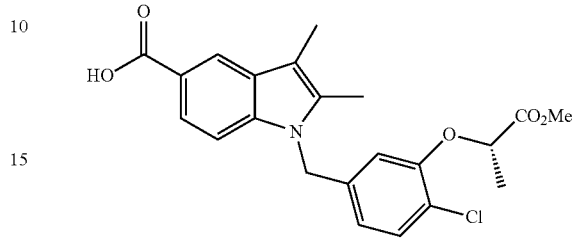

The title compound was prepared following the same general protocol as described for the synthesis of the (S)-1-(2-chloro-5-((1-methoxy-1-oxopropan-2-yl)oxy)benzyl)-2,3-dimethyl-1H-indole-5-carboxylic acid (Step 4, Example 26), using the (S)-allyl 1-(4-chloro-3-((1-methoxy-1-oxopropan-2-yl)oxy)benzyl)-2,3-dimethyl-1H-indole-5-carboxylate instead of the (S)-allyl 1-(2-chloro-5-((1-methoxy-1-oxopropan-2-yl)oxy)benzyl)-2,3-dimethyl-1H-indole-5-carboxylate.
ESI-MS (m/z): 416 $[M+1]^+$.

Step 5: (S)-Methyl 2-(2-chloro-5-((5-(((S)-1-(3-isopropylphenyl)ethyl)carbamoyl)-2,3-dimethyl-1H-indol-1-yl)methyl)phenoxy)propanoate

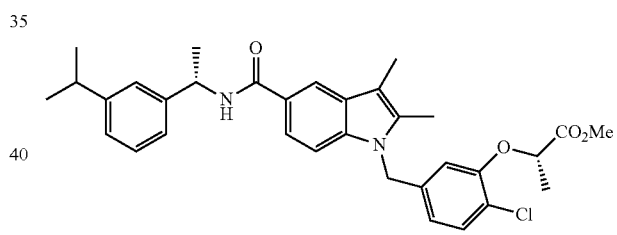

The (S)-1-(4-chloro-3-((1-methoxy-1-oxopropan-2-yl)oxy)benzyl)-2,3-dimethyl-1H-indole-5-carboxylic acid (55 mg, 0.13 mmol), the (S)-1-(3-isopropylphenyl)ethanamine hydrochloride (37 mg, 0.19 mmol) and HATU (61 mg, 0.16 mmol) were dissolved in DMF (3 mL) and DIEA (0.1 mL). It was stirred for 15 h. The solution was filtered and purified by preparative HPLC.

Step 6: (S)-2-(2-Chloro-5-((5-(((S)-1-(3-isopropylphenyl)ethyl)carbamoyl)-2,3-dimethyl-1H-indol-1-yl)methyl)phenoxy)propanoic acid

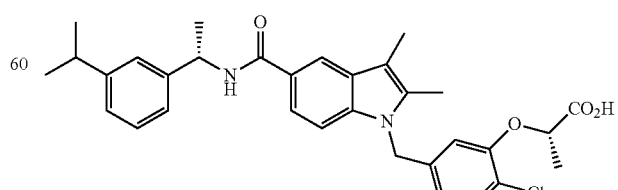

The (S)-methyl 2-(2-chloro-5-((5-(((S)-1-(3-isopropylphenyl)ethyl)carbamoyl)-2,3-dimethyl-1H-indol-1-yl)methyl)phenoxy)propanoate was dissolved in methanol (1.5 mL), DMSO (~1.5 mL) and water (0.1 mL) then NaOH (2 N, 0.1 mL) was added dropwise. The reaction was monitored by LC/MS. It was stirred until all the starting material was consumed (~3 h). It was acidified with trifluoroacetic acid, filtered and purified by preparative HPLC to yield the title compound. ESI-MS (m/z): 547.1 [M+H]⁺.

Example 56

(S)-2-(2-Chloro-5-((5-(((S)-1-(3-cyclopropylphenyl)ethyl)carbamoyl)-2,3-dimethyl-1H-indol-1-yl)methyl)phenoxy)propanoic acid

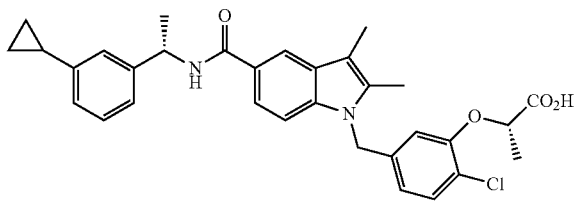 [SMILES: Cc1c(C)n(Cc2ccc(Cl)c(O[C@@H](C)C(=O)O)c2)c2ccc(C(=O)N[C@@H](C)c3cccc(C4CC4)c3)cc12]

A similar procedure was followed as described in the previous example (Example 20) to yield the title compound. ESI-MS (m/z): 545.1 [M+H]⁺.

Example 57

(S)-2-(5-((5-(((S)-1-(4-Bromophenyl)ethyl)carbamoyl)-2,3-dimethyl-1H-indol-1-yl)methyl)-2-chlorophenoxy)propanoic acid

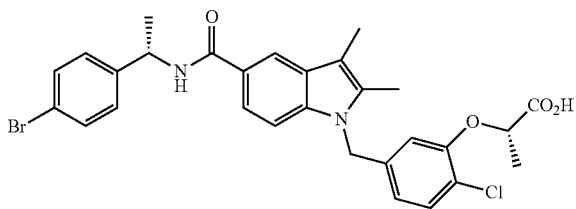 [SMILES: Cc1c(C)n(Cc2ccc(Cl)c(O[C@@H](C)C(=O)O)c2)c2ccc(C(=O)N[C@@H](C)c3ccc(Br)cc3)cc12]

A similar procedure was followed as described in the previous example (Example 20) using (S)-1-(4-bromophenyl)ethanamine to yield the title compound. ESI-MS (m/z): 585.0 [M+H]⁺.

Example 58

(S)-2-(5-((5-(((S)-1-(4-(tert-Butyl)phenyl)ethyl)carbamoyl)-2,3-dimethyl-1H-indol-1-yl)methyl)-2-chlorophenoxy)propanoic acid

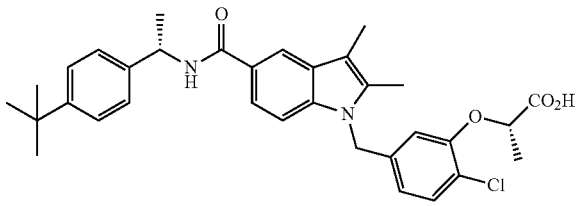

Step 1: (S)-Methyl 2-(5-((5-(((S)-1-(4-(tert-butyl)phenyl)ethyl)carbamoyl)-2,3-dimethyl-1H-indol-1-yl)methyl)-2-chlorophenoxy)propanoate

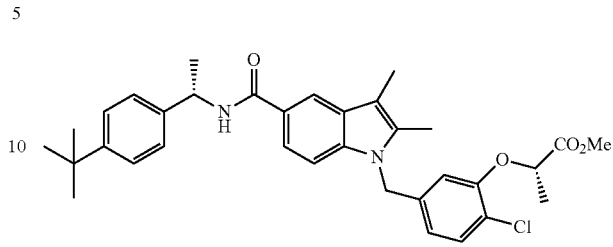

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride the (S)-1-(4-chloro-3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(5-((5-(((S)-1-(4-(tert-Butyl)phenyl)ethyl)carbamoyl)-2,3-dimethyl-1H-indol-1-yl)methyl)-2-chlorophenoxy)propanoic acid

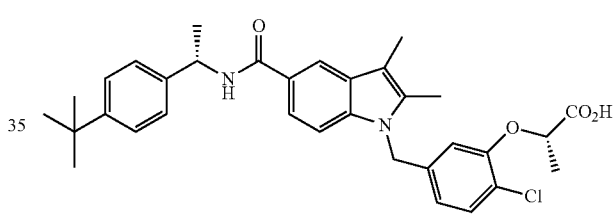

The title compound was prepared following the same protocol as described in Step 6, Example 36, using the (S)-methyl 2-(5-((5-(((S)-1-(4-(tert-butyl)phenyl)ethyl)carbamoyl)-2,3-dimethyl-1H-indol-1-yl)methyl)-2-chlorophenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]⁺

Example 59

(S)-2-(5-((5-(((S)-1-(3-(tert-Butyl)phenyl)ethyl)carbamoyl)-2,3-dimethyl-1H-indol-1-yl)methyl)-2-chlorophenoxy)propanoic acid

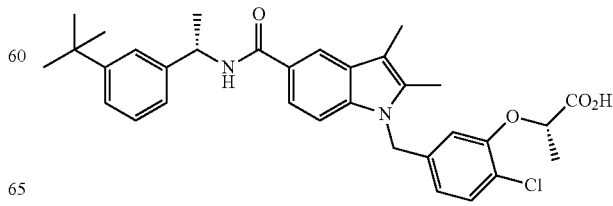

Step 1: (S)-Methyl 2-(5-((5-(((S)-1-(3-(tert-butyl)phenyl)ethyl)carbamoyl)-2,3-dimethyl-1H-indol-1-yl)methyl)-2-chlorophenoxy)propanoate

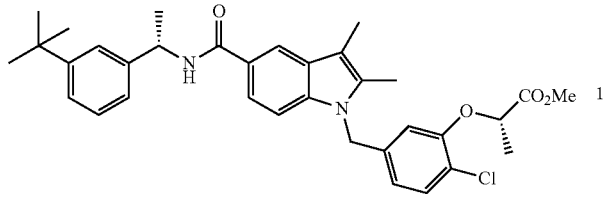

The title compound was prepared following the same protocol as described in Step 5, Example 36, using the (S)-1-(3-(tert-butyl)phenyl)ethanamine hydrochloride instead of the (S)-1-(3-cyclopropylphenyl)ethanamine hydrochloride the (S)-1-(4-chloro-3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(5-((5-(((S)-1-(3-(tert-Butyl)phenyl)ethyl)carbamoyl)-2,3-dimethyl-1H-indol-1-yl)methyl)-2-chlorophenoxy)propanoic acid

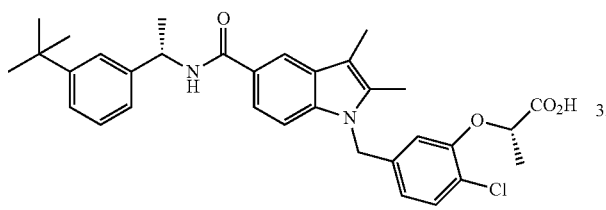

The title compound was prepared following the same protocol as described in Step 6, Example 36, using the (S)-methyl 2-(5-((5-(((S)-1-(4-(tert-butyl)phenyl)ethyl)carbamoyl)-2,3-dimethyl-1H-indol-1-yl)methyl)-2-chlorophenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ Example 60

(S)-2-(2-Chloro-5-((5-(((S)-1-(3-isopropoxyphenyl)ethyl)carbamoyl)-2,3-dimethyl-1H-indol-1-yl)methyl)phenoxy)propanoic acid

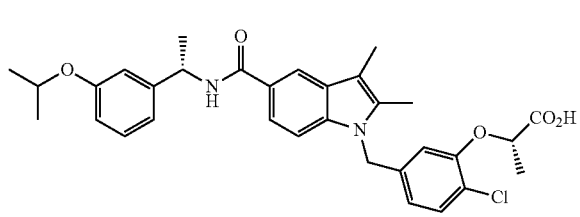 [SMILES: Cc1c(C)n(Cc2ccc(Cl)c(O[C@@H](C)C(=O)O)c2)c2ccc(C(=O)N[C@@H](C)c3cccc(OC(C)C)c3)cc12]

Step 1: (S)-Methyl 2-(5-((5-(((S)-1-(3-isopropoxyphenyl)ethyl)carbamoyl)-2,3-dimethyl-1H-indol-1-yl)methyl)-2-chlorophenoxy)propanoate

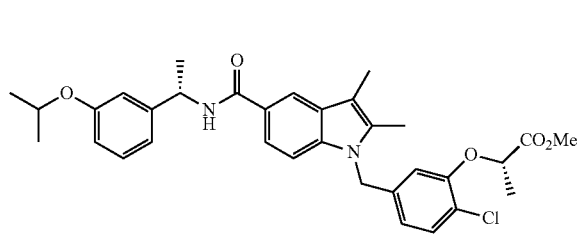 [SMILES: COC(=O)[C@H](C)Oc1cc(Cn2c(C)c(C)c3cc(C(=O)N[C@@H](C)c4cccc(OC(C)C)c4)ccc32)ccc1Cl]

The title compound was prepared following the same protocol as described in Step 5, Example 36, using the (S)-1-(3-isopropoxyphenyl)ethanamine hydrochloride instead of the (S)-1-(3-cyclopropylphenyl)ethanamine hydrochloride and (S)-1-(4-chloro-3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(5-((5-(((S)-1-(3-isopropoxyphenyl)ethyl)carbamoyl)-2,3-dimethyl-1H-indol-1-yl)methyl)-2-chlorophenoxy)propanoic acid

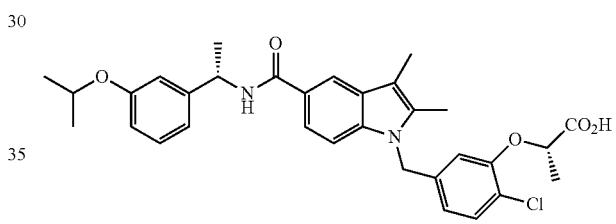

The title compound was prepared following the same protocol as described in Step 6, Example 36, using the (S)-methyl 2-(5-((5-(((S)-1-(3-isopropoxyphenyl)ethyl)carbamoyl)-2,3-dimethyl-1H-indol-1-yl)methyl)-2-chlorophenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ Example 61

(S)-2-(4-Chloro-3-((5-(((S)-1-(3-isopropylphenyl)ethyl)carbamoyl)-2,3-dimethyl-1H-indol-1-yl)methyl)phenoxy)propanoic acid

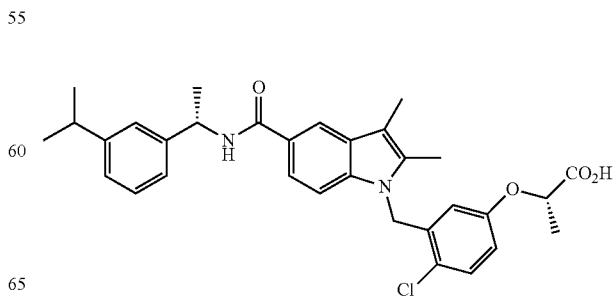

Step 1: (S)-Methyl 2-(4-chloro-3-methylphenoxy)propanoate

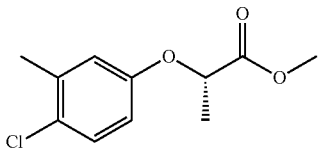

The title compound was prepared following the same general protocol as described for the synthesis of the (S)-methyl 2-(2-chloro-5-methylphenoxy)propanoate (Step 1, Example 55), using the 4-chloro-3-methylphenol instead of the 2-chloro-5-methylphenol.

Step 2: (S)-Methyl 2-(3-(bromomethyl)-4-chlorophenoxy)propanoate

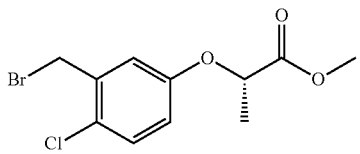

The title compound was prepared following the same general protocol as described for the synthesis of the (S)-methyl 2-(5-(bromomethyl)-2-chlorophenoxy)propanoate (Step 2, Example 55), using the (S)-methyl 2-(4-chloro-3-methylphenoxy)propanoate instead of the (S)-methyl 2-(2-chloro-5-methylphenoxy)propanoate.

Step 3: (S)-Allyl 1-(2-chloro-5-((1-methoxy-1-oxopropan-2-yl)oxy)benzyl)-2,3-dimethyl-1H-indole-5-carboxylate

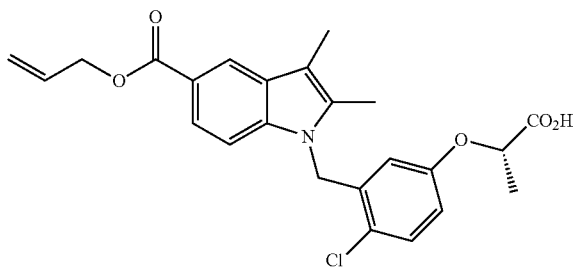 [SMILES: C=CCOC(=O)c1ccc2c(c1)c(C)c(C)n2Cc1cc(O[C@@H](C)C(=O)O)ccc1Cl]

To a solution of the allyl 2,3-dimethyl-1H-indole-5-carboxylate (0.34 g, 1.483 mmol) in anhydrous DMF (3 mL) at 0° C. under argon protection was added NaH (0.08 g, 2.22 mmol). The mixture was stirred at rt for 30 min and re-cooled to 0° C., and then the (S)-methyl 2-(3-(bromomethyl)-4-chlorophenoxy)propanoate (0.55 g, 1.78 mmol) was added. The reaction was stirred at rt for another 1 h. The solvent was removed to obtain the crude, which was dissolved in EtOAc, then washed with water and brine and dried over $Na_2SO_4$. The solvent was removed to obtain the crude. The crude was purified by flash chromatography (AcOEt/Hexane 0-100%) to obtain the title compound. ESI-MS (m/z): 456 [M+1]$^+$.

Step 4: (S)-1-(2-Chloro-5-((1-methoxy-1-oxopropan-2-yl)oxy)benzyl)-2,3-dimethyl-1H-indole-5-carboxylic acid

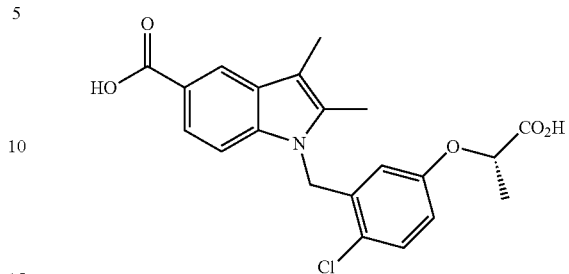

A solution of (S)-allyl 1-(2-chloro-5-((1-methoxy-1-oxopropan-2-yl)oxy)benzyl)-2,3-dimethyl-1H-indole-5-carboxylate (0.327 g, 0.72 mmol) and morpholine (0.63 mL, 7.2 mmol) in anhydrous THF (10 mL) was degassed, then Pd(PPh$_3$)$_4$ (0.083 g, 0.072 mmol) was added under argon protection. The reaction mixture was stirred at rt for 1 h. The solvent was removed and the resulting crude was dissolved in MeOH. The mixture was acidified with 2 N HCl to pH 3. The mixture was filtered and the solid was washed with water. The solid was dried for the next Step with no further purification. ESI-MS (m/z): 416 [M+1]$^+$.

Step 5: (S)-Methyl 2-(4-chloro-3-((5-(((S)-1-(3-isopropylphenyl)ethyl)carbamoyl)-2,3-dimethyl-1H-indol-1-yl)methyl)phenoxy)propanoate

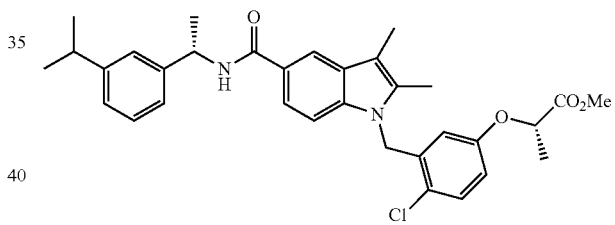

The (S)-1-(2-chloro-5-((1-methoxy-1-oxopropan-2-yl)oxy)benzyl)-2,3-dimethyl-1H-indole-5-carboxylic acid (71 mg, 0.17 mmol), the (S)-1-(3-isopropylphenyl)ethanamine hydrochloride (53 mg, 0.27 mmol) and HATU (88 mg, 0.23 mmol) were dissolved in DMF (3 mL) and DIEA (0.15 mL). It was stirred for 15 h. The solution was filtered and purified by preparative HPLC.

Step 6: (S)-2-(4-Chloro-3-((5-(((S)-1-(3-isopropylphenyl)ethyl)carbamoyl)-2,3-dimethyl-1H-indol-1-yl)methyl)phenoxy)propanoic acid

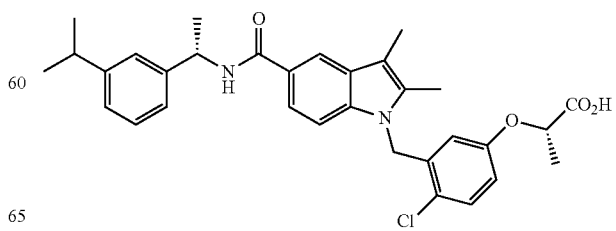

The (S)-methyl 2-(4-chloro-3-((5-(((S)-1-(3-isopropylphenyl)ethyl)carbamoyl)-2,3-dimethyl-1H-indol-1-yl)methyl)phenoxy)propanoate was dissolved in methanol (1.5 mL) and DMSO (~1 mL), water (0.1 mL) and NaOH (2 N, 0.1 mL) were added dropwise. The reaction was monitored by LC/MS. It was stirred until all the starting material was consumed (~3 h). It was acidified with trifluoroacetic acid, filtered and purified by preparative HPLC to yield the title compound. ESI-MS (m/z): 547.1 [M+H]$^+$.

Example 62

(S)-2-(4-Chloro-3-((5-(((S)-1-(3-cyclopropylphenyl)ethyl)carbamoyl)-2,3-dimethyl-1H-indol-1-yl)methyl)phenoxy)propanoic acid

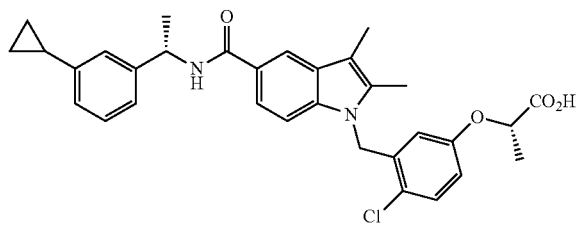 [SMILES: Cc1c(C)n(Cc2cc(O[C@@H](C)C(=O)O)ccc2Cl)c2ccc(C(=O)N[C@@H](C)c3cccc(C4CC4)c3)cc12]

A similar procedure was followed as described in the previous example (Example 61) to yield the title compound. ESI-MS (m/z): 545.1 [M+H]$^+$.

Example 63

(S)-2-(3-((5-(((S)-1-(4-Bromophenyl)ethyl)carbamoyl)-2,3-dimethyl-1H-indol-1-yl)methyl)-4-chlorophenoxy)propanoic acid

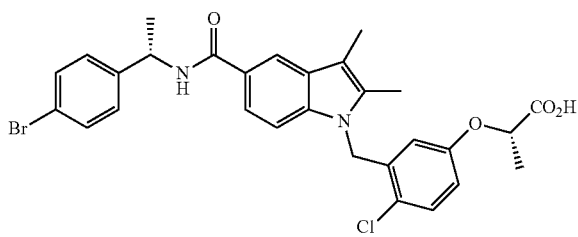 [SMILES: Cc1c(C)n(Cc2cc(O[C@@H](C)C(=O)O)ccc2Cl)c2ccc(C(=O)N[C@@H](C)c3ccc(Br)cc3)cc12]

A similar procedure was followed as described in the previous example (Example 61) to yield the title compound. ESI-MS (m/z): 585.0 [M+H]$^+$.

Example 64

(S)-2-(3-((5-(((S)-1-(4-(tert-Butyl)phenyl)ethyl)carbamoyl)-2,3-dimethyl-1H-indol-1-yl)methyl)-4-chlorophenoxy)propanoic acid

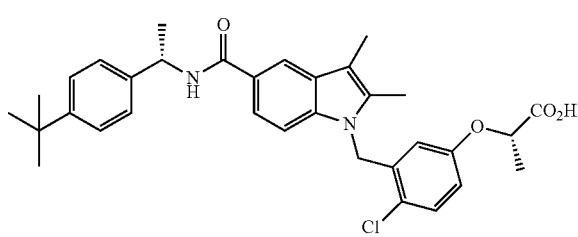 [SMILES: Cc1c(C)n(Cc2cc(O[C@@H](C)C(=O)O)ccc2Cl)c2ccc(C(=O)N[C@@H](C)c3ccc(C(C)(C)C)cc3)cc12]

Step 1: (S)-Methyl 2-(3-((5-(((S)-1-(4-(tert-butyl)phenyl)ethyl)carbamoyl)-2,3-dimethyl-1H-indol-1-yl)methyl)-4-chlorophenoxy)propanoate

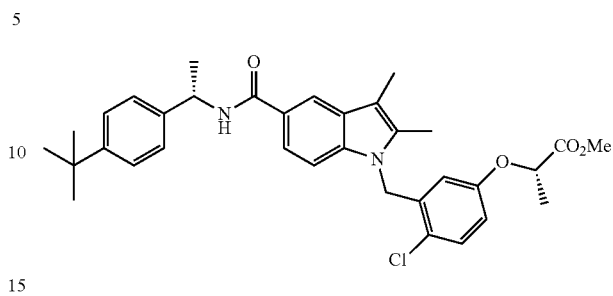

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride the (S)-1-(2-chloro-5-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-(((S)-1-(4-(tert-Butyl)phenyl)ethyl)carbamoyl)-2,3-dimethyl-1H-indol-1-yl)methyl)-4-chlorophenoxy)propanoic acid

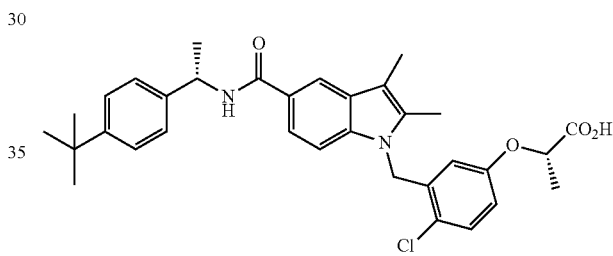

The title compound was prepared following the same protocol as described in Step 6, Example 36, using the (S)-methyl 2-(3-((5-(((S)-1-(4-(tert-butyl)phenyl)ethyl)carbamoyl)-2,3-dimethyl-1H-indol-1-yl)methyl)-4-chlorophenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ Example 65

(S)-2-(3-((5-(((S)-1-(3-(tert-Butyl)phenyl)ethyl)carbamoyl)-2,3-dimethyl-1H-indol-1-yl)methyl)-4-chlorophenoxy)propanoic acid

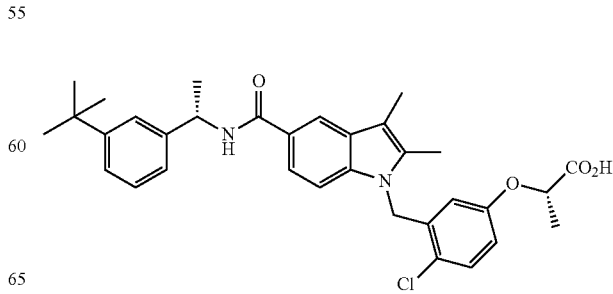

151

Step 1: (S)-Methyl 2-(3-((5-(((S)-1-(3-(tert-butyl)phenyl)ethyl)carbamoyl)-2,3-dimethyl-1H-indol-1-yl)methyl)-4-chlorophenoxy)propanoate

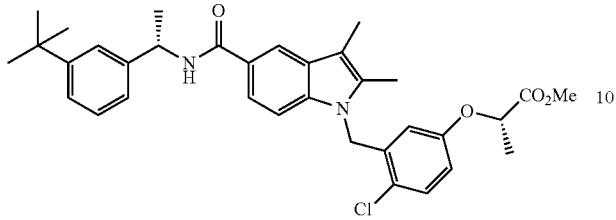

The title compound was prepared following the same protocol as described in Step 5, Example 36, using the (S)-1-(3-(tert-butyl)phenyl)ethanamine hydrochloride instead of the (S)-1-(3-cyclopropylphenyl)ethanamine hydrochloride the (S)-1-(2-chloro-5-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-(((S)-1-(3-(tert-Butyl)phenyl)ethyl)carbamoyl)-2,3-dimethyl-1H-indol-1-yl)methyl)-4-chlorophenoxy)propanoic acid

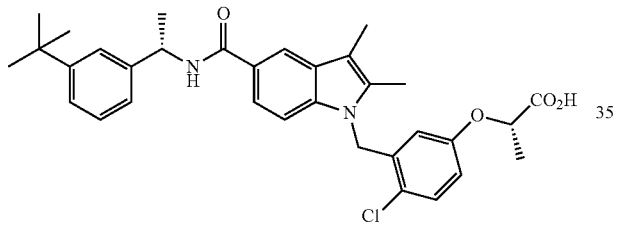

The title compound was prepared following the same protocol as described in Step 6, Example 36, using the (S)-methyl 2-(3-((5-(((S)-1-(4-(tert-butyl)phenyl)ethyl)carbamoyl)-2,3-dimethyl-1H-indol-1-yl)methyl)-4-chlorophenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ Example 66

(S)-2-(4-Chloro-3-((5-(((S)-1-(3-isopropoxyphenyl)ethyl)carbamoyl)-2,3-dimethyl-1H-indol-1-yl)methyl)phenoxy)propanoic acid

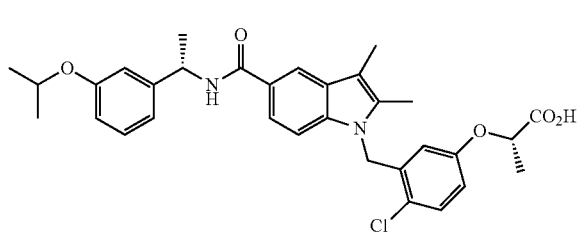 [SMILES: Cc1c(C)n(Cc2cc(O[C@@H](C)C(=O)O)ccc2Cl)c2ccc(C(=O)N[C@@H](C)c3cccc(OC(C)C)c3)cc12]

152

Step 1: (S)-Methyl 2-(3-((5-(((S)-1-(3-isopropoxyphenyl)ethyl)carbamoyl)-2,3-dimethyl-1H-indol-1-yl)methyl)-4-chlorophenoxy)propanoate

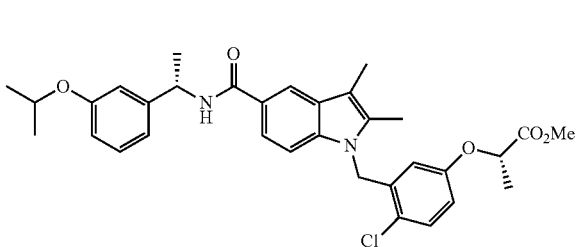 [SMILES: COC(=O)[C@H](C)Oc1ccc(Cl)c(Cn2c(C)c(C)c3cc(C(=O)N[C@@H](C)c4cccc(OC(C)C)c4)ccc32)c1]

The title compound was prepared following the same protocol as described in Step 5, Example 36, using the (S)-1-(3-isopropoxyphenyl)ethanamine hydrochloride instead of the (S)-1-(3-cyclopropylphenyl)ethanamine hydrochloride the (S)-1-(2-chloro-5-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(4-Chloro-3-((5-(((S)-1-(3-isopropoxyphenyl)ethyl)carbamoyl)-2,3-dimethyl-1H-indol-1-yl)methyl)phenoxy)propanoic acid

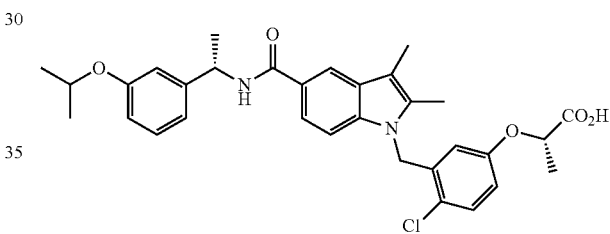

The title compound was prepared following the same protocol as described in Step 6, Example 36, using the (S)-methyl 2-(3-((5-(((S)-1-(3-isopropoxyphenyl)ethyl)carbamoyl)-2,3-dimethyl-1H-indol-1-yl)methyl)-4-chlorophenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ Example 67

(S)-2-(3-chloro-5-((5-(((S)-1-(3-isopropylphenyl)ethyl)carbamoyl)-2,3-dimethyl-1H-indol-1-yl)methyl)phenoxy)propanoic acid

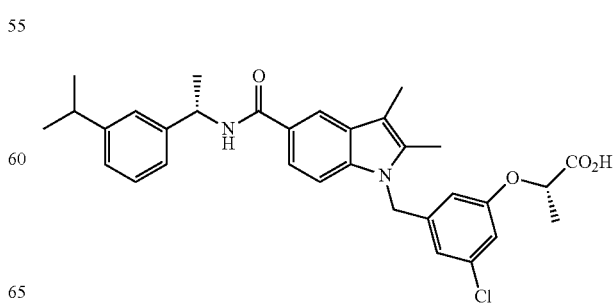

Step 1: (S)-Methyl 2-(3-chloro-5-methylphenoxy)propanoate

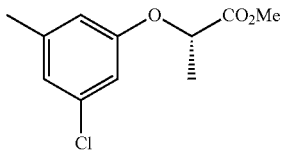

The title compound was prepared following the same protocol as described in Step 1, Example 42, using the 3-chloro-5-methylphenol instead of the m-cresol and the (R)-methyl 2-hydroxypropanoate instead of the (S)-methyl 2-hydroxypropanoate.

Step 2: (S)-Methyl 2-(3-(bromomethyl)-5-chlorophenoxy)propanoate

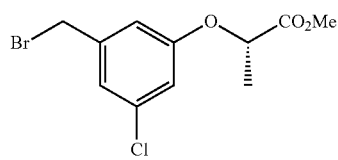 [SMILES: COC(=O)[C@H](C)Oc1cc(Cl)cc(CBr)c1]

The title compound was prepared following the same protocol as described in Step 2, Example 36, using the (S)-methyl 2-(3-chloro-5-methylphenoxy)propanoate instead of the methyl 2-(p-tolyloxy)acetate.

Step 3: (S)-Allyl 1-(3-chloro-5-((1-methoxy-1-oxopropan-2-yl)oxy)benzyl)-2,3-dimethyl-1H-indole-5-carboxylate

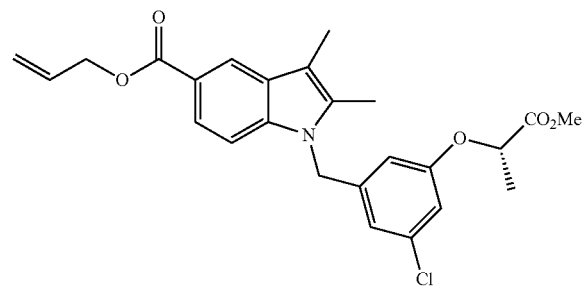 [SMILES: C=CCOC(=O)c1ccc2c(c1)c(C)c(C)n2Cc1cc(Cl)cc(O[C@@H](C)C(=O)OC)c1]

The title compound was prepared following the same general protocol as described in Step 3, Example 36, using the (S)-methyl 2-(3-(bromomethyl)-5-chlorophenoxy)propanoate instead of the methyl 2-(4-(bromomethyl)phenoxy)acetate. ESI-MS (m/z): 456/457/458 [M+H]$^+$.

Step 4: (S)-1-(3-Chloro-5-((1-methoxy-1-oxopropan-2-yl)oxy)benzyl)-2,3-dimethyl-1H-indole-5-carboxylic acid

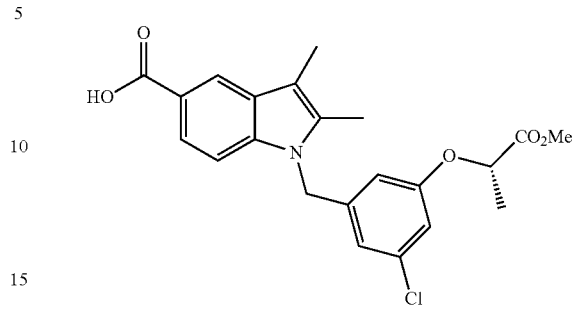

The title compound was prepared following the same general protocol as described in Step 4, Example 36, using the (S)-allyl 1-(3-chloro-5-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.
ESI-MS (m/z): 416/417/418 [M+H]$^+$.

Step 5: (S)-methyl 2-(3-chloro-5-((5-(((S)-1-(3-isopropylphenyl)ethyl)carbamoyl)-2,3-dimethyl-1H-indol-1-yl)methyl)phenoxy)propanoate

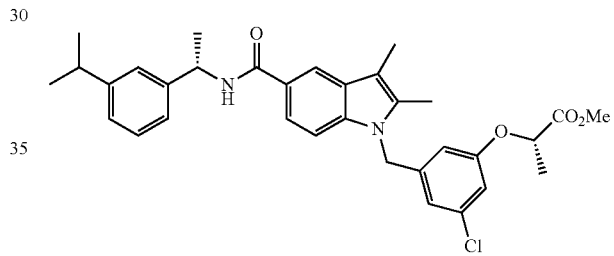

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(3-chloro-5-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-chloro-5-((5-(((S)-1-(3-isopropylphenyl)ethyl)carbamoyl)-2,3-dimethyl-1H-indol-1-yl)methyl)phenoxy)propanoic acid

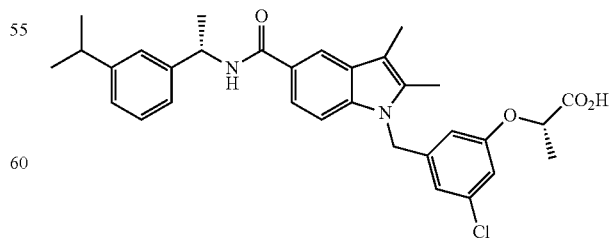

The title compound was prepared following the same protocol as described in Step 6, Example 36, using the (S)-methyl 2-(3-chloro-5-((5-(((S)-1-(3-isopropylphenyl)ethyl)carbamoyl)-2,3-dimethyl-1H-indol-1-yl)methyl)phenoxy)pro-
panoate instead of the (S)-methyl 2-(4-((5-(((1-(3-cyclopro-
pylphenyl)ethyl)carbamoyl)-2,3-dimethyl-1H-indol-1-yl)
methyl)phenoxy)acetate. ESI-MS (m/z): 547/548/549
[M+H]+.

Example 68

(S)-2-(2-chloro-3-((5-(((S)-1-(3-isopropylphenyl)
ethyl)carbamoyl)-2,3-dimethyl-1H-indol-1-yl)me-
thyl)phenoxy)propanoic acid

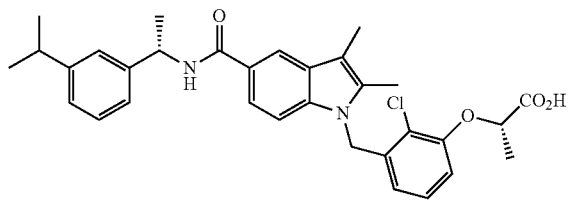 [SMILES: Cc1c(C)n(Cc2cccc(O[C@@H](C)C(=O)O)c2Cl)c2ccc(C(=O)N[C@@H](C)c3cccc(C(C)C)c3)cc12]

Step 1: (S)-Methyl
2-(2-chloro-3-methylphenoxy)propanoate

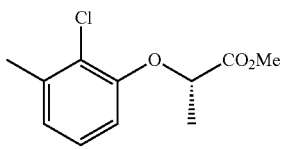

The title compound was prepared following the same protocol as described in Step 1, Example 42, using the 2-chloro-3-methylphenol instead of the m-cresol and the (R)-methyl 2-hydroxypropanoate instead of the (S)-methyl 2-hydroxypropanoate.

Step 2: (S)-Methyl 2-(3-(bromomethyl)-2-chlorophe-
noxy)propanoate

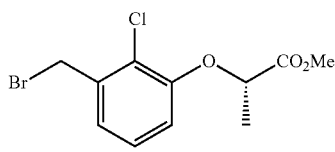 [SMILES: COC(=O)[C@H](C)Oc1cccc(CBr)c1Cl]

The title compound was prepared following the same protocol as described in Step 2, Example 36, using the (S)-methyl 2-(2-chloro-3-methylphenoxy)propanoate instead of the methyl 2-(p-tolyloxy)acetate.

Step 3: (S)-Allyl 1-(2-chloro-3-((1-methoxy-1-oxo-
propan-2-yl)oxy)benzyl)-2,3-dimethyl-1H-indole-5-
carboxylate

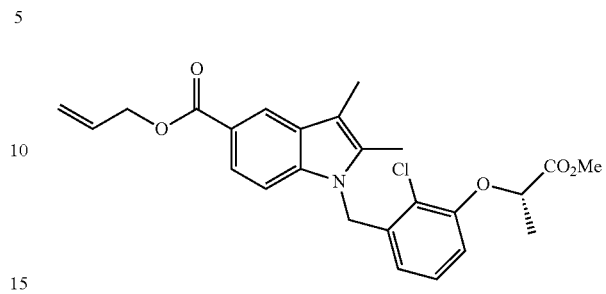

The title compound was prepared following the same general protocol as described in Step 3, Example 36, using the (S)-methyl 2-(3-(bromomethyl)-2-chlorophenoxy)propanoate instead of the methyl 2-(4-(bromomethyl)phenoxy)acetate. ESI-MS (m/z): 456/457/458 [M+H]+.

Step 4: (S)-1-(2-Chloro-3-((1-methoxy-1-oxopropan-
2-yl)oxy)benzyl)-2,3-dimethyl-1H-indole-5-car-
boxylic acid

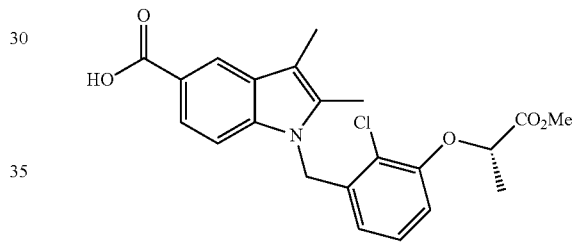

The title compound was prepared following the same general protocol as described in Step 4, Example 36, using the (S)-allyl 1-(2-chloro-3-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.
ESI-MS (m/z): 416/417/418 [M+H]+.

Step 5: (S)-methyl 2-(2-chloro-3-((5-(((S)-1-(3-iso-
propylphenyl)ethyl)carbamoyl)-2,3-dimethyl-1H-
indol-1-yl)methyl)phenoxy)propanoate

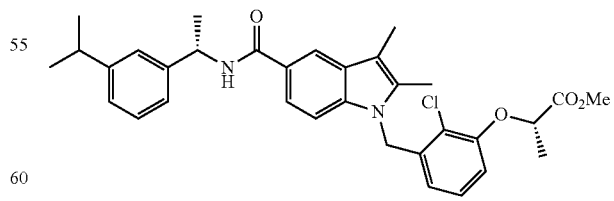

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(2-chloro-3-((1-methoxy-1-oxopropan-2-yl)oxy)

benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(2-chloro-3-((5-(((S)-1-(3-isopropylphenyl)ethyl)carbamoyl)-2,3-dimethyl-1H-indol-1-yl)methyl)phenoxy)propanoic acid

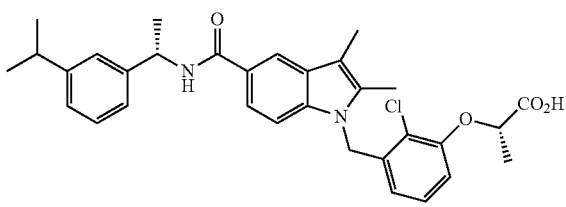 [SMILES: Cc1c(C)n(Cc2cccc(O[C@@H](C)C(=O)O)c2Cl)c2ccc(C(=O)N[C@@H](C)c3cccc(C(C)C)c3)cc12]

The title compound was prepared following the same protocol as described in Step 6, Example 36, using the (S)-methyl 2-(2-chloro-3-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [M+H]$^+$ Example 69

(R)-2-(2-Chloro-5-((5-(((S)-1-(3-isopropylphenyl)ethyl)carbamoyl)-2,3-dimethyl-1H-indol-1-yl)methyl)phenoxy)propanoic acid

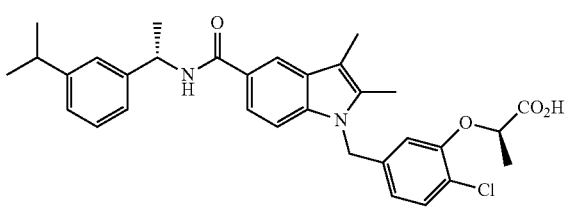

Step 1: (R)-Methyl 2-(2-chloro-5-methylphenoxy)propanoate

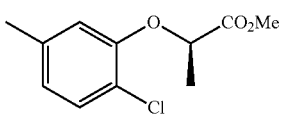

The title compound was prepared following the same protocol as described in Step 1, Example 42, using the 2-chloro-5-methylphenol instead of the m-cresol.

Step 2: (R)-Methyl 2-(5-(bromomethyl)-2-chlorophenoxy)propanoate

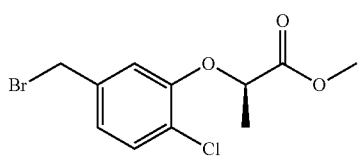 [SMILES: COC(=O)[C@@H](C)Oc1cc(CBr)ccc1Cl]

The title compound was prepared following the same protocol as described in Step 2, Example 36, using the (R)-methyl 2-(2-chloro-5-methylphenoxy)propanoate instead of the methyl 2-(p-tolyloxy)acetate.

Step 3: (R)-Allyl 1-(4-chloro-3-((1-methoxy-1-oxopropan-2-yl)oxy)benzyl)-2,3-dimethyl-1H-indole-5-carboxylate

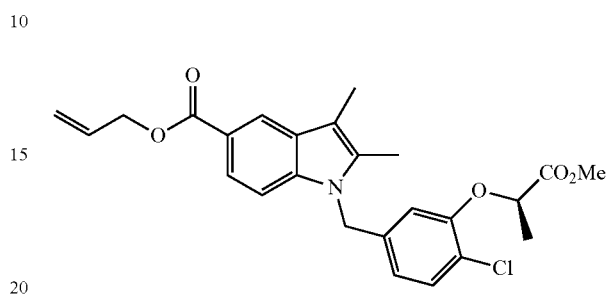

The title compound was prepared following the same general protocol as described in step 3, Example 36, using the (R)-methyl 2-(5-(bromomethyl)-2-chlorophenoxy)propanoate instead of the methyl 2-(4-(bromomethyl)phenoxy)acetate ESI-MS (m/z): 456 [M+1]$^+$.

Step 4: (R)-1-(4-Chloro-3-((1-methoxy-1-oxopropan-2-yl)oxy)benzyl)-2,3-dimethyl-1H-indole-5-carboxylic acid

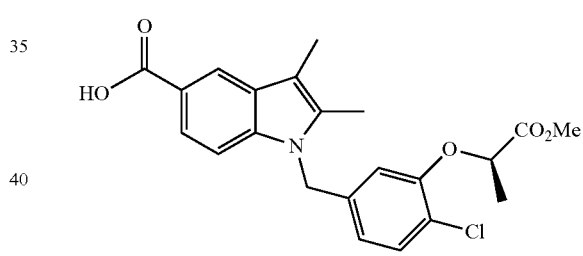

The title compound was prepared following the same general protocol as described in Step 4, Example 36, using the (R)-allyl 1-(4-chloro-3-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.
ESI-MS (m/z): 416 [M+1]$^+$.

Step 5: (R)-Methyl 2-(2-chloro-5-((5-(((S)-1-(3-isopropylphenyl)ethyl)carbamoyl)-2,3-dimethyl-1H-indol-1-yl)methyl)phenoxy)propanoate

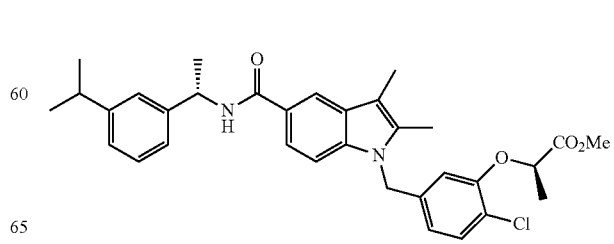

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(4-chloro-3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(2-Chloro-5-((5-(((S)-1-(3-isopropylphenyl)ethyl)carbamoyl)-2,3-dimethyl-1H-indol-1-yl)methyl)phenoxy)propanoic acid

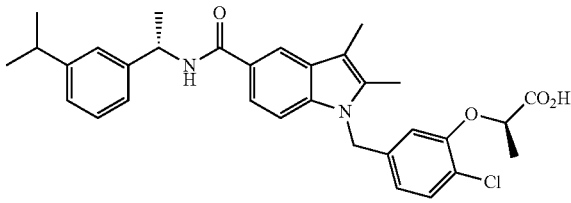 [SMILES: Cc1c(C)n(Cc2ccc(Cl)c(O[C@H](C)C(=O)O)c2)c2ccc(C(=O)N[C@@H](C)c3cccc(C(C)C)c3)cc12]

The title compound was prepared following the same protocol as described in Step 6, Example 36, using the (R)-methyl 2-(2-chloro-5-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [M+H]$^+$ Example 70

(R)-2-(4-Chloro-3-((5-(((S)-1-(3-isopropylphenyl)ethyl)carbamoyl)-2,3-dimethyl-1H-indol-1-yl)methyl)phenoxy)propanoic acid

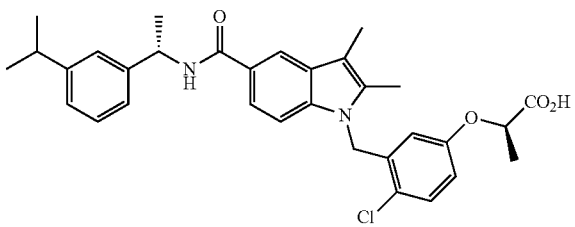 [SMILES: Cc1c(C)n(Cc2cc(O[C@H](C)C(=O)O)ccc2Cl)c2ccc(C(=O)N[C@@H](C)c3cccc(C(C)C)c3)cc12]

Step 1: (R)-Methyl 2-(4-chloro-3-methylphenoxy)propanoate

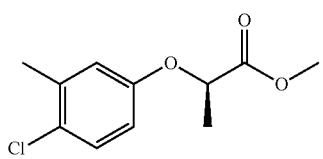

The title compound was prepared following the same protocol as described in Step 1, Example 42, using the 4-chloro-3-methylphenol instead of the m-cresol Step 2: (R)-Methyl 2-(3-(bromomethyl)-4-chlorophenoxy)propanoate

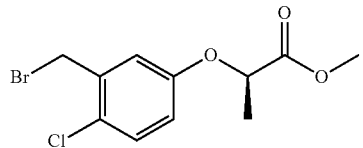 [SMILES: COC(=O)[C@@H](C)Oc1ccc(Cl)c(CBr)c1]

The title compound was prepared following the same protocol as described in Step 2, Example 36, using the (R)-methyl 2-(4-chloro-3-methylphenoxy)propanoate instead of the methyl 2-(p-tolyloxy)acetate.

Step 3: (R)-Allyl 1-(2-chloro-5-((1-methoxy-1-oxopropan-2-yl)oxy)benzyl)-2,3-dimethyl-1H-indole-5-carboxylate

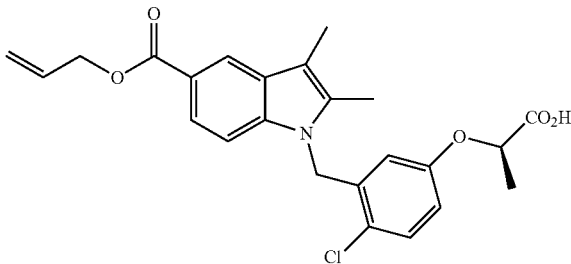 [SMILES: C=CCOC(=O)c1ccc2c(c1)c(C)c(C)n2Cc1cc(O[C@H](C)C(=O)O)ccc1Cl]

The title compound was prepared following the same general protocol as described in step 3, Example 36, using the (R)-methyl 2-(3-(bromomethyl)-4-chlorophenoxy)propanoate instead of the methyl 2-(4-(bromomethyl)phenoxy)acetate ESI-MS (m/z): 456 [M+1]$^+$.

Step 4: (R)-1-(2-Chloro-5-((1-methoxy-1-oxopropan-2-yl)oxy)benzyl)-2,3-dimethyl-1H-indole-5-carboxylic acid

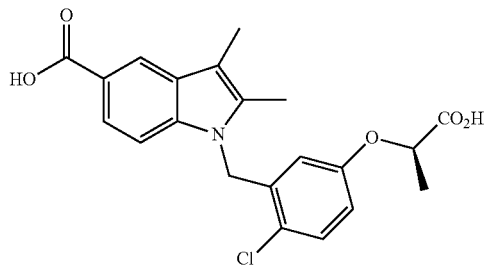 [SMILES: Cc1c(C)n(Cc2cc(O[C@H](C)C(=O)O)ccc2Cl)c2ccc(C(=O)O)cc12]

The title compound was prepared following the same general protocol as described in Step 4, Example 36, using the (R)-allyl 1-(2-chloro-5-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.

ESI-MS (m/z): 416 [M+1]$^+$.

Step 5: (R)-Methyl 2-(3-chloro-4-((5-(((S)-1-(3-iso-propylphenyl)ethyl)carbamoyl)-2,3-dimethyl-1H-indol-1-yl)methyl)phenoxy)propanoate

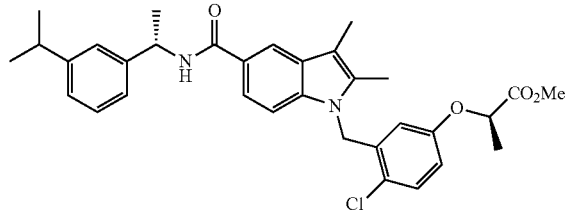 [SMILES: COC(=O)[C@@H](C)Oc1ccc(Cl)c(Cn2c(C)c(C)c3cc(C(=O)N[C@@H](C)c4cccc(C(C)C)c4)ccc32)c1]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(2-chloro-5-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-Chloro-4-((5-(((S)-1-(3-isopropylphenyl)ethyl)carbamoyl)-2,3-dimethyl-1H-indol-1-yl)methyl)phenoxy)propanoic acid

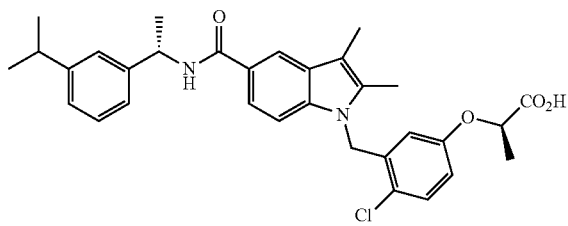 [SMILES: Cc1c(C)n(Cc2cc(O[C@H](C)C(=O)O)ccc2Cl)c2ccc(C(=O)N[C@@H](C)c3cccc(C(C)C)c3)cc12]

The title compound was prepared following the same protocol as described in Step 6, Example 36, using the (R)-methyl 2-(3-chloro-4-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [M+H]$^+$

Example 71

(R)-2-(3-chloro-5-((5-(((S)-1-(3-isopropylphenyl)ethyl)carbamoyl)-2,3-dimethyl-1H-indol-1-yl)methyl)phenoxy)propanoic acid

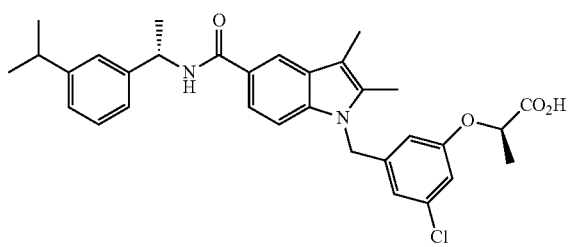 [SMILES: Cc1c(C)n(Cc2cc(Cl)cc(O[C@H](C)C(=O)O)c2)c2ccc(C(=O)N[C@@H](C)c3cccc(C(C)C)c3)cc12]

Step 1: (R)-Methyl 2-(3-chloro-5-methylphenoxy)propanoate

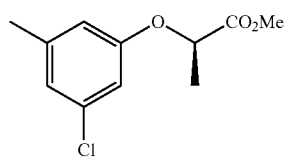

The title compound was prepared following the same protocol as described in Step 1, Example 42, using the 3-chloro-5-methylphenol instead of the m-cresol.

Step 2: (R)-Methyl 2-(3-(bromomethyl)-5-chlorophenoxy)propanoate

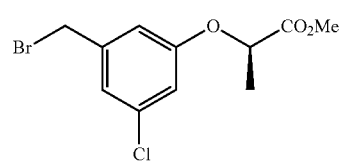

The title compound was prepared following the same protocol as described in Step 2, Example 36, using the (R)-methyl 2-(3-chloro-5-methylphenoxy)propanoate instead of the methyl 2-(p-tolyloxy)acetate.

Step 3: (R)-Allyl 1-(3-chloro-5-((1-methoxy-1-oxopropan-2-yl)oxy)benzyl)-2,3-dimethyl-1H-indole-5-carboxylate

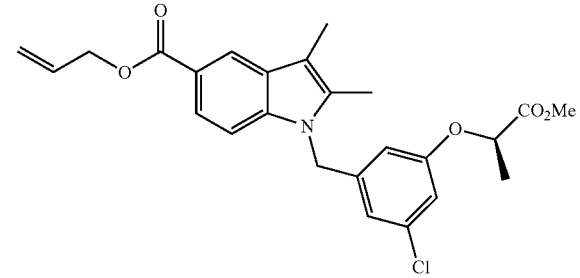 [SMILES: C=CCOC(=O)c1ccc2c(c1)c(C)c(C)n2Cc1cc(Cl)cc(O[C@H](C)C(=O)OC)c1]

The title compound was prepared following the same general protocol as described in Step 3, Example 36, using the (R)-methyl 2-(3-(bromomethyl)-5-chlorophenoxy)propanoate instead of the methyl 2-(4-(bromomethyl)phenoxy)acetate. ESI-MS (m/z): 456/457/458 [M+H]$^+$.

Step 4: (R)-1-(3-Chloro-5-((1-methoxy-1-oxopropan-2-yl)oxy)benzyl)-2,3-dimethyl-1H-indole-5-carboxylic acid

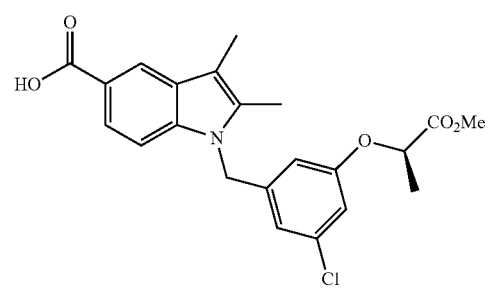 [SMILES: COC(=O)[C@@H](C)Oc1cc(Cl)cc(Cn2c(C)c(C)c3cc(C(=O)O)ccc32)c1]

The title compound was prepared following the same general protocol as described in Step 4, Example 36, using the (R)-allyl 1-(3-chloro-5-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.

ESI-MS (m/z): 416/417/418 [M+H]+.

Step 5: (R)-methyl 2-(3-chloro-5-((5-(((S)-1-(3-isopropylphenyl)ethyl)carbamoyl)-2,3-dimethyl-1H-indol-1-yl)methyl)phenoxy)propanoate

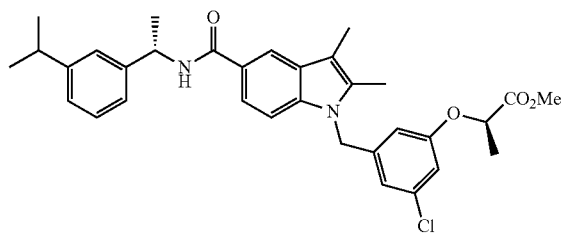

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(3-chloro-5-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-chloro-5-((5-(((S)-1-(3-isopropylphenyl)ethyl)carbamoyl)-2,3-dimethyl-1H-indol-1-yl)methyl)phenoxy)propanoic acid

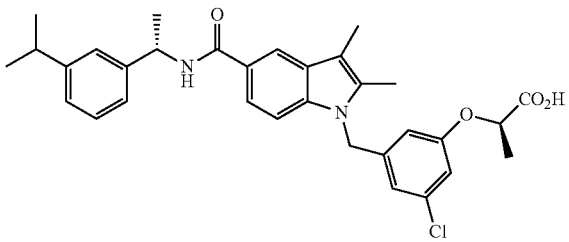 [SMILES: Cc1c(C)n(Cc2cc(Cl)cc(O[C@H](C)C(=O)O)c2)c2ccc(C(=O)N[C@@H](C)c3cccc(C(C)C)c3)cc12]

The title compound was prepared following the same protocol as described in Step 6, Example 36, using the (R)-methyl 2-(3-chloro-5-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [M+H]+

Example 72

(R)-2-(2-chloro-3-((5-(((S)-1-(3-isopropylphenyl)ethyl)carbamoyl)-2,3-dimethyl-1H-indol-1-yl)methyl)phenoxy)propanoic acid

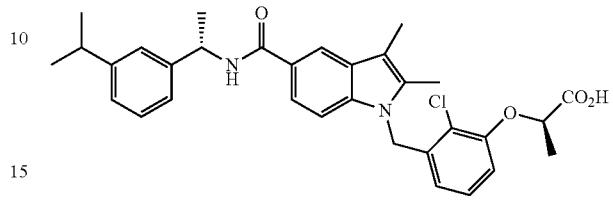

Step 1: (R)-Methyl 2-(2-chloro-3-methylphenoxy)propanoate

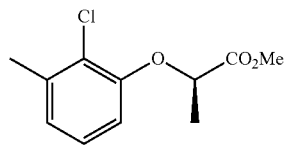

The title compound was prepared following the same protocol as described in Step 1, Example 42, using the 2-chloro-3-methylphenol instead of the m-cresol.

Step 2: (R)-Methyl 2-(3-(bromomethyl)-2-chlorophenoxy)propanoate

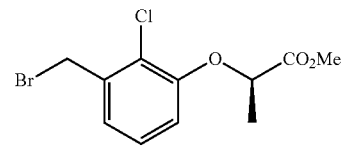 [SMILES: COC(=O)[C@@H](C)Oc1cccc(CBr)c1Cl]

The title compound was prepared following the same protocol as described in Step 2, Example 36, using the (R)-methyl 2-(2-chloro-3-methylphenoxy)propanoate instead of the methyl 2-(p-tolyloxy)acetate.

Step 3: (R)-Allyl 1-(2-chloro-3-((1-methoxy-1-oxopropan-2-yl)oxy)benzyl)-2,3-dimethyl-1H-indole-5-carboxylate

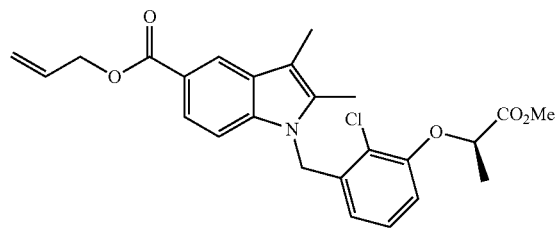 [SMILES: C=CCOC(=O)c1ccc2c(c1)c(C)c(C)n2Cc1cccc(O[C@H](C)C(=O)OC)c1Cl]

The title compound was prepared following the same general protocol as described in Step 3, Example 36, using the (R)-methyl 2-(3-(bromomethyl)-2-chlorophenoxy)propanoate instead of the methyl 2-(4-(bromomethyl)phenoxy)acetate. ESI-MS (m/z): 456/457/458 [M+H]$^+$.

Step 4: (R)-1-(2-Chloro-3-((1-methoxy-1-oxopropan-2-yl)oxy)benzyl)-2,3-dimethyl-1H-indole-5-carboxylic acid

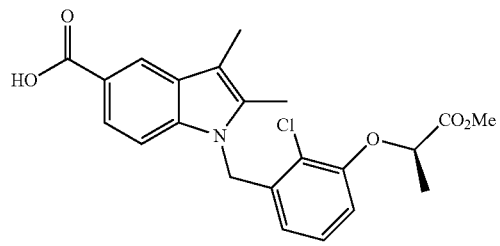 [SMILES: COC(=O)[C@@H](C)Oc1cccc(Cn2c(C)c(C)c3cc(C(=O)O)ccc32)c1Cl]

The title compound was prepared following the same general protocol as described in Step 4, Example 36, using the (R)-allyl 1-(2-chloro-3-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.

ESI-MS (m/z): 416/417/418 [M+H]$^+$.

Step 5: (R)-methyl 2-(2-chloro-3-((5-(((S)-1-(3-isopropylphenyl)ethyl)carbamoyl)-2,3-dimethyl-1H-indol-1-yl)methyl)phenoxy)propanoate

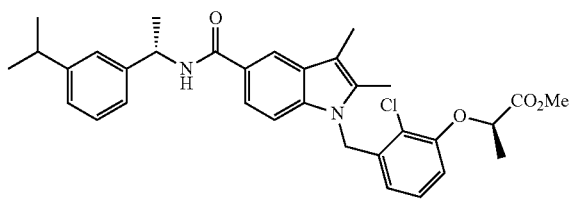 [SMILES: COC(=O)[C@@H](C)Oc1cccc(Cn2c(C)c(C)c3cc(C(=O)N[C@@H](C)c4cccc(C(C)C)c4)ccc32)c1Cl]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(2-chloro-3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(2-chloro-3-((5-(((S)-1-(3-isopropylphenyl)ethyl)carbamoyl)-2,3-dimethyl-1H-indol-1-yl)methyl)phenoxy)propanoic acid

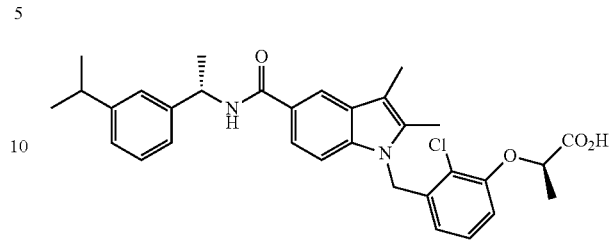

The title compound was prepared following the same protocol as described in Step 6, Example 36, using the (R)-methyl 2-(2-chloro-3-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [M+H]$^+$

Example 73

(S)-2-(2-chloro-4-((5-(((S)-1-(3-Isopropylphenyl)ethyl)carbamoyl)-2,3-dimethyl-1H-indol-1-yl)methyl)phenoxy)propanoic acid

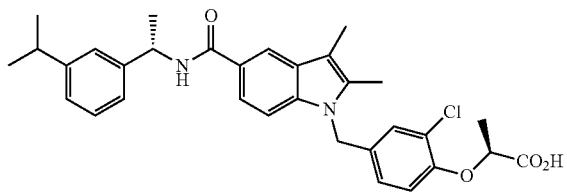 [SMILES: Cc1c(C)n(Cc2ccc(O[C@@H](C)C(=O)O)c(Cl)c2)c2ccc(C(=O)N[C@@H](C)c3cccc(C(C)C)c3)cc12]

Step 1: (S)-Methyl 2-(2-chloro-4-methylphenoxy)propanoate

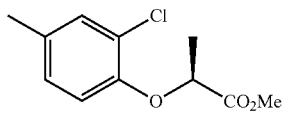

The title compound was prepared following the same protocol as described in Step 1, Example 42, using the 2-chloro-4-methylphenol instead of the m-cresol and the (R)-methyl 2-hydroxypropanoate instead of the (S)-methyl 2-hydroxypropanoate.

Step 2: (S)-Methyl 2-(4-(bromomethyl)-2-chlorophenoxy)propanoate

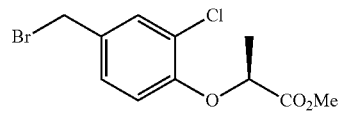

The title compound was prepared following the same protocol as described in Step 2, Example 36, using the (S)-methyl 2-(2-chloro-4-methylphenoxy)propanoate instead of the methyl 2-(p-tolyloxy)acetate.

Step 3: (S)-Allyl 1-(3-chloro-4-((1-methoxy-1-oxopropan-2-yl)oxy)benzyl)-2,3-dimethyl-1H-indole-5-carboxylate

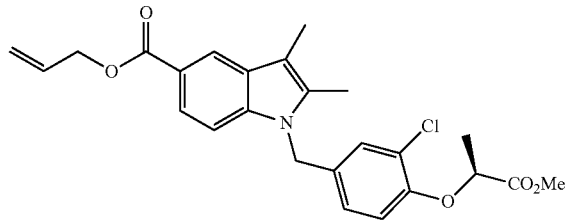 [SMILES: C=CCOC(=O)c1ccc2c(c1)c(C)c(C)n2Cc1ccc(O[C@@H](C)C(=O)OC)c(Cl)c1]

The title compound was prepared following the same general protocol as described in Step 3, Example 36, using the (S)-methyl 2-(4-(bromomethyl)-2-chlorophenoxy)propanoate instead of the methyl 2-(4-(bromomethyl)phenoxy)acetate. ESI-MS (m/z): 456/457/458 [M+H]+.

Step 4: (S)-1-(3-chloro-4-((1-Methoxy-1-oxopropan-2-yl)oxy)benzyl)-2,3-dimethyl-1H-indole-5-carboxylic acid

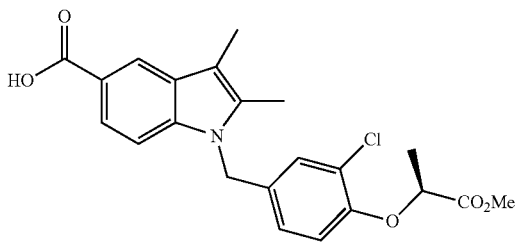 [SMILES: COC(=O)[C@H](C)Oc1ccc(Cn2c(C)c(C)c3cc(C(=O)O)ccc32)cc1Cl]

The title compound was prepared following the same general protocol as described in Step 4, Example 36, using the (S)-allyl 1-(3-chloro-4-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.
ESI-MS (m/z): 416/417/418 [M+H]+.

Step 5: (S)-Methyl 2-(2-chloro-4-((5-(((S)-1-(3-isopropylphenyl)ethyl)carbamoyl)-2,3-dimethyl-1H-indol-1-yl)methyl)phenoxy)propanoate

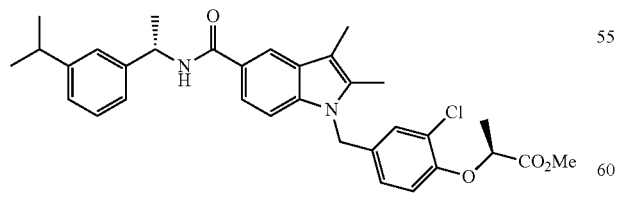

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(3-chloro-4-((1-methoxy-1-oxopropan-2-yl)oxy) benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(2-chloro-4-((5-(((S)-1-(3-Isopropylphenyl)ethyl)carbamoyl)-2,3-dimethyl-1H-indol-1-yl)methyl)phenoxy)propanoic acid

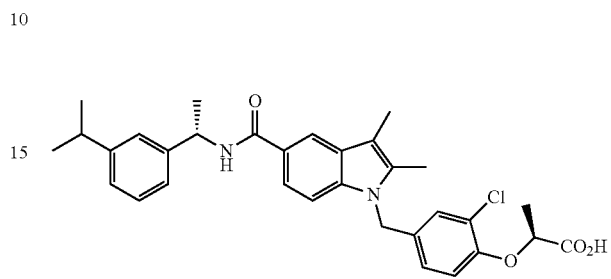

The title compound was prepared following the same protocol as described in Step 6, Example 36, using the (S)-methyl 2-(2-chloro-4-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [MH]+

Example 74

(S)-2-(3-chloro-4-((5-(((S)-1-(3-Isopropylphenyl)ethyl)carbamoyl)-2,3-dimethyl-1H-indol-1-yl)methyl)phenoxy)propanoic acid

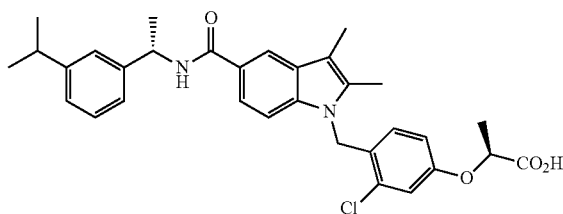 [SMILES: Cc1c(C)n(Cc2ccc(O[C@@H](C)C(=O)O)cc2Cl)c2ccc(C(=O)N[C@@H](C)c3cccc(C(C)C)c3)cc12]

Step 1: (S)-Methyl 2-(3-chloro-4-methylphenoxy)propanoate

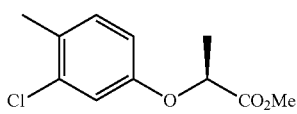

The title compound was prepared following the same protocol as described in Step 1, Example 42, using the 3-chloro-4-methylphenol instead of the m-cresol and the (R)-methyl 2-hydroxypropanoate instead of the (S)-methyl 2-hydroxypropanoate.

Step 2: (S)-Methyl 2-(4-(bromomethyl)-3-chlorophenoxy)propanoate

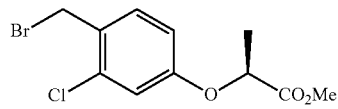

The title compound was prepared following the same protocol as described in Step 2, Example 36, using the (S)-methyl 2-(3-chloro-4-methylphenoxy)propanoate instead of the methyl 2-(p-tolyloxy)acetate.

Step 3: (S)-Allyl 1-(2-chloro-4-((1-methoxy-1-oxopropan-2-yl)oxy)benzyl)-2,3-dimethyl-1H-indole-5-carboxylate

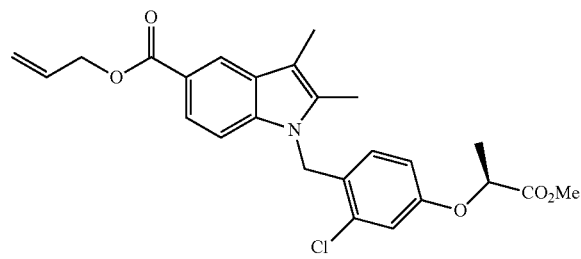 [SMILES: C=CCOC(=O)c1ccc2c(c1)c(C)c(C)n2Cc1ccc(O[C@@H](C)C(=O)OC)cc1Cl]

The title compound was prepared following the same general protocol as described in Step 3, Example 36, using the (S)-methyl 2-(4-(bromomethyl)-3-chlorophenoxy)propanoate instead of the methyl 2-(4-(bromomethyl)phenoxy)acetate. ESI-MS (m/z): 456/457/458 [M+H]⁺.

Step 4: (S)-1-(2-chloro-4-((1-Methoxy-1-oxopropan-2-yl)oxy)benzyl)-2,3-dimethyl-1H-indole-5-carboxylic acid

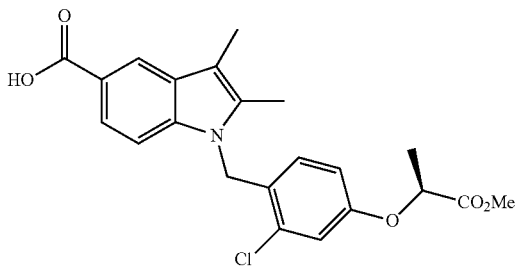 [SMILES: COC(=O)[C@H](C)Oc1ccc(Cn2c(C)c(C)c3cc(C(=O)O)ccc32)c(Cl)c1]

The title compound was prepared following the same general protocol as described in Step 4, Example 36, using the (S)-allyl 1-(2-chloro-4-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.

ESI-MS (m/z): 416/417/418 [M+H]⁺.

Step 5: (S)-Methyl 2-(3-chloro-4-((5-(((S)-1-(3-isopropylphenyl)ethyl)carbamoyl)-2,3-dimethyl-1H-indol-1-yl)methyl)phenoxy)propanoate

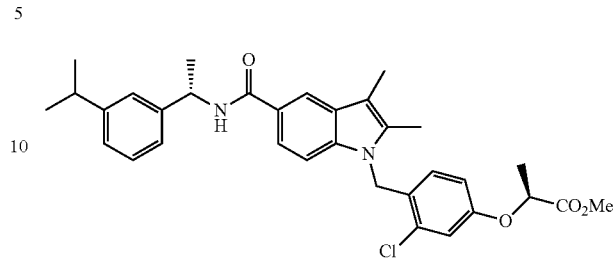

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(2-chloro-4-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-chloro-4-((5-(((S)-1-(3-Isopropylphenyl)ethyl)carbamoyl)-2,3-dimethyl-1H-indol-1-yl)methyl)phenoxy)propanoic acid

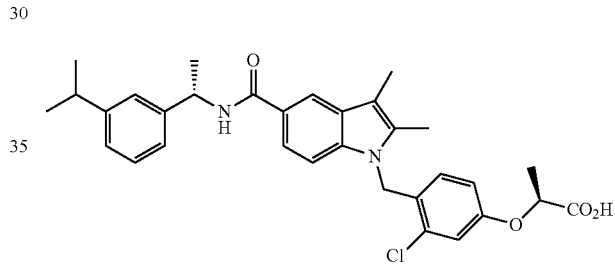

The title compound was prepared following the same protocol as described in Step 6, Example 36, using the (S)-methyl 2-(3-chloro-4-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [MH]⁺

Example 75

(R)-2-(2-chloro-4-((5-(((S)-1-(3-Isopropylphenyl)ethyl)carbamoyl)-2,3-dimethyl-1H-indol-1-yl)methyl)phenoxy)propanoic acid

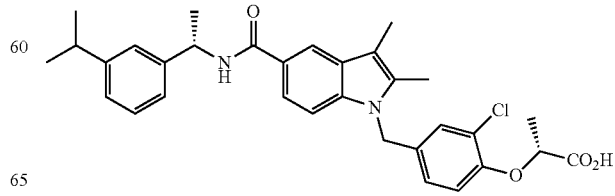

Step 1: (R)-Methyl 2-(2-chloro-4-methylphenoxy)propanoate

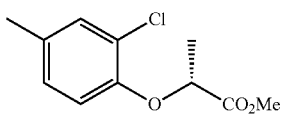

The title compound was prepared following the same protocol as described in Step 1, Example 42, using the 2-chloro-4-methylphenol instead of the m-cresol.

Step 2: (R)-Methyl 2-(4-(bromomethyl)-2-chlorophenoxy)propanoate

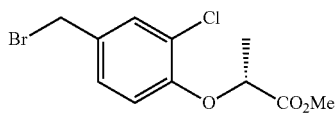 [SMILES: COC(=O)[C@@H](C)Oc1ccc(CBr)cc1Cl]

The title compound was prepared following the same protocol as described in Step 2, Example 36, using the (R)-methyl 2-(2-chloro-4-methylphenoxy)propanoate instead of the methyl 2-(p-tolyloxy)acetate.

Step 3: (R)-Allyl 1-(3-chloro-4-((1-methoxy-1-oxopropan-2-yl)oxy)benzyl)-2,3-dimethyl-1H-indole-5-carboxylate

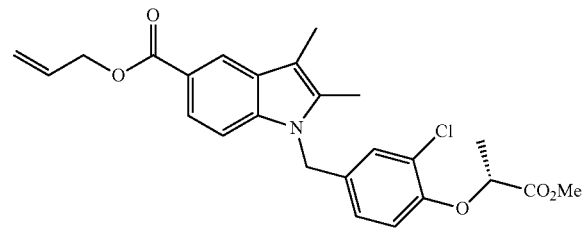 [SMILES: C=CCOC(=O)c1ccc2c(c1)c(C)c(C)n2Cc1ccc(O[C@H](C)C(=O)OC)c(Cl)c1]

The title compound was prepared following the same general protocol as described in Step 3, Example 36, using the (R)-methyl 2-(4-(bromomethyl)-2-chlorophenoxy)propanoate instead of the methyl 2-(4-(bromomethyl)phenoxy)acetate. ESI-MS (m/z): 456/457/458 [M+H]+.

Step 4: (R)-1-(3-chloro-4-((1-Methoxy-1-oxopropan-2-yl)oxy)benzyl)-2,3-dimethyl-1H-indole-5-carboxylic acid

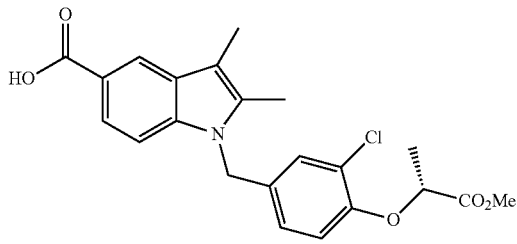 [SMILES: COC(=O)[C@@H](C)Oc1ccc(Cn2c(C)c(C)c3cc(C(=O)O)ccc32)cc1Cl]

The title compound was prepared following the same general protocol as described in Step 4, Example 36, using the (R)-allyl 1-(3-chloro-4-((1-methoxy-1-oxopropan-2-yl)oxy) benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.
ESI-MS (m/z): 416/417/418 [M+H]+.

Step 5: (R)-Methyl 2-(2-chloro-4-((5-(((S)-1-(3-isopropylphenyl)ethyl)carbamoyl)-2,3-dimethyl-1H-indol-1-yl)methyl)phenoxy)propanoate

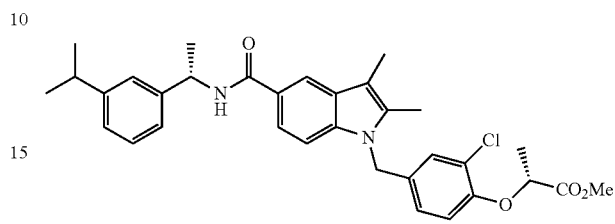

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(3-chloro-4-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(2-chloro-4-((5-(((S)-1-(3-Isopropylphenyl)ethyl)carbamoyl)-2,3-dimethyl-1H-indol-1-yl)methyl)phenoxy)propanoic acid

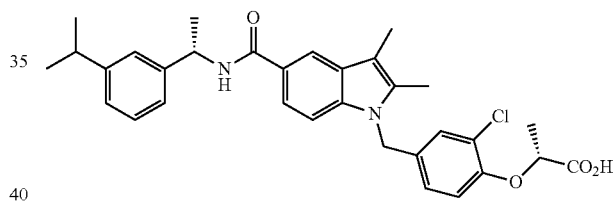

The title compound was prepared following the same protocol as described in Step 6, Example 36, using the (R)-methyl 2-(2-chloro-4-((5-(((S)-1-(3-isopropylphenyl)ethyl) carbamoyl)-2,3-dimethyl-1H-indol-1-yl)methyl)phenoxy) propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [MH]+

Example 76

(R)-2-(3-chloro-4-((5-(((S)-1-(3-Isopropylphenyl)ethyl)carbamoyl)-2,3-dimethyl-1H-indol-1-yl)methyl)phenoxy)propanoic acid

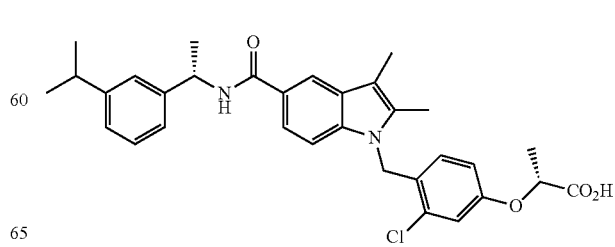

Step 1: (R)-Methyl 2-(3-chloro-4-methylphenoxy)propanoate

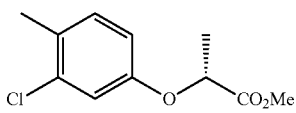

The title compound was prepared following the same protocol as described in Step 1, Example 42, using the 3-chloro-4-methylphenol instead of the m-cresol.

Step 2: (R)-Methyl 2-(4-(bromomethyl)-3-chlorophenoxy)propanoate

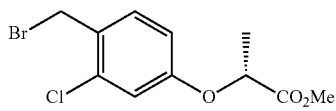 [SMILES: COC(=O)[C@@H](C)Oc1ccc(CBr)c(Cl)c1]

The title compound was prepared following the same protocol as described in Step 2, Example 36, using the (R)-methyl 2-(3-chloro-4-methylphenoxy)propanoate instead of the methyl 2-(p-tolyloxy)acetate.

Step 3: (R)-Allyl 1-(2-chloro-4-((1-methoxy-1-oxopropan-2-yl)oxy)benzyl)-2,3-dimethyl-1H-indole-5-carboxylate

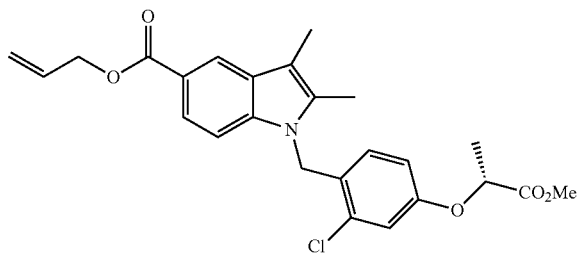 [SMILES: C=CCOC(=O)c1ccc2c(c1)c(C)c(C)n2Cc1ccc(O[C@H](C)C(=O)OC)cc1Cl]

The title compound was prepared following the same general protocol as described in Step 3, Example 36, using the (R)-methyl 2-(4-(bromomethyl)-3-chlorophenoxy)propanoate instead of the methyl 2-(4-(bromomethyl)phenoxy)acetate. ESI-MS (m/z): 456/457/458 [M+H]$^+$.

Step 4: (R)-1-(2-chloro-4-((1-Methoxy-1-oxopropan-2-yl)oxy)benzyl)-2,3-dimethyl-1H-indole-5-carboxylic acid

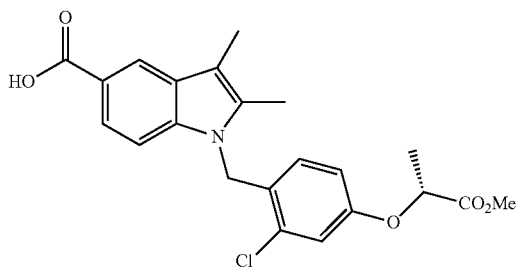 [SMILES: COC(=O)[C@@H](C)Oc1ccc(Cn2c(C)c(C)c3cc(C(=O)O)ccc32)c(Cl)c1]

The title compound was prepared following the same general protocol as described in Step 4, Example 36, using the (R)-allyl 1-(2-chloro-4-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.
ESI-MS (m/z): 416/417/418 [M+H]$^+$.

Step 5: (R)-Methyl 2-(3-chloro-4-((5-(((S)-1-(3-isopropylphenyl)ethyl)carbamoyl)-2,3-dimethyl-1H-indol-1-yl)methyl)phenoxy)propanoate

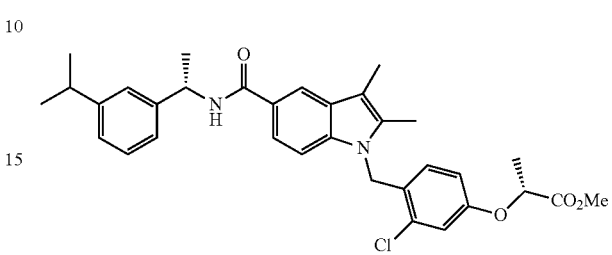

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(2-chloro-4-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-chloro-4-((5-(((S)-1-(3-Isopropylphenyl)ethyl)carbamoyl)-2,3-dimethyl-1H-indol-1-yl)methyl)phenoxy)propanoic acid

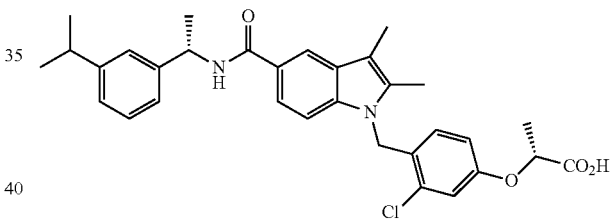

The title compound was prepared following the same protocol as described in Step 6, Example 36, using the (R)-methyl 2-(3-chloro-4-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [MH]$^+$ Example 77

(S)-2-(3-((5-(((S)-1-(3-Isopropylphenyl)ethyl)carbamoyl)-2,3-dimethyl-1H-indol-1-yl)methyl)phenoxy)butanoic acid

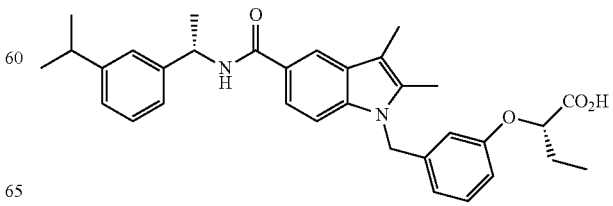

Step 1: (S)-Methyl 2-(m-tolyloxy)butanoate

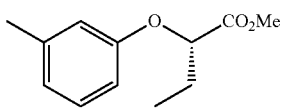

The title compound was prepared following the same protocol as described in Step 1, Example 42, using the (R)-methyl 2-hydroxybutanoate instead of the (S)-methyl 2-hydroxypropanoate.

Step 2: (S)-Methyl 2-(3-(bromomethyl)phenoxy)butanoate

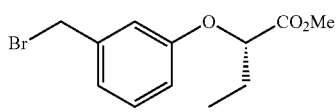 [SMILES: CC[C@H](Oc1cccc(CBr)c1)C(=O)OC]

The title compound was prepared following the same protocol as described in Step 2, Example 36, using the (S)-methyl 2-(m-tolyloxy)butanoate instead of the methyl 2-(p-tolyloxy)acetate.

Step 3: (S)-Allyl 1-(3-((1-methoxy-1-oxobutan-2-yl)oxy)benzyl)-2,3-dimethyl-1H-indole-5-carboxylate

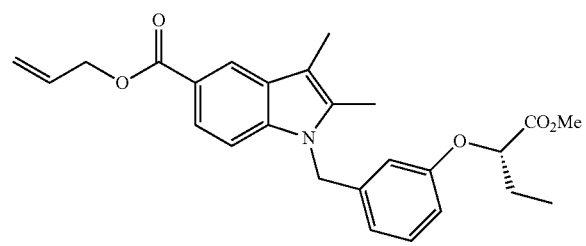 [SMILES: C=CCOC(=O)c1ccc2c(c1)c(C)c(C)n2Cc1cccc(O[C@@H](CC)C(=O)OC)c1]

The title compound was prepared following the same general protocol as described in Step 3, Example 36, using the (S)-methyl 2-(3-(bromomethyl)phenoxy)butanoate instead of the methyl 2-(4-(bromomethyl)phenoxy)acetate. ESI-MS (m/z): 436 [M+H]$^+$.

Step 4: (S)-1-(3-((1-Methoxy-1-oxobutan-2-yl)oxy)benzyl)-2,3-dimethyl-1H-indole-5-carboxylic acid

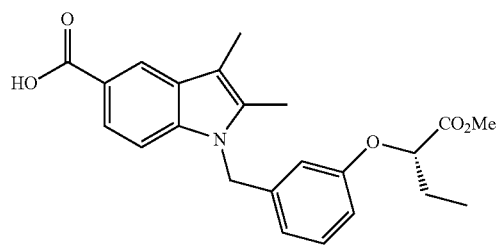 [SMILES: CC[C@H](Oc1cccc(Cn2c(C)c(C)c3cc(C(=O)O)ccc32)c1)C(=O)OC]

The title compound was prepared following the same general protocol as described in Step 4, Example 36, using the (S)-allyl 1-(3-((1-methoxy-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 382 [M+H]$^+$.

Step 5: (S)-Methyl 2-(3-((5-(((S)-1-(3-isopropylphenyl)ethyl)carbamoyl)-2,3-dimethyl-1H-indol-1-yl)methyl)phenoxy)butanoate

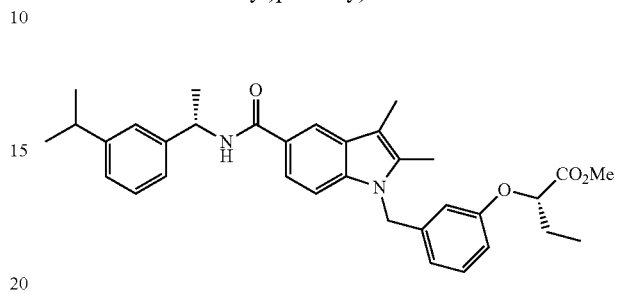

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(3-((1-methoxy-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-((5-(((S)-1-(3-Isopropylphenyl)ethyl)carbamoyl)-2,3-dimethyl-1H-indol-1-yl)methyl)phenoxy)butanoic acid

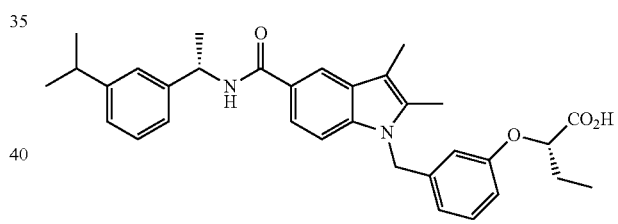

The title compound was prepared following the same protocol as described in Step 6, Example 36, using the (S)-methyl 2-(3-((5-(((S)-1-(3-isopropylphenyl)ethyl)carbamoyl)-2,3-dimethyl-1H-indol-1-yl)methyl)phenoxy)butanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 527 [M+H]$^+$

Example 78

(R)-2-(3-((5-(((S)-1-(3-Isopropylphenyl)ethyl)carbamoyl)-2,3-dimethyl-1H-indol-1-yl)methyl)phenoxy)butanoic acid

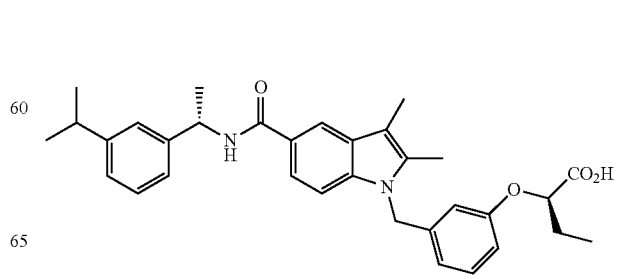

Step 1: (R)-Methyl 2-(m-tolyloxy)butanoate

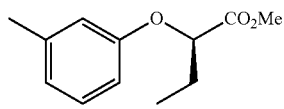

The title compound was prepared following the same protocol as described in Step 1, Example 42, using the (S)-methyl 2-hydroxybutanoate instead of the (S)-methyl 2-hydroxypropanoate.

Step 2: (R)-Methyl 2-(3-(bromomethyl)phenoxy)butanoate

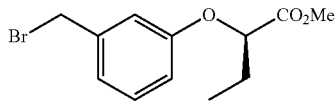 [SMILES: CC[C@@H](Oc1cccc(CBr)c1)C(=O)OC]

The title compound was prepared following the same protocol as described in Step 2, Example 36, using the (R)-methyl 2-(m-tolyloxy)butanoate instead of the methyl 2-(p-tolyloxy)acetate.

Step 3: (R)-Allyl 1-(3-((1-methoxy-1-oxobutan-2-yl)oxy)benzyl)-2,3-dimethyl-1H-indole-5-carboxylate

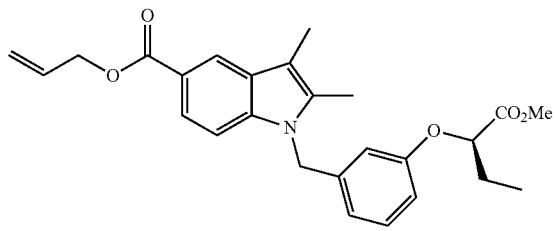 [SMILES: C=CCOC(=O)c1ccc2c(c1)c(C)c(C)n2Cc1cccc(O[C@H](CC)C(=O)OC)c1]

The title compound was prepared following the same general protocol as described in Step 3, Example 36, using the (R)-methyl 2-(3-(bromomethyl)phenoxy)butanoate instead of the methyl 2-(4-(bromomethyl)phenoxy)acetate. ESI-MS (m/z): 436 [M+H]+.

Step 4: (R)-1-(3-((1-Methoxy-1-oxobutan-2-yl)oxy)benzyl)-2,3-dimethyl-1H-indole-5-carboxylic acid

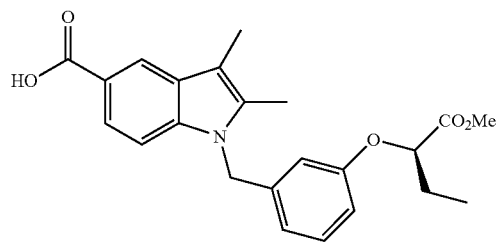 [SMILES: CC[C@@H](Oc1cccc(Cn2c(C)c(C)c3cc(C(=O)O)ccc32)c1)C(=O)OC]

The title compound was prepared following the same general protocol as described in Step 4, Example 36, using the (R)-allyl 1-(3-((1-methoxy-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 382 [M+H]+.

Step 5: (R)-Methyl 2-(3-((5-(((S)-1-(3-isopropylphenyl)ethyl)carbamoyl)-2,3-dimethyl-1H-indol-1-yl)methyl)phenoxy)butanoate

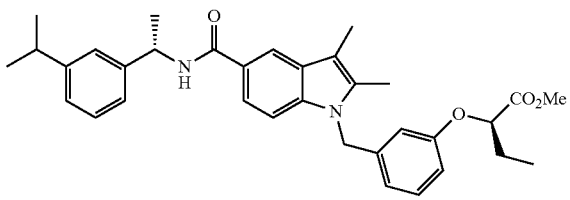 [SMILES: CC[C@@H](Oc1cccc(Cn2c(C)c(C)c3cc(C(=O)N[C@@H](C)c4cccc(C(C)C)c4)ccc32)c1)C(=O)OC]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(3-((1-methoxy-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-((5-(((S)-1-(3-Isopropylphenyl)ethyl)carbamoyl)-2,3-dimethyl-1H-indol-1-yl)methyl)phenoxy)butanoic acid

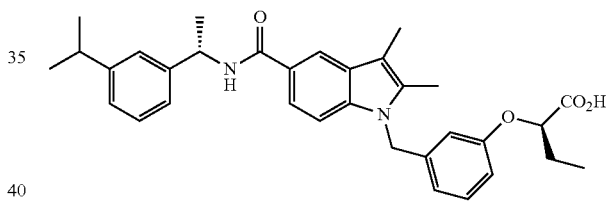

The title compound was prepared following the same protocol as described in Step 6, Example 36, using the (R)-methyl 2-(3-((5-(((S)-1-(3-isopropylphenyl)ethyl)carbamoyl)-2,3-dimethyl-1H-indol-1-yl)methyl)phenoxy)butanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 527 [M+H]+

Example 79

(S)-2-(3-((5-(((S)-1-(3-Isopropylphenyl)ethyl)carbamoyl)-2,3-dimethyl-1H-indol-1-yl)methyl)phenoxy)-3-methylbutanoic acid

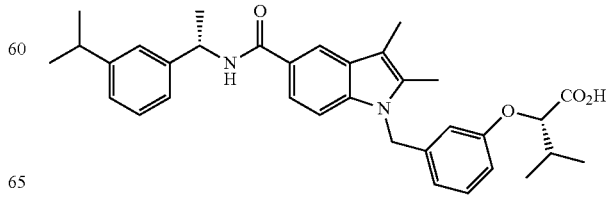

Step 1: (S)-Methyl 3-methyl-2-(m-tolyloxy)butanoate

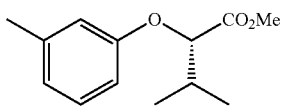 [SMILES: COC(=O)[C@@H](Oc1cccc(C)c1)C(C)C]

The title compound was prepared following the same protocol as described in Step 1, Example 42, using the (R)-methyl 2-hydroxy-3-methylbutanoate instead of the (S)-methyl 2-hydroxypropanoate.

Step 2: (S)-Methyl 2-(3-(bromomethyl)phenoxy)-3-methylbutanoate

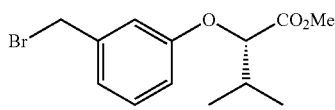 [SMILES: COC(=O)[C@@H](Oc1cccc(CBr)c1)C(C)C]

The title compound was prepared following the same protocol as described in Step 2, Example 36, using the (S)-methyl 3-methyl-2-(m-tolyloxy)butanoate instead of the methyl 2-(p-tolyloxy)acetate.

Step 3: (S)-Allyl 1-(3-((1-methoxy-3-methyl-1-oxobutan-2-yl)oxy)benzyl)-2,3-dimethyl-1H-indole-5-carboxylate

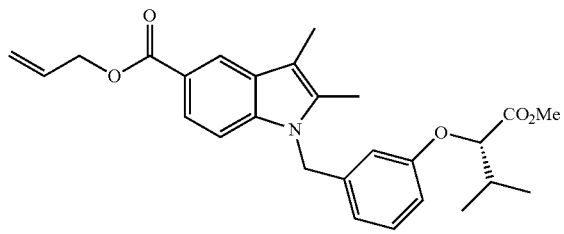 [SMILES: C=CCOC(=O)c1ccc2c(c1)c(C)c(C)n2Cc1cccc(O[C@H](C(=O)OC)C(C)C)c1]

The title compound was prepared following the same general protocol as described in Step 3, Example 36, using the (S)-methyl 2-(3-(bromomethyl)phenoxy)-3-methylbutanoate instead of the methyl 2-(4-(bromomethyl)phenoxy)acetate. ESI-MS (m/z): 450 [M+H]+.

Step 4: (S)-1-(3-((1-Methoxy-3-methyl-1-oxobutan-2-yl)oxy)benzyl)-2,3-dimethyl-1H-indole-5-carboxylic acid

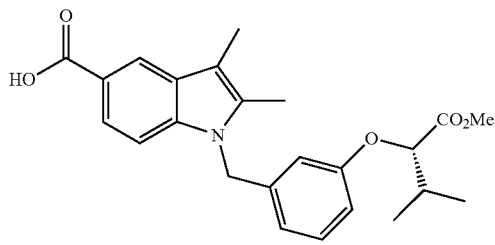

The title compound was prepared following the same general protocol as described in Step 4, Example 36, using the (S)-allyl 1-(3-((1-methoxy-3-methyl-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.
ESI-MS (m/z): 396 [M+H]+.

Step 5: (S)-Methyl 2-(3-((5-(((S)-1-(3-isopropylphenyl)ethyl)carbamoyl)-2,3-dimethyl-1H-indol-1-yl)methyl)phenoxy)-3-methylbutanoate

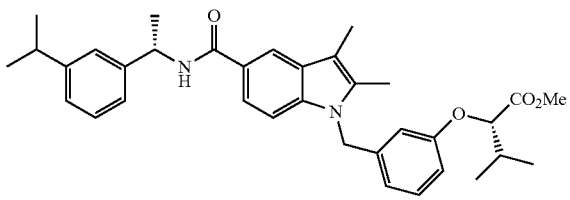 [SMILES: COC(=O)[C@@H](Oc1cccc(Cn2c(C)c(C)c3cc(C(=O)N[C@@H](C)c4cccc(C(C)C)c4)ccc32)c1)C(C)C]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(3-((1-methoxy-3-methyl-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-((5-(((S)-1-(3-Isopropylphenyl)ethyl)carbamoyl)-2,3-dimethyl-1H-indol-1-yl)methyl)phenoxy)-3-methylbutanoic acid

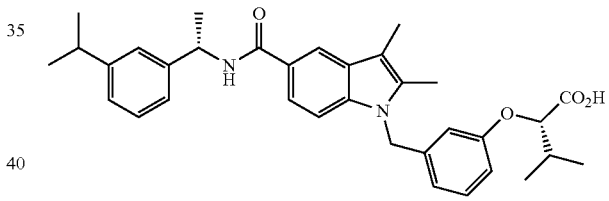

The title compound was prepared following the same protocol as described in Step 6, Example 36, using the (S)-methyl 2-(3-((5-(((S)-1-(3-isopropylphenyl)ethyl)carbamoyl)-2,3-dimethyl-1H-indol-1-yl)methyl)phenoxy)-3-methylbutanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 541 [M+H]+

Example 80

(R)-2-(3-((5-(((S)-1-(3-Isopropylphenyl)ethyl)carbamoyl)-2,3-dimethyl-1H-indol-1-yl)methyl)phenoxy)-3-methylbutanoic acid

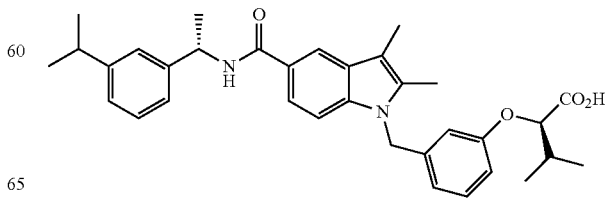

Step 1: (R)-Methyl 3-methyl-2-(m-tolyloxy)butanoate

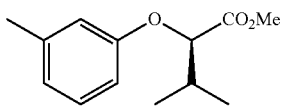 [SMILES: COC(=O)[C@H](Oc1cccc(C)c1)C(C)C]

The title compound was prepared following the same protocol as described in Step 1, Example 42, using the (S)-methyl 2-hydroxy-3-methylbutanoate instead of the (S)-methyl 2-hydroxypropanoate.

Step 2: (R)-Methyl 2-(3-(bromomethyl)phenoxy)-3-methylbutanoate

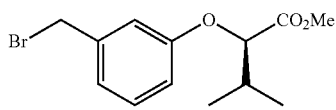 [SMILES: COC(=O)[C@H](Oc1cccc(CBr)c1)C(C)C]

The title compound was prepared following the same protocol as described in Step 2, Example 36, using the (R)-methyl 3-methyl-2-(m-tolyloxy)butanoate instead of the methyl 2-(p-tolyloxy)acetate.

Step 3: (R)-Allyl 1-(3-((1-methoxy-3-methyl-1-oxobutan-2-yl)oxy)benzyl)-2,3-dimethyl-1H-indole-5-carboxylate

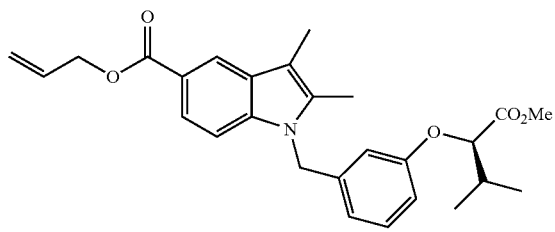 [SMILES: C=CCOC(=O)c1ccc2c(c1)c(C)c(C)n2Cc1cccc(O[C@@H](C(=O)OC)C(C)C)c1]

The title compound was prepared following the same general protocol as described in Step 3, Example 36, using the (R)-methyl 2-(3-(bromomethyl)phenoxy)-3-methylbutanoate instead of the methyl 2-(4-(bromomethyl)phenoxy)acetate. ESI-MS (m/z): 450 [M+H]+.

Step 4: (R)-1-(3-((1-Methoxy-3-methyl-1-oxobutan-2-yl)oxy)benzyl)-2,3-dimethyl-1H-indole-5-carboxylic acid

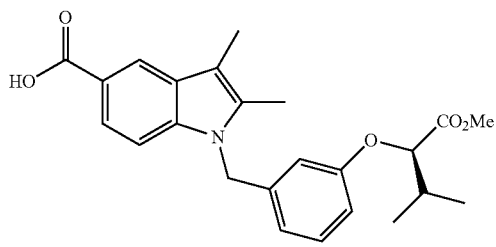 [SMILES: COC(=O)[C@H](Oc1cccc(Cn2c(C)c(C)c3cc(C(=O)O)ccc32)c1)C(C)C]

The title compound was prepared following the same general protocol as described in Step 4, Example 36, using the (R)-allyl 1-(3-((1-methoxy-3-methyl-1-oxobutan-2-yl)oxy) benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.
ESI-MS (m/z): 396 [M+H]+.

Step 5: (R)-Methyl 2-(3-((5-(((S)-1-(3-isopropylphenyl)ethyl)carbamoyl)-2,3-dimethyl-1H-indol-1-yl)methyl)phenoxy)-3-methylbutanoate

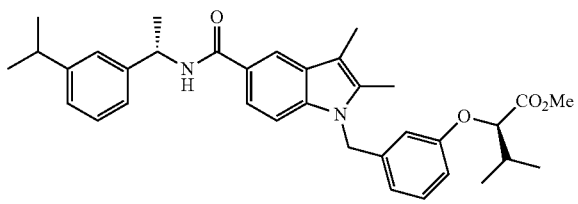

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(3-((1-methoxy-3-methyl-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-((5-(((S)-1-(3-Isopropylphenyl)ethyl)carbamoyl)-2,3-dimethyl-1H-indol-1-yl)methyl)phenoxy)-3-methylbutanoic acid

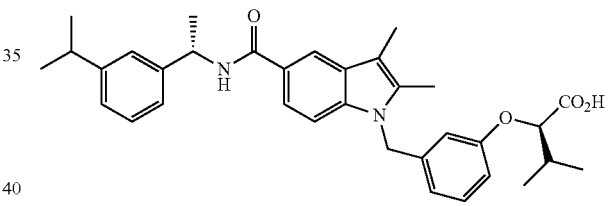

The title compound was prepared following the same protocol as described in Step 6, Example 36, using the (R)-methyl 2-(3-((5-(((S)-1-(3-isopropylphenyl)ethyl)carbamoyl)-2,3-dimethyl-1H-indol-1-yl)methyl)phenoxy)-3-methylbutanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 541 [M+H]+

Example 81

(S)-2-(2-Chloro-5-((5-(((S)-1-(3-isopropylphenyl)ethyl)carbamoyl)-2,3-dimethyl-1H-indol-1-yl)methyl)phenoxy)butanoic acid

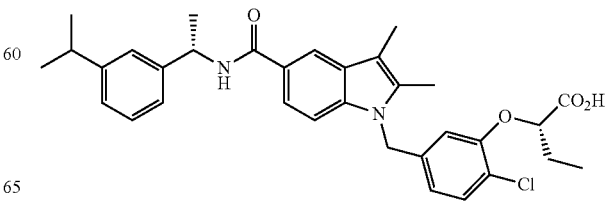

Step 1: (S)-Methyl 2-(2-chloro-5-methylphenoxy)butanoate

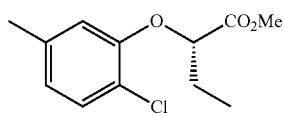 [SMILES: CC[C@H](Oc1cc(C)ccc1Cl)C(=O)OC]

The title compound was prepared following the same protocol as described in Step 1, Example 42, using the (R)-methyl 2-hydroxybutanoate instead of the (S)-methyl 2-hydroxypropanoate and the 2-chloro-5-methylphenol instead of the m-cresol.

Step 2: (S)-Methyl 2-(5-(bromomethyl)-2-chlorophenoxy)butanoate

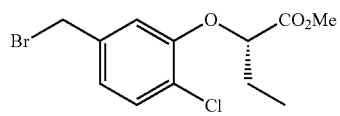 [SMILES: CC[C@H](Oc1cc(CBr)ccc1Cl)C(=O)OC]

The title compound was prepared following the same protocol as described in Step 2, Example 36, using the (S)-methyl 2-(2-chloro-5-methylphenoxy)butanoate instead of the methyl 2-(p-tolyloxy)acetate.

Step 3: (S)-Allyl 1-(4-chloro-3-((1-methoxy-1-oxobutan-2-yl)oxy)benzyl)-2,3-dimethyl-1H-indole-5-carboxylate

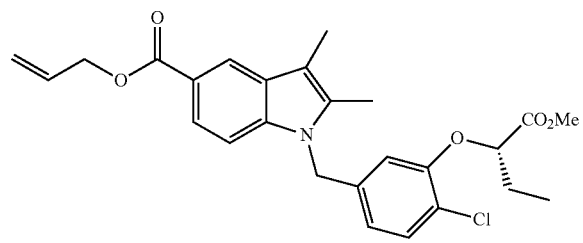 [SMILES: C=CCOC(=O)c1ccc2c(c1)c(C)c(C)n2Cc1ccc(Cl)c(O[C@@H](CC)C(=O)OC)c1]

The title compound was prepared following the same general protocol as described in Step 3, Example 36, using the (S)-methyl 2-(5-(bromomethyl)-2-chlorophenoxy)butanoate instead of the methyl 2-(4-(bromomethyl)phenoxy)acetate. ESI-MS (m/z): 470/471/472 [M+H]$^+$.

Step 4: (S)-1-(4-Chloro-3-((1-methoxy-1-oxobutan-2-yl)oxy)benzyl)-2,3-dimethyl-1H-indole-5-carboxylic acid

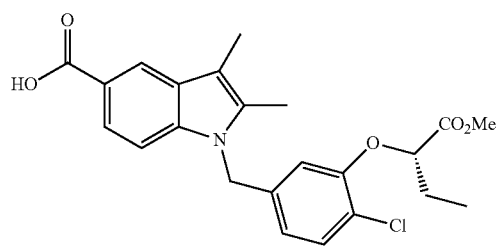 [SMILES: CC[C@H](Oc1cc(Cn2c(C)c(C)c3cc(C(=O)O)ccc32)ccc1Cl)C(=O)OC]

The title compound was prepared following the same general protocol as described in Step 4, Example 36, using the (S)-allyl 1-(4-chloro-3-((1-methoxy-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 [M+H]$^+$.

Step 5: (S)-Methyl 2-(2-chloro-5-((5-(((S)-1-(3-isopropylphenyl)ethyl)carbamoyl)-2,3-dimethyl-1H-indol-1-yl)methyl)phenoxy)butanoate

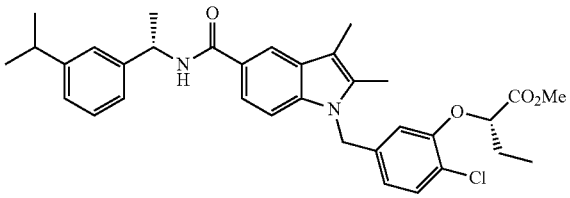 [SMILES: CC[C@H](Oc1cc(Cn2c(C)c(C)c3cc(C(=O)N[C@@H](C)c4cccc(C(C)C)c4)ccc32)ccc1Cl)C(=O)OC]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(4-chloro-3-((1-methoxy-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(2-Chloro-5-((5-(((S)-1-(3-isopropylphenyl)ethyl)carbamoyl)-2,3-dimethyl-1H-indol-1-yl)methyl)phenoxy)butanoic acid

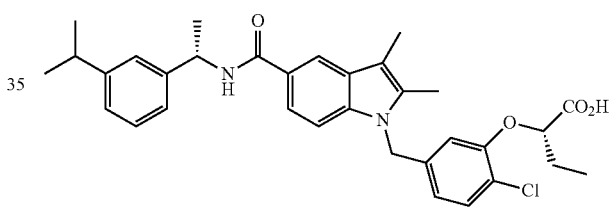

The title compound was prepared following the same protocol as described in Step 6, Example 36, using the (S)-methyl 2-(2-chloro-5-((5-(((S)-1-(3-isopropylphenyl)ethyl)carbamoyl)-2,3-dimethyl-1H-indol-1-yl)methyl)phenoxy)butanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$

Example 82

(S)-2-(4-Chloro-3-((5-(((S)-1-(3-isopropylphenyl)ethyl)carbamoyl)-2,3-dimethyl-1H-indol-1-yl)methyl)phenoxy)butanoic acid

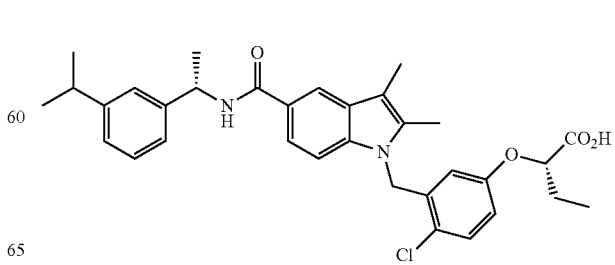

Step 1: (S)-Methyl 2-(4-chloro-3-methylphenoxy)butanoate

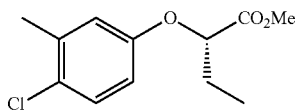 [SMILES: CC[C@H](Oc1ccc(Cl)c(C)c1)C(=O)OC]

The title compound was prepared following the same protocol as described in Step 1, Example 42, using the (R)-methyl 2-hydroxybutanoate instead of the (S)-methyl 2-hydroxypropanoate and the 4-chloro-3-methylphenol instead of the m-cresol.

Step 2: (S)-Methyl 2-(3-(bromomethyl)-4-chlorophenoxy)butanoate

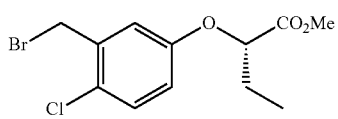 [SMILES: CC[C@H](Oc1ccc(Cl)c(CBr)c1)C(=O)OC]

The title compound was prepared following the same protocol as described in Step 2, Example 36, using the (S)-methyl 2-(4-chloro-3-methylphenoxy)butanoate instead of the methyl 2-(p-tolyloxy)acetate.

Step 3: (S)-Allyl 1-(2-chloro-5-((1-methoxy-1-oxobutan-2-yl)oxy)benzyl)-2,3-dimethyl-1H-indole-5-carboxylate

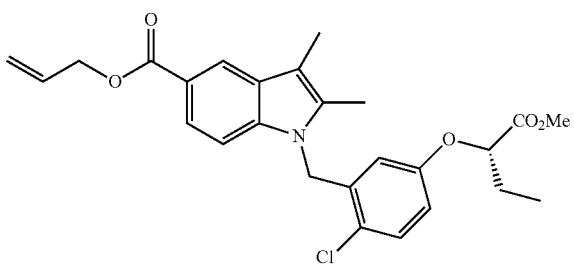 [SMILES: C=CCOC(=O)c1ccc2c(c1)c(C)c(C)n2Cc1cc(O[C@@H](CC)C(=O)OC)ccc1Cl]

The title compound was prepared following the same general protocol as described in Step 3, Example 36, using the (S)-methyl 2-(3-(bromomethyl)-4-chlorophenoxy)butanoate instead of the methyl 2-(4-(bromomethyl)phenoxy)acetate. ESI-MS (m/z): 470/471/472 [M+H]$^+$.

Step 4: (S)-1-(2-Chloro-5-((1-methoxy-1-oxobutan-2-yl)oxy)benzyl)-2,3-dimethyl-1H-indole-5-carboxylic acid

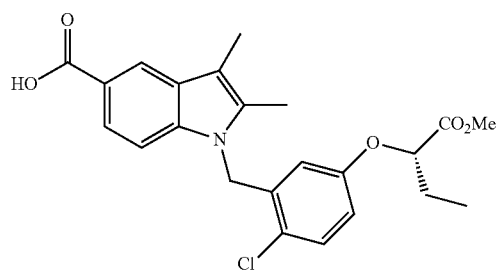 [SMILES: CC[C@H](Oc1ccc(Cl)c(Cn2c(C)c(C)c3cc(C(=O)O)ccc32)c1)C(=O)OC]

The title compound was prepared following the same general protocol as described in Step 4, Example 36, using the (S)-allyl 1-(2-chloro-5-((1-methoxy-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.
ESI-MS (m/z): 430/431/432 [M+H]$^+$.

Step 5: (S)-Methyl 2-(4-chloro-3-((5-(((S)-1-(3-isopropylphenyl)ethyl)carbamoyl)-2,3-dimethyl-1H-indol-1-yl)methyl)phenoxy)butanoate

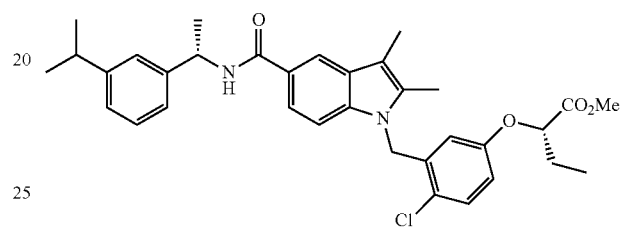

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(2-chloro-5-((1-methoxy-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(4-Chloro-3-((5-(((S)-1-(3-isopropylphenyl)ethyl)carbamoyl)-2,3-dimethyl-1H-indol-1-yl)methyl)phenoxy)butanoic acid

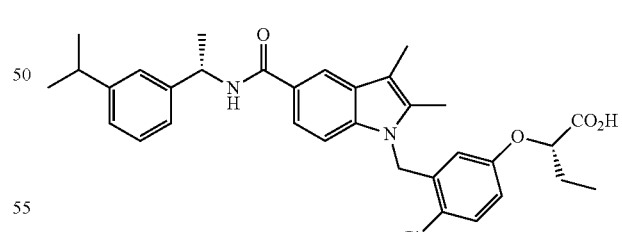

The title compound was prepared following the same protocol as described in Step 6, Example 36, using the (S)-methyl 2-(4-chloro-3-((5-(((S)-1-(3-isopropylphenyl)ethyl)carbamoyl)-2,3-dimethyl-1H-indol-1-yl)methyl)phenoxy)butanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$

Example 83

(R)-2-(2-Chloro-5-((5-(((S)-1-(3-isopropylphenyl)ethyl)carbamoyl)-2,3-dimethyl-1H-indol-1-yl)methyl)phenoxy)butanoic acid

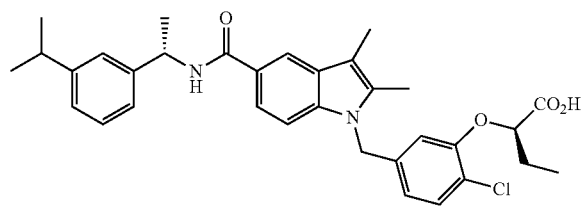 [SMILES: CC[C@@H](Oc1cc(Cn2c(C)c(C)c3cc(C(=O)N[C@@H](C)c4cccc(C(C)C)c4)ccc32)ccc1Cl)C(=O)O]

Step 1: (R)-Methyl 2-(2-chloro-5-methylphenoxy)butanoate

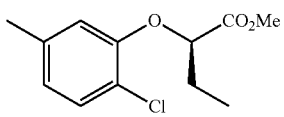 [SMILES: CC[C@@H](Oc1cc(C)ccc1Cl)C(=O)OC]

The title compound was prepared following the same protocol as described in Step 1, Example 42, using the (S)-methyl 2-hydroxybutanoate instead of the (S)-methyl 2-hydroxypropanoate and the 2-chloro-5-methylphenol instead of the m-cresol.

Step 2: (R)-Methyl 2-(5-(bromomethyl)-2-chlorophenoxy)butanoate

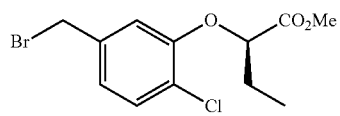 [SMILES: CC[C@@H](Oc1cc(CBr)ccc1Cl)C(=O)OC]

The title compound was prepared following the same protocol as described in Step 2, Example 36, using the (R)-methyl 2-(2-chloro-5-methylphenoxy)butanoate instead of the methyl 2-(p-tolyloxy)acetate.

Step 3: (R)-Allyl 1-(4-chloro-3-((1-methoxy-1-oxobutan-2-yl)oxy)benzyl)-2,3-dimethyl-1H-indole-5-carboxylate

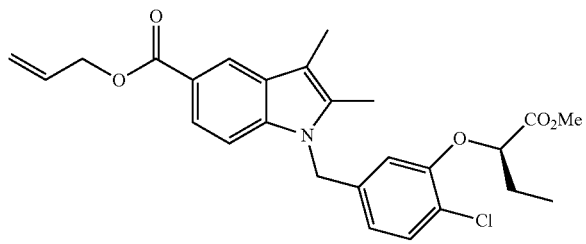 [SMILES: C=CCOC(=O)c1ccc2c(c1)c(C)c(C)n2Cc1ccc(Cl)c(O[C@H](CC)C(=O)OC)c1]

The title compound was prepared following the same general protocol as described in Step 3, Example 36, using the (R)-methyl 2-(5-(bromomethyl)-2-chlorophenoxy)butanoate instead of the methyl 2-(4-(bromomethyl)phenoxy)acetate.
ESI-MS (m/z): 470/471/472 [M+H]$^+$.

Step 4: (R)-1-(4-Chloro-3-((1-methoxy-1-oxobutan-2-yl)oxy)benzyl)-2,3-dimethyl-1H-indole-5-carboxylic acid

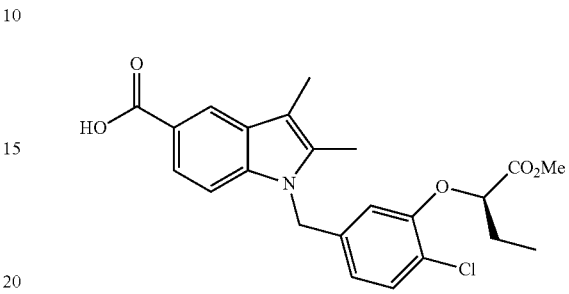

The title compound was prepared following the same general protocol as described in Step 4, Example 36, using the (R)-allyl 1-(4-chloro-3-((1-methoxy-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.
ESI-MS (m/z): 430/431/432 [M+H]$^+$.

Step 5: (R)-Methyl 2-(2-chloro-5-((5-(((S)-1-(3-isopropylphenyl)ethyl)carbamoyl)-2,3-dimethyl-1H-indol-1-yl)methyl)phenoxy)butanoate

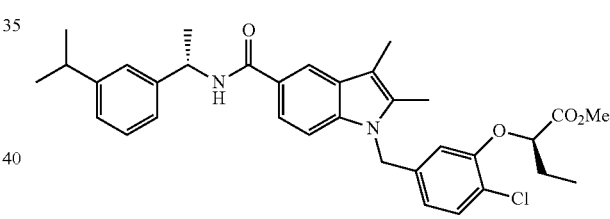

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(4-chloro-3-((1-methoxy-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(2-chloro-5-((5-(((S)-1-(3-Isopropylphenyl)ethyl)carbamoyl)-2,3-dimethyl-1H-indol-1-yl)methyl)phenoxy)butanoic acid

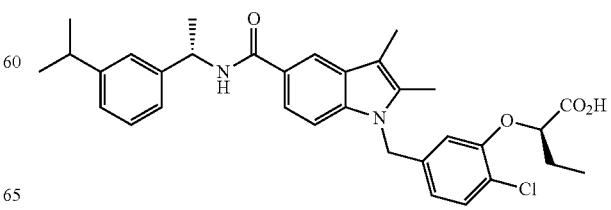

The title compound was prepared following the same protocol as described in Step 6, Example 36, using the (R)-methyl 2-(2-chloro-5-(((S)-1-(3-isopropylphenyl)ethyl)carbamoyl)-2,3-dimethyl-1H-indol-1-yl)methyl)phenoxy)butanoate instead of the (S)-methyl 2-(4-((5-(((1-(3-cyclopropylphenyl)ethyl)carbamoyl)-2,3-dimethyl-1H-indol-1-yl)methyl)phenoxy)acetate. ESI-MS (m/z): 561/562/563 [M+H]+.

Example 84

(R)-2-(4-Chloro-3-((5-(((S)-1-(3-isopropylphenyl)ethyl)carbamoyl)-2,3-dimethyl-1H-indol-1-yl)methyl)phenoxy)butanoic acid

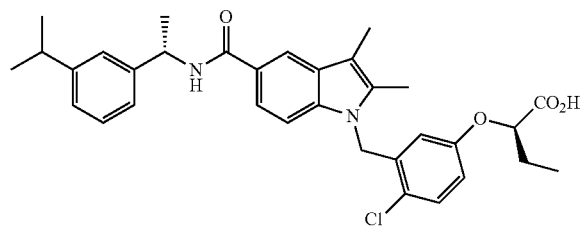 [SMILES: CC[C@@H](Oc1ccc(Cl)c(Cn2c(C)c(C)c3cc(C(=O)N[C@@H](C)c4cccc(C(C)C)c4)ccc32)c1)C(=O)O]

Step 1: (R)-Methyl 2-(4-chloro-3-methylphenoxy)butanoate

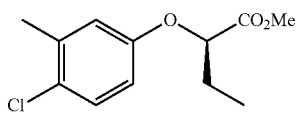 [SMILES: CC[C@@H](Oc1ccc(Cl)c(C)c1)C(=O)OC]

The title compound was prepared following the same protocol as described in Step 1, Example 42, using the (S)-methyl 2-hydroxybutanoate instead of the (S)-methyl 2-hydroxypropanoate and the 4-chloro-3-methylphenol instead of the m-cresol.

Step 2: (R)-Methyl 2-(3-(bromomethyl)-4-chlorophenoxy)butanoate

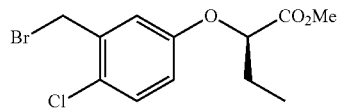 [SMILES: CC[C@@H](Oc1ccc(Cl)c(CBr)c1)C(=O)OC]

The title compound was prepared following the same protocol as described in Step 2, Example 36, using the (R)-methyl 2-(4-chloro-3-methylphenoxy)butanoate instead of the methyl 2-(p-tolyloxy)acetate.

Step 3: (R)-Allyl 1-(2-chloro-5-((1-methoxy-1-oxobutan-2-yl)oxy)benzyl)-2,3-dimethyl-1H-indole-5-carboxylate

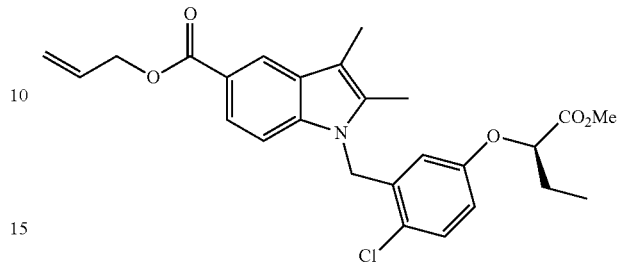

The title compound was prepared following the same general protocol as described in Step 3, Example 36, using the (R)-methyl 2-(3-(bromomethyl)-4-chlorophenoxy)butanoate instead of the methyl 2-(4-(bromomethyl)phenoxy)acetate. ESI-MS (m/z): 470/471/472 [M+H]+.

Step 4: (R)-1-(2-Chloro-5-((1-methoxy-1-oxobutan-2-yl)oxy)benzyl)-2,3-dimethyl-1H-indole-5-carboxylic acid

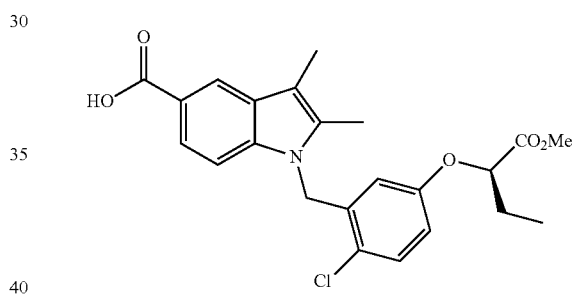

The title compound was prepared following the same general protocol as described in Step 4, Example 36, using the (R)-allyl 1-(2-chloro-5-((1-methoxy-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate.
ESI-MS (m/z): 430/431/432 [M+H]+.

Step 5: (R)-Methyl 2-(4-chloro-3-((5-(((S)-1-(3-isopropylphenyl)ethyl)carbamoyl)-2,3-dimethyl-1H-indol-1-yl)methyl)phenoxy)butanoate

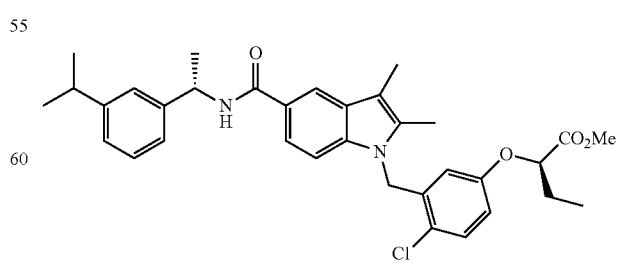

The title compound was prepared following the same protocol as described in Step 5, Example 36, using the (S)-1-(3- isopropylphenyl)ethanamine hydrochloride instead of the (S)-1-(3-cyclopropylphenyl)ethanamine hydrochloride and the (R)-1-(2-chloro-5-((1-methoxy-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(4-Chloro-3-((5-(((S)-1-(3-isopropylphenyl)ethyl)carbamoyl)-2,3-dimethyl-1H-indol-1-yl)methyl)phenoxy)butanoic acid

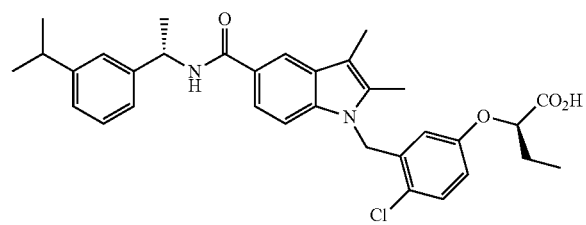 [SMILES: CC[C@@H](Oc1ccc(Cl)c(Cn2c(C)c(C)c3cc(C(=O)N[C@@H](C)c4cccc(C(C)C)c4)ccc32)c1)C(=O)O]

The title compound was prepared following the same protocol as described in Step 6, Example 36, using the (R)-methyl 2-(4-chloro-3-((5-(((S)-1-(3-isopropylphenyl)ethyl)carbamoyl)-2,3-dimethyl-1H-indol-1-yl)methyl)phenoxy)butanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ Example 85

(S)-2-(2-Chloro-5-((5-(((S)-1-(3-isopropylphenyl)ethyl)carbamoyl)-2,3-dimethyl-1H-indol-1-yl)methyl)phenoxy)-3-methylbutanoic acid

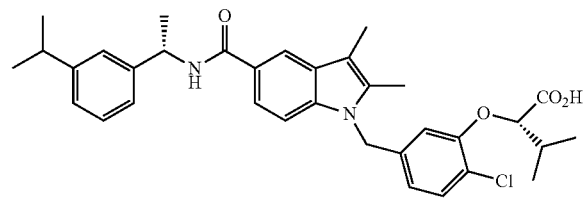 [SMILES: Cc1c(C)n(Cc2ccc(Cl)c(O[C@H](C(=O)O)C(C)C)c2)c2ccc(C(=O)N[C@@H](C)c3cccc(C(C)C)c3)cc12]

Step 1: (S)-Methyl 2-(2-chloro-5-methylphenoxy)-3-methylbutanoate

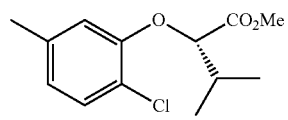 [SMILES: COC(=O)[C@@H](Oc1cc(C)ccc1Cl)C(C)C]

The title compound was prepared following the same protocol as described in Step 1, Example 42, using the (R)-methyl 2-hydroxy-3-methylbutanoate instead of the (S)-methyl 2-hydroxypropanoate and the 2-chloro-5-methylphenol instead of the m-cresol.

Step 2: (S)-Methyl 2-(5-(bromomethyl)-2-chlorophenoxy)-3-methylbutanoate

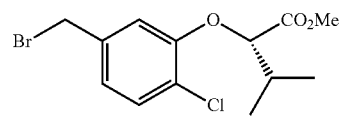 [SMILES: COC(=O)[C@@H](Oc1cc(CBr)ccc1Cl)C(C)C]

The title compound was prepared following the same protocol as described in Step 2, Example 36, using the (S)-methyl 2-(2-chloro-5-methylphenoxy)-3-methylbutanoate instead of the methyl 2-(p-tolyloxy)acetate.

Step 3: (S)-Allyl 1-(4-chloro-3-((1-methoxy-3-methyl-1-oxobutan-2-yl)oxy)benzyl)-2,3-dimethyl-1H-indole-5-carboxylate

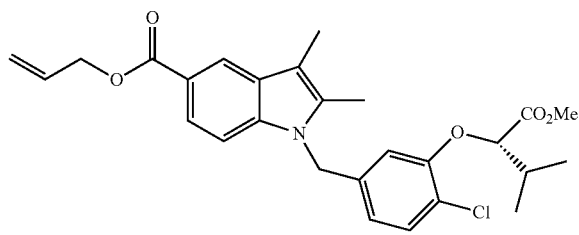 [SMILES: C=CCOC(=O)c1ccc2c(c1)c(C)c(C)n2Cc1ccc(Cl)c(O[C@H](C(=O)OC)C(C)C)c1]

The title compound was prepared following the same general protocol as described in Step 3, Example 36, using the (S)-methyl 2-(5-(bromomethyl)-2-chlorophenoxy)-3-methylbutanoate instead of the methyl 2-(4-(bromomethyl)phenoxy)acetate. ESI-MS (m/z): 470/471/472 [M+H]$^+$.

Step 4: (S)-1-(4-Chloro-3-((1-methoxy-3-methyl-1-oxobutan-2-yl)oxy)benzyl)-2,3-dimethyl-1H-indole-5-carboxylic acid

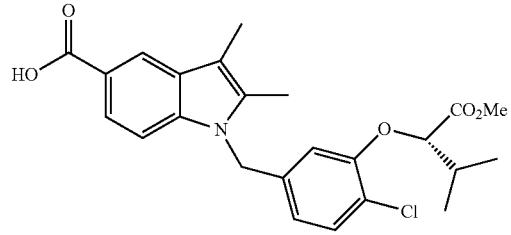 [SMILES: COC(=O)[C@@H](Oc1cc(Cn2c(C)c(C)c3cc(C(=O)O)ccc32)ccc1Cl)C(C)C]

The title compound was prepared following the same general protocol as described in Step 4, Example 36, using the (S)-allyl 1-(4-chloro-3-((1-methoxy-3-methyl-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 [M+H]$^+$.

Step 5: (S)-Methyl 2-(2-chloro-5-((5-(((S)-1-(3-isopropylphenyl)ethyl)carbamoyl)-2,3-dimethyl-1H-indol-1-yl)methyl)phenoxy)-3-methylbutanoate

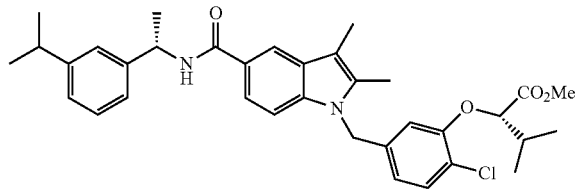 [SMILES: COC(=O)[C@@H](Oc1cc(Cn2c(C)c(C)c3cc(C(=O)N[C@@H](C)c4cccc(C(C)C)c4)ccc32)ccc1Cl)C(C)C]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(4-chloro-3-((1-methoxy-3-methyl-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(2-Chloro-5-((5-(((S)-1-(3-isopropylphenyl)ethyl)carbamoyl)-2,3-dimethyl-1H-indol-1-yl)methyl)phenoxy)-3-methylbutanoic acid

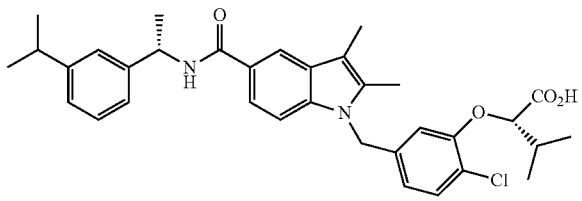 [SMILES: Cc1c(C)n(Cc2ccc(Cl)c(O[C@H](C(=O)O)C(C)C)c2)c2ccc(C(=O)N[C@@H](C)c3cccc(C(C)C)c3)cc12]

The title compound was prepared following the same protocol as described in Step 6, Example 36, using the (S)-methyl 2-(2-chloro-5-((5-(((S)-1-(3-isopropylphenyl)ethyl)carbamoyl)-2,3-dimethyl-1H-indol-1-yl)methyl)phenoxy)-3-methylbutanoate instead of the (S)-methyl 2-(4-((5-(((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$

Example 86

(S)-2-(4-Chloro-3-((5-(((S)-1-(3-isopropylphenyl)ethyl)carbamoyl)-2,3-dimethyl-1H-indol-1-yl)methyl)phenoxy)-3-methylbutanoic acid

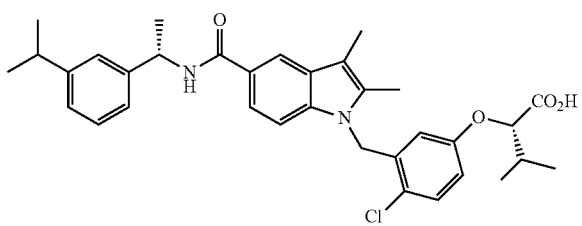 [SMILES: Cc1c(C)n(Cc2cc(O[C@H](C(=O)O)C(C)C)ccc2Cl)c2ccc(C(=O)N[C@@H](C)c3cccc(C(C)C)c3)cc12]

Step 1: (S)-Methyl 2-(4-chloro-3-methylphenoxy)-3-methylbutanoate

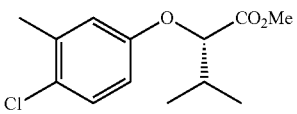 [SMILES: COC(=O)[C@@H](Oc1ccc(Cl)c(C)c1)C(C)C]

The title compound was prepared following the same protocol as described in Step 1, Example 42, using the (R)-methyl 2-hydroxy-3-methylbutanoate instead of the (S)-methyl 2-hydroxypropanoate and the 4-chloro-3-methylphenol instead of the m-cresol.

Step 2: (S)-Methyl 2-(3-(bromomethyl)-4-chlorophenoxy)-3-methylbutanoate

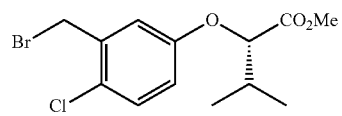 [SMILES: COC(=O)[C@@H](Oc1ccc(Cl)c(CBr)c1)C(C)C]

The title compound was prepared following the same protocol as described in Step 2, Example 36, using the (S)-methyl 2-(4-chloro-3-methylphenoxy)-3-methylbutanoate instead of the methyl 2-(p-tolyloxy)acetate.

Step 3: (S)-Allyl 1-(2-chloro-5-((1-methoxy-3-methyl-1-oxobutan-2-yl)oxy)benzyl)-2,3-dimethyl-1H-indole-5-carboxylate

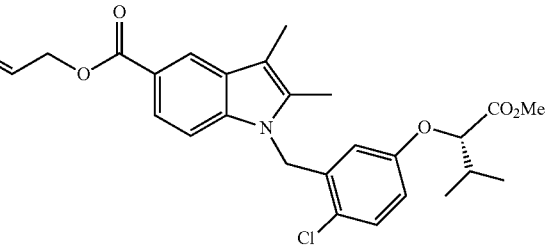

The title compound was prepared following the same general protocol as described in Step 3, Example 36, using the (S)-methyl 2-(3-(bromomethyl)-4-chlorophenoxy)-3-methylbutanoate instead of the methyl 2-(4-(bromomethyl)phenoxy)acetate. ESI-MS (m/z): 470/471/472 [M+H]$^+$.

Step 4: (S)-1-(2-Chloro-5-((1-methoxy-3-methyl-1-oxobutan-2-yl)oxy)benzyl)-2,3-dimethyl-1H-indole-5-carboxylic acid

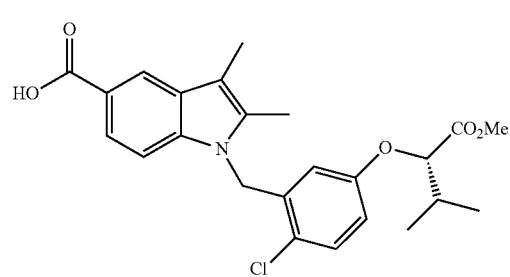 [SMILES: COC(=O)[C@@H](Oc1ccc(Cl)c(Cn2c(C)c(C)c3cc(C(=O)O)ccc32)c1)C(C)C]

The title compound was prepared following the same general protocol as described in Step 4, Example 36, using the (S)-allyl 1-(2-chloro-5-((1-methoxy-3-methyl-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 [M+H]⁺.

Step 5: (S)-Methyl 2-(4-chloro-3-((5-(((S)-1-(3-isopropylphenyl)ethyl)carbamoyl)-2,3-dimethyl-1H-indol-1-yl)methyl)phenoxy)-3-methylbutanoate

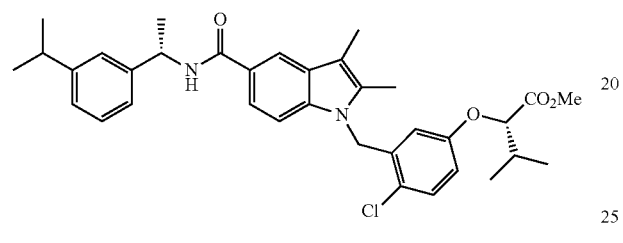

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(2-chloro-5-((1-methoxy-3-methyl-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(4-Chloro-3-((5-(((S)-1-(3-isopropylphenyl)ethyl)carbamoyl)-2,3-dimethyl-1H-indol-1-yl)methyl)phenoxy)-3-methylbutanoic acid

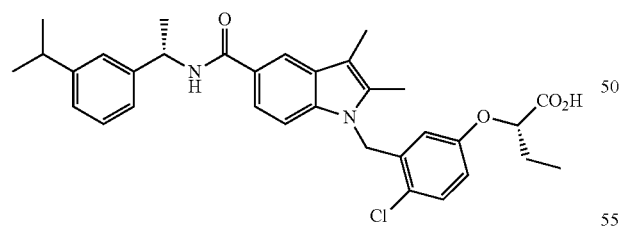

The title compound was prepared following the same protocol as described in Step 6, Example 36, using the (S)-methyl 2-(4-chloro-3-((5-(((S)-1-(3-isopropylphenyl)ethyl)carbamoyl)-2,3-dimethyl-1H-indol-1-yl)methyl)phenoxy)-3-methylbutanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]⁺

Example 87

(R)-2-(2-Chloro-5-((5-(((S)-1-(3-isopropylphenyl)ethyl)carbamoyl)-2,3-dimethyl-1H-indol-1-yl)methyl)phenoxy)-3-methylbutanoic acid

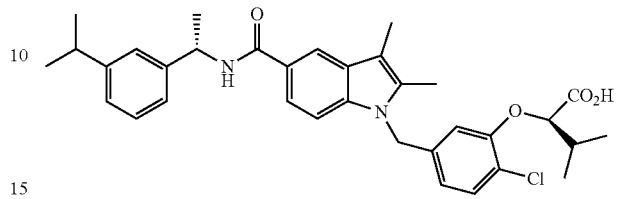

Step 1: (R)-Methyl 2-(2-chloro-5-methylphenoxy)-3-methylbutanoate

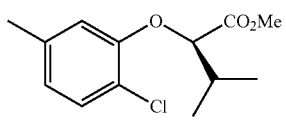 [SMILES: COC(=O)[C@H](Oc1cc(C)ccc1Cl)C(C)C]

The title compound was prepared following the same protocol as described in Step 1, Example 42, using the (S)-methyl 2-hydroxy-3-methylbutanoate instead of the (S)-methyl 2-hydroxypropanoate and the 2-chloro-5-methylphenol instead of the m-cresol.

Step 2: (R)-Methyl 2-(5-(bromomethyl)-2-chlorophenoxy)-3-methylbutanoate

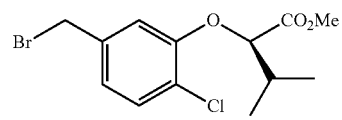

The title compound was prepared following the same protocol as described in Step 2, Example 36, using the (R)-methyl 2-(2-chloro-5-methylphenoxy)-3-methylbutanoate instead of the methyl 2-(p-tolyloxy)acetate.

Step 3: (R)-Allyl 1-(4-chloro-3-((1-methoxy-3-methyl-1-oxobutan-2-yl)oxy)benzyl)-2,3-dimethyl-1H-indole-5-carboxylate

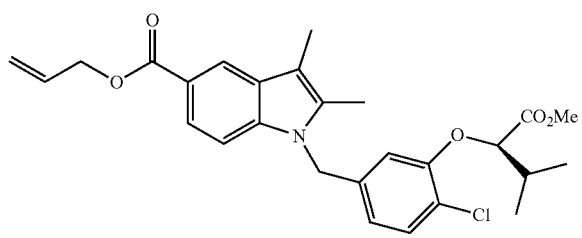 [SMILES: C=CCOC(=O)c1ccc2c(c1)c(C)c(C)n2Cc1ccc(Cl)c(O[C@@H](C(=O)OC)C(C)C)c1]

The title compound was prepared following the same general protocol as described in Step 3, Example 36, using the (R)-methyl 2-(5-(bromomethyl)-2-chlorophenoxy)-3-methylbutanoate instead of the methyl 2-(4-(bromomethyl)phenoxy)acetate. ESI-MS (m/z): 470/471/472 [M+H]+.

Step 4: (R)-1-(4-Chloro-3-((1-methoxy-3-methyl-1-oxobutan-2-yl)oxy)benzyl)-2,3-dimethyl-1H-indole-5-carboxylic acid

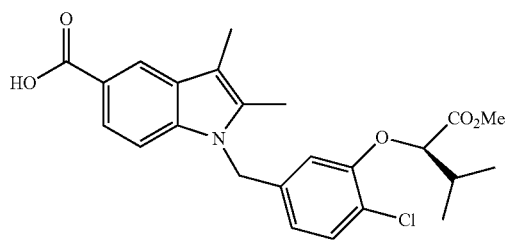 [SMILES: COC(=O)[C@H](Oc1cc(Cn2c(C)c(C)c3cc(C(=O)O)ccc32)ccc1Cl)C(C)C]

The title compound was prepared following the same general protocol as described in Step 4, Example 36, using the (R)-allyl 1-(4-chloro-3-((1-methoxy-3-methyl-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 [M+H]+.

Step 5: (R)-Methyl 2-(2-chloro-5-((5-(((S)-1-(3-isopropylphenyl)ethyl)carbamoyl)-2,3-dimethyl-1H-indol-1-yl)methyl)phenoxy)-3-methylbutanoate

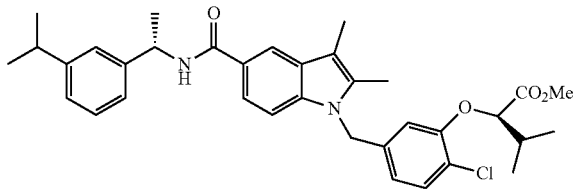 [SMILES: COC(=O)[C@H](Oc1cc(Cn2c(C)c(C)c3cc(C(=O)N[C@@H](C)c4cccc(C(C)C)c4)ccc32)ccc1Cl)C(C)C]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(4-chloro-3-((1-methoxy-3-methyl-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(2-Chloro-5-((5-(((S)-1-(3-isopropylphenyl)ethyl)carbamoyl)-2,3-dimethyl-1H-indol-1-yl)methyl)phenoxy)-3-methylbutanoic acid

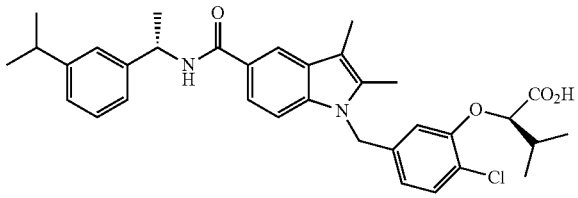 [SMILES: Cc1c(C)n(Cc2ccc(Cl)c(O[C@@H](C(=O)O)C(C)C)c2)c2ccc(C(=O)N[C@@H](C)c3cccc(C(C)C)c3)cc12]

The title compound was prepared following the same protocol as described in Step 6, Example 36, using the (R)-methyl 2-(2-chloro-5-((5-(((S)-1-(3-isopropylphenyl)ethyl)carbamoyl)-2,3-dimethyl-1H-indol-1-yl)methyl)phenoxy)-3-methylbutanoate instead of the (S)-methyl 2-(4-((5-(((1-(3-cyclopropylphenyl)ethyl)carbamoyl)-2,3-dimethyl-1H-indol-1-yl)methyl)phenoxy)acetate. ESI-MS (m/z): 561/562/563 [M+H]+

Example 88

(R)-2-(4-Chloro-3-((5-(((S)-1-(3-isopropylphenyl)ethyl)carbamoyl)-2,3-dimethyl-1H-indol-1-yl)methyl)phenoxy)-3-methylbutanoic acid

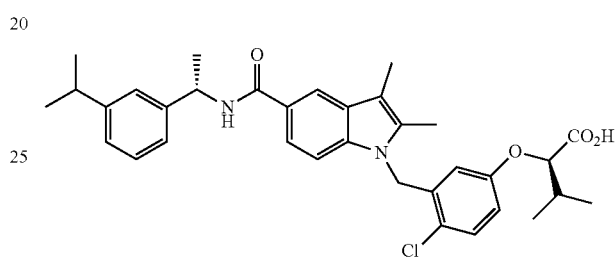

Step 1: (R)-Methyl 2-(4-chloro-3-methylphenoxy)-3-methylbutanoate

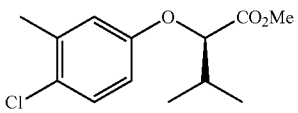 [SMILES: COC(=O)[C@H](Oc1ccc(Cl)c(C)c1)C(C)C]

The title compound was prepared following the same protocol as described in Step 1, Example 42, using the (S)-methyl 2-hydroxybutanoate instead of the (S)-methyl 2-hydroxy-3-methylpropanoate and the 4-chloro-3-methylphenol instead of the m-cresol.

Step 2: (R)-Methyl 2-(3-(bromomethyl)-4-chlorophenoxy)-3-methylbutanoate

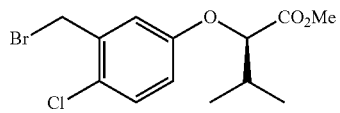

The title compound was prepared following the same protocol as described in Step 2, Example 36, using the (R)-methyl 2-(4-chloro-3-methylphenoxy)-3-methylbutanoate instead of the methyl 2-(p-tolyloxy)acetate.

Step 3: (R)-Allyl 1-(2-chloro-5-((1-methoxy-3-methyl-1-oxobutan-2-yl)oxy)benzyl)-2,3-dimethyl-1H-indole-5-carboxylate

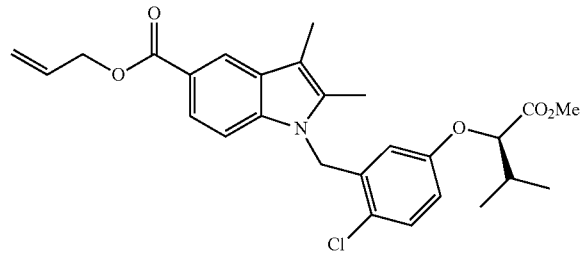 [SMILES: C=CCOC(=O)c1ccc2c(c1)c(C)c(C)n2Cc1cc(O[C@@H](C(=O)OC)C(C)C)ccc1Cl]

The title compound was prepared following the same general protocol as described in Step 3, Example 36, using the (R)-methyl 2-(3-(bromomethyl)-4-chlorophenoxy)-3-methylbutanoate instead of the methyl 2-(4-(bromomethyl)phenoxy)acetate. ESI-MS (m/z): 470/471/472 [M+H]⁺.

Step 4: (R)-1-(2-Chloro-5-((1-methoxy-3-methyl-1-oxobutan-2-yl)oxy)benzyl)-2,3-dimethyl-1H-indole-5-carboxylic acid

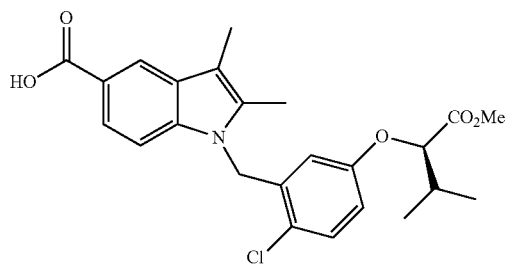 [SMILES: COC(=O)[C@H](Oc1ccc(Cl)c(Cn2c(C)c(C)c3cc(C(=O)O)ccc32)c1)C(C)C]

The title compound was prepared following the same general protocol as described in Step 4, Example 36, using the (R)-allyl 1-(2-chloro-5-((1-methoxy-3-methyl-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 [M+H]⁺.

Step 5: (R)-Methyl 2-(4-chloro-3-((5-(((S)-1-(3-isopropylphenyl)ethyl)carbamoyl)-2,3-dimethyl-1H-indol-1-yl)methyl)phenoxy)-3-methylbutanoate

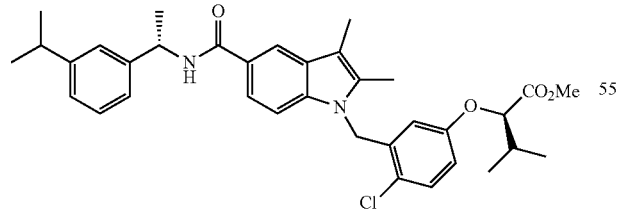

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(2-chloro-5-((1-methoxy-3-methyl-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(4-Chloro-3-((5-(((S)-1-(3-isopropylphenyl)ethyl)carbamoyl)-2,3-dimethyl-1H-indol-1-yl)methyl)phenoxy)-3-methylbutanoic acid

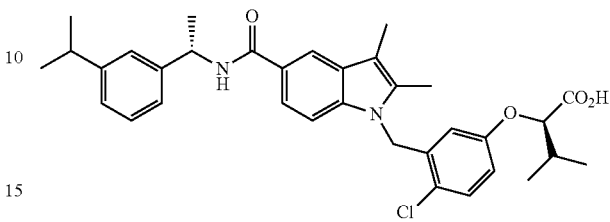

The title compound was prepared following the same protocol as described in Step 6, Example 36, using the (R)-methyl 2-(4-chloro-3-((5-(((S)-1-(3-isopropylphenyl)ethyl)carbamoyl)-2,3-dimethyl-1H-indol-1-yl)methyl)phenoxy)-3-methylbutanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]⁺.

Example 89

1-(4-((2,3-dimethyl-5-((1-phenylpropyl)carbamoyl)-1H-indol-1-yl)methyl)phenyl)cyclopropanecarboxylic acid

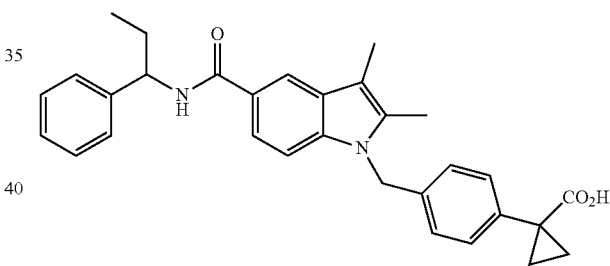

The title compound was prepared following the same protocol as described in Step 5 and 8, Example 35, using the 1-phenylpropanamine instead of the (S)-1-(3-bromophenyl)ethanamine. ESI-MS (m/z): 481 [MH]⁺.

Example 90

(S)-1-(4-((5-((1-(4-bromophenyl)ethyl)carbamoyl)-2,3-dimethyl-1H-indol-1-yl)methyl)phenyl)cyclopropanecarboxylic acid

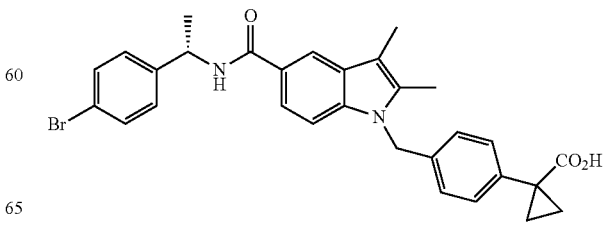

The title compound was prepared following the same protocol as described in Step 5 and 8, Example 35, using the (S)-1-(4-bromophenyl)ethanamine instead of the (S)-1-(3-bromophenyl)ethanamine. ESI-MS (m/z): 545/547 [MH]$^+$.

Example 91

(S)-1-(4-((5-(((1-(4-isopropylphenyl)ethyl)carbamoyl)-2,3-dimethyl-1H-indol-1-yl)methyl)phenyl)cyclopropanecarboxylic acid

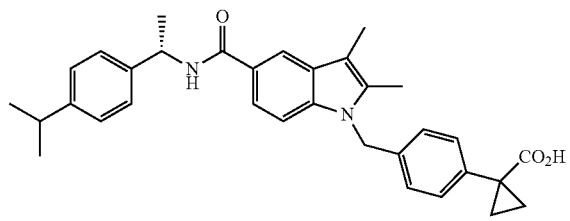 [SMILES: Cc1c(C)n(Cc2ccc(C3(C(=O)O)CC3)cc2)c2ccc(C(=O)N[C@@H](C)c3ccc(C(C)C)cc3)cc12]

The title compound was prepared following the same protocol as described in Step 5-8, Example 35, using the (S)-1-(4-bromophenyl)ethanamine instead of the (S)-1-(3-bromophenyl)ethanamine. ESI-MS (m/z): 509 [MH]$^+$.

Example 92

(S)-2-(3-chloro-5-((5-(((S)-1-(3-cyclopropylphenyl)ethyl)carbamoyl)-2,3-dimethyl-1H-indol-1-yl)methyl)phenoxy)propanoic acid

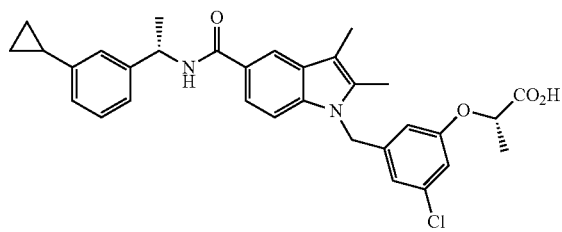 [SMILES: Cc1c(C)n(Cc2cc(Cl)cc(O[C@@H](C)C(=O)O)c2)c2ccc(C(=O)N[C@@H](C)c3cccc(C4CC4)c3)cc12]

The title compound was prepared following the same protocol as described in Step 5-6, Example 67, using the (S)-1-(3-cyclopropylphenyl)ethanamine hydrochloride instead of the (S)-1-(3-isopropylphenyl)ethanamine hydrochloride. ESI-MS (m/z): 545/546/547 [MH]$^+$.

Example 93

(S)-2-(3-((5-(((S)-1-(4-(tert-butyl)phenyl)ethyl)carbamoyl)-2,3-dimethyl-1H-indol-1-yl)methyl)-5-chlorophenoxy)propanoic acid

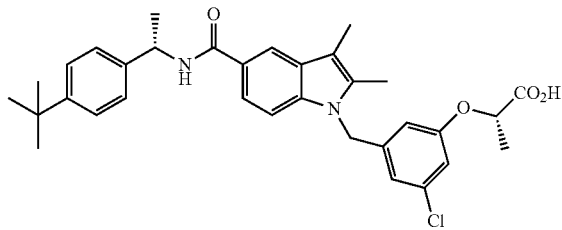 [SMILES: Cc1c(C)n(Cc2cc(Cl)cc(O[C@@H](C)C(=O)O)c2)c2ccc(C(=O)N[C@@H](C)c3ccc(C(C)(C)C)cc3)cc12]

The title compound was prepared following the same protocol as described in Step 5-6, Example 67, using the (S)-1-(4-tert-butylphenyl)ethanamine hydrochloride instead of the (S)-1-(3-isopropylphenyl)ethanamine hydrochloride. ESI-MS (m/z): 561/562/563 [MH]$^+$.

Example 94

(S)-2-(2-chloro-4-((5-(((S)-1-(3-cyclopropylphenyl)ethyl)carbamoyl)-2,3-dimethyl-1H-indol-1-yl)methyl)phenoxy)propanoic acid

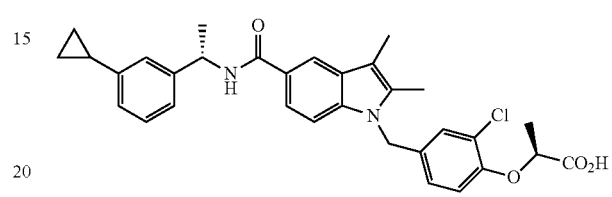

The title compound was prepared following the same protocol as described in Step 5-6, Example 73, using the (S)-1-(3-cyclopropylphenyl)ethanamine hydrochloride instead of the (S)-1-(3-isopropylphenyl)ethanamine hydrochloride. ESI-MS (m/z): 545/546/547 [MH]$^+$.

Example 95

(S)-2-(4-((5-(((S)-1-(4-(tert-butyl)phenyl)ethyl)carbamoyl)-2,3-dimethyl-1H-indol-1-yl)methyl)-2-chlorophenoxy)propanoic acid

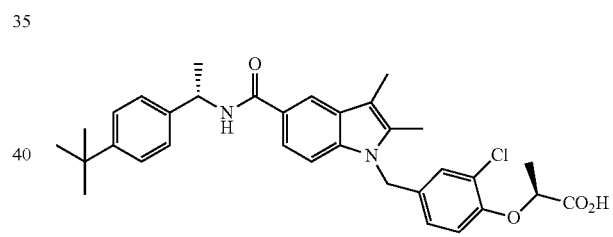

The title compound was prepared following the same protocol as described in Step 5-6, Example 73, using the (S)-1-(4-tert-butylphenyl)ethanamine hydrochloride instead of the (S)-1-(3-isopropylphenyl)ethanamine hydrochloride. ESI-MS (m/z): 561/562/563 [MH]$^+$.

Example 96

(S)-2-(2-chloro-3-((5-(((S)-1-(3-cyclopropylphenyl)ethyl)carbamoyl)-2,3-dimethyl-1H-indol-1-yl)methyl)phenoxy)propanoic acid

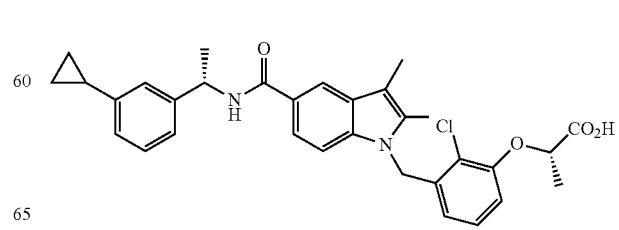

The title compound was prepared following the same protocol as described in Step 5-6, Example 68, using the (S)-1-(3-cyclopropylphenyl)ethanamine hydrochloride instead of the (S)-1-(3-isopropylphenyl)ethanamine hydrochloride.
ESI-MS (m/z): 545/546/547 [MH]+.

Example 97

(S)-2-(3-((5-(((S)-1-(4-(tert-butyl)phenyl)ethyl)carbamoyl)-2,3-dimethyl-1H-indol-1-yl)methyl)-2-chlorophenoxy)propanoic acid

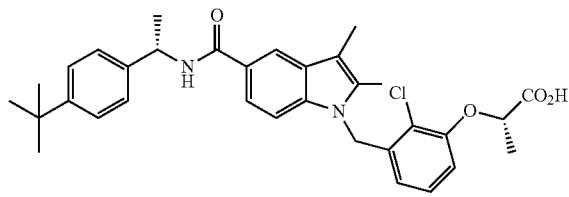 [SMILES: Cc1c(C)n(Cc2cccc(O[C@@H](C)C(=O)O)c2Cl)c2ccc(C(=O)N[C@@H](C)c3ccc(C(C)(C)C)cc3)cc12]

The title compound was prepared following the same protocol as described in Step 5-6, Example 68, using the (S)-1-(4-tert-butylphenyl)ethanamine hydrochloride instead of the (S)-1-(3-isopropylphenyl)ethanamine hydrochloride.
ESI-MS (m/z): 561/562/563 [MH]+.

Example 98

1-(3-(((S)-1-amino-1-oxopropan-2-yl)oxy)-4-chlorobenzyl)-N-((S)-1-(4-(tert-butyl)phenyl)ethyl)-2,3-dimethyl-1H-indole-5-carboxamide

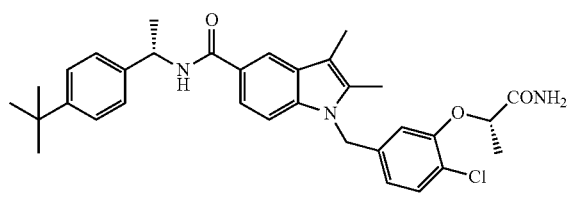 [SMILES: Cc1c(C)n(Cc2ccc(Cl)c(O[C@@H](C)C(N)=O)c2)c2ccc(C(=O)N[C@@H](C)c3ccc(C(C)(C)C)cc3)cc12]

A solution of (S)-2-(5-((5-(((S)-1-(4-(tert-butyl)phenyl)ethyl)carbamoyl)-2,3-dimethyl-1H-indol-1-yl)methyl)-2-chlorophenoxy)propanoic acid (20 mg, 0.036 mmol), NH4Cl (19 mg, 0.36 mmol), HATU (14 mg, 0.036 mmol) and DIEA (25 µl, 0.144 mmol) in DCM (0.5 ml) was stirred at rt for 1 h. After concentration, the obtained oil was purified by reverse phase prep-HPLC (MeOH/Acetonitrile/water) to afford a white powder (18 mg). ESI-MS (m/z): 560/561/562 [MH]+.

Example 99

1-(5-(((S)-1-amino-1-oxopropan-2-yl)oxy)-2-chlorobenzyl)-N-((S)-1-(4-(tert-butyl)phenyl)ethyl)-2,3-dimethyl-1H-indole-5-carboxamide

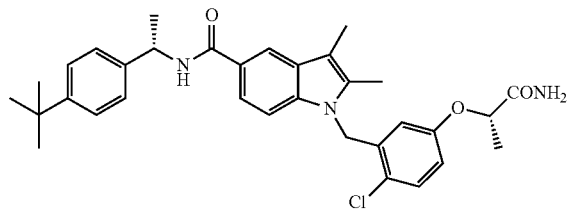 [SMILES: Cc1c(C)n(Cc2cc(O[C@@H](C)C(N)=O)ccc2Cl)c2ccc(C(=O)N[C@@H](C)c3ccc(C(C)(C)C)cc3)cc12]

A solution of (S)-2-(3-((5-(((S)-1-(4-(tert-butyl)phenyl)ethyl)carbamoyl)-2,3-dimethyl-1H-indol-1-yl)methyl)-4-chlorophenoxy)propanoic acid (20 mg, 0.036 mmol), NH4Cl (19 mg, 0.36 mmol), HATU (14 mg, 0.036 mmol) and DIEA (25 µl, 0.144 mmol) in DCM (0.5 ml) was stirred at rt for 1 h. After concentration, the obtained oil was purified by reverse phase prep-HPLC (MeOH/Acetonitrile/water) to afford a white powder (18 mg). ESI-MS (m/z): 560/561/562 [MH]+.

Example 100

1-(3-(((S)-1-amino-1-oxopropan-2-yl)oxy)benzyl)-N-((S)-1-(4-(tert-butyl)phenyl)ethyl)-2,3-dimethyl-1H-indole-5-carboxamide

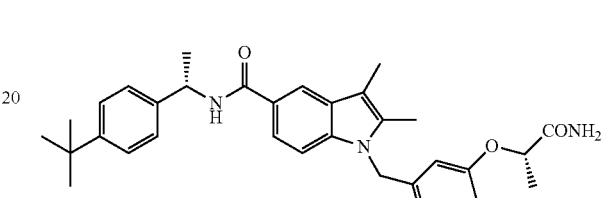

A solution of (S)-2-(3-((5-(((S)-1-(4-(tert-butyl)phenyl)ethyl)carbamoyl)-2,3-dimethyl-1H-indol-1-yl)methyl)phenoxy)propanoic acid (20 mg, 0.036 mmol), NH4Cl (19 mg, 0.36 mmol), HATU (14 mg, 0.036 mmol) and DIEA (25 µl, 0.144 mmol) in DCM (0.5 ml) was stirred at rt for 1 h. After concentration, the obtained oil was purified by reverse phase prep-HPLC (MeOH/Acetonitrile/water) to afford a white powder (18 mg). ESI-MS (m/z): 526 [MH]+.

Example 101

(S)-1-(3-(2-cyanopropan-2-yl)benzyl)-N-(1-(3-cyclopropylphenyl)ethyl)-2,3-dimethyl-1H-indole-5-carboxamide

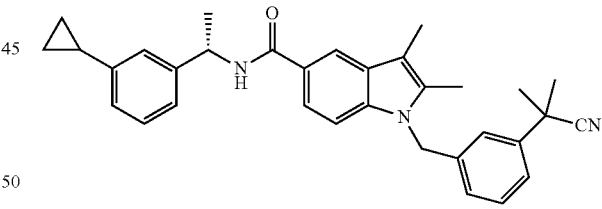

Step 1: 2-methyl-2-(m-tolyl)propanenitrile

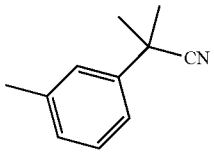

2-(m-tolyl)acetonitrile (3.75 g, 28.6 mmol) in dry THF (20 mL) was cooled at ice bath, and then NaH (60% in dispension, 2.9 g, 71.5 mmol) was added gradually. The mixture was stirred at room temperature for 30 min, and recooled at ice bath. MeI (3.91 mL, 62.8 mmol) was then added dropwise. The reaction mixture was stirred at room temperature for 16 hr. isopropanol was carefully added to the mixture followed by ethyl acetate. The organic layer was washed with water and brine, dried over anhydrous sodium sulfate. The solvent was removed and the residue was purified by silica gel to obtain the title compound. $^1$H NMR (400 MHz, CDCl$_3$) δ 7.28-7.24 (m, 3H), 7.11 (s, 1H), 2.36 (s, 3H), 1.70 (s, 6H)

Step 2:
2-(3-(bromomethyl)phenyl)-2-methylpropanenitrile

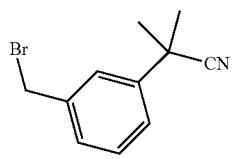

The title compound was prepared following the same general protocol as described in Step 2, Example 35, using 2-methyl-2-(m-tolyl)propanenitrile.

Step 3: allyl 1-(3-(2-cyanopropan-2-yl)benzyl)-2,3-dimethyl-1H-indole-5-carboxylate

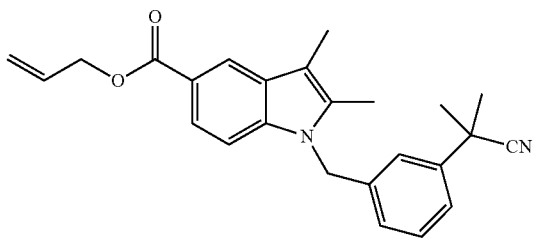 [SMILES: C=CCOC(=O)c1ccc2c(c1)c(C)c(C)n2Cc1cccc(C(C)(C)C#N)c1]

The title compound was prepared following the same general protocol as described in Step 2, Example 1, using 2-(3-(bromomethyl)phenyl)-2-methylpropanenitrile and allyl 2,3-dimethyl-1H-indole-5-carboxylate. ESI-MS (m/z): 387 [M+H]$^+$.

Step 4: 1-(3-(2-cyanopropan-2-yl)benzyl)-2,3-dimethyl-1H-indole-5-carboxylic acid

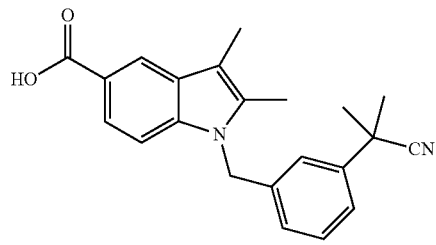

The mixture of allyl 1-(3-(2-cyanopropan-2-yl)benzyl)-2,3-dimethyl-1H-indole-5-carboxylate (0.688 g, 1.78 mmol) and morpholine (1.6 mL, 17.8 mmol) in THF (5 mL) was degassed and then Pd(PPh3)4 (0.21 g, 0.18 mmol) was added. The mixture was stirred at room temperature for 1 h. The solvent was removed and the residue was dissolved in Methanol and acidified to pH4. The solvent was removed and the residue was purified by silica gel to obtain the title compound. ESI-MS (m/z): 347 [M+H]$^+$.

Step 5: (S)-1-(3-(2-cyanopropan-2-yl)benzyl)-N-(1-(3-cyclopropylphenyl)ethyl)-2,3-dimethyl-1H-indole-5-carboxamide The title compound was prepared following the same general protocol as described in Step 4, Example 1, using (S)-1-(3-cyclopropylphenyl)ethanamine hydrochloride and 1-(3-(2-cyanopropan-2-yl)benzyl)-2,3-dimethyl-1H-indole-5-carboxylic acid. ESI-MS (m/z): 490 [M+H]$^+$.

Example 102

(S)-1-(3-(1-amino-2-methyl-1-oxopropan-2-yl)benzyl)-N-(1-(3-cyclopropylphenyl)ethyl)-2,3-dimethyl-1H-indole-5-carboxamide and (S)-2-(3-((5-(1-(3-cyclopropylphenyl)ethyl)carbamoyl)-2,3-dimethyl-1H-indol-1-yl)methyl)phenyl)-2-methylpropanoic acid

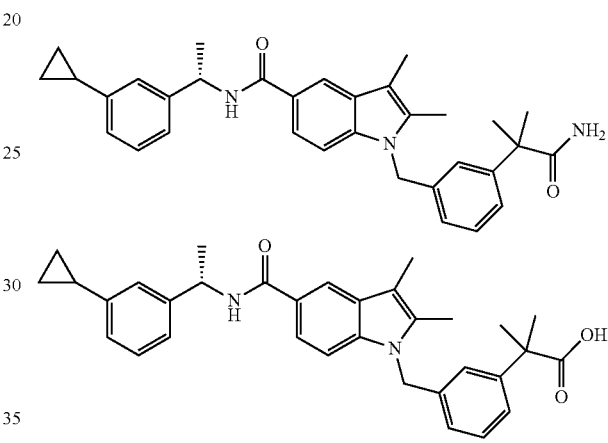

To (S)-1-(3-(2-cyanopropan-2-yl)benzyl)-N-(1-(3-cyclopropylphenyl)ethyl)-2,3-dimethyl-1H-indole-5-carboxamide (0.1 g, 0.2 mmol) in ethanol added NaOH (5 N, 1 mL). The mixture was heated at 130° C. oil bath for 2 days. The mixture was cooled to room temperature and acidified to pH 4. The solvent was removed and residue was purified by preparative-HPLC to obtain the title compounds. (S)-1-(3-(1-amino-2-methyl-1-oxopropan-2-yl)benzyl)-N-(1-(3-cyclopropylphenyl)ethyl)-2,3-dimethyl-1H-indole-5-carboxamide ESI-MS (m/z): 508 [M+H]$^+$; (S)-2-(3-((5-((1-(3-cyclopropylphenyl)ethyl)carbamoyl)-2,3-dimethyl-1H-indol-1-yl)methyl)phenyl)-2-methylpropanoic acid. ESI-MS (m/z): 509 [M+H]$^+$.

Example 103

(2S)-2-(3-(1-(5-(((S)-1-(3-cyclopropylphenyl)ethyl)carbamoyl)-2,3-dimethyl-1H-indol-1-yl)ethyl)phenoxy)propanoic acid

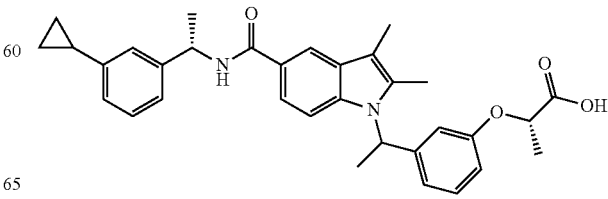

Step 1: (S)-methyl 2-(3-ethylphenoxy)propanoate

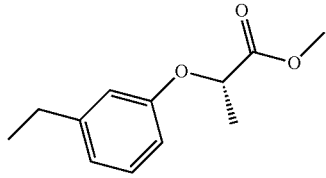

To 3-ethylphenol (3.42 g, 28 mmol) in THF (20 mL) at ice bath was added triphenylphosphine (9.5 g, 36.4 mmol) and then (R)-methyl 2-hydroxypropanoate (2.94 mL, 31 mmol). And then DIAD (8.2 mL, 42 mmol) was added dropwise to the above cole solution. The mixture was stirred at room temperature for 16 hr. The solvent was removed and the residue was purified by silica gel to obtain the title compound.

Step 2: (2S)-methyl 2-(3-(1-bromoethyl)phenoxy)propanoate

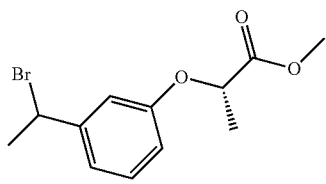 [SMILES: COC(=O)[C@H](C)Oc1cccc(C(C)Br)c1]

The title compound was prepared following the same general protocol as described in Step 2, Example 35, using (S)-methyl 2-(3-ethylphenoxy)propanoate.

Step 3: Allyl 1-(1-(3-(((S)-1-methoxy-1-oxopropan-2-yl)oxy)phenyl)ethyl)-2,3-dimethyl-1H-indole-5-carboxylate

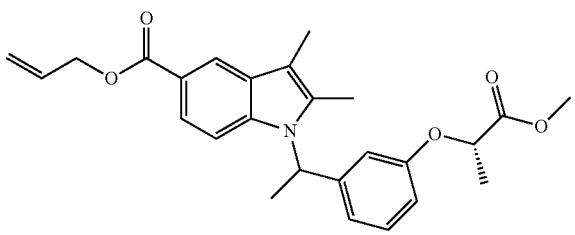 [SMILES: C=CCOC(=O)c1ccc2c(c1)c(C)c(C)n2C(C)c1cccc(O[C@@H](C)C(=O)OC)c1]

The title compound was prepared following the same general protocol as described in Step 2, Example 1, using (2S)-methyl 2-(3-(1-bromoethyl)phenoxy)propanoate and allyl 2,3-dimethyl-1H-indole-5-carboxylate.
ESI-MS (m/z): 436 [M+H]$^+$.

Step 4: 1-(1-(3-(((S)-1-methoxy-1-oxopropan-2-yl)oxy)phenyl)ethyl)-2,3-dimethyl-1H-indole-5-carboxylic acid

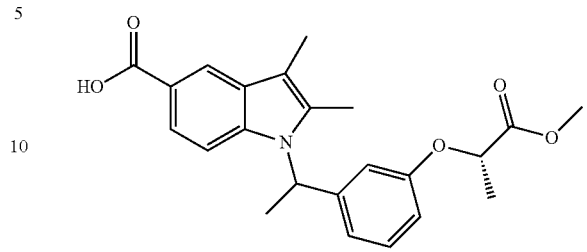

The title compound was prepared following the same general protocol as described in Step 4. Example 36, using allyl 1-(1-(3-(((S)-1-methoxy-1-oxopropan-2-yl)oxy)phenyl)ethyl)-2,3-dimethyl-1H-indole-5-carboxylate. ESI-MS (m/z): 396 [M+H]$^+$.

Step 5: (2S)-methyl 2-(3-(1-(5-(((S)-1-(3-cyclopropylphenyl)ethyl)carbamoyl)-2,3-dimethyl-1H-indol-1-yl)ethyl)phenoxy)propanoate

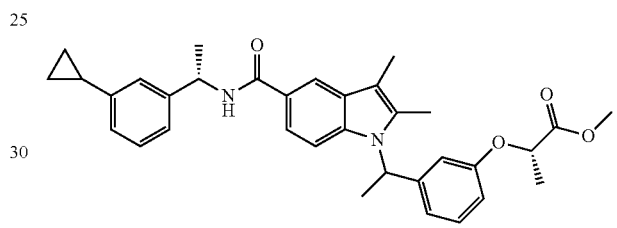

The title compound was prepared following the same general protocol as described in Step 4, Example 1, using (S)-1-(3-cyclopropylphenyl)ethanamine hydrochloride and 1-(3-(2-cyanopropan-2-yl)benzyl)-2,3-dimethyl-1H-indole-5-carboxylic acid. ESI-MS (m/z): 539 [M+H]$^+$.

Step 6: (2S)-2-(3-(1-(5-(((S)-1-(3-cyclopropylphenyl)ethyl)carbamoyl)-2,3-dimethyl-1H-indol-1-yl)ethyl)phenoxy)propanoic acid NaOH (2 N, 0.1 mL, 0.2 mmol) was added to (2S)-methyl 2-(3-(1-(5-(((S)-1-(3-cclopropylphenyl)ethyl)carbamoyl)-2,3-dimethyl-1H-indol-1-yl)ethyl)phenoxy)propanoate (0.03 g, 0.06 mmol) in Methanol (0.5 mL). The reaction mixture was acidified to pH 4. The solvent was removed and the residue was purified by preparative-HPLC to obtain the title compound. ESI-MS (m/z): 525 [M+H]$^+$.

Example 104

(2S)-2-(3-(1-(5-(((S)-1-(4-(tert-butyl)phenyl)ethyl)carbamoyl)-2,3-dimethyl-1H-indol-1-yl)ethyl)phenoxy)propanoic acid

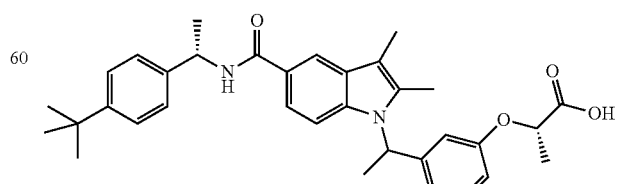

The title compound was prepared following the same general protocol as described in Step 5-6. Example 103, using (S)-1-(4-(tert-butyl)phenyl)ethanamine hydrochloride. ESI-MS (m/z): 541 [M+H]+.

Example 105

(S)-2-(3-((5-(((S)-1-(3-isopropoxyphenyl)ethyl)carbamoyl)-2,3-dimethyl-1H-indol-1-yl)methyl)phenoxy)propanoic acid

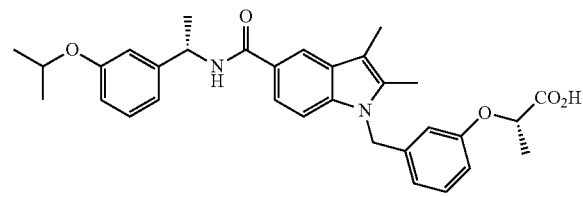 [SMILES: Cc1c(C)n(Cc2cccc(O[C@@H](C)C(=O)O)c2)c2ccc(C(=O)N[C@@H](C)c3cccc(OC(C)C)c3)cc12]

Step 1: (S)-methyl 2-(m-tolyloxy)propanoate

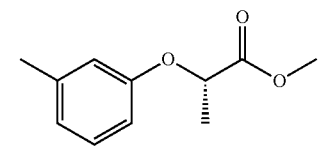

To a solution of m-cresol (5.0 g, 46 mmol, 1 equiv), methyl-D(+) lactate (4.8 g, 46 mmol, 1 equiv) and PPh$_3$ (14.5 g, 55.2 mmol, 1.2 equiv) in anhydrous THF (200 mL) under argon and at 0° C., was added dropwise DIAD (9.96 g, 48.2 mmol, 1.5 equiv). The reaction mixture was stirred at 0° C. until room temperature overnight. The crude mixture was dissolved in AcOEt (200 mL) and washed with a 0.5 N HCl aqueous solution (×2), a saturated NaHCO$_3$ solution (×2), brine and then dried over Na$_2$SO$_4$. After filtration, solvent was evaporated. The crude product was purified by flash chromatography on silica gel (AcOEt/hexane 0->60%) to obtain the title compound.

Step 2: (S)-methyl 2-(3-(bromomethyl)phenoxy)propanoate

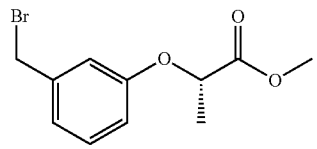

To a 250 mL round-bottom flask was (S)-methyl 2-(m-tolyloxy)propanoate (2.0 g, 10.3 mmol, 1 equiv), NBS (1.83 g, 10.3 mmol, 1 equiv), AIBN (169 mg, 1.03 mmol, 0.1 equiv) and CCl$_4$ (100 mL). The reaction mixture was refluxed for 16 h at 80° C. The completion of the reaction was monitored by analytical HPLC. The reaction mixture was allowed to cool to room temperature. The crude mixture was dissolved in AcOEt (100 mL) and washed with a 0.5N HCl aqueous solution (×2), a saturated NaHCO$_3$ solution (×2) and brine, dried over Na$_2$SO$_4$. The filtrate was concentrated to obtain the crude product which was purified by flash chromatography (AcOEt/Hexane 0->60%) to obtain the title compound.

Step 3: (S)-allyl 1-(3-((1-methoxy-1-oxopropan-2-yl)oxy)benzyl)-2,3-dimethyl-1H-indole-5-carboxylate

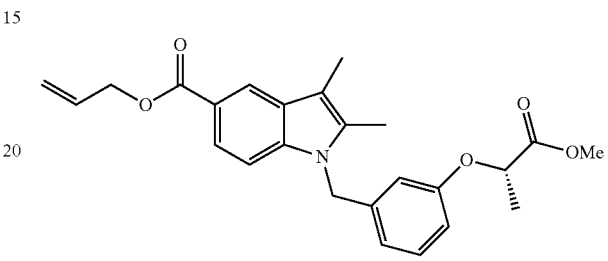

To a solution of allyl 2,3-dimethyl-1H-indole-5-carboxylate (1.0 g, 4.4 mmol, 1 equiv) and (S)-methyl 2-(3-(bromomethyl)phenoxy)propanoate (1.30 g, 4.84 mmol, 1.1 equiv) in anhydrous DMF (30 mL) under argon atmosphere was added sodium hydride (211 mg, 8.8 mmol, 2 equiv) in small portions. The mixture was stirred 2 h at room temperature. The reaction mixture was then quenched slowly with a solution of HCl 0.5 N. The residue was dissolved in AcOEt, washed with a saturated NaHCO$_3$ solution and brine, dried over MgSO$_4$. The crude was purified by flash chromatography (AcOEt/Hexane 0->60%) to afford the title compound.

Step 4: (S)-1-(3-((1-methoxy-1-oxopropan-2-yl)oxy)benzyl)-2,3-dimethyl-1H-indole-5-carboxylic acid

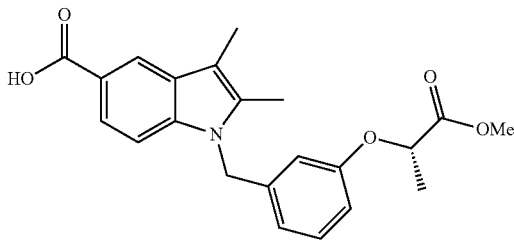 [SMILES: COC(=O)[C@H](C)Oc1cccc(Cn2c(C)c(C)c3cc(C(=O)O)ccc32)c1]

A mixture of (S)-allyl 1-(3-((1-methoxy-1-oxopropan-2-yl)oxy)benzyl)-2,3-dimethyl-1H-indole-5-carboxylate (1.0 g, 2.37 mmol, 1 equiv), Pd(PPh$_3$)$_4$ (277 mg, 0.24 mmol, 0.1 equiv), and morpholine (2 mL, 23.7 mmol, 10 equiv) in anhydrous THF (30 mL) was stirred at room temperature under argon atmosphere for 16 h. The completion of the reaction was monitored by anal. HPLC. The crude mixture was dissolved in AcOEt (100 mL) and washed with a 0.5N HCl aqueous solution (×2) and brine, then dried over Na$_2$SO$_4$. The filtrate was concentrated to obtain the crude product which was purified by flash chromatography (AcOEt/Hexane 0->60%) to obtain the title compound.

Step 5: (S)-methyl 2-(3-((5-(((S)-1-(3-isopropoxyphenyl)ethyl)carbamoyl)-2,3-dimethyl-1H-indol-1-yl)methyl)phenoxy)propanoate

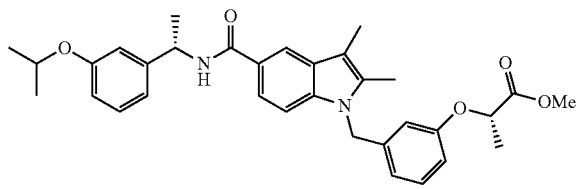 [SMILES: COC(=O)[C@H](C)Oc1cccc(Cn2c(C)c(C)c3cc(C(=O)N[C@@H](C)c4cccc(OC(C)C)c4)ccc32)c1]

To a solution of (S)-1-(3-((1-methoxy-1-oxopropan-2-yl)oxy)benzyl)-2,3-dimethyl-1H-indole-5-carboxylic acid (50 mg, 0.13 mmol, 1 equiv) in DCM (2 mL) was added (S)-1-(3-isopropoxyphenyl)ethanamine (34 mg, 0.16 mmol, 1.2 equiv), DIEA (70 µL, 0.39 mmol, 3 equiv) and HATU (50 mg, 0.13 mmol, 1 equiv). The reaction mixture was stirred 2 h at room temperature. The solvent was removed in vacuo. The residue was dissolved in AcOEt and washed with a 0.5N HCl aqueous solution, a saturated NaHCO₃ solution and brine, dried over MgSO₄. The filtrate was concentrated to obtain the crude product which was purified by flash chromatography (AcOEt/Hexane 0->50%) to obtain the title compound.

Step 6: (S)-2-(3-((5-(((S)-1-(3-isopropoxyphenyl)ethyl)carbamoyl)-2,3-dimethyl-1H-indol-1-yl)methyl)phenoxy)propanoic acid

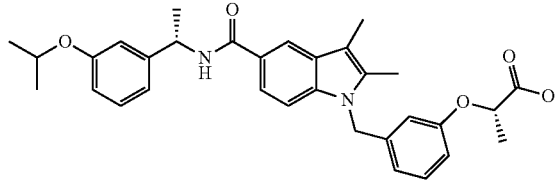

To a solution of (S)-methyl 2-(3-((5(((S)-1-(3-isopropoxyphenyl)ethyl) carbamoyl)-2,3-dimethyl-1H-indol-1-yl)methyl)phenoxy)propanoate (70 mg, 0.13 mmol, 1 equiv) in THF (2 mL) was added a 1 N LiOH aqueous solution of (1 mL). The reaction mixture was stirred 6 h at room temperature, then acidified with a 0.5 N HCl aqueous solution. The mixture was filtered and the precipitate was dissolved in methanol and concentrated to obtain the crude product which was purified by prep. HPLC (MeOH/Acetonitrile/water 0.1% TFA) to obtain the title compound.
ESI-MS (m/z): 529 [M+H]⁺.

Example 106

(S)-2-(3-((5-(((S)-1-(3-(tert-butyl)phenyl)ethyl)carbamoyl)-2,3-dimethyl-1H-indol-1-yl)methyl)phenoxy)propanoic acid

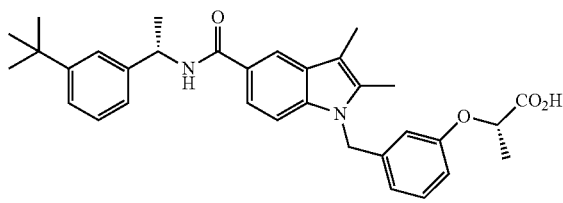 [SMILES: Cc1c(C)n(Cc2cccc(O[C@@H](C)C(=O)O)c2)c2ccc(C(=O)N[C@@H](C)c3cccc(C(C)(C)C)c3)cc12]

The title compound was prepared following the same protocol as described in Steps 4-6, Example 105, using (S)-1-(3-(tert-butyl)phenyl)ethanamine instead of the (S)-1-(3-isopropoxyphenyl)ethanamine ESI-MS (m/z): 527 [M+H]⁺.

Example 107

(S)-2-(3-((5-(((S)-1-(4-bromophenyl)ethyl)carbamoyl)-2,3-dimethyl-1H-indol-1-yl)methyl)phenoxy)propanoic acid

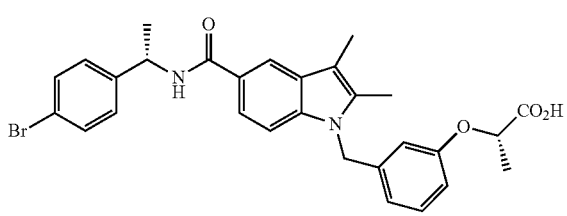

The title compound was prepared following the same protocol as described in Steps 4-6, Example 105, using (S)-1-(4-bromophenyl)ethanamine instead of the (S)-1-(3-isopropoxyphenyl)ethanamine. ESI-MS (m/z): 549 [M+H]⁺.

Example 108

(S)-2-(3-((2,3-dimethyl-5-(((S)-1-(4-(trifluoromethyl)phenyl)ethyl)carbamoyl)-1H-indol-1-yl)methyl)phenoxy)propanoic acid

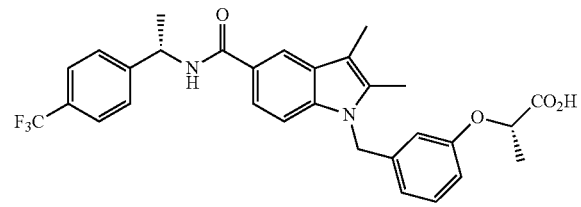 [SMILES: Cc1c(C)n(Cc2cccc(O[C@@H](C)C(=O)O)c2)c2ccc(C(=O)N[C@@H](C)c3ccc(C(F)(F)F)cc3)cc12]

The title compound was prepared following the same protocol as described in Steps 4-6, Example 105, using (S)-1-(3-(trifluoromethyl)phenyl)ethanamine instead of the (S)-1-(3-isopropoxyphenyl)ethanamine. ESI-MS (m/z): 539 [M+H]⁺.

Example 109

(S)-2-(3-((5-(((S)-1-(3-chlorophenyl)ethyl)carbamoyl)-2,3-dimethyl-1H-indol-1-yl)methyl)phenoxy)propanoic acid

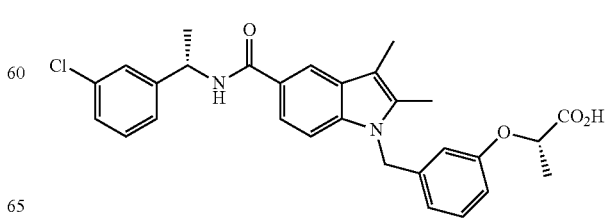

The title compound was prepared following the same protocol as described in Steps 4-6, Example 105, using (S)-1-(3-chlorophenyl)ethanamine instead of the (S)-1-(3-isopropoxyphenyl)ethanamine. ESI-MS (m/z): 505 [M+H]+.

Example 110

(S)-2-(3-((5-(((S)-1-(4-chlorophenyl)ethyl)carbamoyl)-2,3-dimethyl-1H-indol-1-yl)methyl)phenoxy)propanoic acid

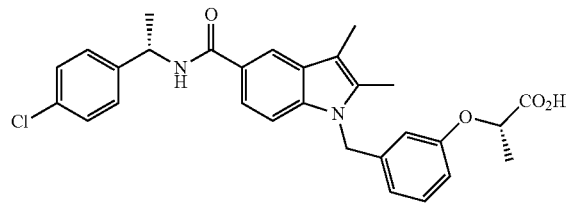 [SMILES: Cc1c(C)n(Cc2cccc(O[C@@H](C)C(=O)O)c2)c2ccc(C(=O)N[C@@H](C)c3ccc(Cl)cc3)cc12]

The title compound was prepared following the same protocol as described in Steps 4-6, Example 105, using (S)-1-(4-chlorophenyl)ethanamine instead of the (S)-1-(3-isopropoxyphenyl)ethanamine. ESI-MS (m/z): 505 [M+H]+.

Example 111

(S)-2-(3-((5-(((S)-1-(2-chlorophenyl)ethyl)carbamoyl)-2,3-dimethyl-1H-indol-1-yl)methyl)phenoxy)propanoic acid

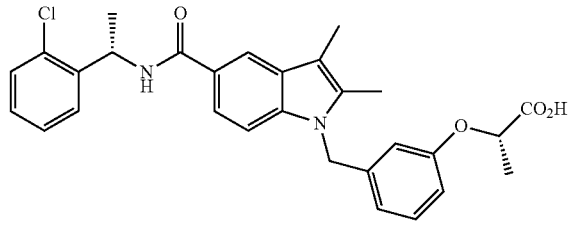 [SMILES: Cc1c(C)n(Cc2cccc(O[C@@H](C)C(=O)O)c2)c2ccc(C(=O)N[C@@H](C)c3ccccc3Cl)cc12]

The title compound was prepared following the same protocol as described in Steps 4-6, Example 105, using (S)-1-(2-chlorophenyl)ethanamine instead of the (S)-1-(3-isopropoxyphenyl)ethanamine. ESI-MS (m/z): 505 [M+H]+.

Example 112

(S)-2-(5-((5-(((S)-1-(4-(tert-butyl)phenyl)ethyl)carbamoyl)-2,3-dimethyl-1H-indol-1-yl)methyl)-2-methoxyphenoxy)propanoic acid

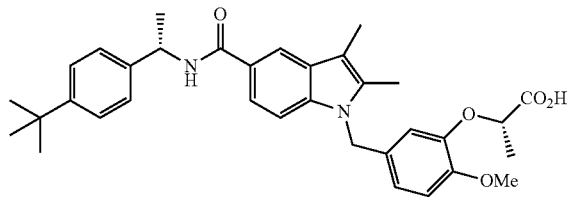 [SMILES: COc1ccc(Cn2c(C)c(C)c3cc(C(=O)N[C@@H](C)c4ccc(C(C)(C)C)cc4)ccc32)cc1O[C@@H](C)C(=O)O]

The title compound was prepared following the same protocol as described in Steps 4-6, Example 105, using (S)-1-(4-(tert-butyl)phenyl)ethanamine instead of the (S)-1-(3-isopropoxyphenyl)ethanamine ESI-MS (m/z): 557 [M+H]+.

Example 113

(S)-2-(5-((5-(((S)-1-(3-cyclopropylphenyl)ethyl)carbamoyl)-2,3-dimethyl-1H-indol-1-yl)methyl)-2-methoxyphenoxy)propanoic acid

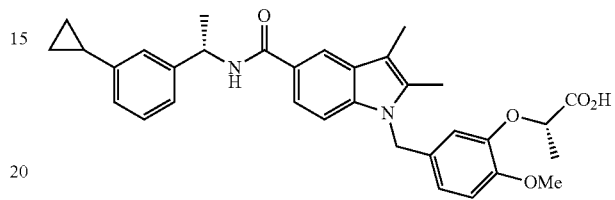

The title compound was prepared following the same protocol as described in Steps 4-6, Example 105, using (S)-1-(3-cyclopropylphenyl)ethanamine instead of the (S)-1-(3-isopropoxyphenyl)ethanamine ESI-MS (m/z): 541 [M+H]+.

Example 114

(S)-2-(3-((5-(((S)-1-(4-(tert-butyl)phenyl)ethyl)carbamoyl)-2,3-dimethyl-1H-indol-1-yl)methyl)-4-fluorophenoxy)propanoic acid

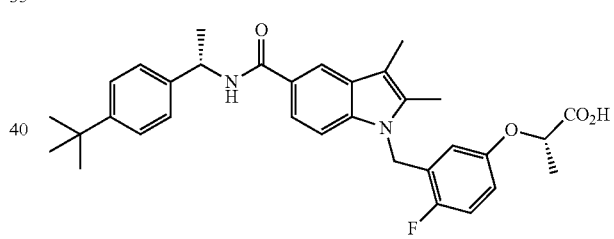

The title compound was prepared following the same protocol as described in Steps 4-6, Example 105, using (S)-1-(4-(tert-butyl)phenyl)ethanamine instead of the (S)-1-(3-isopropoxyphenyl)ethanamine ESI-MS (m/z): 545 [M+H]+.

Example 115

(S)-2-(5-((5-(((S)-1-(4-(tert-butyl)phenyl)ethyl)carbamoyl)-2,3-dimethyl-1H-indol-1-yl)methyl)-2-fluorophenoxy)propanoic acid

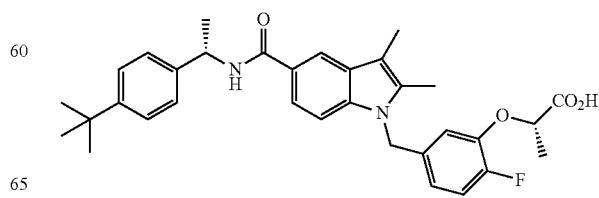

215

The title compound was prepared following the same protocol as described in Steps 4-6, Example 105, using (S)-1-(4-(tert-butyl)phenyl)ethanamine instead of the (S)-1-(3-isopropoxyphenyl)ethanamine ESI-MS (m/z): 545 [M+H]⁺.

Example 116

(S)-2-(5-((5-(((S)-1-(3-cyclopropylphenyl)ethyl)carbamoyl)-2,3-dimethyl-1H-indol-1-yl)methyl)-2-fluorophenoxy)propanoic acid

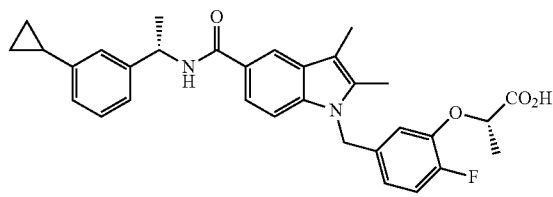 [SMILES: Cc1c(C)n(Cc2ccc(F)c(O[C@@H](C)C(=O)O)c2)c2ccc(C(=O)N[C@@H](C)c3cccc(C4CC4)c3)cc12]

The title compound was prepared following the same protocol as described in Steps 4-6, Example 105, using (S)-1-(3-cyclopropylphenyl)ethanamine instead of the (S)-1-(3-isopropoxyphenyl)ethanamine ESI-MS (m/z): 529 [M+H]⁺.

Example 117

(S)-2-(3-((5-(((S)-1-(4-methoxyphenyl)ethyl)carbamoyl)-2,3-dimethyl-1H-indol-1-yl)methyl)phenoxy)propanoic acid

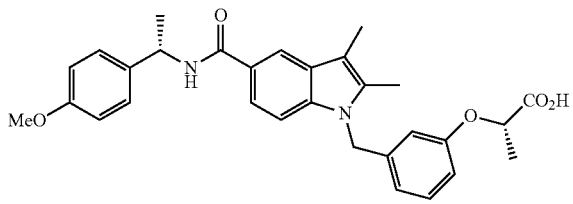 [SMILES: COc1ccc([C@H](C)NC(=O)c2ccc3c(c2)c(C)c(C)n3Cc2cccc(O[C@@H](C)C(=O)O)c2)cc1]

The title compound was prepared following the same protocol as described in Steps 4-6, Example 105, using (S)-1-(4-methoxyphenyl)ethanamine instead of the (S)-1-(3-isopropoxyphenyl)ethanamine. ESI-MS (m/z): 501 [M+H]⁺.

Example 118

(2S)-2-(4-(1-(5-(((S)-1-(4-(tert-butyl)phenyl)ethyl)carbamoyl)-2,3-dimethyl-1H-indol-1-yl)ethyl)phenoxy)propanoic acid

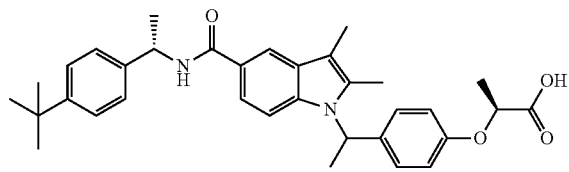 [SMILES: Cc1c(C)n(C(C)c2ccc(O[C@@H](C)C(=O)O)cc2)c2ccc(C(=O)N[C@@H](C)c3ccc(C(C)(C)C)cc3)cc12]

216

Step 1: 4-Ethylphenyl acetate

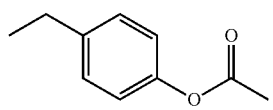

To a stirred solution of 4-ethylphenol (3.38 g, 27.67 mmol) in DCM (50 mL) in an ice bath was added TEA (7.2 mL, 55.34 mmol), followed by the dropwise addition of acetyl chloride (2.2 mL, 30.44 mmol). The mixture was stirred at room temperature for 30 min. The reaction mixture was quenched with water (40 mL) and extracted with DCM (3×50 mL). The combined organic layers were washed with brine, dried over Na₂SO₄, filtered and concentrated under reduced pressure and purified by silica gel chromatography to obtain the title compound.

Step 2: 4-(1-Bromoethyl)phenyl acetate

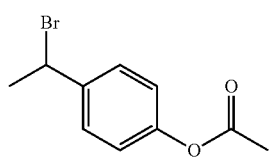

The title compound was prepared following the same general protocol as described in Step 2, Example 35, using 4-ethylphenyl acetate.

¹H NMR (400 MHz, CDCl₃) δ 7.45 (d, J=8.8 Hz, 2H), 7.06 (d, J=8.8 Hz, 2H), 5.21 (q, J=7.2 Hz, 1H), 2.99 (s, 3H), 2.04 (d, J=6.8 Hz, 3H).

Step 3: Allyl 1-(1-(4-hydroxyphenyl)ethyl)-2,3-dimethyl-1H-indole-5-carboxylate

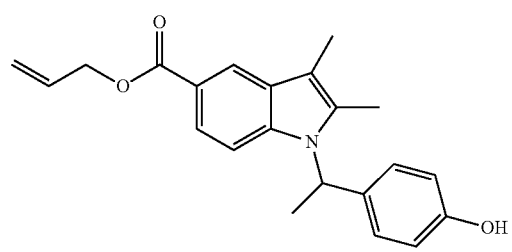 [SMILES: C=CCOC(=O)c1ccc2c(c1)c(C)c(C)n2C(C)c1ccc(O)cc1]

The title compound was prepared following the same general protocol as described in Step 2, Example 1, using 4-(1-bromoethyl)phenyl acetate and allyl 2,3-dimethyl-1H-indole-5-carboxylate.

To the above reaction mixture was added saturated Na₂CO₃ solution (20 mL) and the mixture was stirred at room temperature for 1 h. The mixture was diluted with EtOAc, followed by the addition of a saturated NH₄Cl solution. The aqueous layer was removed and the organic layer was washed with water and then brine and dried over Na₂SO₄. The solvent was removed under reduced pressure and the residue was purified by silica gel chromatography to obtain the title compound. ESI-MS (m/z): 350 [M+H]+.

Step 4: Allyl 1-(1-(4-(((S)-1-methoxy-1-oxopropan-2-yl)oxy)phenyl)ethyl)-2,3-dimethyl-1H-indole-5-carboxylate

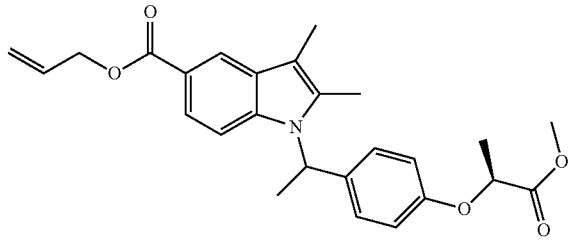 [SMILES: C=CCOC(=O)c1ccc2c(c1)c(C)c(C)n2C(C)c1ccc(O[C@@H](C)C(=O)OC)cc1]

To allyl 1-(1-(4-hydroxyphenyl)ethyl)-2,3-dimethyl-1H-indole-5-carboxylate (0.286 g, 0.82 mmol) in THF (0.8 mL) in an ice bath was added triphenylphosphine (0.28 g, 1.07 mmol) and then (R)-methyl 2-hydroxypropanoate (0.093 mL, 0.98 mmol). DIAD (0.24 mL, 1.23 mmol) was added dropwise to the cold solution. The mixture was stirred at room temperature for 16 hr. The solvent was removed and the residue was purified by silica gel chromatography to obtain the title compound. ESI-MS (m/z): 436 [M+H]+.

Step 5: 1-(1-(4-(((S)-1-Methoxy-1-oxopropan-2-yl)oxy)phenyl)ethyl)-2,3-dimethyl-1H-indole-5-carboxylic acid

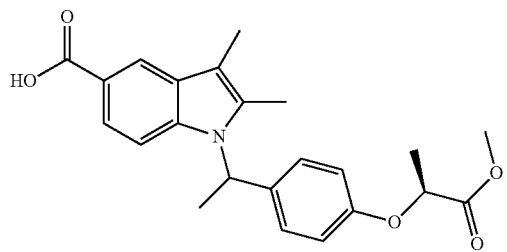 [SMILES: COC(=O)[C@H](C)Oc1ccc(C(C)n2c(C)c(C)c3cc(C(=O)O)ccc32)cc1]

The mixture of allyl 1-(1-(4-(((S)-1-methoxy-1-oxopropan-2-yl)oxy)phenyl)ethyl)-2,3-dimethyl-1H-indole-5-carboxylate (0.55 g, 1.26 mmol) and morpholine (1.0 mL, 12.6 mmol) in THF (5 mL) was degassed and then Pd(PPh3)4 (0.15 g, 0.13 mmol) was added. The mixture was stirred at room temperature for 1 h. The solvent was removed and the residue was dissolved in Methanol and acidified to pH 4. The solvent was removed and the residue was purified by silica gel chromatography to obtain the title compound. ESI-MS (m/z): 396 [M+H]+.

Step 6: (2S)-Methyl 2-(4-(1-(5-(((S)-1-(4-(tert-butyl)phenyl)ethyl)carbamoyl)-2,3-dimethyl-1H-indol-1-yl)ethyl)phenoxy)propanoate

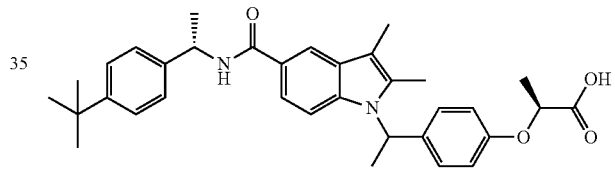

The title compound was prepared following the same general protocol as described in Step 5, Example 35, using (S)-1-(4-(tert-butyl)phenyl)ethanamine instead of (S)-1-(3-bromophenyl)ethylamine and 1-(1-(4-(((S)-1-methoxy-1-oxopropan-2-yl)oxy)phenyl)ethyl)-2,3-dimethyl-1H-indole-5-carboxylic acid instead of 1-(4-(1-(methoxycarbonyl)cyclopropyl)benzyl)-2,3-dimethyl-1H-indole-5-carboxylic acid'

Step 7: (2S)-2-(4-(1-(5-(((S)-1-(4-(tert-butyl)phenyl)ethyl)carbamoyl)-2,3-dimethyl-1H-indol-1-yl)ethyl)phenoxy)propanoic acid

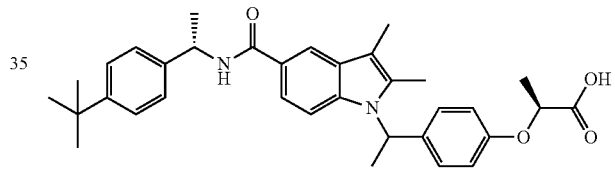

A solution of (2S)-methyl 2-(4-(1-(5-(((S)-1-(4-(tert-butyl)phenyl)ethyl)carbamoyl)-2,3-dimethyl-1H-indol-1-yl)ethyl)phenoxy)propanoate (~0.07 mmol) and NaOH (2 M, 0.2 mL) in MeOH (2 mL) and DMF (1 mL) was stirred at rt for 5 h. It was neutralized and purified by preparative HPLC to yield the title compound as a white solid. ESI-MS (m/z): 541 [M+H]+.

Example 119

(2S)-2-(4-(1-(5-(((S)-1-(3-Cyclopropylphenyl)ethyl)carbamoyl)-2,3-dimethyl-1H-indol-1-yl)ethyl)phenoxy)propanoic acid

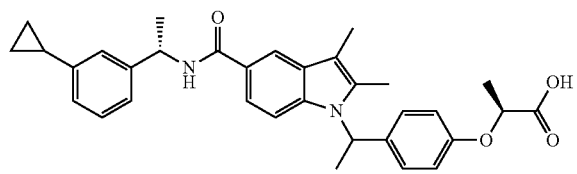 [SMILES: Cc1c(C)n(C(C)c2ccc(O[C@@H](C)C(=O)O)cc2)c2ccc(C(=O)N[C@@H](C)c3cccc(C4CC4)c3)cc12]

The title compound was prepared following the same general protocol as described in the previous example. ESI-MS (m/z): 525 [M+H]⁺.

Example 120

(S)-1-(3-((5-((1-(3-Cyclopropylphenyl)ethyl)carbamoyl)-2,3-dimethyl-1H-indol-1-yl)methyl)phenyl)cyclopropanecarboxylic acid

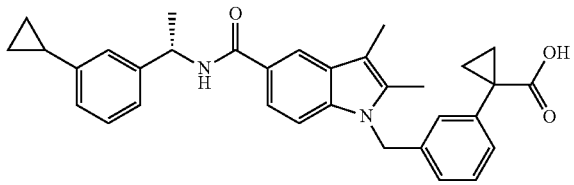 [SMILES: Cc1c(C)n(Cc2cccc(C3(C(=O)O)CC3)c2)c2ccc(C(=O)N[C@@H](C)c3cccc(C4CC4)c3)cc12]

Step 1: 1-(m-Tolyl)cyclopropanecarbonitrile

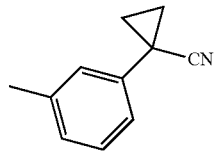

To a stirred solution of 2-(m-tolyl)acetonitrile (4.2 g, 32 mmol) in toluene (15 mL) was added sodium hydroxide (30 mL, 50% w/w in water, 375 mmol), 1-bromo-2-chloroethane (9.3 mL, 112 mmol) and (n-Bu)₄Br (0.5 g, 1.55 mmol). The mixture was heated at 60° C. overnight. After cooling to room temperature, the reaction mixture was diluted with water (40 mL) and extracted with EtOAc (3×50 mL). The combined organic layers were washed with brine, dried over Na₂SO₄, filtered and concentrated under reduced pressure and purified by silica gel chromatography to obtain the title compound.

¹H NMR (400 MHz, CDCl₃) δ 7.26-7.22 (m, 1H), 7.13-7.05 (m, 3H), 2.36 (s, 3H), 1.72-1.68 (m, 2H), 1.41-1.38 (m, 2H).

Step 2: 1-(3-(Bromomethyl)phenyl)cyclopropanecarbonitrile

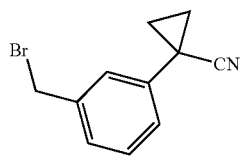 [SMILES: N#CC1(c2cccc(CBr)c2)CC1]

The title compound was prepared following the same general protocol as described in Step 2, Example 35, using 1-(m-tolyl)cyclopropanecarbonitrile.

Step 3: Allyl 1-(3-(1-cyanocyclopropyl)benzyl)-2,3-dimethyl-1H-indole-5-carboxylate

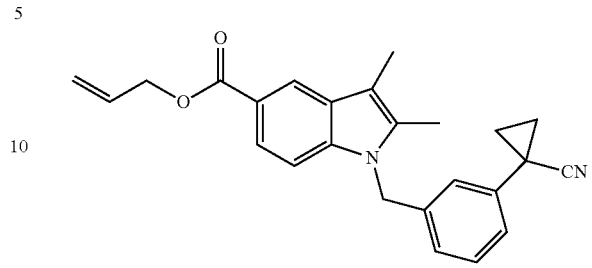

The title compound was prepared following the same general protocol as described in Step 2, Example 1, using 1-(3-(bromomethyl)phenyl)cyclopropanecarbonitrile and allyl 2,3-dimethyl-1H-indole-5-carboxylate.

Step 4: 1-(3-(1-Cyanocyclopropyl)benzyl)-2,3-dimethyl-1H-indole-5-carboxylic acid

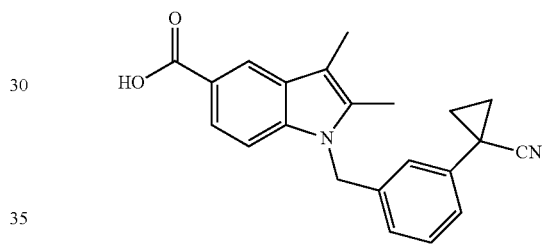

The mixture of allyl 1-(3-(1-cyanocyclopropyl)benzyl)-2,3-dimethyl-1H-indole-5-carboxylate (375 mg, 0.98 mmol) and morpholine (0.8 mL, 9.2 mmol) in THF (8 mL) was degassed and then Pd(PPh₃)₄ (117 mg, 0.10 mmol) was added. The mixture was stirred at room temperature for 1 h. The solvent was removed and the residue was dissolved in Methanol and acidified to pH 4. The precipitate was collected and washed with water to obtain the title compound.

Step 5: (S)-1-(3-(1-Cyanocyclopropyl)benzyl)-N-(1-(3-cyclopropylphenyl)ethyl)-2,3-dimethyl-1H-indole-5-carboxamide

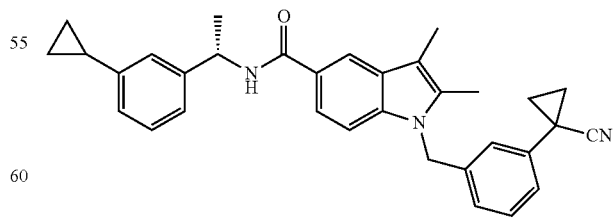

The title compound was prepared following the same general protocol as described in Step 5, Example 35, using 1-(3-(1-cyanocyclopropyl)benzyl)-2,3-dimethyl-1H-indole-5-carboxylic acid and (S)-1-(3-cyclopropylphenyl)ethanamine.

Step 6: (S)-1-(3-((5-((1-(3-Cyclopropylphenyl)ethyl)carbamoyl)-2,3-dimethyl-1H-indol-1-yl)methyl)phenyl)cyclopropanecarboxylic acid

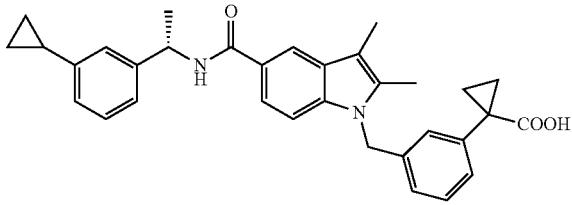 [SMILES: Cc1c(C)n(Cc2cccc(C3(C(=O)O)CC3)c2)c2ccc(C(=O)N[C@@H](C)c3cccc(C4CC4)c3)cc12]

To a solution of (S)-1-(3-(1-Cyanocyclopropyl)benzyl)-N-(1-(3-cyclopropylphenyl)ethyl)-2,3-dimethyl-1H-indole-5-carboxamide (~0.2 mmol) in Ethanol was added NaOH (5 N, 1 mL). The mixture was heated at 130° C. in an oil bath for 14 days. The mixture was cooled to room temperature and acidified to pH 4. The solvent was removed and the residue was purified by preparative-HPLC to obtain the title compound. ESI-MS (m/z): 507 [M+H]$^+$.

Example 121

((S)-3-((5-((1-(3-Cyclopropylphenyl)ethyl)carbamoyl)-2,3-dimethyl-1H-indol-1-yl)methyl)benzoic acid

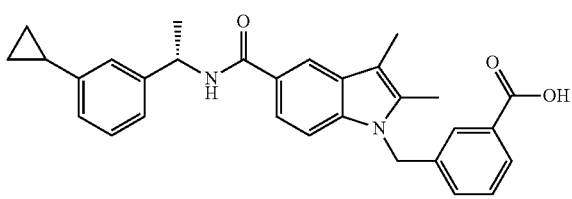 [SMILES: Cc1c(C)n(Cc2cccc(C(=O)O)c2)c2ccc(C(=O)N[C@@H](C)c3cccc(C4CC4)c3)cc12]

Step 1: Allyl 1-(3-(methoxycarbonyl)benzyl)-2,3-dimethyl-1H-indole-5-carboxylate

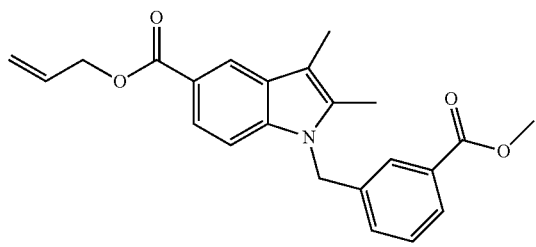 [SMILES: C=CCOC(=O)c1ccc2c(c1)c(C)c(C)n2Cc1cccc(C(=O)OC)c1]

The title compound was prepared following the same general protocol as described in Step 2, Example 1, using methyl 3-(bromomethyl)benzoate and allyl 2,3-dimethyl-1H-indole-5-carboxylate.

Step 4: 1-(3-(Methoxycarbonyl)benzyl)-2,3-dimethyl-1H-indole-5-carboxylic acid

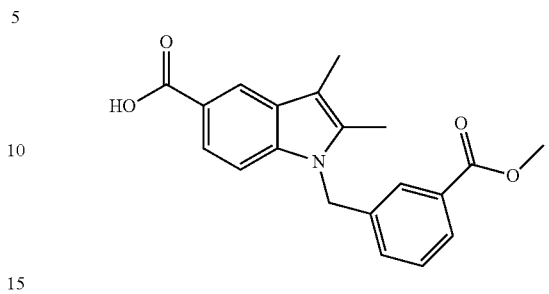

The mixture of allyl 1-(3-(methoxycarbonyl)benzyl)-2,3-dimethyl-1H-indole-5-carboxylate (133 mg, 0.35 mmol) and morpholine (0.3 mL, 3.4 mmol) in THF (4 mL) was degassed and then Pd(PPh$_3$)$_4$ (41 mg, 0.035 mmol) was added. The mixture was stirred at room temperature for 1 h. The solvent was removed and the residue was dissolved in Methanol and acidified to pH 4. The precipitate was collected and washed with water to obtain the title compound.

Step 5: (S)-Methyl 3-((5-((1-(3-cyclopropylphenyl)ethyl)carbamoyl)-2,3-dimethyl-1H-indol-1-yl)methyl)benzoate

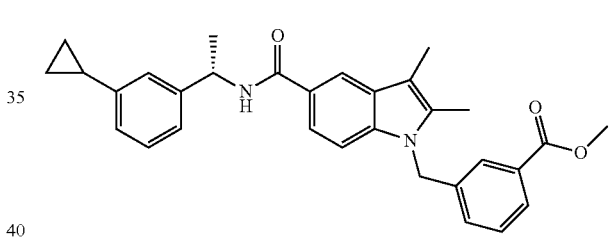

The title compound was prepared following the same general protocol as described in Step 5, Example 35, using 1-(3-(methoxycarbonyl)benzyl)-2,3-dimethyl-1H-indole-5-carboxylic acid and (S)-1-(3-cyclopropylphenyl)ethanamine.

Step 6: ((S)-3-((5-((1-(3-Cyclopropylphenyl)ethyl)carbamoyl)-2,3-dimethyl-1H-indol-1-yl)methyl)benzoic acid

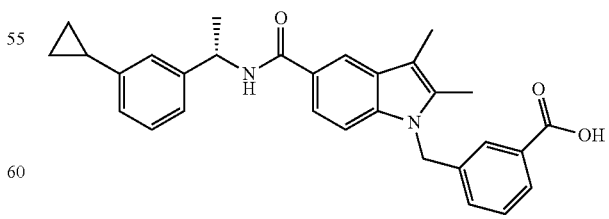

A solution of (S)-Methyl 3-((5-((1-(3-cyclopropylphenyl)ethyl)carbamoyl)-2,3-dimethyl-1H-indol-1-yl)methyl)benzoate (~0.07 mmol) and NaOH (2 M, 0.5 mL) in MeOH (2 mL) and DMSO (1 mL) was stirred at rt for 15 h. It was

Example 122

(S)-1-(3-Carbamoylbenzyl)-N-(1-(3-cyclopropylphenyl)ethyl)-2,3-dimethyl-1H-indole-5-carboxamide

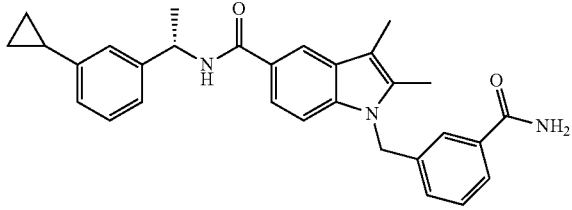 [SMILES: Cc1c(C)n(Cc2cccc(C(N)=O)c2)c2ccc(C(=O)N[C@@H](C)c3cccc(C4CC4)c3)cc12]

The title compound was prepared following the same general protocol as described in Step 5, Example 35. ESI-MS (m/z): 466 [M+H]+.

Example 123

(S)-2-(5-(((S)-1-(3-isopropylphenyl)ethyl)carbamoyl)-2,3-dimethyl-1H-indol-1-yl)methyl)-2-methoxyphenoxy)propanoic acid

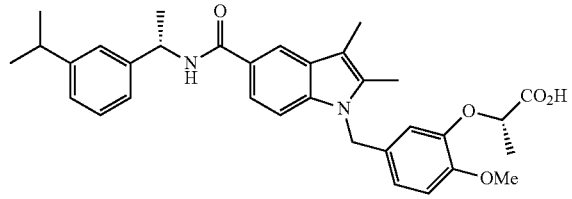 [SMILES: COc1ccc(Cn2c(C)c(C)c3cc(C(=O)N[C@@H](C)c4cccc(C(C)C)c4)ccc32)cc1O[C@@H](C)C(=O)O]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride, followed by an ester hydrolysis step as outlined in Step 6, example 36.

Example 124

(S)-2-(2-fluoro-5-((5-(((S)-1-(3-isopropylphenyl)ethyl)carbamoyl)-2,3-dimethyl-1H-indol-1-yl)methyl)phenoxy)propanoic acid

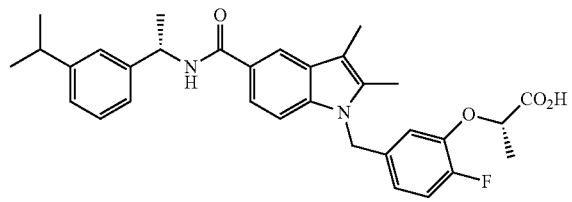 [SMILES: Cc1c(C)n(Cc2ccc(F)c(O[C@@H](C)C(=O)O)c2)c2ccc(C(=O)N[C@@H](C)c3cccc(C(C)C)c3)cc12]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and (S)-1-(4-fluoro-3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid, followed by an ester hydrolysis step as outlined in Step 6, example 36.

Bioassay Procedures

Lanthascreen PPARG Competitive Binding Assay (Invitrogen)

The assay was performed according to manufacturer protocol. A mixture of 5 nM GST-PPARG-LBD, 5 nM Tb-GST-antibody, 5 nM Fluormone Pan-PPAR Green, and serial dilutions of the experimental compound, beginning at 10 µM downwards, was added to wells of black 384-well low-volume plates (Greiner) to a total volume of 18 µL. All dilutions were made in TR-FRET assay buffer C. DMSO at 2% final concentration was used as a no-ligand control. Experiment was performed in triplicate, and incubated for 2 hours in the dark prior to assay read in Perkin Elmer ViewLux ultra HTS microplate reader. FRET signal was measured by excitation at 340 nm and emission at 520 nm for fluorescein and 490 nm for terbium. Fold change over DMSO was calculated using GraphPad Prism Software (La Jolla, Calif.) by calculating 520 nm/490 nm ratio. Graphs were plotted as fold change of FRET signal for compound treatment over DMSO-only control.

Cell-based Transactivation Assays:

PPRE is a DNA that contains a binding site for PPARG; thus PPRE is a PPAR response element, used herein as a promoter reporter. The binding site is a DR1 response element with the sequence AGGTCA repeated 3 times in tandem and then fused to a construct for luciferase.

Thus, PPRE is the basis of the cell based transactivation assay described below. The plasmid DNA is co-transfected along with a plasmid for PPARG into COS-1 cells. After an overnight incubation, cells are treated with DMSO or compounds. In this assay rosiglitazone activates the reporter about 5 fold. Partial agonists such as MRL24 transactivate the reporter about 25% of rosiglitazone response. Compounds of the invention which are non-activators afford no transactivation of the reporter.

Confluent COS-1 cells were transfected with 4.5 µg murine PPARg2-pSV Sport or full-length human PPARg-pSport6, 4.5 µg 3×PPRE-luciferase reporter and 27 µL X-treme Gene 9 transfection reagent in serum-free opti-mem media (Gibco), followed by overnight incubation at 37° C., 5% $CO_2$. Transfected cells were plated in white Perkin Elmer 384-well plates and incubated 4 hours. Cells were treated with DMSO vehicle only or experimental compounds in increasing doses from 2 µM-220 pM for mouse receptor and 10 µM-111 fM for human. After 18 hour incubation, treated cells were developed with Brite Lite Plus (Perkin Elmer) and read in 384-well Luminescence Perkin Elmer EnVision Multilabel plate reader. Graphs were plotted in triplicate in GraphPad Prism Software as fold change of treated cells over DMSO control cells.

Biodata Tables 1-3, below, provides biological data for the specifically claimed compounds as shown in Table 1, above, showing compound examples of the invention. Each line in the Biodata Tables represents biodata for a single compound of the set of compounds listed in Table 1 with respect to $IC_{50}$ as determined by the Lanthascreen procedure and $EC_{50}$ as determined by the cell-based transactivation assay. A compound with a relatively low $IC_{50}$ concentration is indicated to have potent PPARG binding activity, whereas a compound with a relatively high $EC_{50}$ value in the cell-based transactivation assay is indicated to possess non-agonistic properties.

In various embodiments, the invention provides compounds combining these two properties, non-agonistic and PPARG binding.

The human PPAR nuclear receptor ligand binding domain (LBD) is fused to the DNA-Binding Domain of the yeast GAL4 transcription factor. The hybrid fusion-protein nuclear receptor can activate the luciferase reporter under the control of the GAL4 Upstream Activator Sequence (UAS).

The plasmid Gal4-PPAR DNA is co-transfected along with a plasmid for UAS-luc into HEK 293T cells. After an overnight incubation, cells are treated with DMSO or compounds. In this assay rosiglitazone activates the reporter about 100-fold. Partial agonists transactivate the reporter about 30-40% of rosiglitazone response. Compounds of the invention which are non-activators exhibit <5% transactivation of the receptor at 1 µM.

HEK 293T cells were transfected with 4.5 µg of Gal4-PPARg, 4.5 µg UAS-luciferase reporter and 27 µL X-treme Gene 9 transfection reagent in serum-free opti-mem media (Gibco), followed by overnight incubation at 37° C., 5% $CO_2$. Transfected cells were replated in white Perkin Elmer 384-well plates and incubated 4 hours. Cells were treated with DMSO vehicle only or experimental compounds in doses from 10 µM-111 fM. After 18 hour incubation, treated cells were developed with Brite Lite Plus (Perkin Elmer) and read in 384-well Luminescence Perkin Elmer EnVision Multilabel plate reader. Graphs were plotted in triplicate in GraphPad Prism Software as fold change of treated cells over DMSO control cells.

Evaluations

It is within ordinary skill to evaluate any compound disclosed and claimed herein for effectiveness in non-agonistic binding to PPARG and in the various cellular assays using the procedures described above or found in the scientific literature. Accordingly, the person of ordinary skill can prepare and evaluate any of the claimed compounds without undue experimentation.

Any compound found to be an effective non-agonist PPARG binding molecular entity can likewise be tested in animal models and in human clinical studies using the skill and experience of the investigator to guide the selection of dosages and treatment regimens.

BIODATA TABLE 1

| Ex. | $IC_{50}$ (nM) Lantha | $EC_{50}$ (nM) PPRE |
|---|---|---|
| 1 | 317 | 400 (15%) |
| 2 | >1000 | NT |
| 3 | 300 | 450 (13%) |
| 4 | 292 | NT |
| 5 | 154 | NT |
| 7 | 9 | 4 (38%) |
| 8 | 1 | 0.5 (37%) |
| 9 | 5 | 24 (13%) |
| 10 | 31 | 12 (12%) |
| 11 | 4 | 13 (11%) |
| 12 | 7 | 3 (11%) |
| 14 | >1000 | NT |
| 15 | 49 | 65 (8%) |
| 16 | 14 | 41 (17%) |
| 17 | <1 | <1 (14%) |
| 18 | >1000 | NT |
| 19 | 6700 | NT |
| 20 | 147 | NT |
| 21 | <1 | <1 (37%) |
| 22 | 29 | 21 (15%) |
| 24 | >1000 | NT |
| 25 | 1000 | NT |
| 26 | >1000 | NT |
| 27 | 563 | 275 (18%) |
| 28 | 98 | 10 (21%) |
| 30 | 7 | 25 (25%) |
| 32 | 3 | 10 (19%) |
| 35 | 44 | NT |
| 36 | 126 | NA (0%)* |
| 37 | 124 | 6000 (5%)* |
| 38 | 370 | NA (0%)* |
| 39 | 56 | NA (0%)* |
| 40 | 69 | NA (0%)* |

*GAL-4 transactivation data; NA = no activity; NT = not tested; $EC_{50}$'s measured at 10 µM drug

BIODATA TABLE 2

| Ex. | $IC_{50}$ (nM) Lantha | $EC_{50}$ (nM) GAL4 |
|---|---|---|
| 41 | 131 | NA (0%) |
| 42 | 550 | NT |
| 43 | >1000 | NT |
| 44 | 76 | 4000 (4%) |
| 45 | 60 | 1204 (1%) |
| 46 | 59 | NA (0%) |
| 47 | 107 | 980 (8%) |
| 48 | 321 | 7260 (4%) |
| 49 | 74 | 653 (20%) |
| 50 | 107 | 1500 (18%) |
| 51 | 313 | 6121 (10%) |
| 53 | 107 | 3783 (10%) |
| 54 | 101 | NA (0%) |
| 55 | 0.6 | 187 (3%) |
| 56 | 0.6 | 202 (3%) |
| 57 | 0.7 | 311 (10%) |
| 58 | 0.2 | NA (0%) |
| 59 | 1.6 | NA (0%) |
| 60 | 5 | NA (0%) |
| 61 | 0.06 | NA (0%) |
| 62 | 0.6 | NA (0%) |
| 63 | 0.3 | 564 (15%) |
| 64 | 0.2 | NA (0%) |
| 65 | 1.6 | NA (0%) |
| 66 | 5 | 595 (20%) |
| 90 | 31 | 1274 (10%) |
| 91 | 318 | NA (0%) |
| 92 | 76 | 4000 (4%) |
| 93 | 25 | 916 (5%) |
| 94 | 67 | NT |

NA = no activity; NT = not tested; $EC_{50}$'s measured at 10 µM drug

BIODATA TABLE 3

| Ex. | $IC_{50}$ (nM) Lantha | $EC_{50}$ (nM) GAL4 |
|---|---|---|
| 95 | 143 | NT |
| 96 | 351 | NT |
| 97 | 4000 | NT |
| 98 | 263 | NT |
| 99 | 151 | NT |
| 100 | 358 | NT |
| 101 | 120 | NT |
| 102 | 233; 24 | NT; 470 (5%) |
| 103 | 97 | 4861 (10%) |
| 104 | 255 | NT |
| 105 | 59 | NA (0%) |
| 106 | 82 | NA (0%) |
| 107 | 104 | NT |
| 108 | 213 | NT |
| 109 | 61 | 1276 (10%) |
| 110 | 82 | NT |
| 111 | 40 | 1129 (15%) |
| 112 | 61 | NA (0%) |
| 113 | 70 | NT |
| 114 | 10 | NA (0%) |
| 115 | 16 | NA (0%) |
| 116 | 20 | 431 (4%) |

BIODATA TABLE 3-continued

| Ex. | IC$_{50}$ (nM) Lantha | EC$_{50}$ (nM) GAL4 |
|---|---|---|
| 120 | 13 | 123 (8%) |
| 121 | 39 | 310 (10%) |
| 123 | 77 | 242 (4%) |

NA = no activity; NT = not tested; EC$_{50}$'s measured at 10 μM drug

Statements of the Invention

1. A non-agonist PPARG modulatory compound of formula (I) or a pharmaceutically acceptable salt thereof:

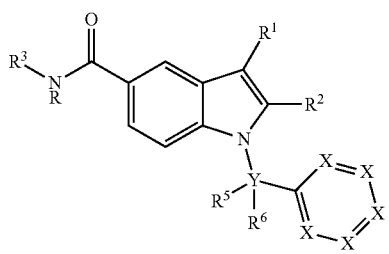

wherein:

R is H, (C$_1$-C$_6$)alkyl, (C$_3$-C$_9$)cycloalkyl, or (C$_1$-C$_6$)haloalkyl;

each X is independently N, CH, or CR$^4$, provided that no more than two instances of X are N, and no more than three instances of X are CR$^4$;

R$^1$ and R$^2$ are independently H, (C$_1$-C$_6$)alkyl, (C$_3$-C$_9$)cycloalkyl, or (C$_1$-C$_6$)haloalkyl; or R$^1$ and R$^2$ together with the atoms to which they are bonded form a 5- to 9-membered ring, comprising 0-3 heteroatoms selected from the group consisting of O, NR, and SO$_q$ wherein q is 0, 1, or 2, and optionally mono- or pluri-substituted with independently selected (C$_1$-C$_6$)alkyl, (C$_2$-C$_6$)alkenyl, (C$_2$-C$_6$)alkynyl, (C$_6$-C$_{10}$)aryl, (C$_3$-C$_9$)cycloalkyl, halo, (C$_1$-C$_6$)haloalkyl, nitro, cyano-(C$_0$-C$_6$)alkyl, R'O$_2$C—(C$_0$-C$_6$)alkyl, methylenedioxy, R'O—(C$_0$-C$_6$)alkyl, (R')$_2$N—(C$_0$-C$_6$)alkyl, (R')$_2$NC(=O)—(C$_0$-C$_6$)alkyl, (C$_1$-C$_6$)alkyl-S(O)$_q$(C$_0$-C$_6$)alkyl, aryl, aroyl, or SO$_2$NR'$_2$;

R$^3$ is optionally mono- or multi-substituted (C$_1$-C$_6$)alkyl, (C$_1$-C$_6$)alkenyl, (C$_1$-C$_6$)alkynyl, aryl, arylalkyl, heteroaryl, heteroarylalkyl, cycloalkyl, heterocyclyl, cycloalkylalkyl, or heterocyclylalkyl; wherein if present each substituent on R$^3$ is independently selected from the group consisting of (C$_1$-C$_6$)alkyl, (C$_2$-C$_6$)alkenyl, (C$_2$-C$_6$)alkynyl, (C$_6$-C$_{10}$)aryl, (C$_3$-C$_9$)cycloalkyl, 3-9 membered mono- and bicyclic heterocyclyl, 3-9 membered mono- and bicyclic heteroaryl, halo, haloalkyl, haloalkoxy, nitro, cyano, CO$_2$R', methylenedioxy, OR', N(R')$_2$, C(O)N(R')$_2$, (C$_1$-C$_4$)alkyl-S(O)$_q$, SO$_2$NR'$_2$, and (C$_1$-C$_6$)alkoxyl, wherein R' is independently H, (C$_1$-C$_6$) alkyl, (C$_1$-C$_6$) haloalkyl, or (C$_3$-C$_9$)cycloalkyl, or wherein two R' bonded to an atom together with the atom form a 3-8 membered ring optionally further comprising a heteroatom selected from the group consisting of O, NR', and S(O)$_q$, and wherein alkyl, alkenyl, alkynyl, aryl, arylalkyl, or cycloalkyl is optionally mono- or independently multi-substituted with (C$_1$-C$_6$)alkyl, (C$_1$-C$_6$)haloalkyl, (C$_1$-C$_6$)alkoxy, (C$_1$-C$_6$)haloalkoxy, halo, OR', N(R')$_2$, aryl, or aroyl; and wherein an alkyl or an alkyl group of a cycloalkylalkyl, heterocyclylalkyl, arylalkyl or heteroarylalkyl can be substituted with oxo;

each R$^4$ is independently halo, nitro, (C$_1$-C$_6$)fluoroalkyl, R"-(C$_1$-C$_6$)alkyl, R"O$_2$C—(C$_0$-C$_6$)alkyl, NC—(C$_0$-C$_6$)alkyl, R"O—(C$_0$-C$_6$)alkyl, (R")$_2$N—(C$_0$-C$_6$)alkyl, (R')$_2$NC(=O)—(C$_0$-C$_6$)alkyl, C-bonded tetrazolyl, (1,3,4-oxadiazol-2(3H)-on)-yl, (1,2,4-oxadiazol-5(4H)-on)-3-yl, (C$_1$-C$_6$)alkyl-S(O)$_q$(C$_0$-C$_6$)alkyl, an unsubstituted or substituted aryl, an unsubstituted or substituted heteroaryl, (C$_1$-C$_6$)alkyl or (C$_3$-C$_9$)cycloalkyl-(C$_0$-C$_6$)alkyl, wherein any alkyl or cycloalkyl is optionally mono- or independently multi-substituted with R", OR", N(R")$_2$, C-bonded tetrazolyl, (C$_1$-C$_6$)alkyl-S(O)$_q$(C$_0$-C$_6$)alkyl, an unsubstituted or substituted aryl, or an unsubstituted or substituted heteroaryl; or R$^4$ is —(C(R")$_2$)$_m$CO$_2$R", —(C(R")$_2$)$_m$CON(R")$_2$, or —(C(R")$_2$)$_m$CN; m is 1, 2, 3, 4, 5, or 6;

R" is independently H, OH, (C$_1$-C$_6$)alkyl or (C$_3$-C$_9$)cycloalkyl-(C$_0$-C$_6$)alkyl; or R" is independently (C$_1$-C$_6$)haloalkyl, —(C(R')$_2$)$_m$CO$_2$R, —(C(R')$_2$)$_m$CON(R)$_2$, —(C(R')$_2$)$_m$CON(R)OH, or —(C(R')$_2$)$_m$CN; or R" is C-bonded tetrazolyl, C-bonded oxadiazolonyl, (C$_1$-C$_6$)alkyl-(1,3,4-oxadiazol-2(3H)-on)-yl, (C$_1$-C$_6$)alkyl-(1,2,4-oxadiazol-5(4H)-on)-3-yl, (C$_1$-C$_4$)alkyl-S(O)$_q$(C$_0$-C$_6$)alkyl, an unsubstituted or substituted aryl, or an unsubstituted or substituted heteroaryl; or two R" bonded to an atom together with the atom form a 3-8 membered ring optionally further comprising a heteroatom selected from the group consisting of O, NR, and S(O)$_q$; and wherein any alkyl or cycloalkyl moiety of R" is optionally mono- or independently multi-substituted with (C$_1$-C$_6$)alkyl, (C$_1$-C$_6$)haloalkyl, (C$_1$-C$_6$)alkoxy, (C$_1$-C$_6$)haloalkoxy, halo, cyano, CO$_2$R, OR, N(R), aryl, or aroyl; and wherein an alkyl, or an alkyl moiety or a cycloalkyl moiety or a heterocyclyl moiety of a cycloalkylalkyl, heterocyclylalkyl, arylalkyl or heteroarylalkyl, can be substituted with oxo;

q is 0, 1, or 2;

Y is (C$_1$-C$_2$)alkyl, or sulfur;

when Y is (C$_1$-C$_2$)alkyl, R$^5$ and R$^6$ are independently H or (C$_1$-C$_4$)alkyl or independently each R$^5$ and R$^6$ together with the carbon atom to which they are bonded form a carbonyl; and, when Y is sulfur, R$^5$ and R$^6$ are both oxygen.

2. The compound of statement 1 wherein R$^1$ and R$^2$ are independently H or methyl.

3. The compound of statement 1 or 2 wherein one instance of X is N.

4. The compound of any one of statements 1-3 wherein R$^3$ is benzyl, α-phenethyl, α-phenpropyl, cycloalkyl or cycloalkylalkyl, any of which is unsubstituted or substituted.

5. The compound of any one of statements 1-3 wherein R$^3$ is unsubstituted or substituted naphthyl or naphthylalkyl.

6. The compound of any one of statements 1-3 wherein R$^3$ is heterocyclyl, heterocyclylalkyl, heteroaryl, or heteroarylalkyl, any of which is unsubstituted or substituted.

7. The compound of any one of statements 1-6 wherein the compound is represented by formula (II)

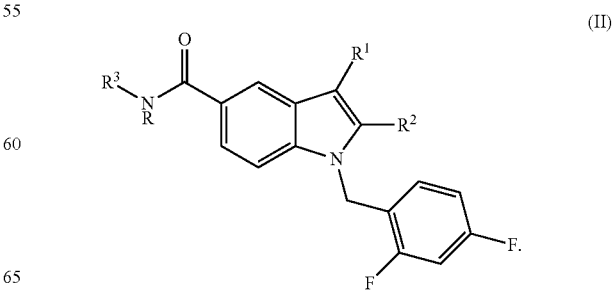

8. The compound of any one of statements 1-6 wherein YR$^5$R$^6$ is SO$_2$.
9. The compound of any one of statements 1-6 wherein Y is C$_1$-alkyl; and R$^5$ and R$^6$ are H, or wherein Y is C$_2$-alkyl, and R$^5$ and R$^6$ are H.
10. The compound of any one of statements 1-6 wherein R$^4$ is
—CO$_2$H, —(CH$_2$)$_m$CO$_2$H,
—O(CH$_2$)$_m$CO$_2$H, —CN, —(CH$_2$)$_m$CN, —O(CH$_2$)$_m$CN, —C(CH$_3$)$_2$CO$_2$H, —C(CH$_3$)$_2$CN,
—OC(CH$_3$)$_2$CO$_2$H, —OC(CH$_3$)$_2$CN, —CH(CH$_3$)CO$_2$H, —CH(CH$_3$)CN, —OCH(CH$_3$)CO$_2$H,
—OCH(CH$_3$)CN; —CH(CH$_2$CH$_3$)CO$_2$H, —CH(CH$_2$CH$_3$)CN, —OCH(CH$_2$CH$_3$)CO$_2$H,
—OCH(CH$_2$CH$_3$)CN; —CH(i-Pr)CO$_2$H, —CH(i-Pr)CN, —OCH(i-Pr)CO$_2$H, —OCH(i-Pr)CN, wherein iPr indicates isopropyl; —CH(t-Bu)CO$_2$H, —CH(t-Bu)CN, —OCH(t-Bu)CO$_2$H, —OCH(t-Bu)CN, wherein t-Bu indicates t-butyl;
—(CHR″)$_m$C(=O)N(R″)$_2$, —O(CHR″)$_m$C(=O)N(R″)$_2$,

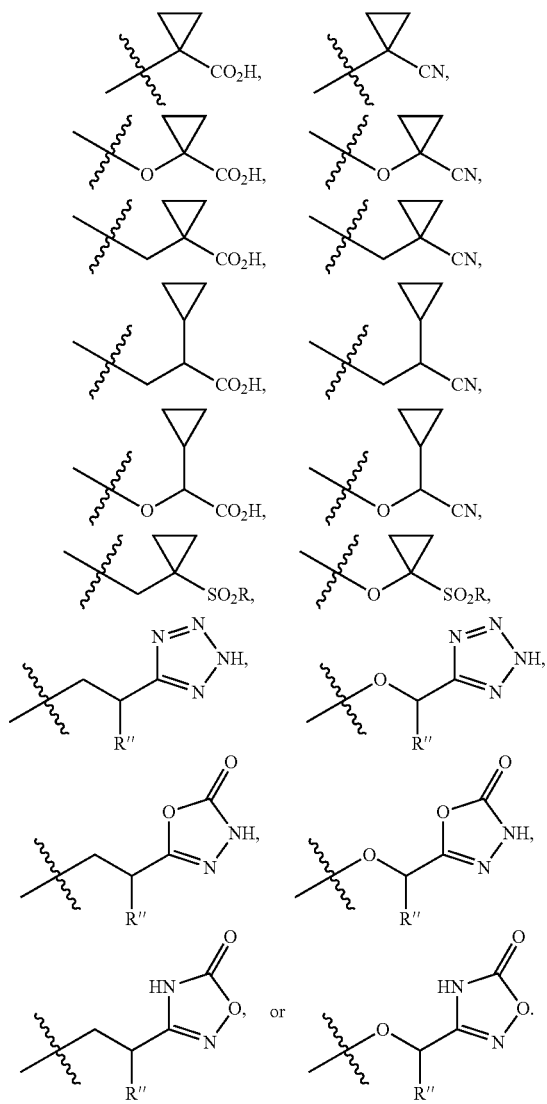

whereas R″ is as defined in statement 1; wherein a wavy line indicates a point of attachment.
11. The compound of statement 10 wherein n is 1 and R$^4$ is disposed para to Y.

12. The compound of statement 1 wherein R$^3$ is any one of:

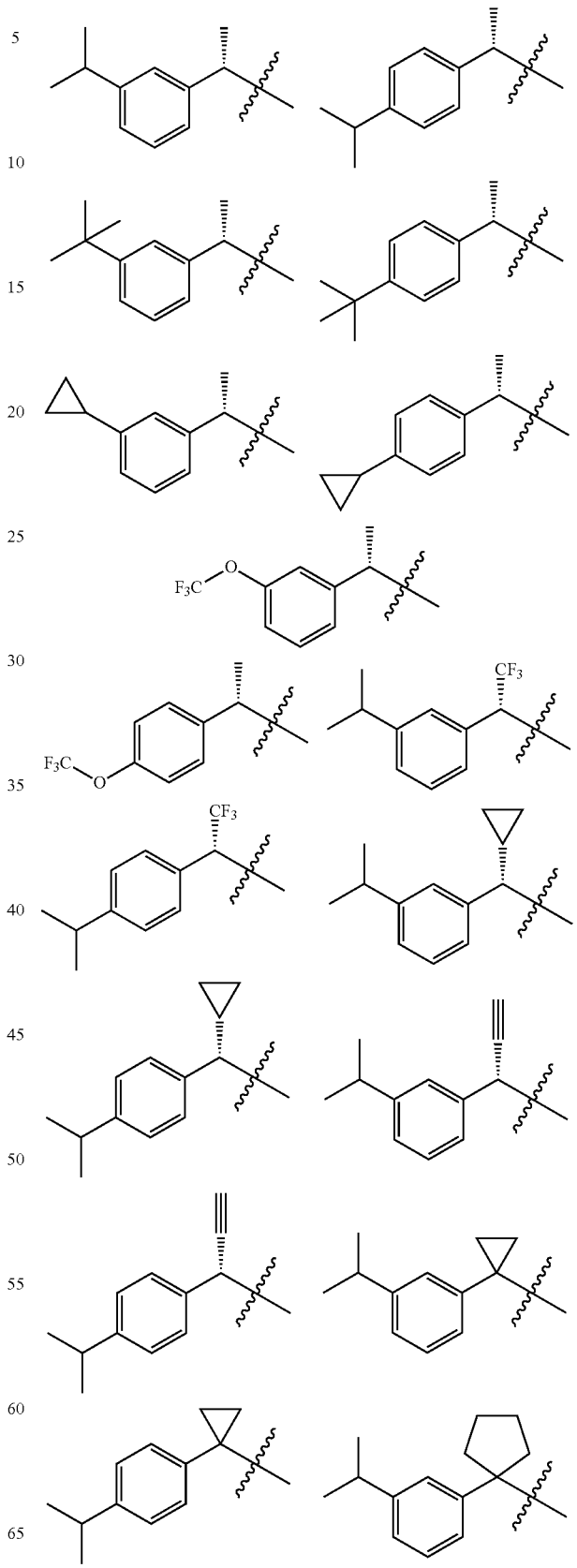

231
-continued
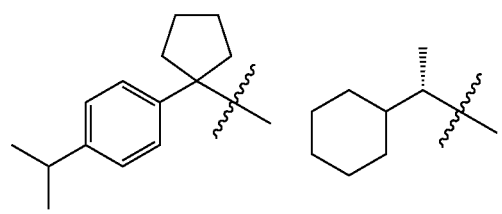
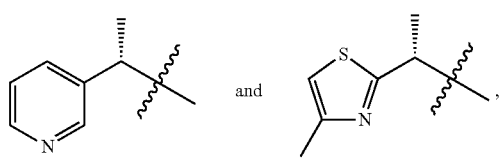 and
wherein a wavy line indicates a point of attachment.
13. The compound of statement 1 wherein the compound is any one of:
1
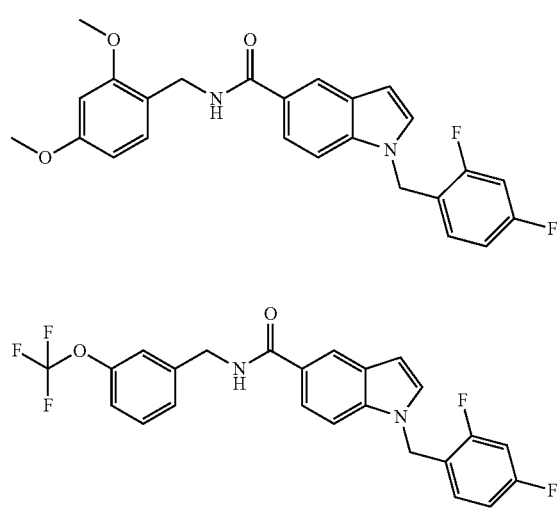
2
3
4
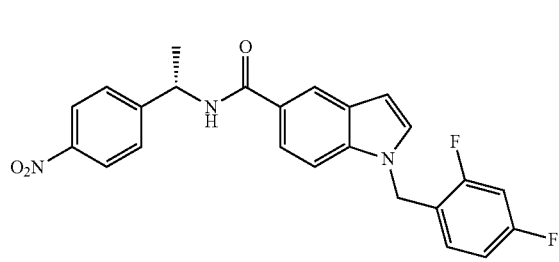
232
-continued
5
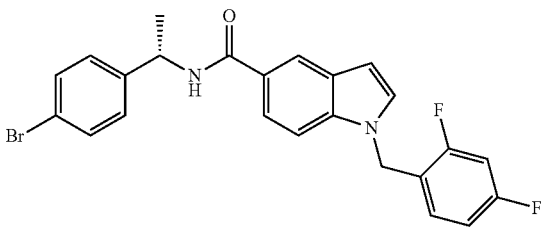
6
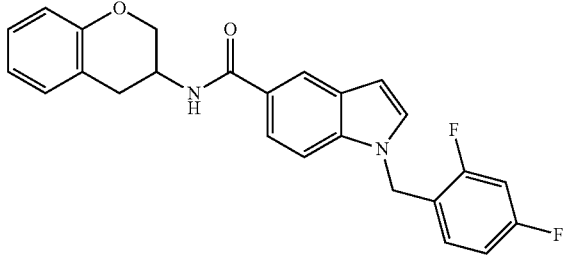
7
8
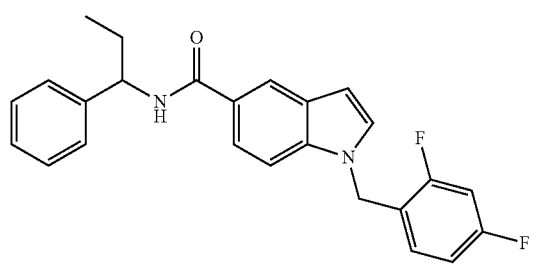
9
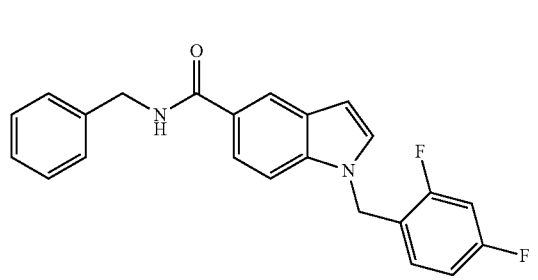
10
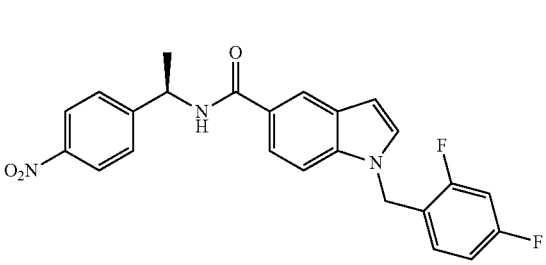

-continued
11
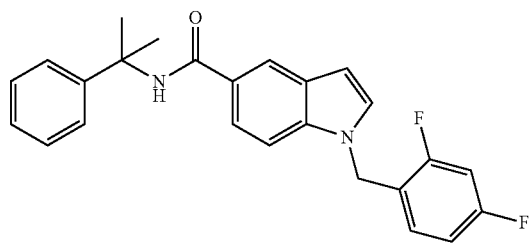
12
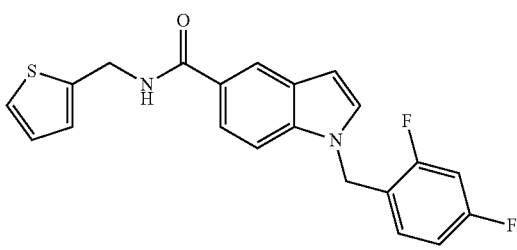
13
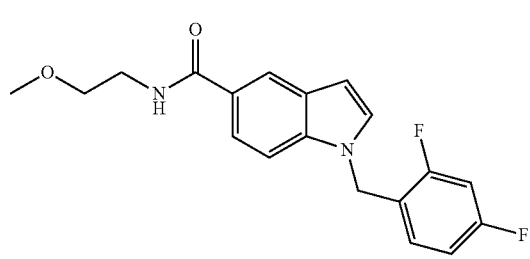
14
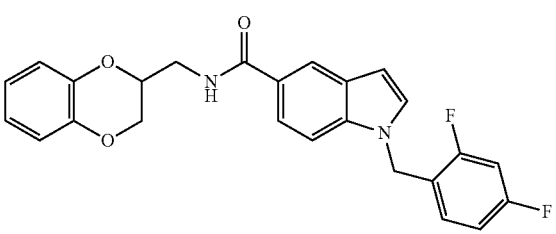
15
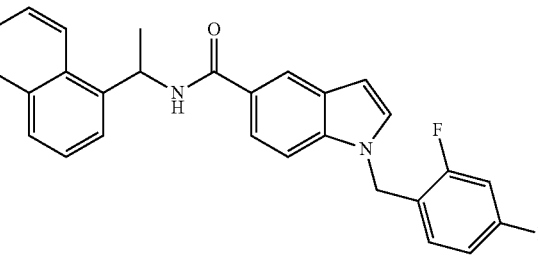
16
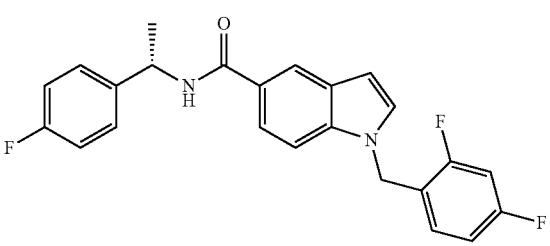
-continued
17
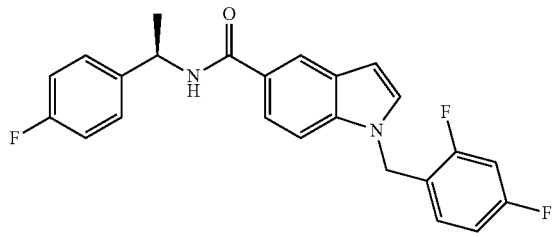
18
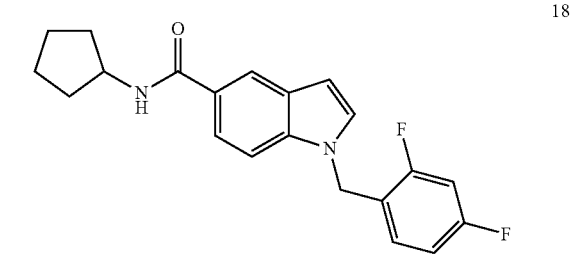
19
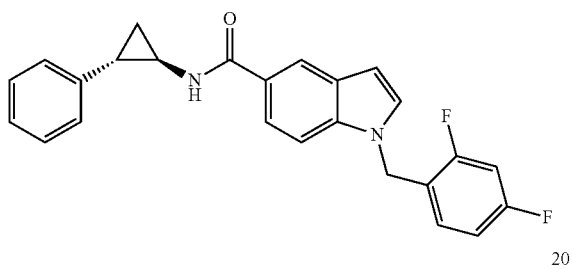
20
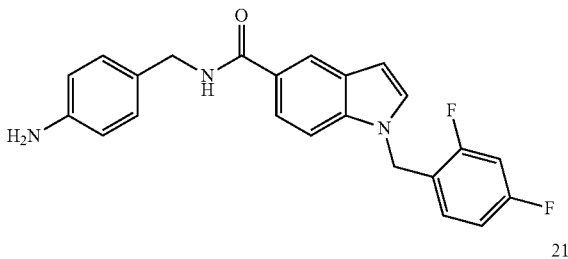
21
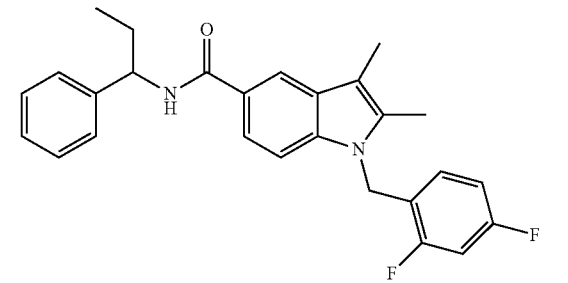
22
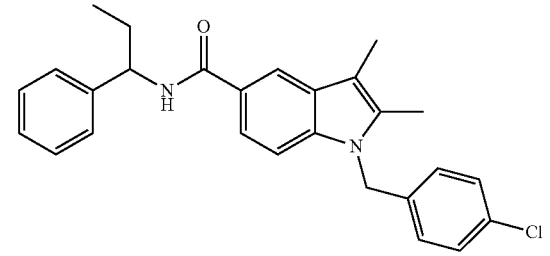

235
-continued
24
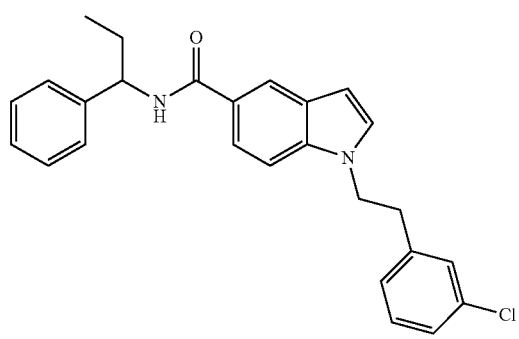
25
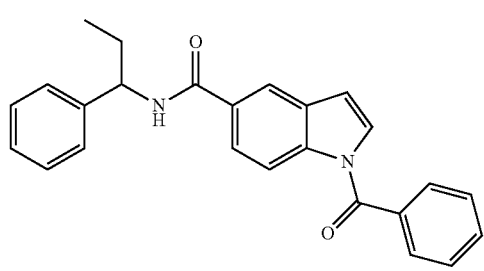
26
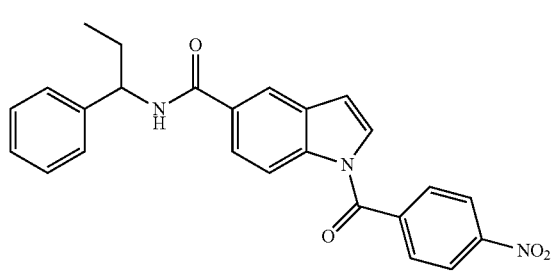
27
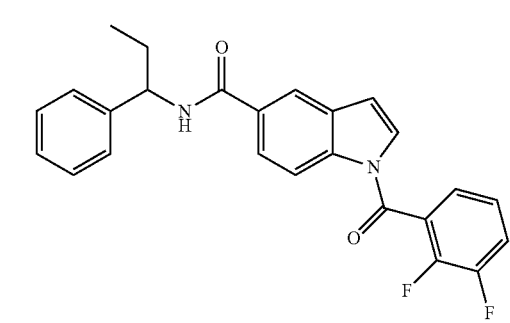
28
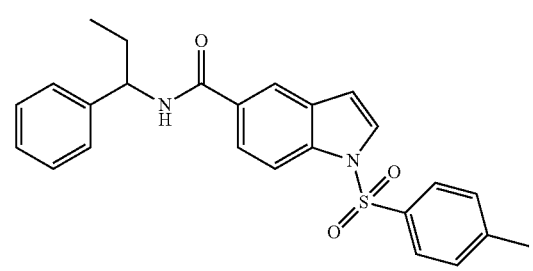
236
-continued
30
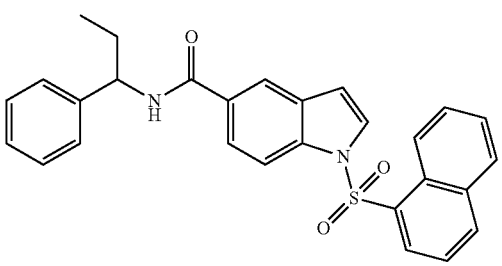
31
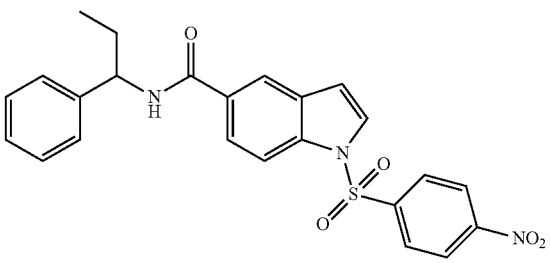
32
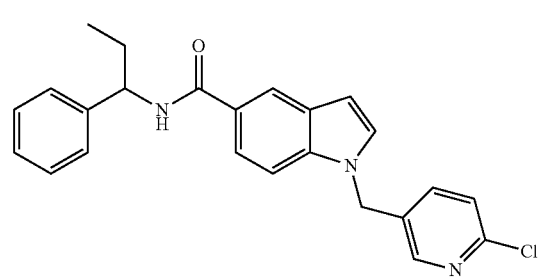
33
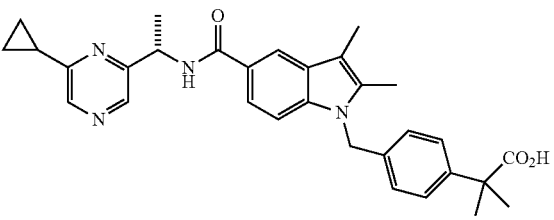
34
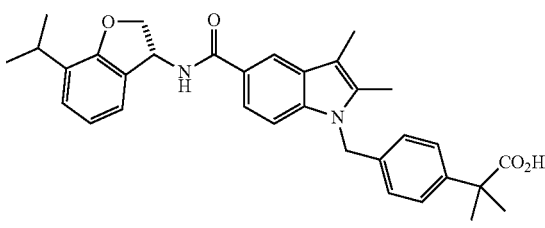
35
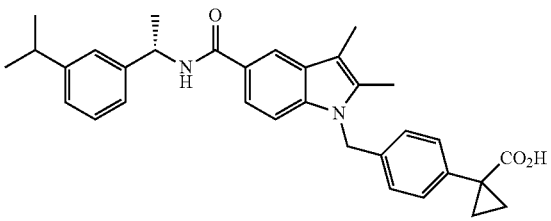

36
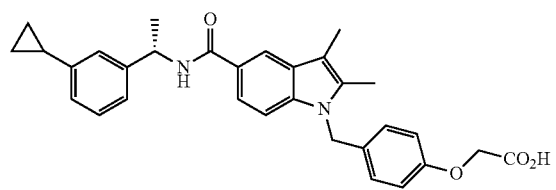
37
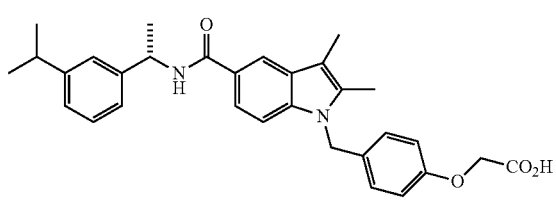
38
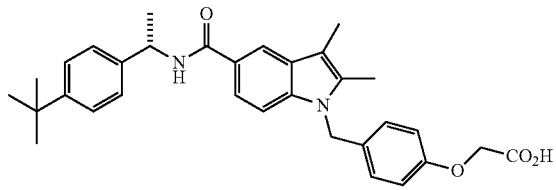
39
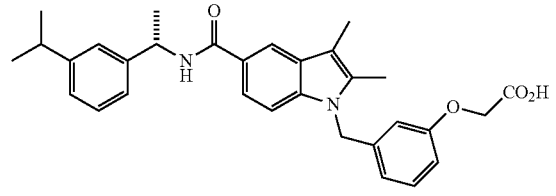
40
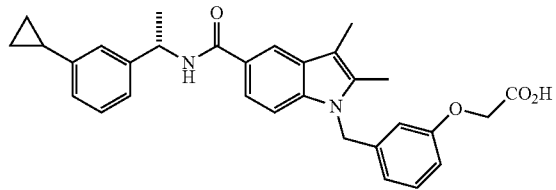
41
42
43
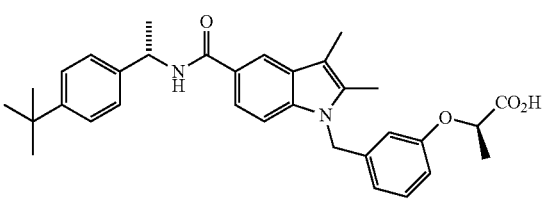
44
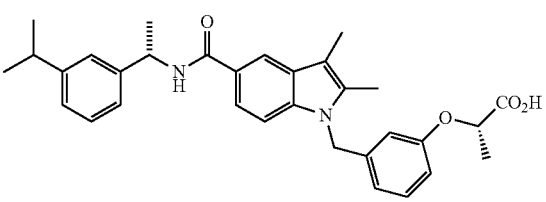
45
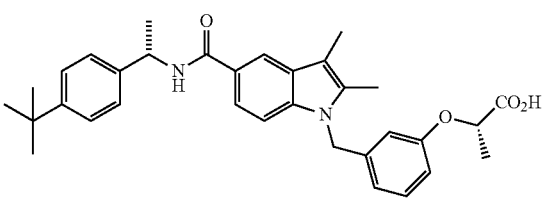
46
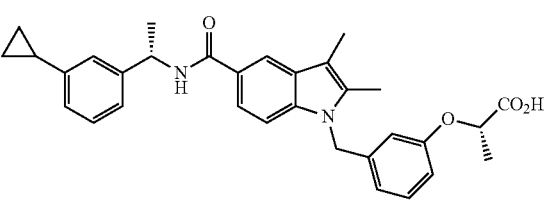
47
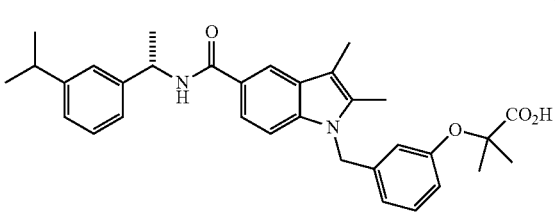
48
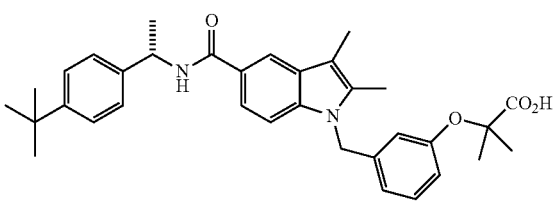
49
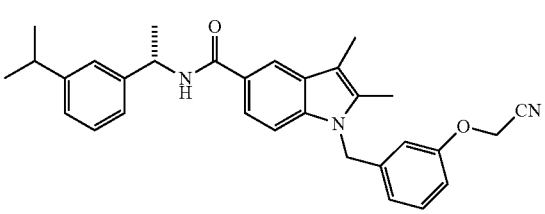

239
50 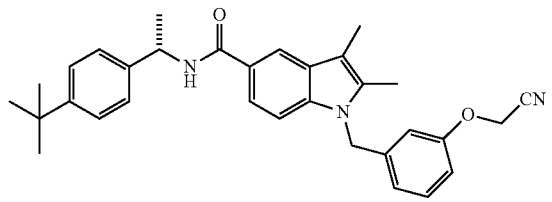
51 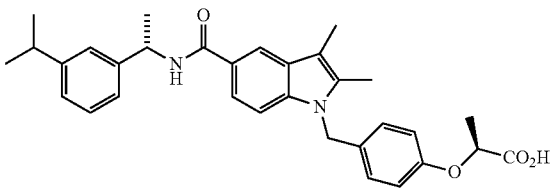
52 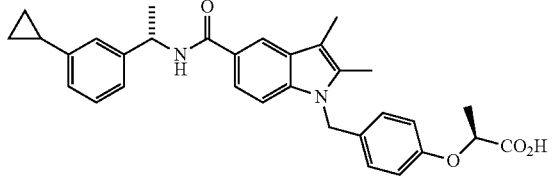
53 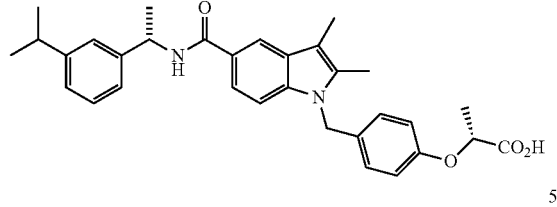
54 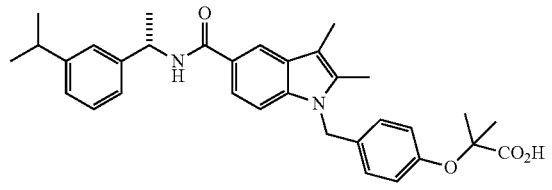
55 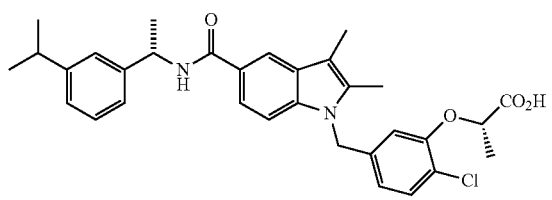
56 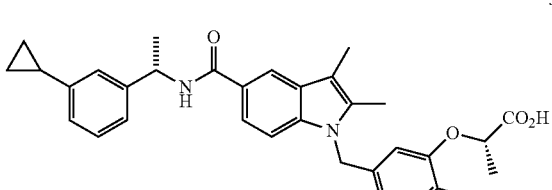
240
57 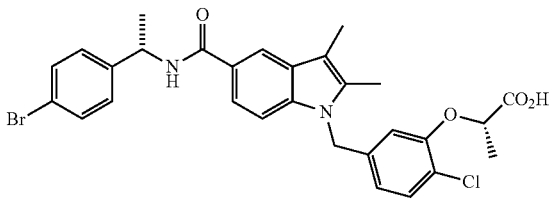
58 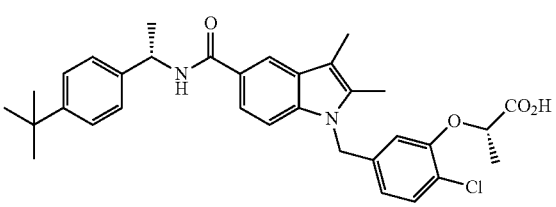
59 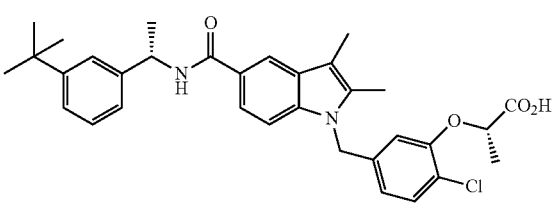
60 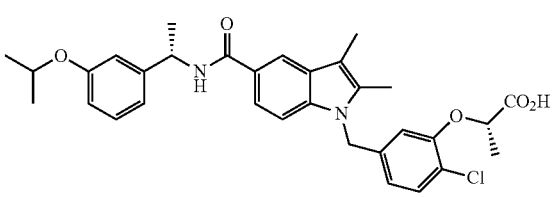
61 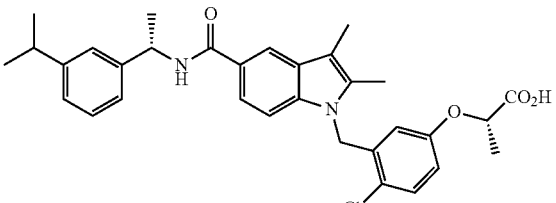
62 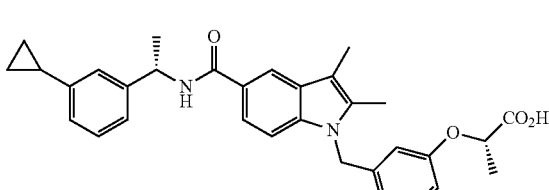
63 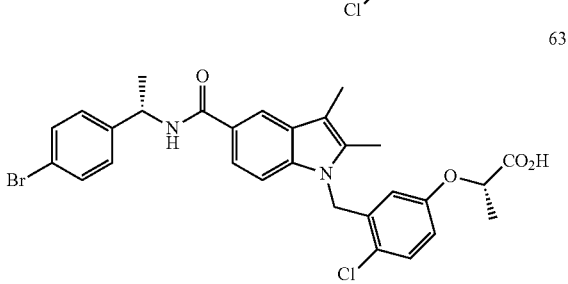

64
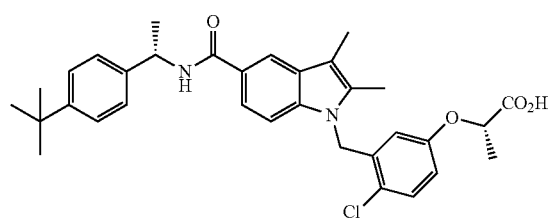
65
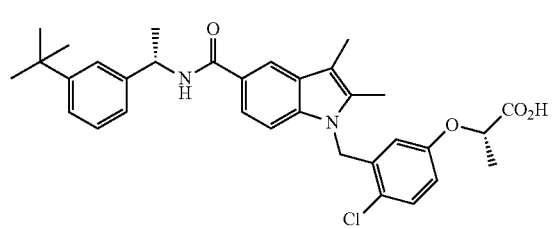
66
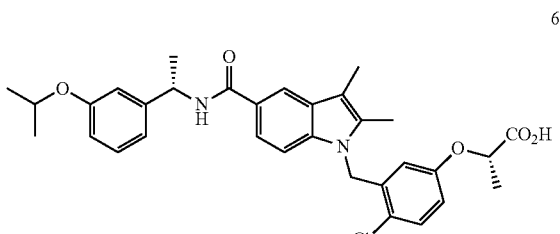
67
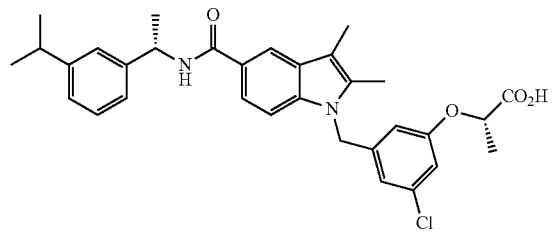
68
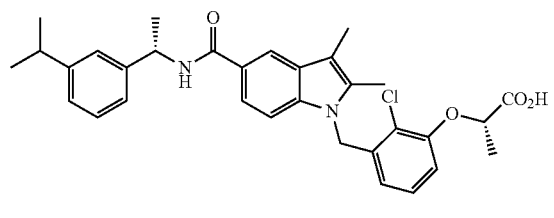
69
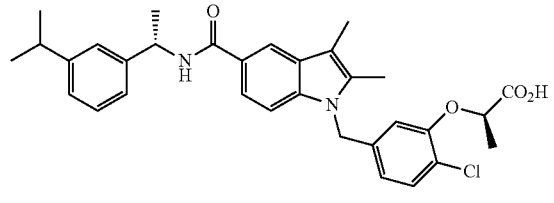
70
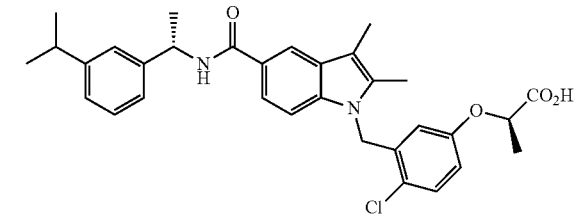
71
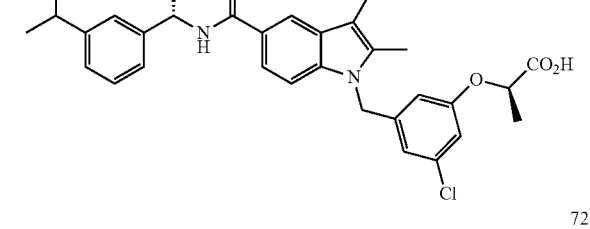
72
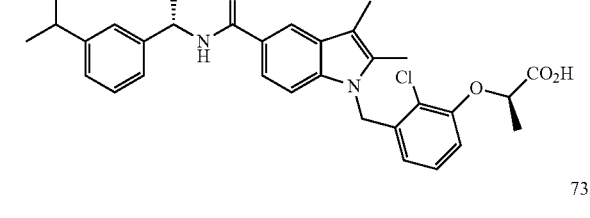
73
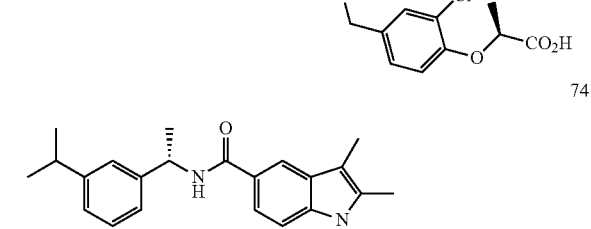
74
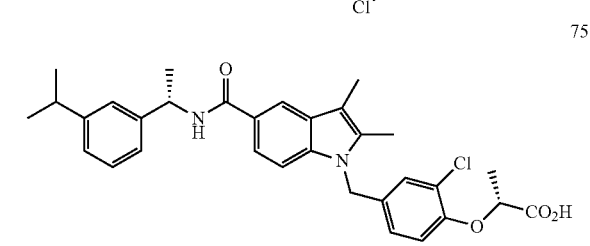
75
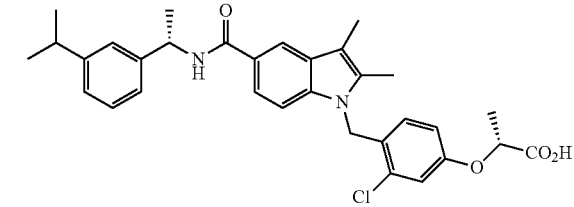
76
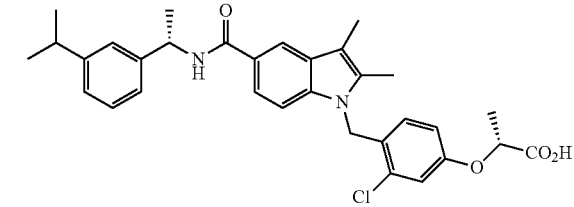

77
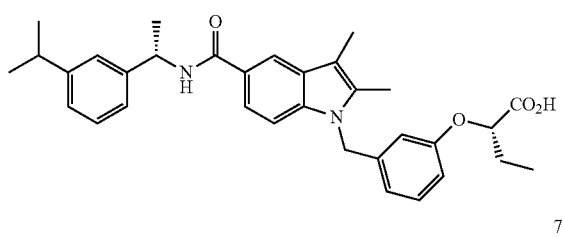
78
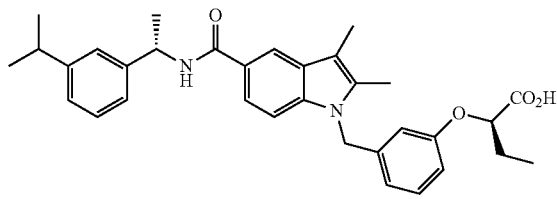
79
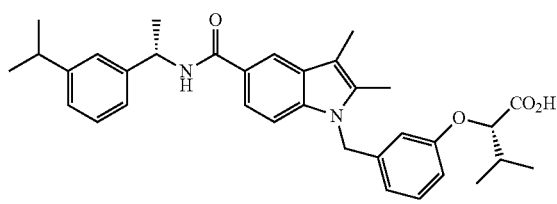
80
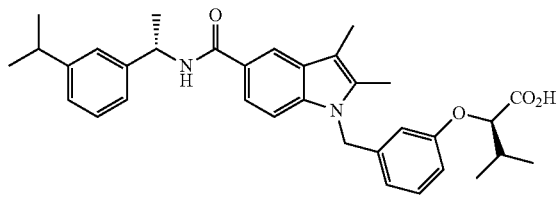
81
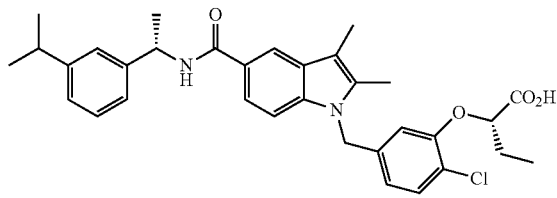
82
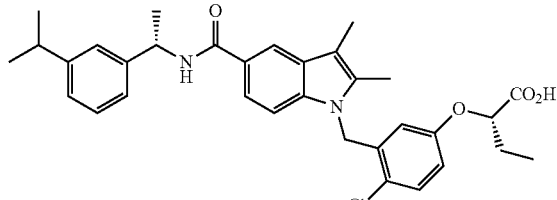
83
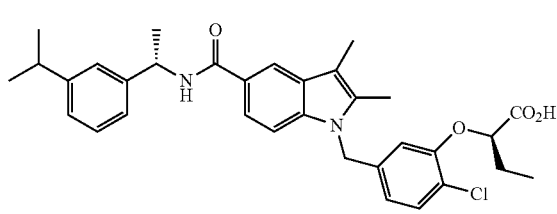
84
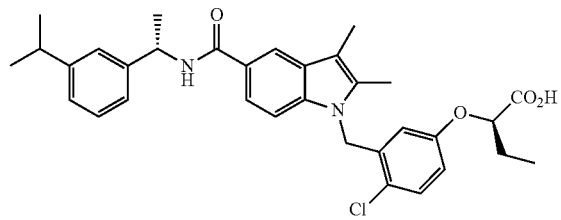
85
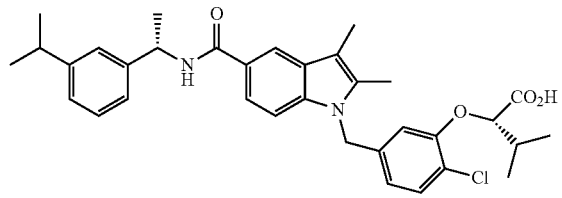
86
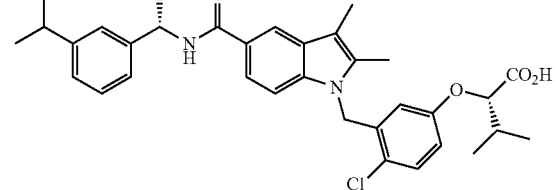
87
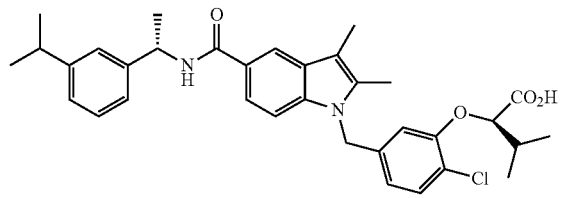
88
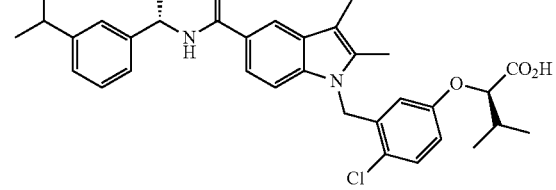
89
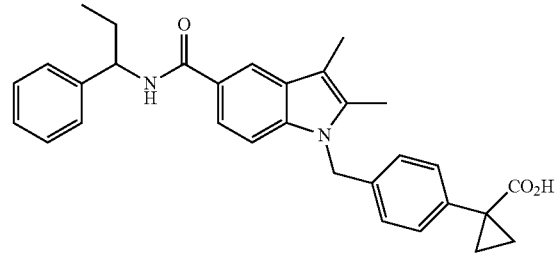

245
90
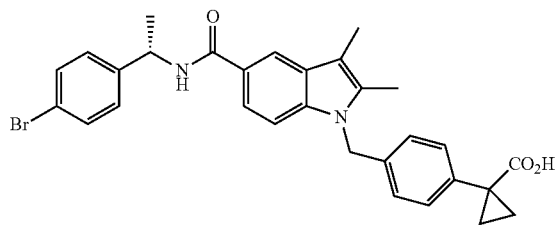
91
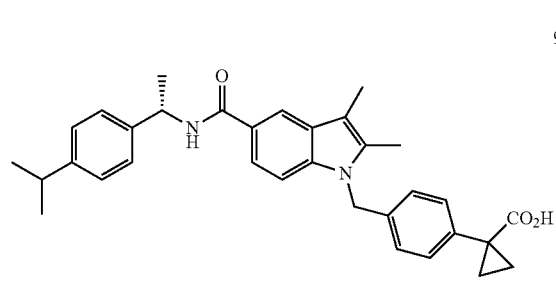
92
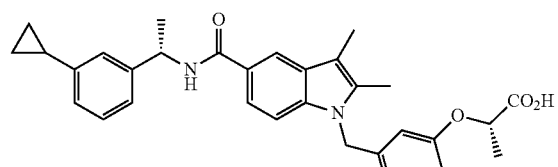
93
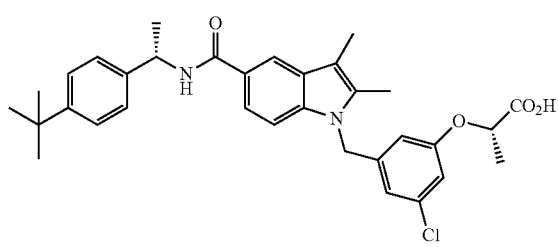
94
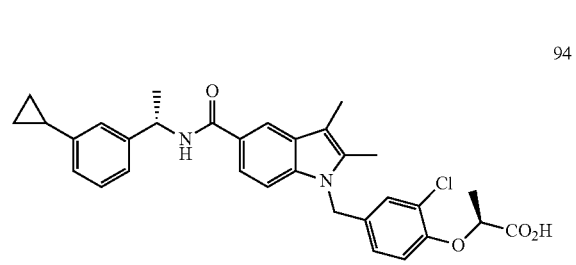
95
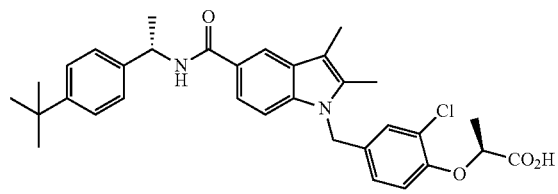
246
96
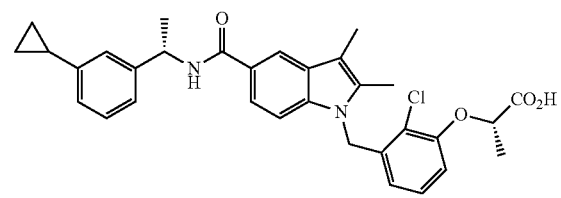
97
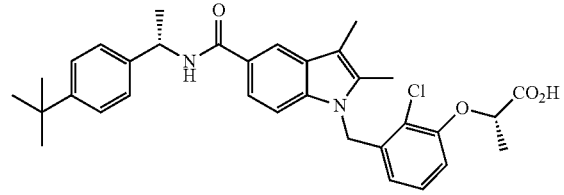
98
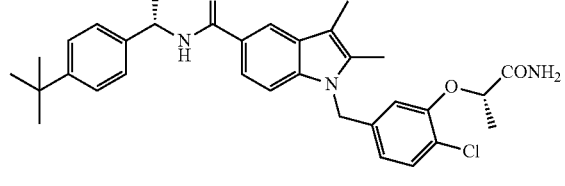
99
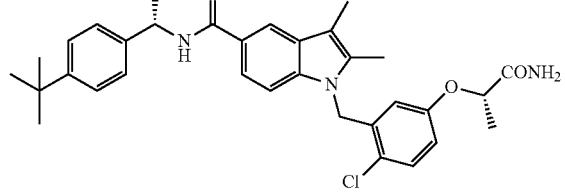
100
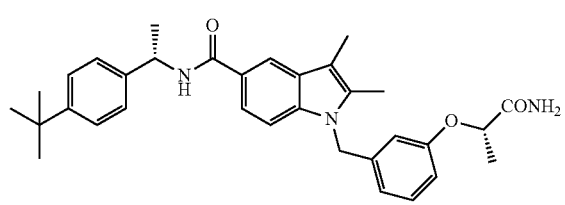
101
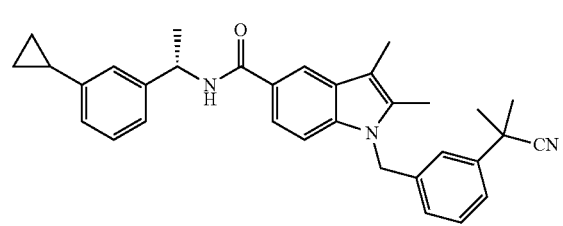
102
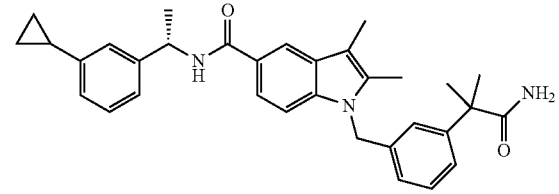

103 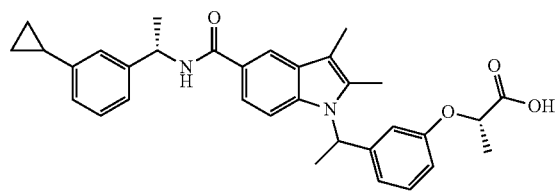
104 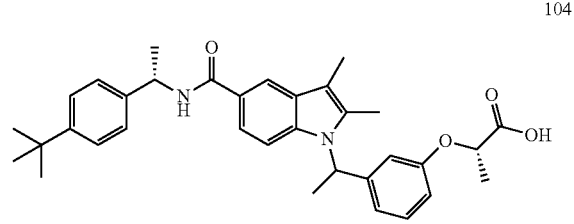
105 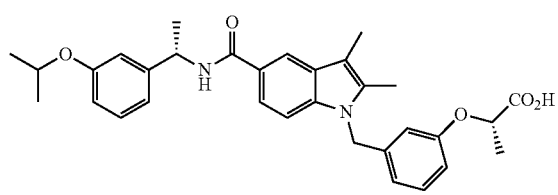
106 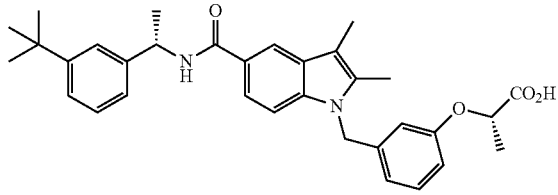
107 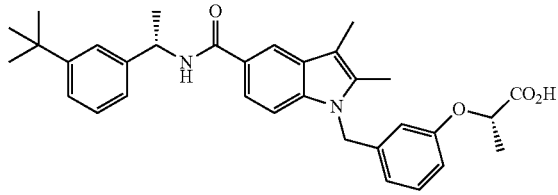
108 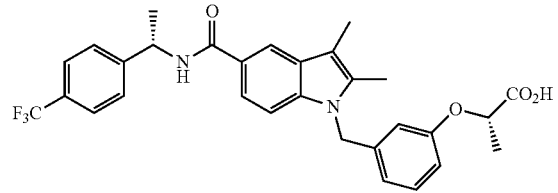
109 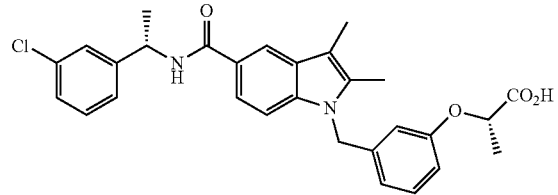
110 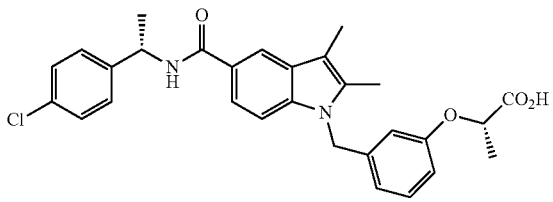
111 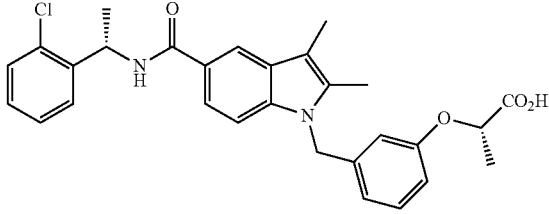
112 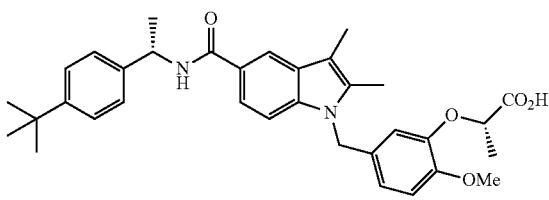
113 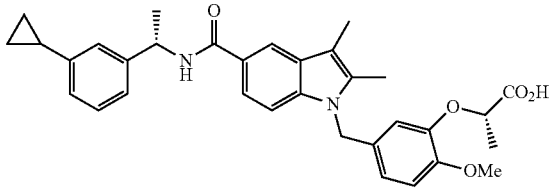
114 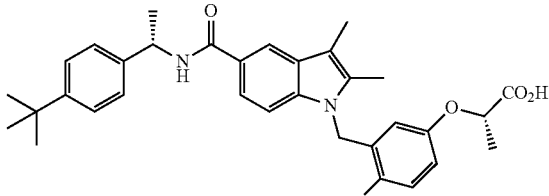
115 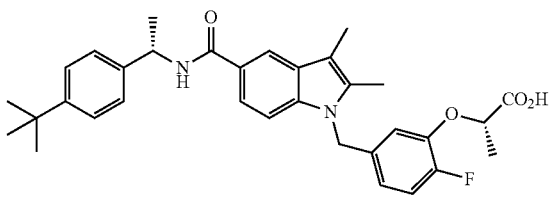
116 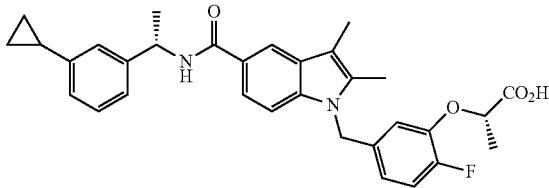

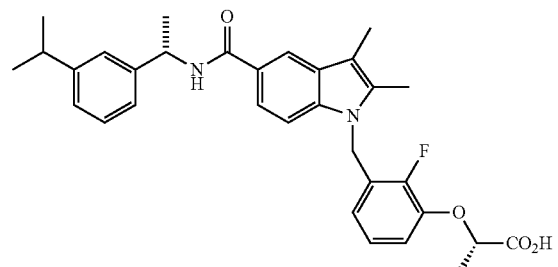
130
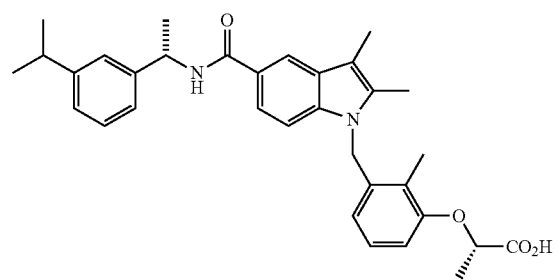
131
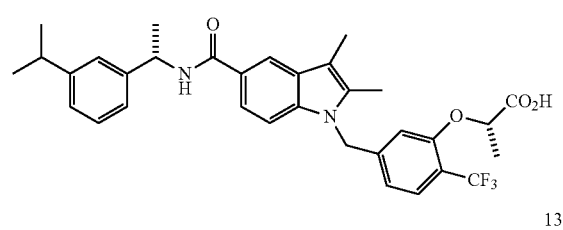
132
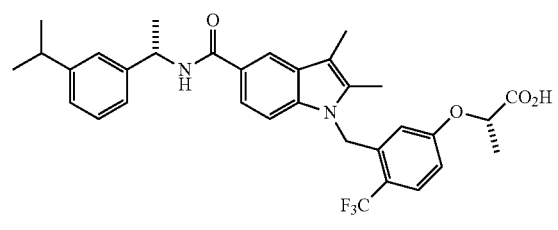
133
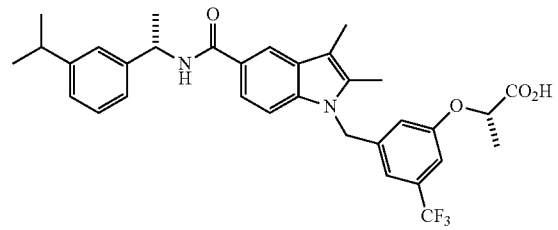
134
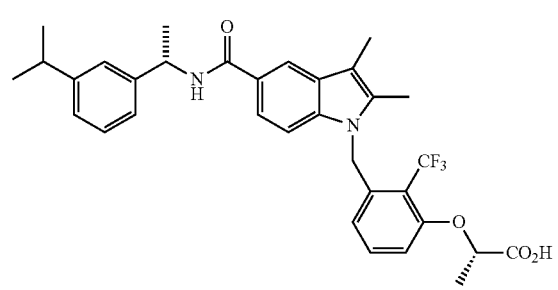
135
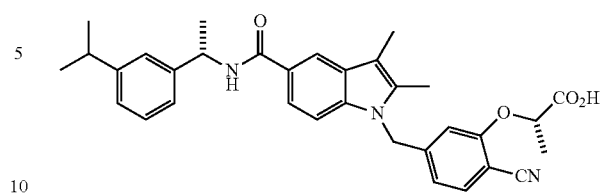
136
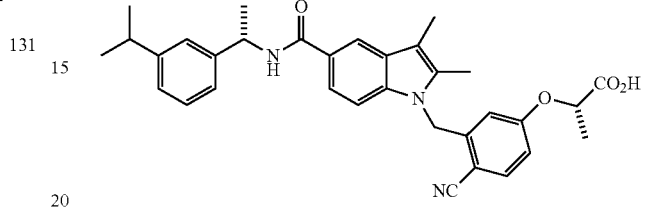
137
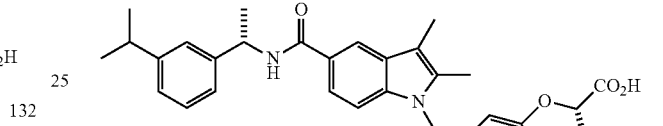
138
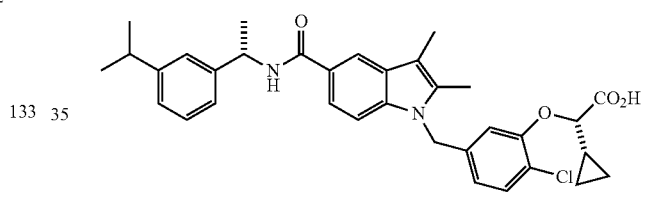
139
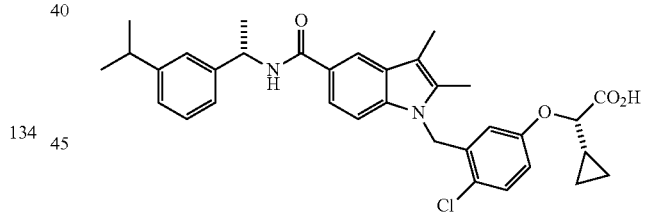
140
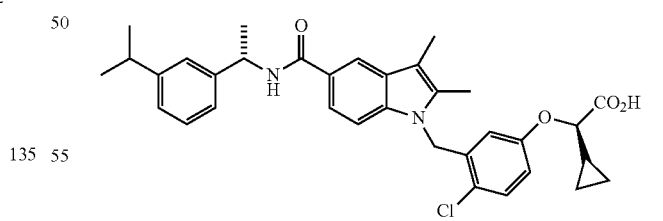
141
142

143
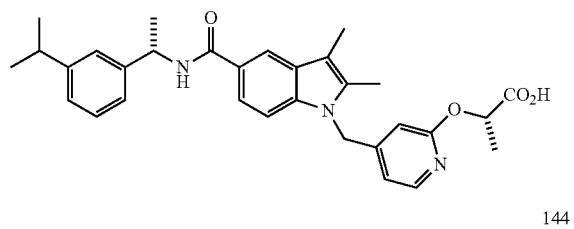
144
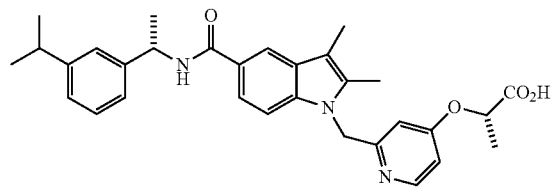
145
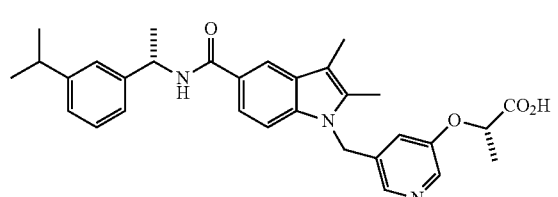
146
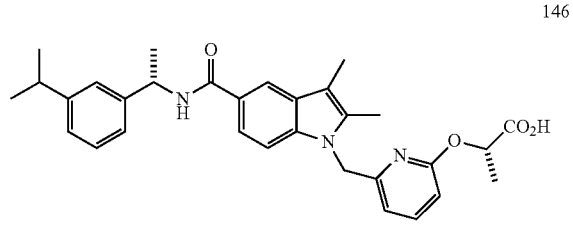
147
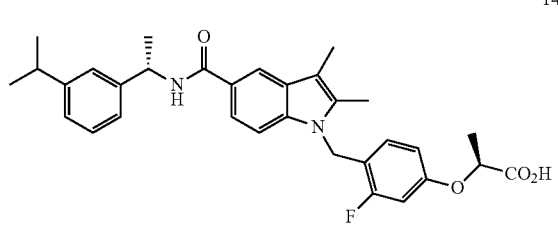
148
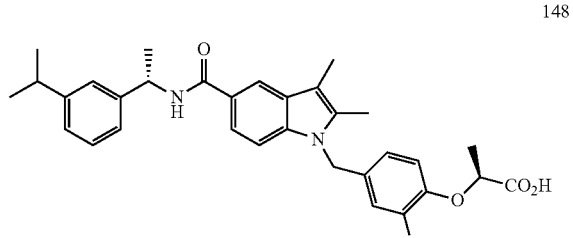
149
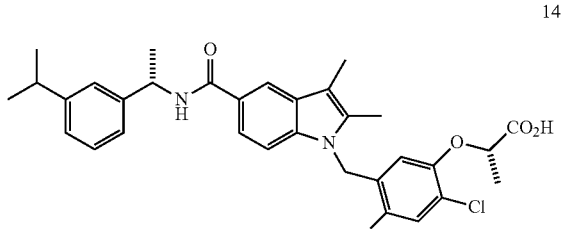
150
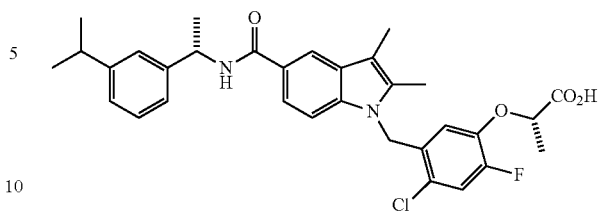
151
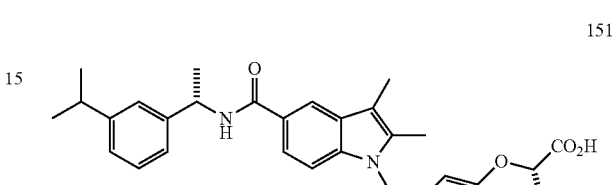
152
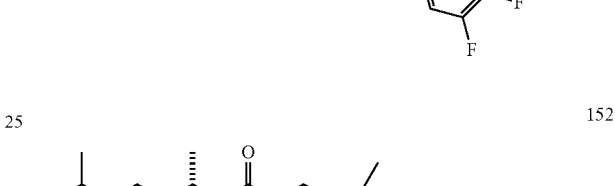
153
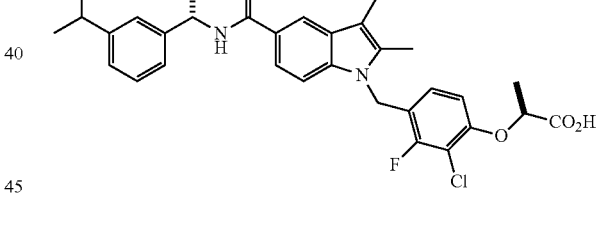
154
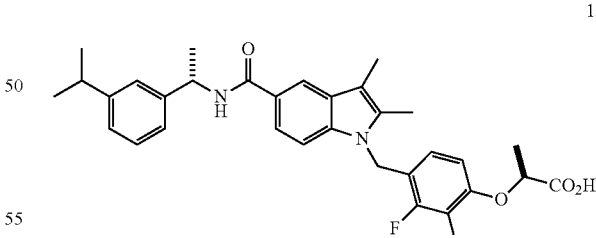
155
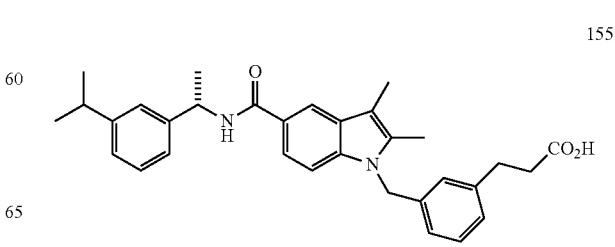

156
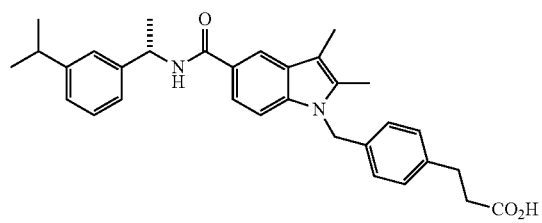
157
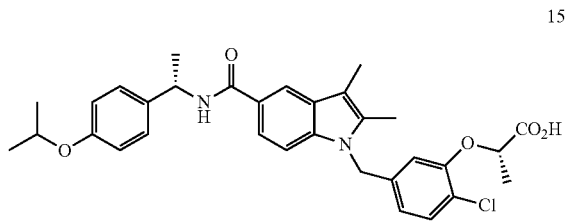
158
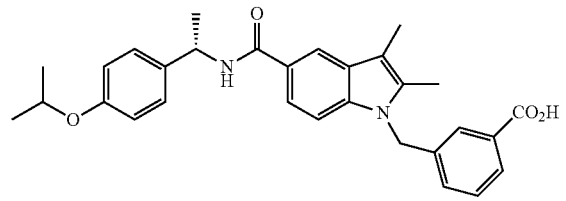
159
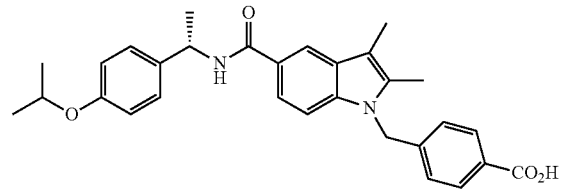
160
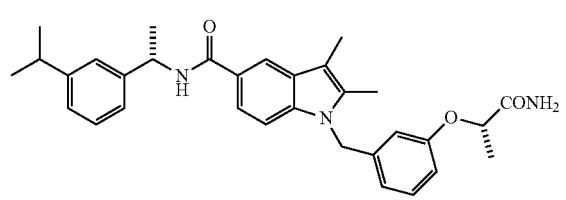
161
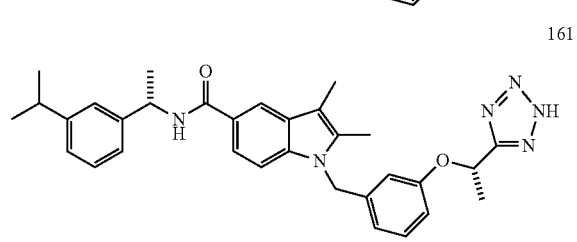
162
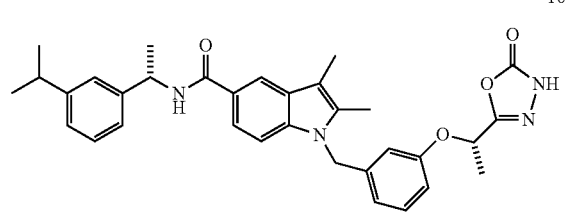
163
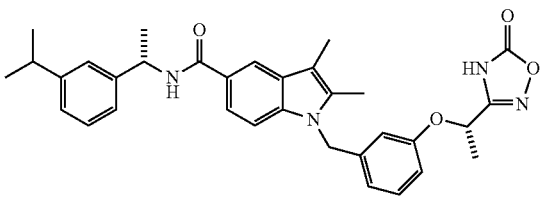
164
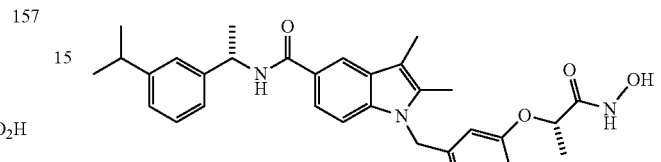
165
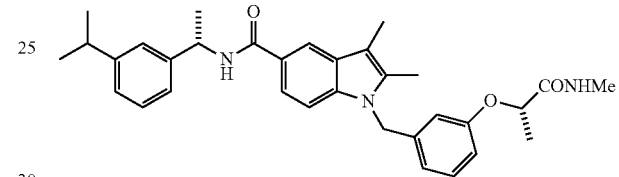
166
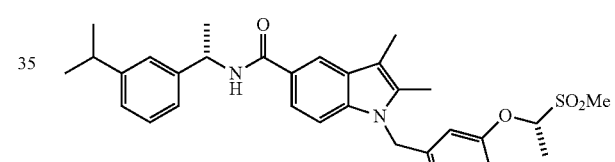
167
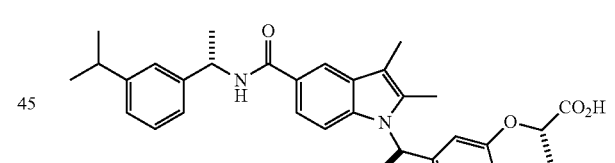
168
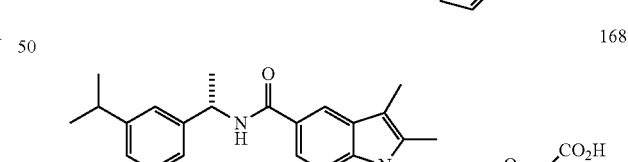
169
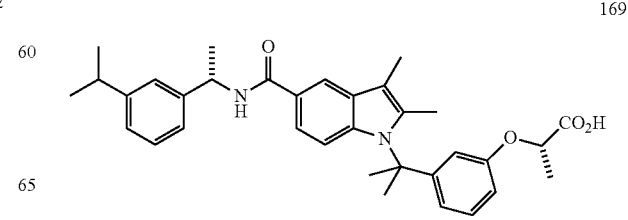

-continued

170

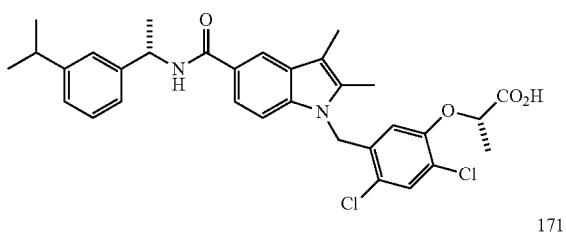

171

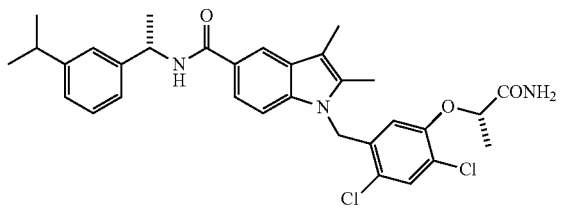

172

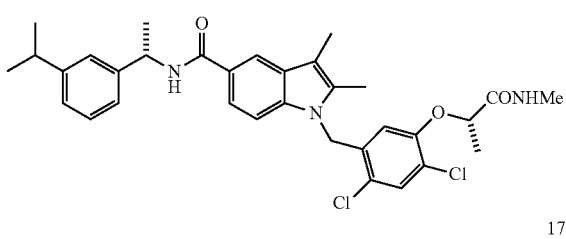

173

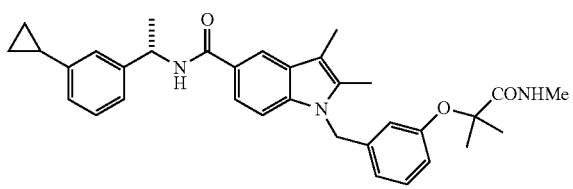

174

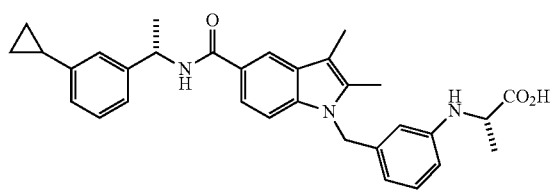

175

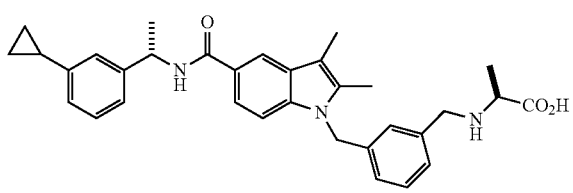

176

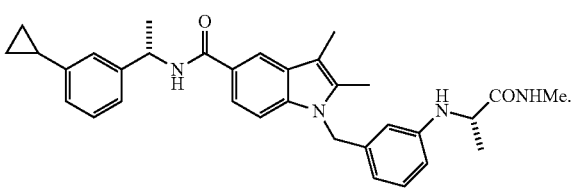

14. A pharmaceutical composition, comprising a compound of any one of statements 1-13; and a pharmaceutically acceptable excipient.

15. A method of inhibiting kinase-mediated phosphorylation of PPARG in a mammal, comprising administering to the mammal an effective amount of a compound of any one of statements 1-13.

16. The method of statement 15 wherein the kinase-mediated phosphorylation of PPARG is cdk5-mediated phosphorylation of PPARG.

17. The method of statement 15 wherein the effective amount of the compound for inhibiting kinase-mediated phosphorylation of PPARG does not produce an agonistic effect on PPARG.

18. A method of treating a condition in a mammal, wherein binding of a ligand to PPARG or inhibition of kinase-mediated phosphorylation of PPARG, or both, is medically indicated, comprising administering to the mammal an effective amount of a compound of any one of statements 1-13 at a frequency of dosing and for a duration of dosing effective to provide a beneficial effect to the mammal.

19. The method of statement 18 wherein the kinase-mediated phosphorylation of PPARG is cdk5-mediated phosphorylation of PPARG.

20. The method of statement 18, wherein the mammal is a human.

21. The method of statement 18, wherein the effective amount, frequency of dosing, and duration of dosing of the compound do not produce an agonistic effect on PPARG.

22. The method of statement 18, wherein the condition is diabetes, insulin resistance, impaired glucose tolerance, pre-diabetes, hyperglycemia, hyperinsulinemia, obesity, or inflammation.

23. The method of statement 22, wherein the effective amount, frequency of dosing, and duration of dosing of the compound does not produce side effects of significant weight gain, edema, impairment of bone growth or formation, or cardiac hypertrophy, or any combination thereof, in the mammal receiving the compound.

24. A method of treating a condition comprising diabetes, insulin resistance, impaired glucose tolerance, pre-diabetes, hyperglycemia, hyperinsulinemia, or inflammation, in a human, comprising administering to the human regularly over a duration of time an effective amount of a compound of any one of statements 1-13, optionally in conjunction with administering an effective amount of a second medicament effective for the treatment of the condition.

All patents and patent and other publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A non-agonist peroxisome proliferator active receptor gamma (PPARG) modulatory compound of formula (I) or a pharmaceutically acceptable salt thereof:

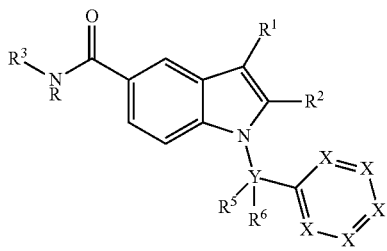

wherein:

R is H, (C₁-C₆)alkyl, (C₃-C₉)cycloalkyl, or (C₁-C₆)haloalkyl;

R' is independently H, (C₁-C₆) alkyl, (C₁-C₆) haloalkyl, or (C₃-C₉)cycloalkyl;

each X is independently N, CH, or CR⁴, provided that no more than two instances of X are N, and no more than three instances of X are CR⁴;

R¹ and R² are independently H, (C₁-C₆)alkyl, (C₃-C₉)cycloalkyl, or (C₁-C₆)haloalkyl;

R³ is any one of:

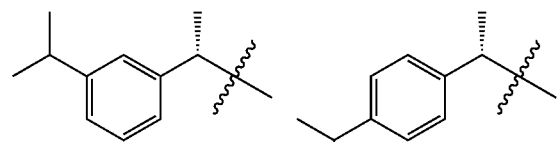

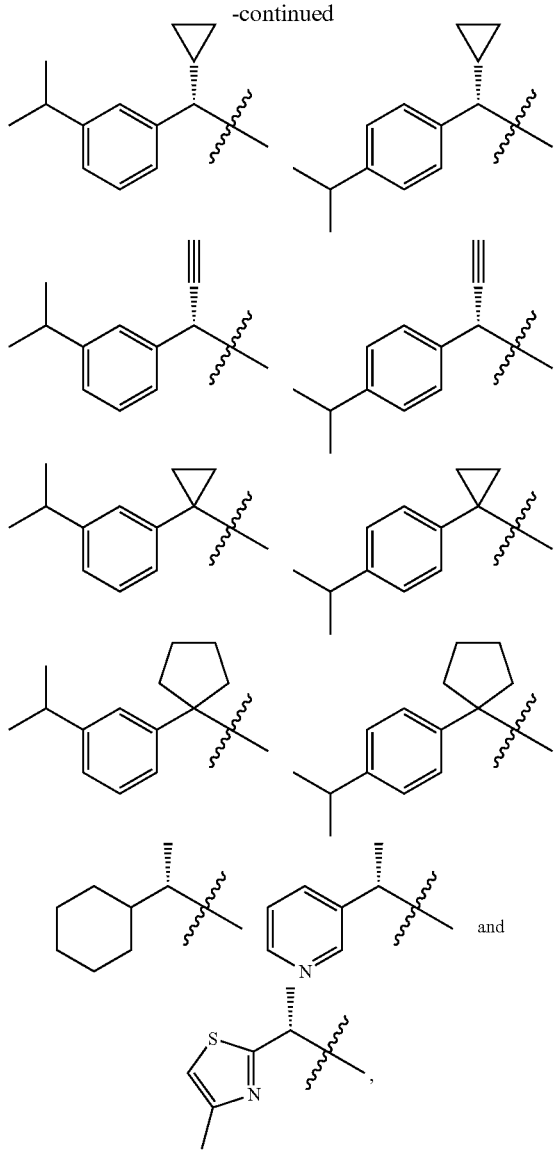

wherein a wavy line indicates a point of attachment, each R₄ is —O(CH₂)ₘCO₂H, —CN, —(CH₂)ₘCN, —O(CH₂)ₘCN, —(CH₃)₂CN, —OC(CH₃)₂CO₂H, —OC(CH₃)₂CN, —CH(CH₃)CN, —OCH(CH₃)CO₂H, —OCH(CH₃)CN; —CH(CH₂CH₃)CN, —OCH(CH₂CH₃)CO₂H, —OCH(CH₂CH₃)CN; —CH(i-Pr)CN, —OCH(i-Pr)CO₂H, —OCH(i-Pr)CN, wherein iPr indicated isopropyl; —CH(t-Bu)CN, —OCH(t-Bu)CO₂H, —OCH(t-Bu)CN, wherein t-Bu indicates t-butyl; —(CHR")ₘC(=O)N(R")₂, —O(CHR")ₘC(=O)N(R")₂,

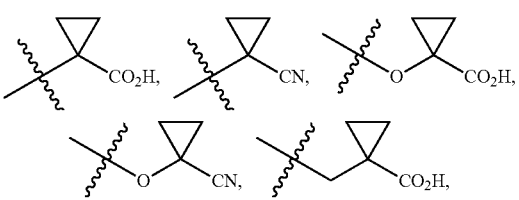

-continued

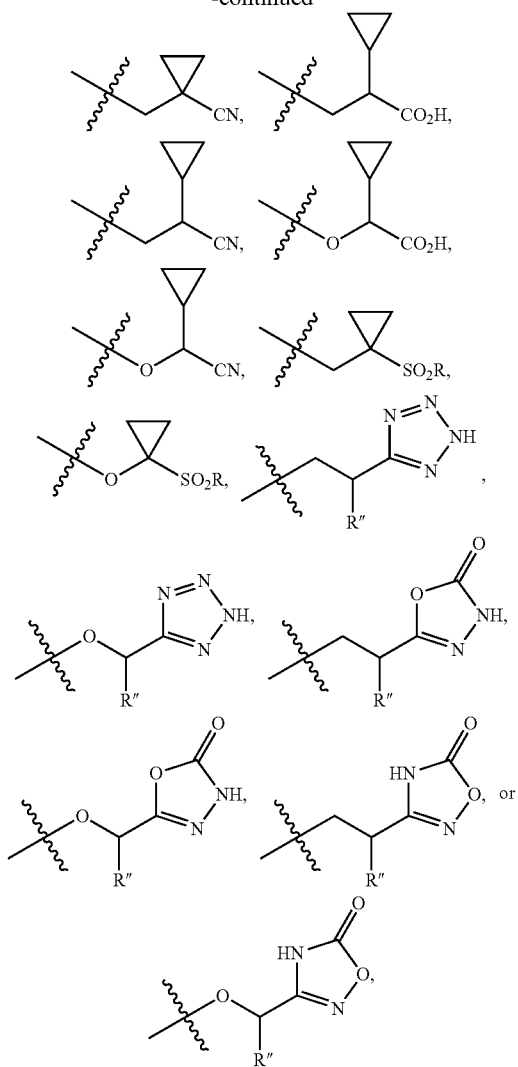

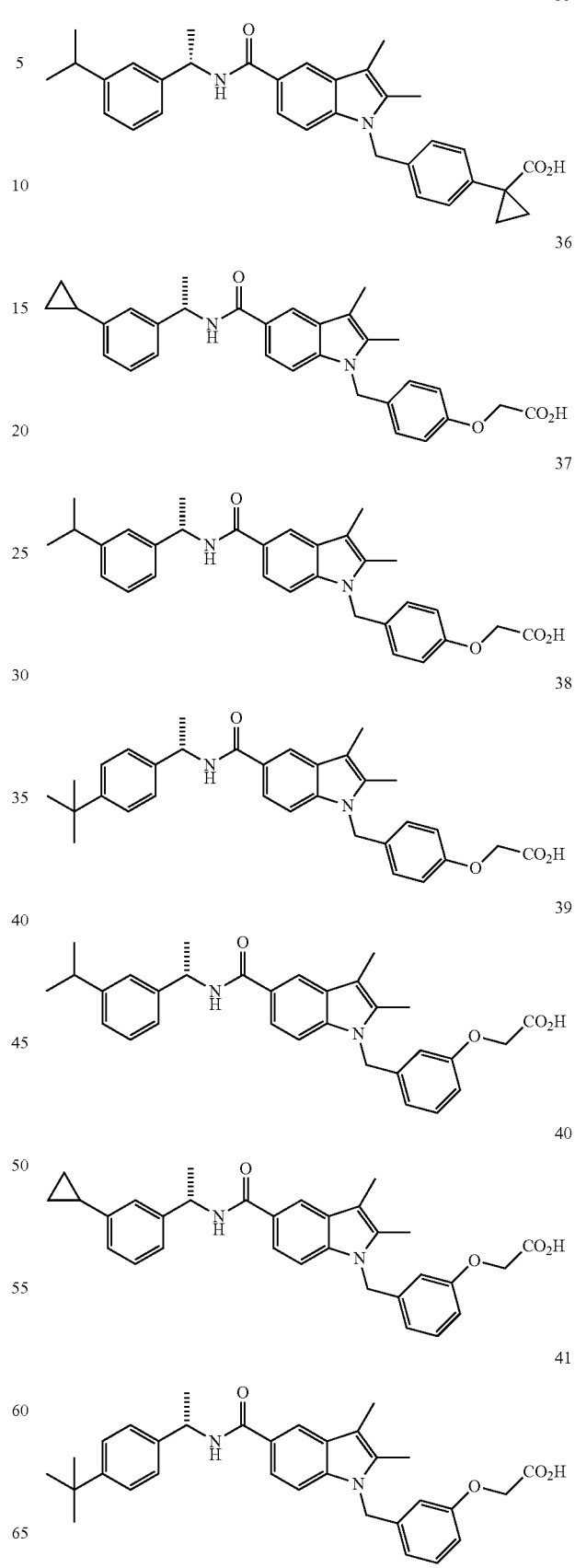

wherein a wavy line indicates a point of attachment;

m is 1,2,3,4,5, or 6;

R" is independently H, OH, (C$_1$-C$_6$)alkyl or (C$_3$-C$_9$)cycloalkyl-(C$_0$-C$_6$)alkyl; or R" is independently -(C$_1$-C$_6$)haloalkyl, —C(R')$_2$)$_m$CO$_2$R, —(C(R')$_2$)$_m$CON(R)$_2$, —(C(R')$_2$)$_m$CON(R)OH, or —(C(R')$_2$)$_m$CN; or R" is C-bonded tetrazolyl, C-bonded oxadiazolonyl, (C$_1$-C$_6$)alkyl-(1,3,4-oxadiazol-2(3H)-on)-yl, (C$_1$-C$_6$)alkyl-(1,2,4-oxadiazol-5(4H)-on)-3-yl, (C$_1$-C$_4$)alkyl-S(O)$_q$(C$_0$-C$_6$)alkyl, an unsubstituted or substituted aryl, or an unsubstituted or substituted heteroaryl;

Y is (C$_1$-C$_2$)alkyl; and

R$^5$ and R$^6$ are independently H or (C$_1$-C$_4$)alkyl or independently each R$^5$ and R$^6$ together with the carbon atom to which they are bonded form a carbonyl.

2. The compound of claim 1 wherein R$^1$ and R$^2$ are independently H or methyl.

3. The compound of claim 1 wherein Y is C$_1$-alkyl; and R$^5$ and R$^6$ are H, or wherein Y is C$_2$-alkyl, and R$^5$ and R$^6$ are H.

4. A non-agonist PPARG modulatory compound selected from the group consisting of:

42
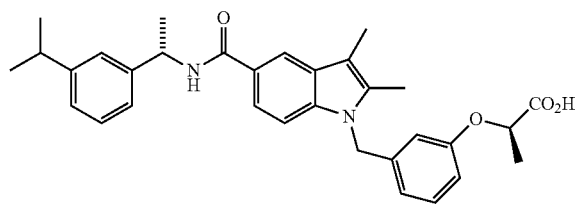
43
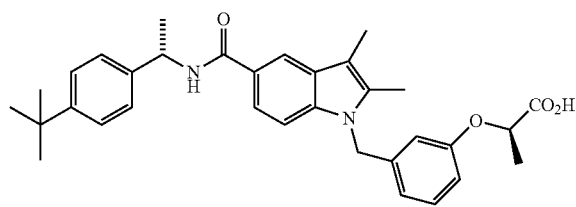
44
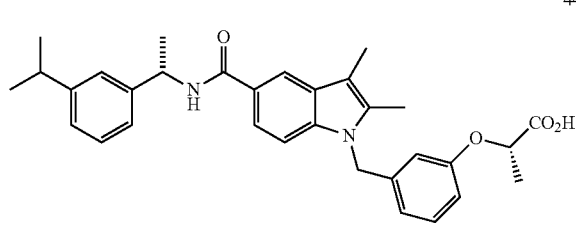
45
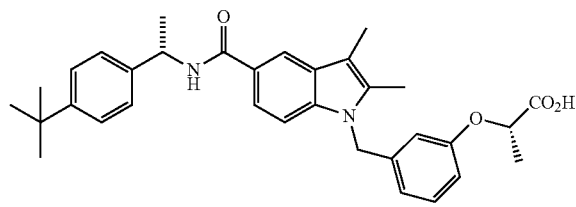
46
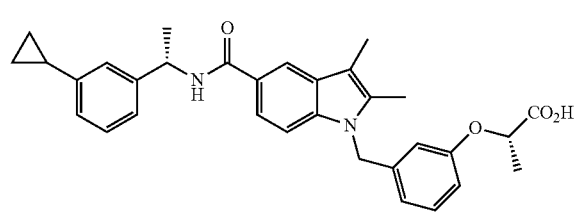
47
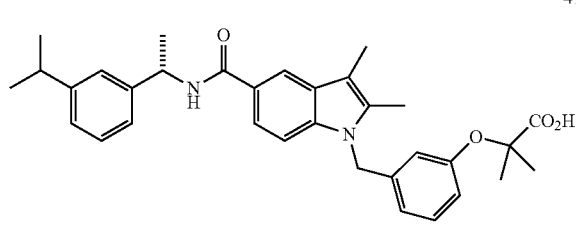
48
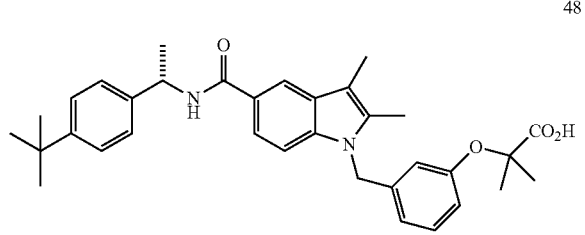
49
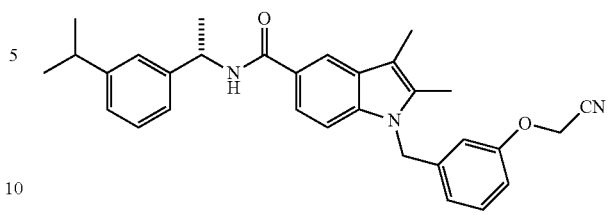
50
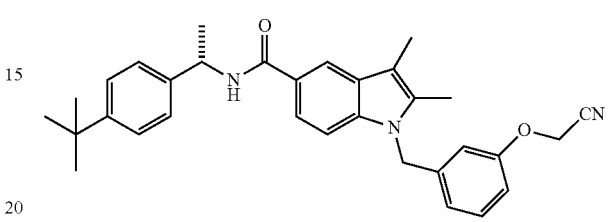
51
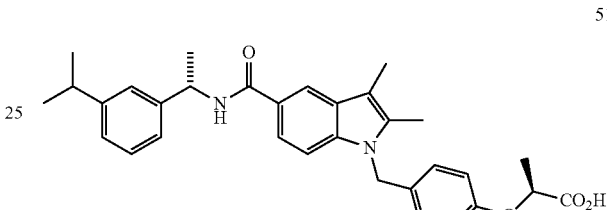
52
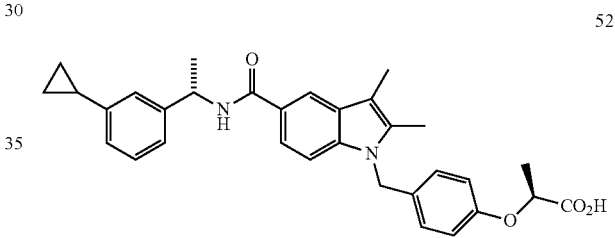
53
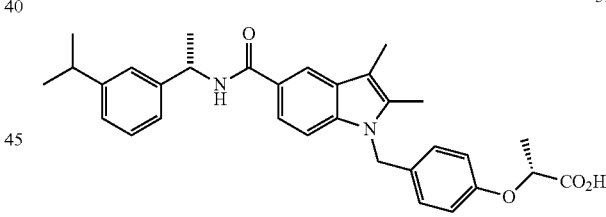
54
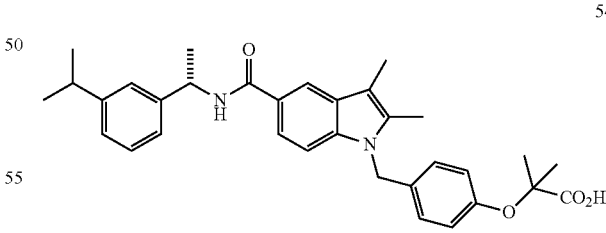
55
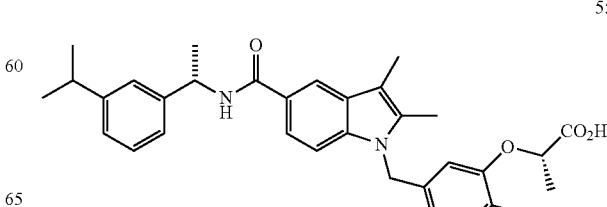

56
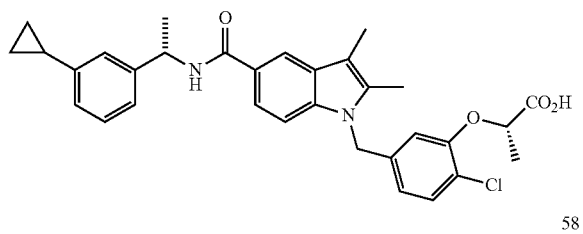
58
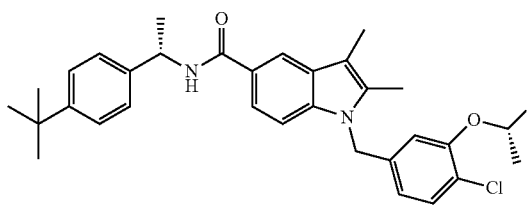
59
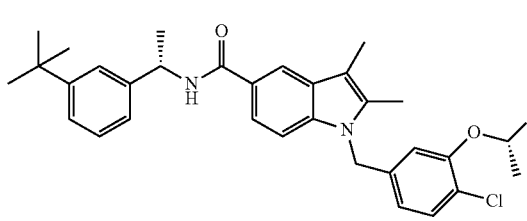
59
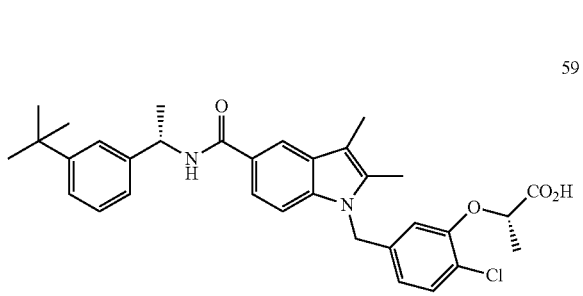
61
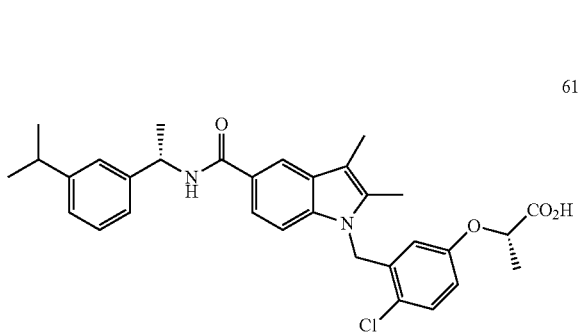
62
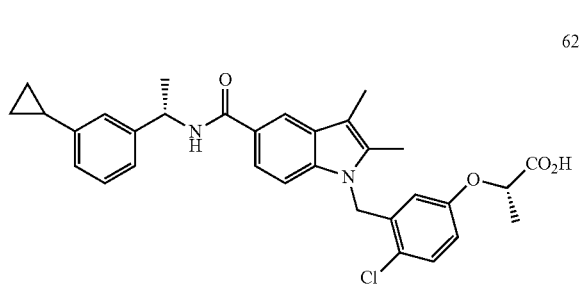
64
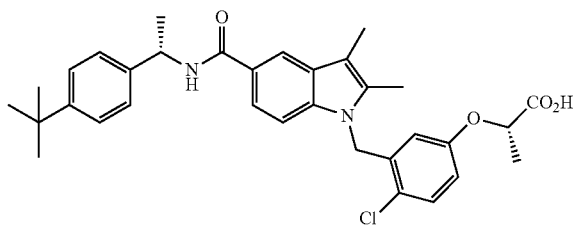
65
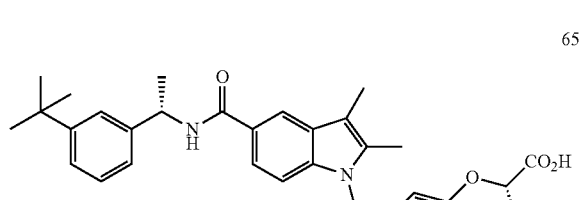
67
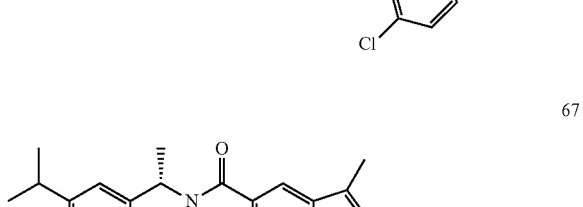
68
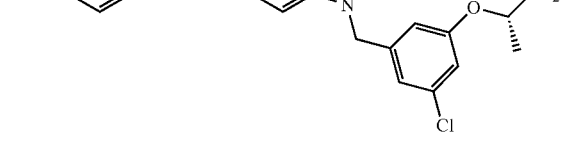
69
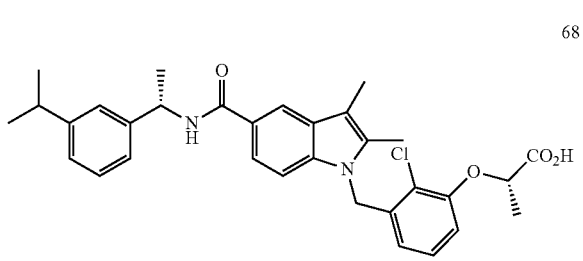
70
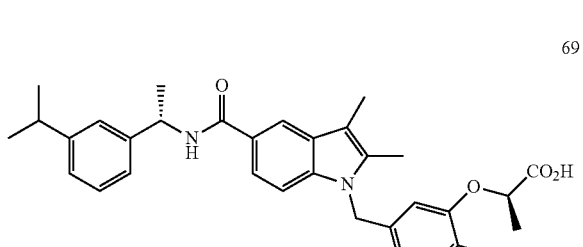

267
-continued
71
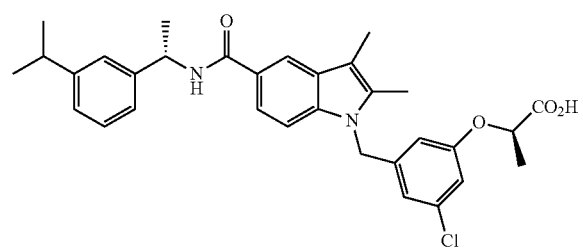
72
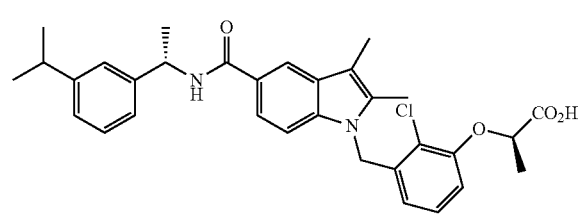
73
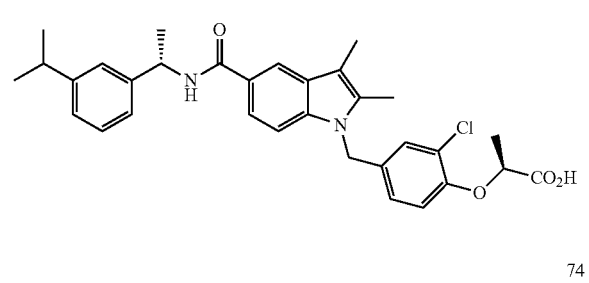
74
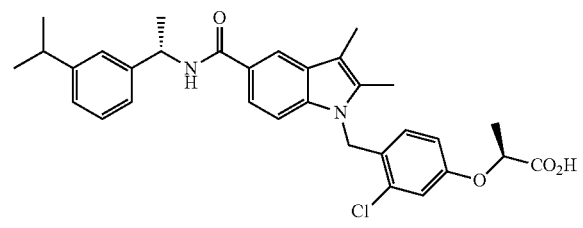
75
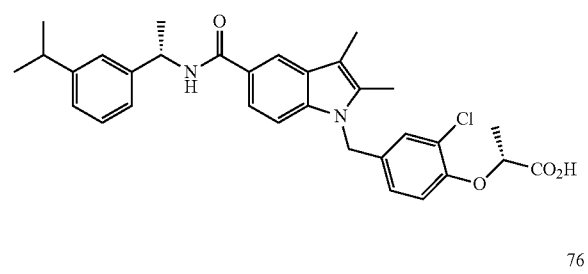
76
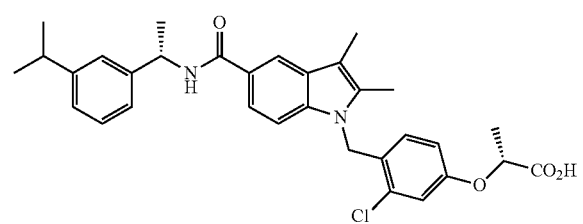
268
-continued
77
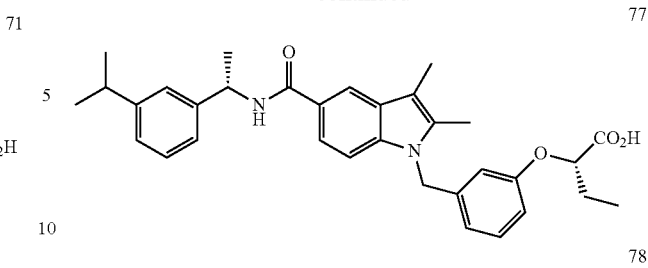
78
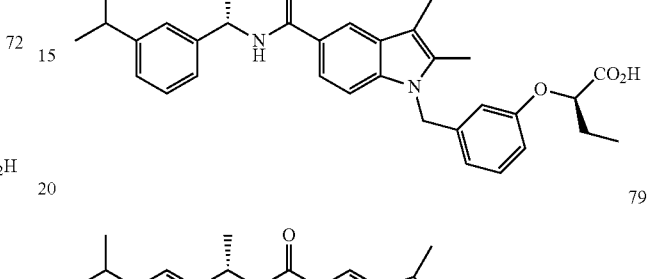
79
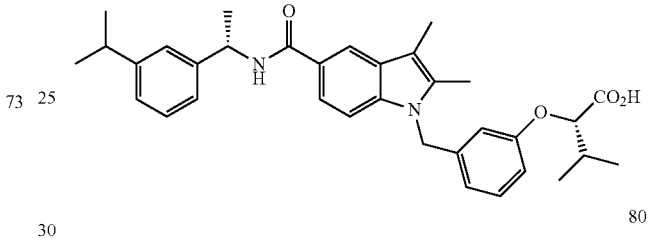
80
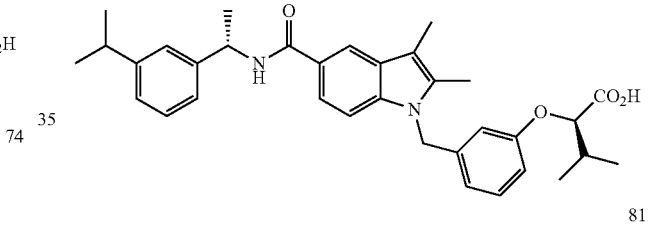
81
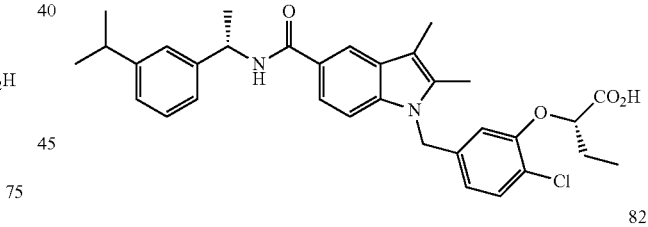
82
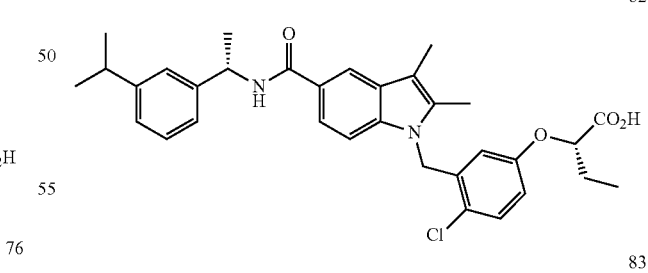
83
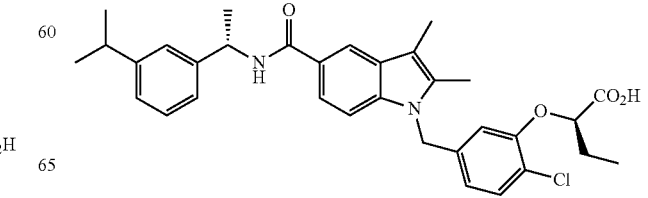

84
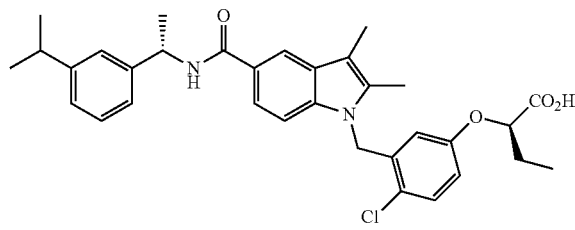
85
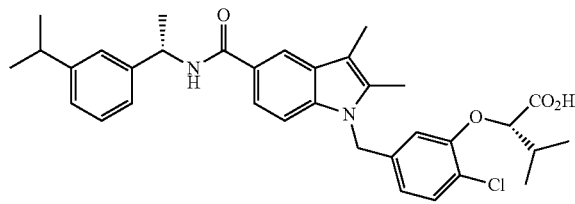
86
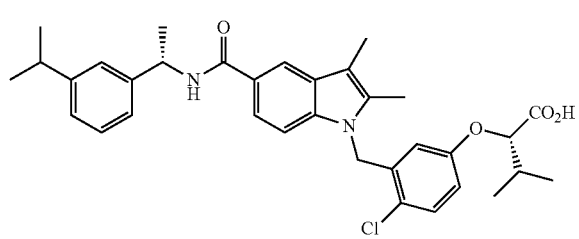
87
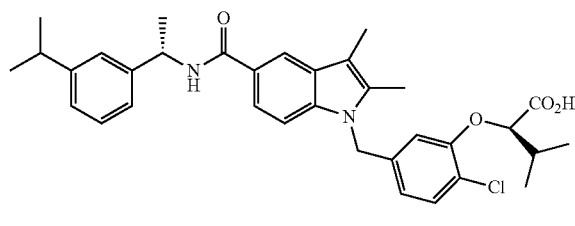
88
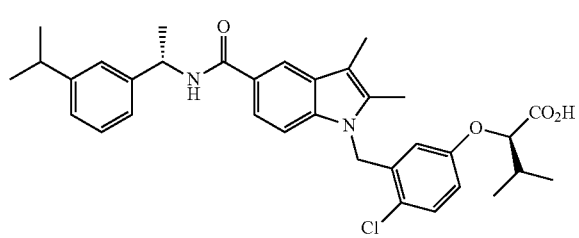
91
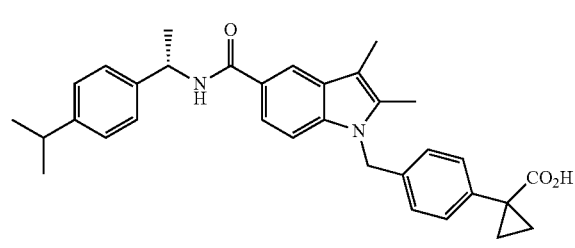
92
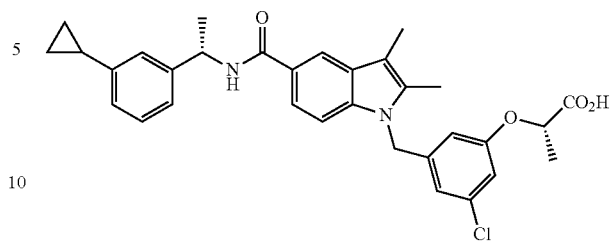
93
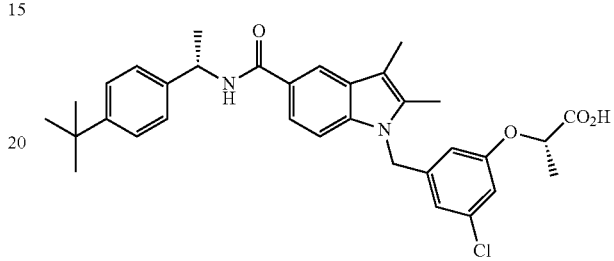
94
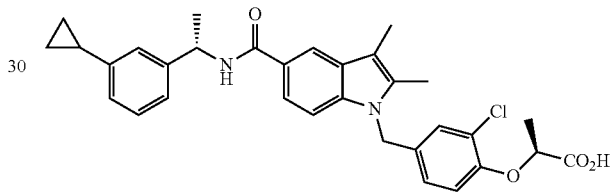
95
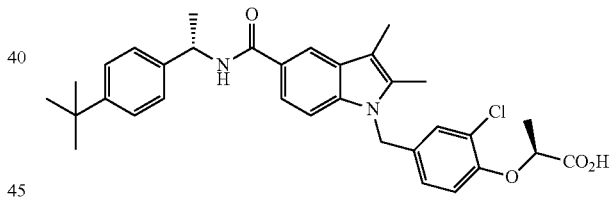
96
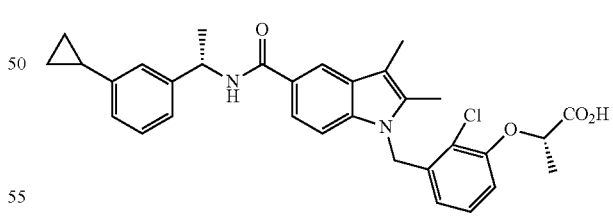
97
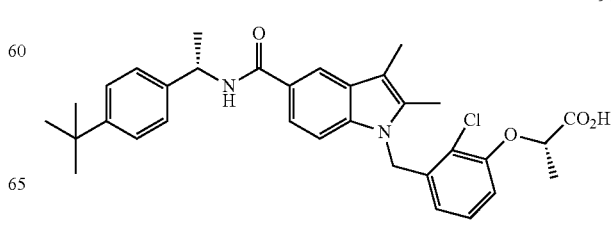

98
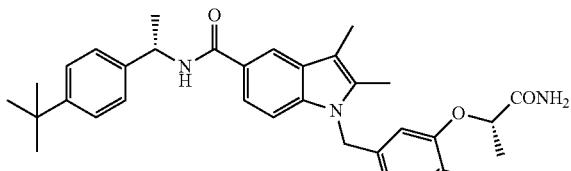
99
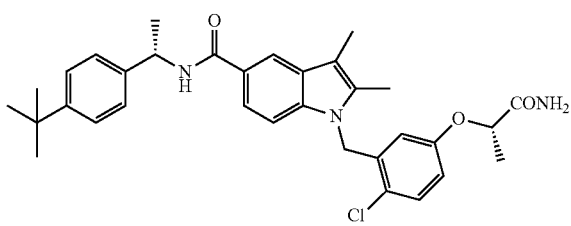
100
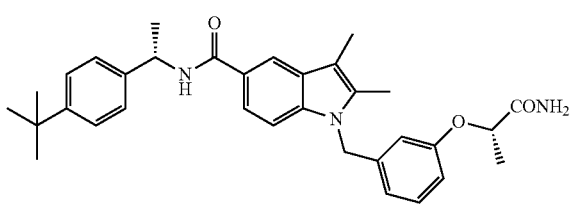
101
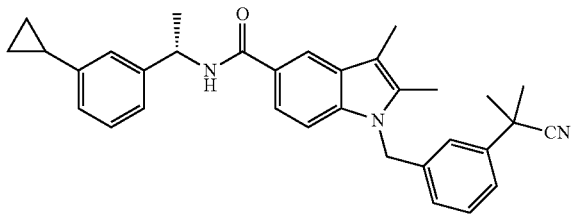
102
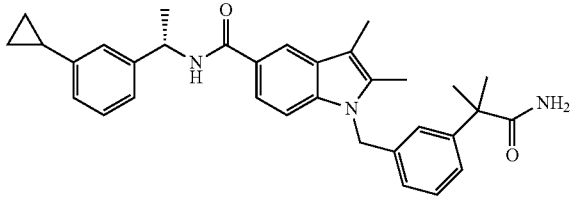
103
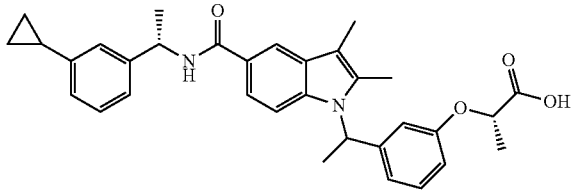
104
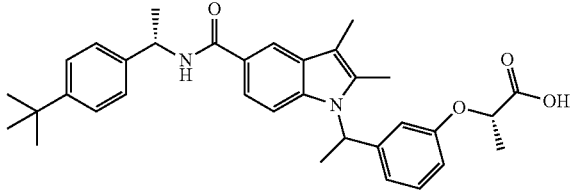
105
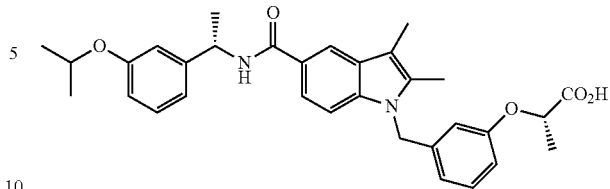
106
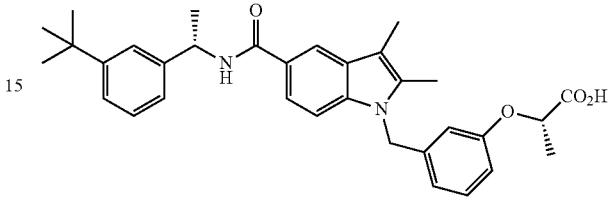
107
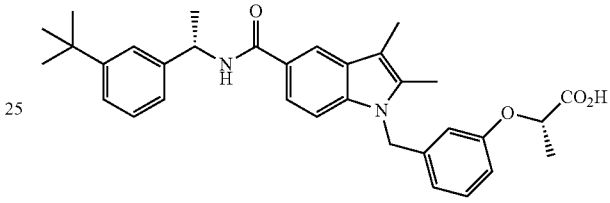
108
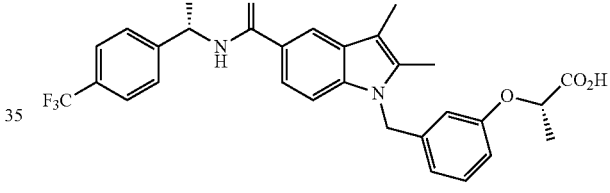
109
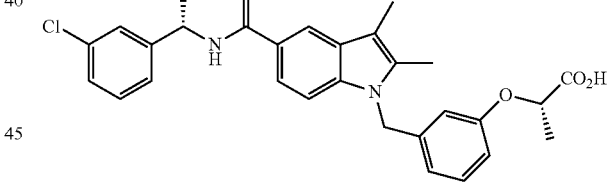
110
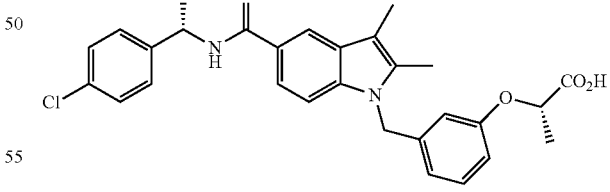
111
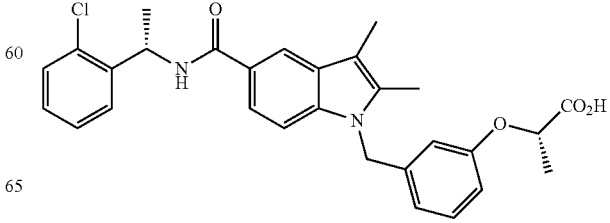

273
-continued
112
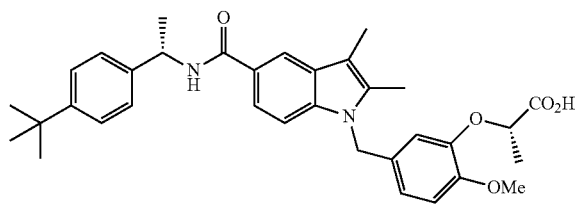
113
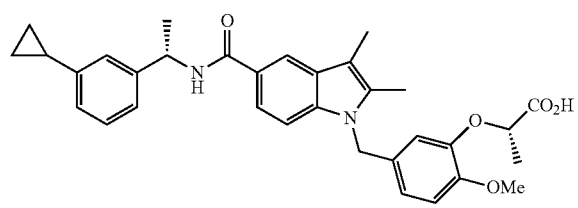
114
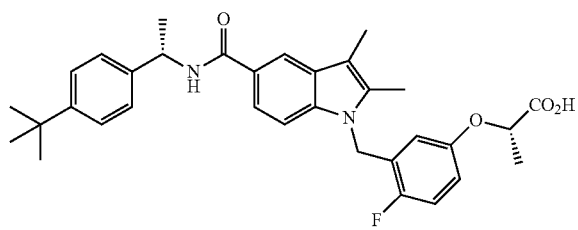
115
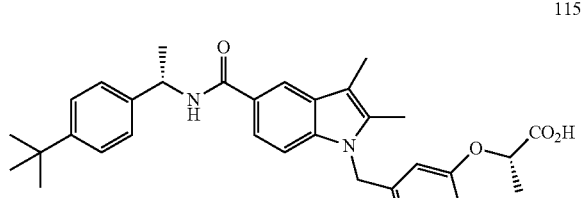
116
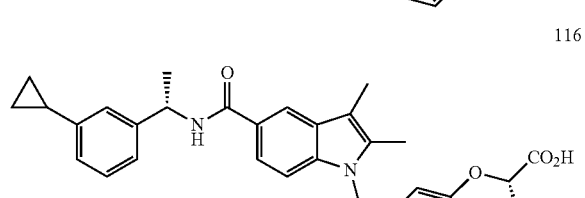
118
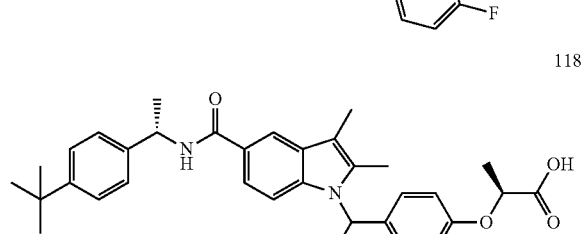
119
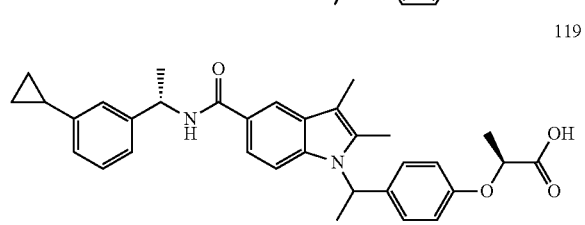
274
-continued
120
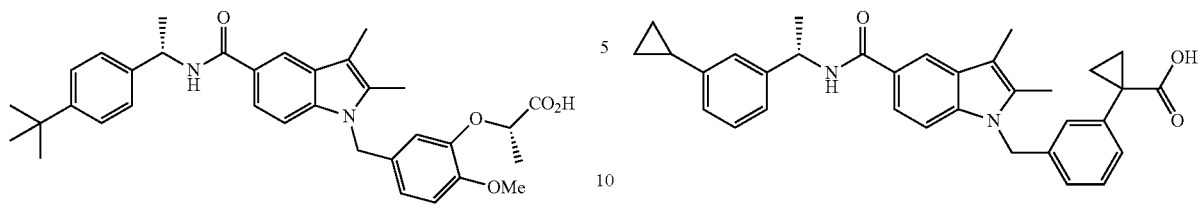
122
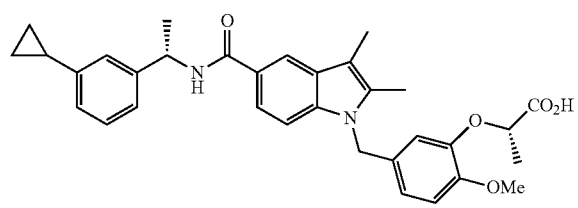
123
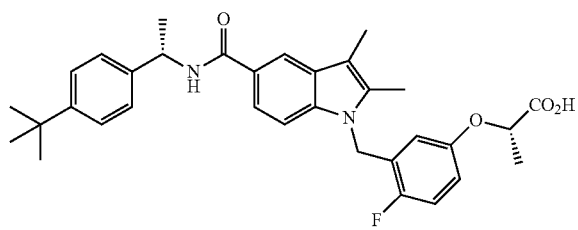
124
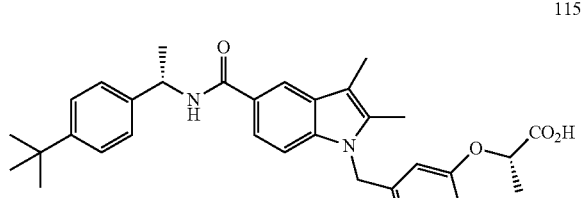
125
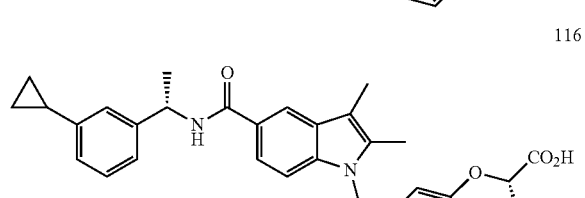
126
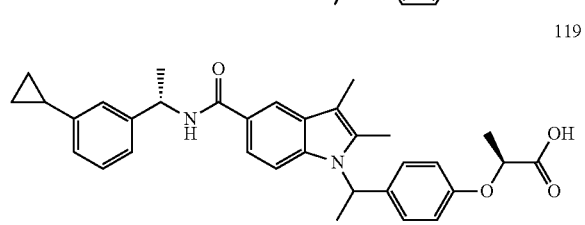

127
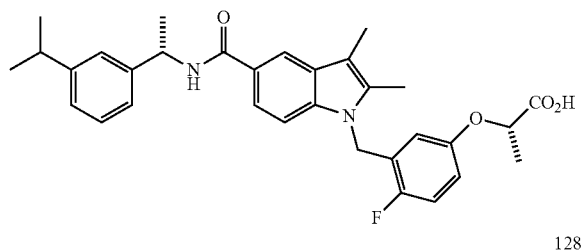
128
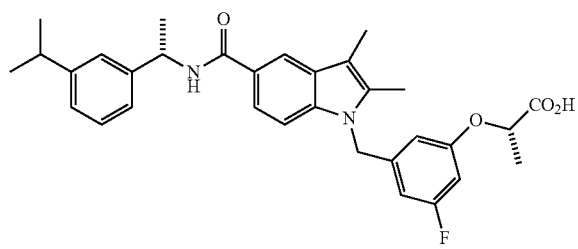
129
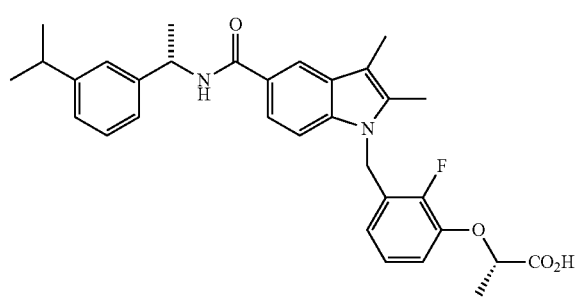
130
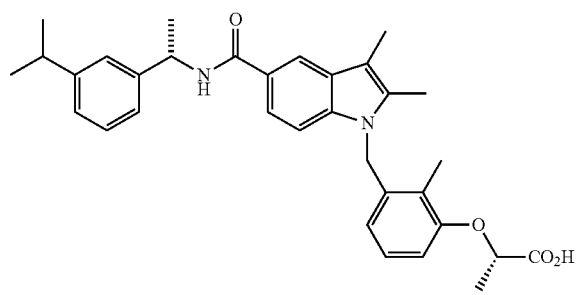
131
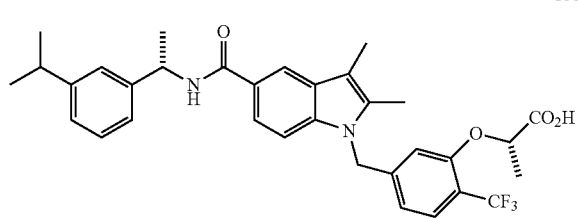
132
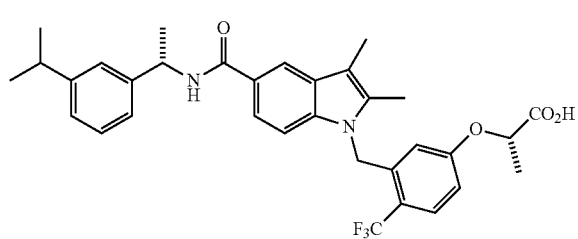
133
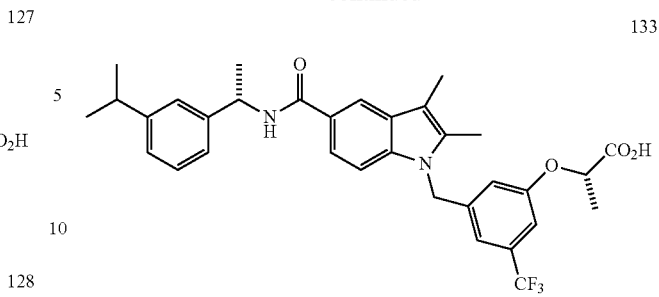
134
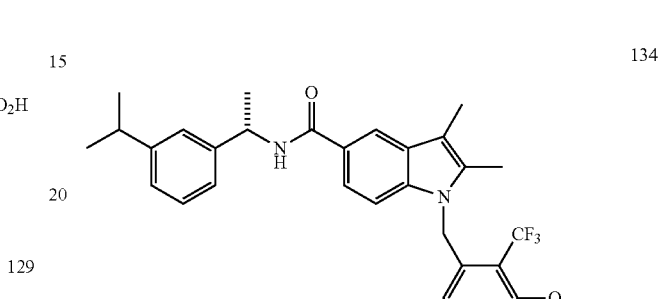
135
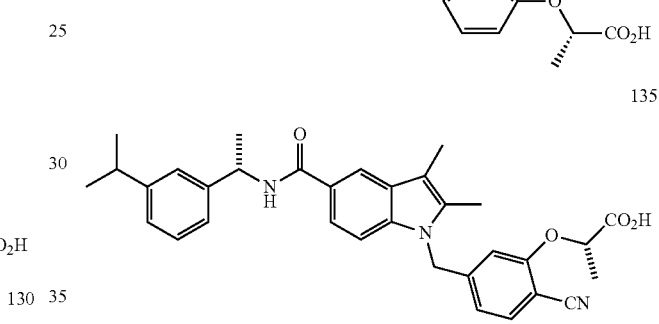
136
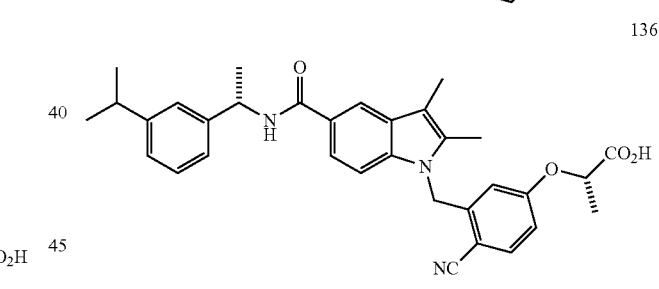
137
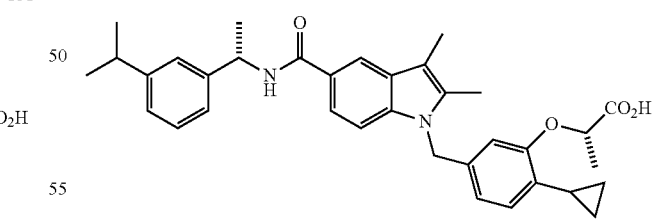
138
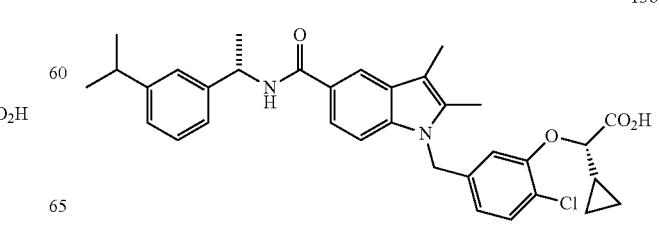

139
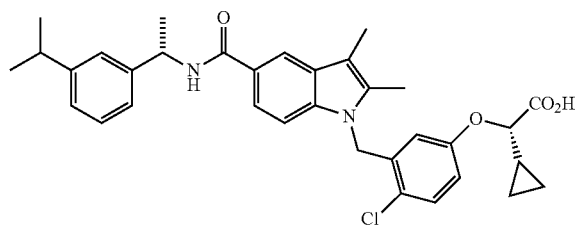
140
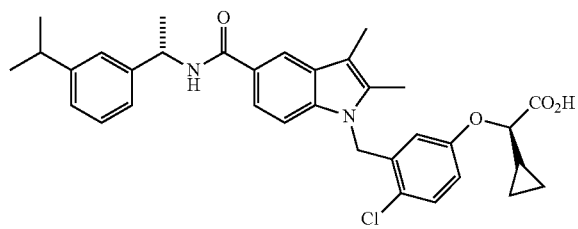
141
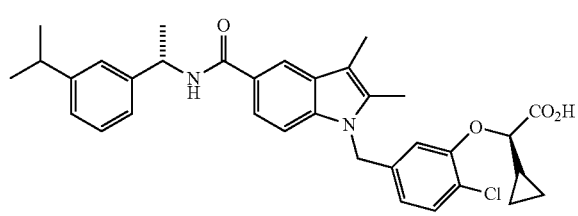
142
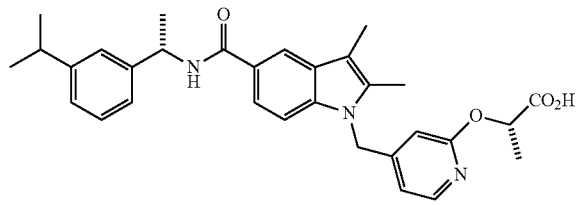
143
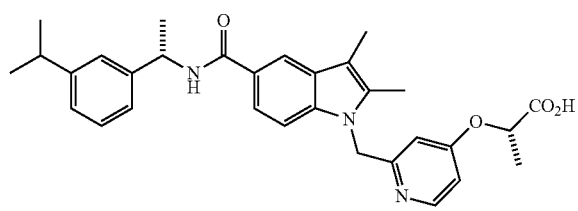
144
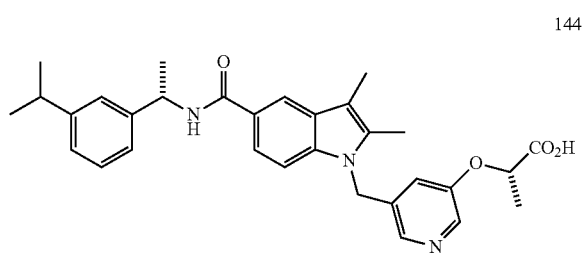
145
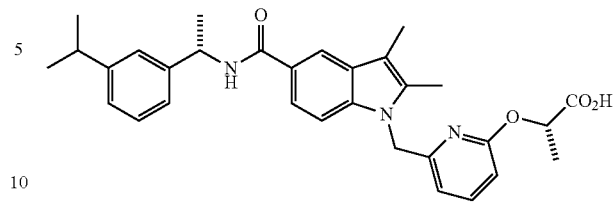
146
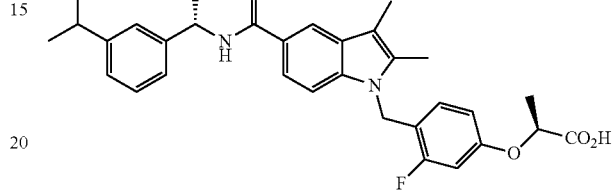
147
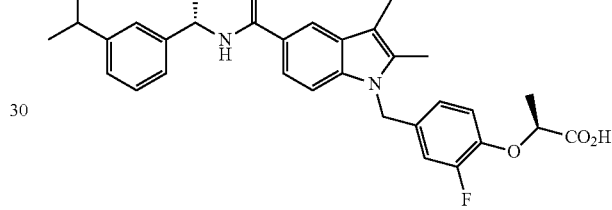
148
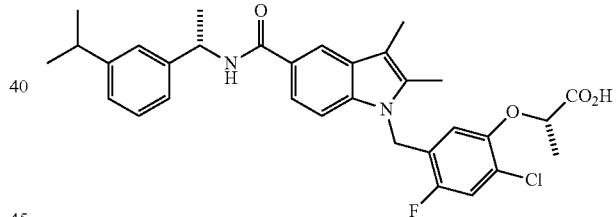
149
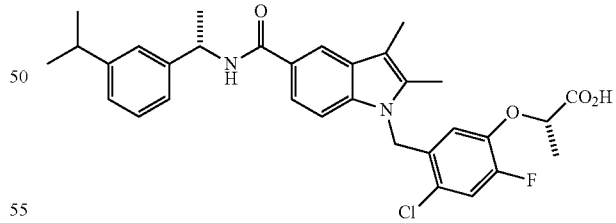
150
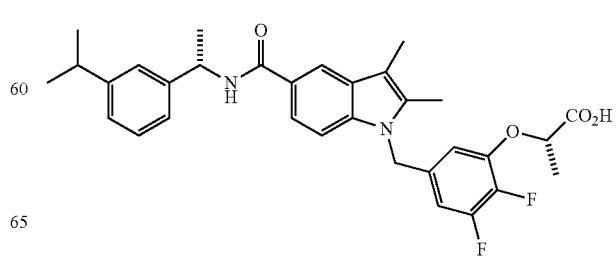

279
-continued
151
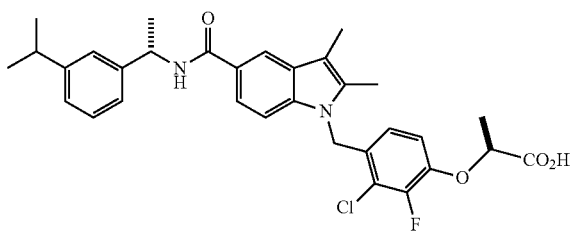
152
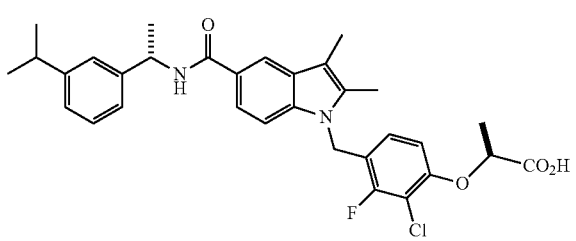
153
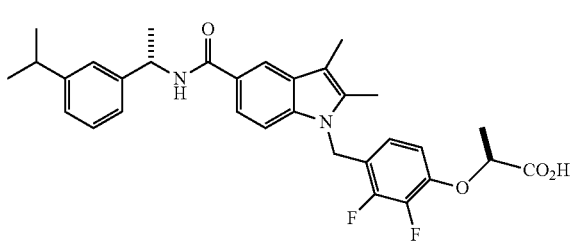
154
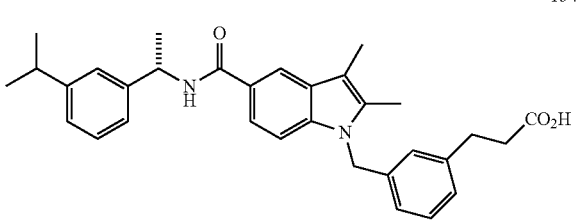
155
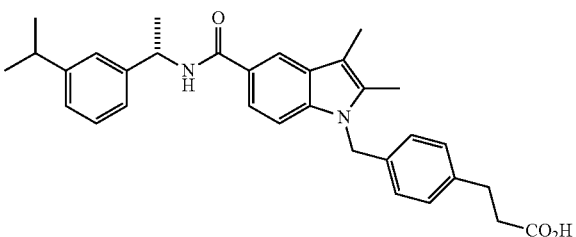
159
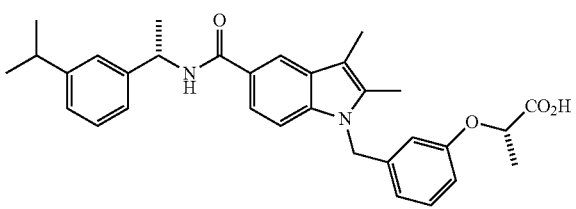
280
-continued
160
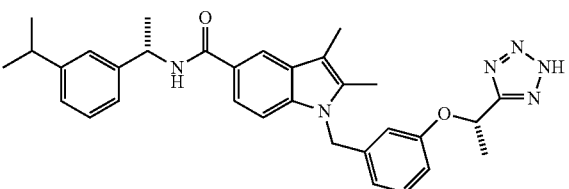
161
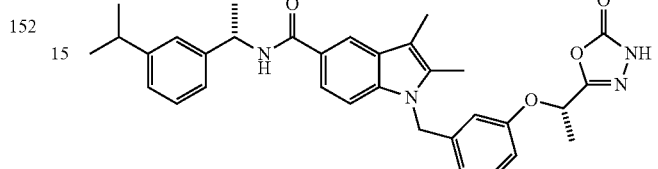
162
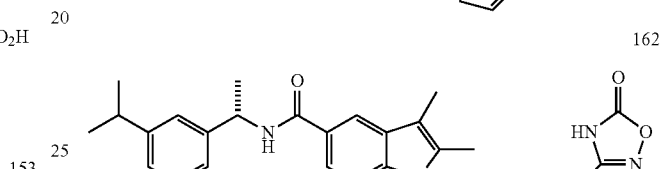
163
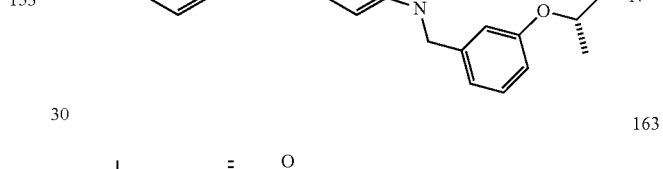
164
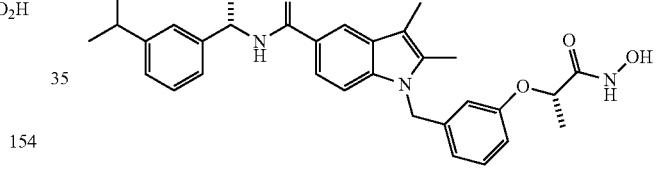
165
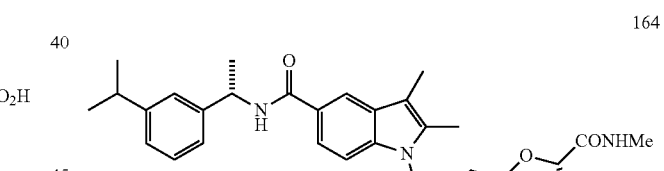
166
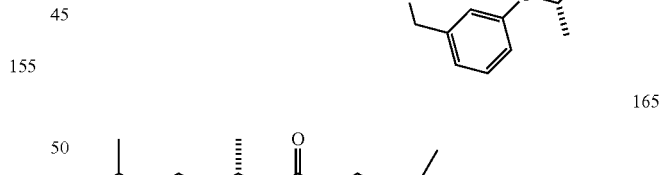

167

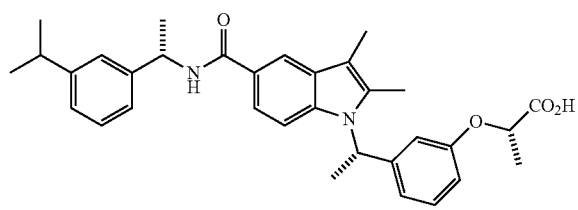

168

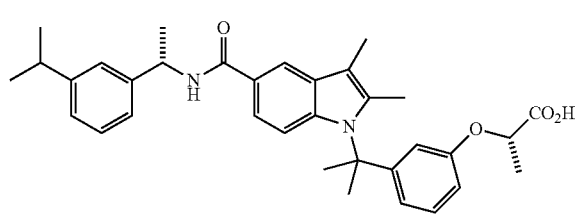

169

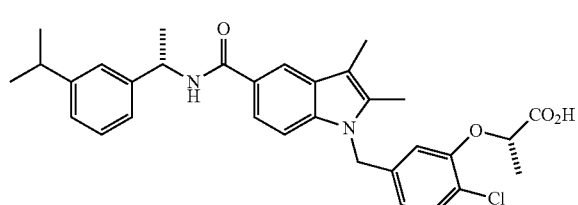

170

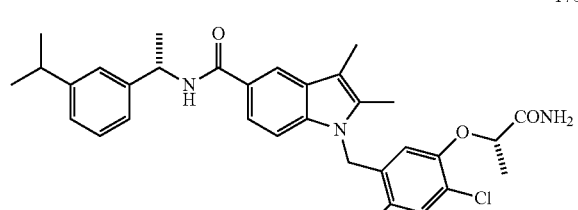

171

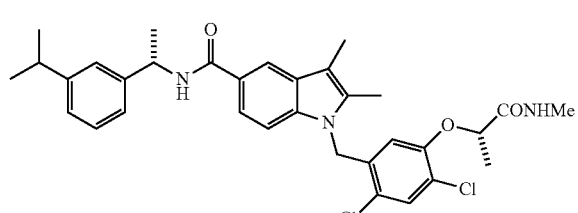

172

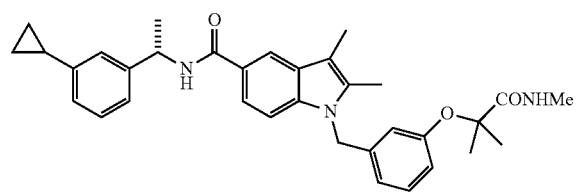

173

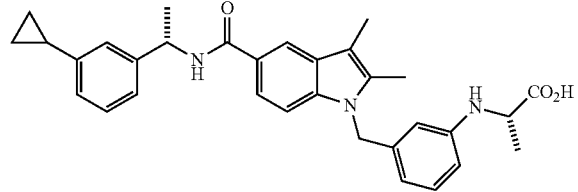

174

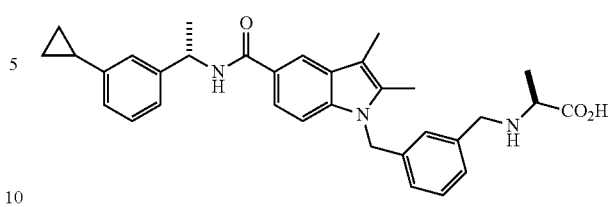

175

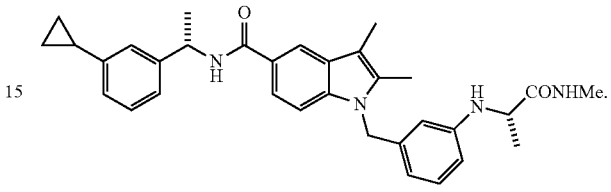

5. A pharmaceutical composition, comprising a compound of claim 1 or claim 4; and a pharmaceutically acceptable excipient.

6. A method of inhibiting kinase-mediate phosphorylation of PPARG in a mammal, comprising administering to the mammal an effective amount of a compound of claim 1.

7. The method of claim 6 wherein the kinase-mediated phosphorylation of PPARG is cdk5-mediated phosphorylation of PPARG.

8. The method of claim 6 wherein the effective amount of the compound for inhibiting kinase-mediated phosphorylation of PPARG does not produce an agonistic effect on PPARG.

9. A method of treating a condition in a mammal, wherein binding of a ligand to PPARG or inhibition of kinase-mediated phosphorylation of PPARG, or both, is medically indicated, comprising administering to the mammal an effective amount of a compound of claim 1.

10. The method of claim 9 wherein the kinase-mediated phosphorylation of PPARG is cdk5-mediated phosphorylation of PPARG.

11. The method of claim 9, wherein the mammal is a human.

12. The method of claim 9, wherein the effective amount, frequency of dosing, and duration of dosing of the compound do not produce an agonistic effect on PPARG.

13. The method of claim 9, wherein the condition is diabetes, insulin resistance, impaired glucose tolerance, pre-diabetes, hyperglycemia, hyperinsulinemia, obesity, or inflammation.

14. The method of claim 13, wherein the effective amount, frequency of dosing, and duration of dosing of the compound does not produce side effects of significant weight gain, edema, impairment of bone growth or formation, or cardiac hypertrophy, or any combination thereof, in the mammal receiving the compound.

15. A method of treating diabetes, insulin resistance, impaired glucose tolerance, pre-diabetes, hyperglycemia, hyperinsulinemia, or inflammation, in a human, comprising administering to the human regularly over a duration of time an effective amount of a compound of claim 1, optionally in conjunction with administering an effective amount of a second medicament effective for the treatment of the condition.

\* \* \* \* \*